US008420779B2

(12) United States Patent
Walker et al.

(10) Patent No.: US 8,420,779 B2
(45) Date of Patent: Apr. 16, 2013

(54) COMPOSITIONS AND METHODS FOR PRODUCING BIOACTIVE FUSION PROTEINS

(75) Inventors: Kenneth W. Walker, Newbury Park, CA (US); Colin V. Gegg, Jr., Newbury Park, CA (US)

(73) Assignee: Amgen Inc., Thousand Oaks, CA (US)

(*) Notice: Subject to any disclaimer, the term of this patent is extended or adjusted under 35 U.S.C. 154(b) by 97 days.

(21) Appl. No.: 12/154,507

(22) Filed: May 22, 2008

(65) Prior Publication Data

US 2009/0118181 A1 May 7, 2009

Related U.S. Application Data

(60) Provisional application No. 60/931,344, filed on May 22, 2007.

(51) Int. Cl.
| A61K 38/16 | (2006.01) |
| C07K 14/00 | (2006.01) |
| C07K 17/00 | (2006.01) |
| C07K 19/00 | (2006.01) |
| C07H 21/04 | (2006.01) |
| C12N 15/63 | (2006.01) |
| C12N 5/10 | (2006.01) |
| C12N 1/21 | (2006.01) |
| C12N 15/09 | (2006.01) |

(52) U.S. Cl.
USPC ........... 530/350; 514/1.1; 514/21.2; 530/402; 536/23.4; 435/69.7; 435/252.3; 435/252.33; 435/320.1; 435/325

(58) Field of Classification Search .................. None
See application file for complete search history.

(56) References Cited

U.S. PATENT DOCUMENTS

| 3,691,016 A | 9/1972 | Patel |
| 3,941,763 A | 3/1976 | Sarantakis |
| 3,969,287 A | 7/1976 | Jaworek et al. |
| 4,083,368 A | 4/1978 | Freezer |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,351,337 A | 9/1982 | Sidman |
| 4,847,325 A | 7/1989 | Shadle et al. |
| 4,849,224 A | 7/1989 | Chang et al. |
| 4,906,159 A | 3/1990 | Sabo et al. |
| 4,906,169 A | 3/1990 | Chien et al. |
| 4,911,916 A | 3/1990 | Cleary |
| 4,925,673 A | 5/1990 | Steiner et al. |
| 4,925,677 A | 5/1990 | Feijen |
| 4,983,395 A | 1/1991 | Chang et al. |
| 4,994,439 A | 2/1991 | Longenecker et al. |
| 5,002,936 A | 3/1991 | Lieberman et al. |
| 5,013,556 A | 5/1991 | Woodle et al. |
| 5,023,084 A | 6/1991 | Chien et al. |
| 5,096,885 A | 3/1992 | Pearlman et al. |
| 5,166,322 A | 11/1992 | Shaw et al. |
| 5,171,264 A | 12/1992 | Merrill |
| 5,206,344 A | 4/1993 | Katre et al. |
| 5,252,714 A | 10/1993 | Harris et al. |
| 5,284,656 A | 2/1994 | Platz et al. |
| 5,302,697 A | 4/1994 | Goodey et al. |
| 5,346,701 A | 9/1994 | Heiber et al. |
| 5,397,702 A | 3/1995 | Cahalan et al. |
| 5,446,090 A | 8/1995 | Harris |
| 5,460,820 A | 10/1995 | Ebert et al. |
| 5,484,895 A | 1/1996 | Meister et al. |
| 5,494,895 A | 2/1996 | Garcia et al. |
| 5,516,523 A | 5/1996 | Heiber et al. |
| 5,567,677 A | 10/1996 | Castensson et al. |
| 5,605,702 A | 2/1997 | Teillaud et al. |
| 5,643,575 A | 7/1997 | Martinez et al. |
| 5,662,925 A | 9/1997 | Ebert et al. |
| 5,714,142 A | 2/1998 | Blaney et al. |
| 5,739,208 A | 4/1998 | Harris |
| 5,739,277 A | 4/1998 | Presta et al. |
| 5,763,478 A | 6/1998 | Baker et al. |

(Continued)

FOREIGN PATENT DOCUMENTS

| EP | 0 219 716 A2 | 4/1987 |
| EP | 0 315 456 B1 | 6/1994 |

(Continued)

OTHER PUBLICATIONS

Kurihara et al. 2001. Journal of Biological Chemistry. 276(44): 41035-41039.*
Fairlie et al, 2002. Protein Expression and Purification. 26: 171-178.*
Zhou et al. 2001. Journal of Biomolecular NMR. 20: 11-14.*
Phillips, A., J Pharm Pharmacology 53: 1169-1174, 2001.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*

(Continued)

Primary Examiner — Zachary Howard
(74) Attorney, Agent, or Firm — Nisan A. Steinberg

(57) ABSTRACT

Disclosed is a composition of matter involving a recombinant fusion protein comprising a a pharmacologically active protein partner, and a small pharmacologically inactive protein domain partner of human origin, such as but not limited to, a $10^{th}$ fibronectin III domain, a SH3 domain, a SH2 domain, a CH2 domain of IgG1, a PDZ domain, a thrombospondin repeat domain, an ubiquitin domain, a leucine-rich repeat domain, a villin headpiece HP35 domain, a villin headpiece HP76 domain, or a fragment or modification of any of these. Also disclosed are nucleic acids (e.g., DNA constructs) encoding the fusion protein, expression vectors and recombinant host cells for expression of the fusion protein, and pharmaceutical compositions containing the recombinant fusion protein and a pharmaceutically acceptable carrier, and method of producing a pharmacologically active recombinant fusion protein.

18 Claims, 20 Drawing Sheets

U.S. PATENT DOCUMENTS

| | | |
|---|---|---|
| 5,770,559 A | 6/1998 | Manning et al. |
| 5,783,208 A | 7/1998 | Venkateshwaran et al. |
| 5,792,451 A | 8/1998 | Sarubbi et al. |
| 5,824,784 A | 10/1998 | Kinstler et al. |
| 5,827,655 A | 10/1998 | Chandy et al. |
| 5,834,431 A | 11/1998 | Stewart et al. |
| 5,849,863 A | 12/1998 | Stewart et al. |
| 5,869,451 A | 2/1999 | Dower et al. |
| 5,900,461 A | 5/1999 | Harris |
| 5,919,455 A | 7/1999 | Greenwald et al. |
| 5,932,462 A | 8/1999 | Harris et al. |
| 5,932,946 A | 8/1999 | Miyasaka et al. |
| 5,981,474 A | 11/1999 | Manning et al. |
| 5,981,485 A | 11/1999 | O'Connor et al. |
| 5,985,265 A | 11/1999 | Kinstler et al. |
| 5,985,608 A | 11/1999 | Luna et al. |
| 5,990,237 A | 11/1999 | Bentley et al. |
| 6,022,952 A | 2/2000 | Weiner et al. |
| 6,077,680 A | 6/2000 | Kem et al. |
| 6,096,891 A | 8/2000 | Carr et al. |
| 6,171,586 B1 | 1/2001 | Lam et al. |
| 6,245,740 B1 | 6/2001 | Goldenberg et al. |
| 6,267,964 B1 | 7/2001 | Nygren et al. |
| 6,273,086 B1 | 8/2001 | Ohki et al. |
| 6,335,178 B1 | 1/2002 | Weiner et al. |
| 6,342,225 B1 | 1/2002 | Jones et al. |
| 6,451,986 B1 | 9/2002 | Pettit |
| 6,548,644 B1 | 4/2003 | Pettit |
| 6,551,821 B1 | 4/2003 | Kandel et al. |
| 6,552,170 B1 | 4/2003 | Thompson et al. |
| 6,602,498 B2 | 8/2003 | Shen |
| 6,610,281 B2 | 8/2003 | Harris |
| 6,632,928 B1 | 10/2003 | Neville et al. |
| 6,660,843 B1 | 12/2003 | Feige et al. |
| 6,689,749 B1 | 2/2004 | Lebrun et al. |
| 6,703,485 B2 | 3/2004 | Kandel et al. |
| 6,740,743 B2 | 5/2004 | Herrmann et al. |
| 6,756,480 B2 | 6/2004 | Kostenuik et al. |
| 6,768,002 B1 | 7/2004 | Herrmann et al. |
| 6,818,418 B1 | 11/2004 | Lipovsek et al. |
| 6,849,714 B1 | 2/2005 | Bridon et al. |
| 6,861,405 B2 | 3/2005 | Desir et al. |
| 6,887,470 B1 | 5/2005 | Bridon et al. |
| 6,887,487 B2 | 5/2005 | Murthy et al. |
| 6,892,728 B2 | 5/2005 | Helgesson et al. |
| 6,894,025 B2 | 5/2005 | Harris |
| 6,900,317 B2 | 5/2005 | Trunk et al. |
| 6,905,688 B2 | 6/2005 | Rosen et al. |
| 6,926,898 B2 | 8/2005 | Rosen et al. |
| 6,932,962 B1 | 8/2005 | Bäckström et al. |
| 6,946,134 B1 | 9/2005 | Rosen et al. |
| 6,989,365 B2 | 1/2006 | Fleer et al. |
| 7,005,436 B2 | 2/2006 | Lloyd et al. |
| 7,029,909 B1 | 4/2006 | Uemura et al. |
| 7,071,172 B2 | 7/2006 | McCown et al. |
| 7,096,942 B1 | 8/2006 | de Rouffignac et al. |
| 7,128,913 B2 | 10/2006 | Burg et al. |
| 7,288,254 B2 | 10/2007 | Neville et al. |
| 7,348,004 B2 | 3/2008 | Peters et al. |
| 7,381,408 B2 | 6/2008 | Mezo et al. |
| 7,404,956 B2 | 7/2008 | Peters et al. |
| 2002/0119946 A1 | 8/2002 | Gen |
| 2003/0069170 A1 | 4/2003 | Soltero et al. |
| 2003/0069395 A1 | 4/2003 | Sato et al. |
| 2003/0104400 A1 | 6/2003 | Ruben et al. |
| 2003/0176352 A1 | 9/2003 | Min et al. |
| 2003/0191056 A1 | 10/2003 | Walker et al. |
| 2003/0195154 A1 | 10/2003 | Walker et al. |
| 2003/0195156 A1 | 10/2003 | Min et al. |
| 2003/0229023 A1 | 12/2003 | Oliner et al. |
| 2003/0236193 A1 | 12/2003 | Oliner et al. |
| 2004/0039167 A1 | 2/2004 | Sabatier et al. |
| 2004/0044188 A1 | 3/2004 | Feige et al. |
| 2004/0121959 A1 | 6/2004 | Boone et al. |
| 2004/0181033 A1 | 9/2004 | Han et al. |
| 2005/0048572 A1 | 3/2005 | Reilly et al. |
| 2005/0054051 A1 | 3/2005 | Rosen et al. |
| 2005/0054570 A1 | 3/2005 | Rosen et al. |
| 2005/0136032 A1* | 6/2005 | Ekwuribe .................. 424/78.27 |
| 2005/0215470 A1 | 9/2005 | Ng et al. |
| 2006/0068469 A1 | 3/2006 | Payne et al. |
| 2006/0140934 A1 | 6/2006 | Gegg et al. |
| 2006/0199812 A1 | 9/2006 | D'Amico et al. |
| 2007/0071764 A1 | 3/2007 | Sullivan et al. |
| 2007/0166308 A1 | 7/2007 | Pullen et al. |
| 2007/0190047 A1 | 8/2007 | Brych et al. |
| 2007/0269369 A1 | 11/2007 | Gegg et al. |
| 2008/0020978 A1 | 1/2008 | Gegg et al. |

FOREIGN PATENT DOCUMENTS

| | | |
|---|---|---|
| EP | 0 668 353 A1 | 8/1995 |
| EP | 0 668 354 A1 | 8/1995 |
| EP | 0 473 084 B1 | 11/1995 |
| EP | 0 469 074 B1 | 7/1996 |
| EP | 0 575 545 B1 | 5/2003 |
| WO | WO 88/06451 A1 | 9/1988 |
| WO | WO 92/02634 A1 | 2/1992 |
| WO | WO 95/03065 A1 | 2/1995 |
| WO | WO 95/13312 A1 | 5/1995 |
| WO | WO 95/18858 A1 | 7/1995 |
| WO | WO 95/21919 A2 | 8/1995 |
| WO | WO 95/21920 A1 | 8/1995 |
| WO | WO 95/26746 A1 | 10/1995 |
| WO | WO 96/05309 A2 | 2/1996 |
| WO | WO 96/11953 A1 | 4/1996 |
| WO | WO 96/32478 A1 | 10/1996 |
| WO | WO 97/23614 A1 | 7/1997 |
| WO | WO 97/34631 A1 | 9/1997 |
| WO | WO 98/23639 A2 | 6/1998 |
| WO | WO 98/39363 A2 | 9/1998 |
| WO | WO 98/46751 A1 | 10/1998 |
| WO | WO 99/24055 A1 | 5/1999 |
| WO | WO 99/38008 A1 | 7/1999 |
| WO | WO 00/24770 C2 | 5/2000 |
| WO | WO 00/24782 A2 | 5/2000 |
| WO | WO 00/38651 A1 | 7/2000 |
| WO | WO 00/38652 A1 | 7/2000 |
| WO | WO 00/69900 A2 | 11/2000 |
| WO | WO 01/83525 A2 | 11/2001 |
| WO | WO 02/11801 A1 | 2/2002 |
| WO | WO 02/098446 A1 | 12/2002 |
| WO | WO 02/100248 A2 | 12/2002 |
| WO | WO 03/031589 A2 | 4/2003 |
| WO | WO 03/057134 A2 | 7/2003 |
| WO | WO 03/093295 A2 | 11/2003 |
| WO | WO 2004/017918 A2 | 3/2004 |
| WO | WO 2004/026329 A1 | 4/2004 |
| WO | WO 2004/043396 A2 | 5/2004 |
| WO | WO 2004/110472 A2 | 12/2004 |
| WO | WO 2005/047337 A1 | 5/2005 |
| WO | WO 2005/105057 A1 | 11/2005 |
| WO | WO2005/105057 A1 | 11/2005 |
| WO | WO 2006/002850 A2 | 1/2006 |
| WO | WO 2006/036834 A2 | 4/2006 |
| WO | WO 2006/042151 A2 | 4/2006 |
| WO | WO 2006/116156 A2 | 11/2006 |
| WO | WO 2007/022070 A2 | 2/2007 |
| WO | WO 2007/045463 A1 | 4/2007 |
| WO | WO 2007/047577 A2 | 4/2007 |
| WO | WO 2007/048026 A2 | 4/2007 |
| WO | 2008/088422 | 7/2008 |
| WO | 2010/054007 A1 | 5/2010 |
| WO | 2010/108154 A2 | 9/2010 |

OTHER PUBLICATIONS

Brenner (1999) Trends in Genetics 15(4): 132.*
U.S. Appl. No. 11/978,076, filed Oct. 25, 2007, Sullivan, et al.
Abdul, et al., "Activity of Potassium Channel-blockers in Breast Cancer", *Anticancer Research*, 23: 3347-3352 (2003).
Abuchowski, et al., "Soluble Polymer-Enzyme Adducts", *Enzymes as Drugs*, pp. 367-383 (1981).
Adams, et al., "Conotoxins and Their Potential Pharmaceutical Applications", *Drug Devel. Research*, 46: 219-234 (1999).
Adjei, et al., "Bioavailability of Leuprolide Following Intratracheal Administration to Beagle Dogs", *Internatl. J Pharmaceutics*, 61: 135-144 (1990).

Adjei, et al., Pulmonary Delivery of Peptide Drugs: Effect of Particle Size on Bioavailability of Leuprolide Acetate in Healthy Male Volunteers, *Pharma. Res.*, 7(6): 565-569 (1990).

"Advanced Chemtech Handbook of Combinatorial and Solid Phase Organic Chemistry—A Guide to Principles, Products & Protocols", Bennett, et al. (ed.), Advanced Chem Tech, Inc., Louisville, Kentucky, (1998) (Provided Table of Contents only).

Akerman, S and Goadsby, PJ, "The Role of Dopamine in a Model of Trigeminovascular Nociception", *J Pharmacology & Experimental Therapeutics*, 314(1): 162-169 (2005).

Akerstrom, et al., "Protein G: A Powerful Tool for Binding and Detection of Monoclonal and Polyclonal Antibodies", *J of Immunol*, 135(4): 2589-2592 (1985).

Alberts, et al., "Synthesis of a Novel Hematopoietic Peptide SK&F 107647", *Thirteenth American Peptide Symposium*, pp. 367-369 (1993).

Altschul, et al., "Gapped BLAST and PSI-BLAST: A New Generation of Protein Database Search Programs", *Nuc. Acids Res.*, 25(17): 3389-3402 (1997).

Andreasen, et al., "Secretion of Glucagon-Like Peptide-1 and Reactive Hypoglycemia after Partial Gastrectomy", *Digestion*, 55: 221-228 (1994).

Arpin, et al., "Sequence of Human Villin: A Large Duplicated Domain Homologous with Other Actin-Severing Proteins and a Unique Small Carboxy-Terminal Domain Related to Villin Specificity", J Cell Biol, 107: 1759-1766 (1988).

Asai, et al., "(Chapter 3) Making Monoclonal Antibodies", *Methods in Cell Biology*, 37: 57-74 (1993).

Azam, et al., "Targeting Effector Memory T Cells With the Small Molecule Kv1.3 Blocker PAP-1 Suppresses Allergic Contact Dermatitis", *J Investigative Dermatology*, 127: 1419-1429 (2007).

Barash, et al., "Human Secretory Signal Peptide Description by Hidden Markov Model and Generation of a Strong Artificial Signal Peptide for Secreted Protein Expression", *Biochemical and Biophysical Research Communications*, 294: 835-842 (2002).

Barrett, A., et al., (ed.), "Handbook of Proteolytic Enzymes", Academic Press, (1998) (Provided Table of Contents only).

Baumgart, et al., "Tacrolimus is Safe and Effective in Patients with Severe Steroid-Refractory or Steroid-Dependent Inflammatory Bowel Disease—A Long-Term Follow-Up", *Amer. J of Gastroenterology*, 101(5): 1048-1056 (2006).

Bednarek, et al., "Chemical Synthesis and Structure-Function Studies of Margatoxin, A Potent Inhibitor of Voltage-Dependent Potassium Channel in Human T Lymphocytes", *Biochemical and Biophysical Research Communications*, 198(2): 619-625 (1994).

Beeton, et al., "Selective Blocking of Voltage-Gated $K^+$ Channels Improves Experimental Autoimmune Encephalomyelitis and Inhibits T Cell Activation[1]", *J of Immunology*, 166: 936-944 (2001).

Beeton, et al., "Targeting Effector Memory T Cells with a Selective Peptide Inhibitor of Kv1.3 Channels for Therapy of Autoimmune Diseases", *Mol. Pharmacol.*, 67(4): 1369-1381 (2005).

Beeton, et al., "Selective Blockade of T Lymphocyte $K^+$ Channels Ameliorates Experimental Autoimmune Encephalomyelitis, a Model for Multiple Sclerosis", *PNAS*, 98(24): 13942-13947 (2001).

Beeton, et al., "Kv1.3 Channels are a Therapeutic Target for T Cell-Mediated Autoimmune Diseases", *PNAS*, 103(46): 17414-17419 (2006).

Begenisich, et al., "Physiological Roles of the Intermediate Conductance, $Ca^{2+}$-activated Potassium Channel Kcnn4", *J of Biological Chem.*, 279(46): 47681-47687 (2004).

Bell, et al., "Exon Duplication and Divergence in the Human Preproglucagon Gene", *Nature*, 304: 368-371 (1983).

Bergerot, et al., "Review Article: Animal Models of Migraine: Looking at the Component Parts of a Complex Disorder", *European J Neuroscience*, 24: 1517-1534 (2006).

Berridge, et al., "Calcium Signalling: Dynamics, Homeostasis and Remodelling", *Nature Reviews—Molecular Cell Biology*, 4: 517-529 (2003).

Bhatnagar, et al., "Structure-Activity Relationships of Novel Hematoregulatory Peptides", *J Med Chem.*, 39(19): 3814-3819 (1996).

Bissonnette, et al., "A Randomized, Multicenter, Double-Blind, Placebo-Controlled Phase 2 Trial of ISA247 in Patients with Chronic Plaque Psoriasis", *J Am. Acad. Dermatol.*, 54(3): 472-478 (2006).

Bodanszky, "Principles of Peptide Synthesis", 2$^{nd}$ Ed., Springer Laboratory (1993) (Provided Table of Contents only).

Bodanszky, et al., "The Practice of Peptide Synthesis", 2$^{nd}$ Revised Ed., Springer-Verlag (1994) (Provided Table of Contents only).

Boehm, et al., "Cellular Response to Interferon-γ", *Annu. Rev. Immunol.*, 15: 749-795 (1997). (Table of Contents also provided).

Bogdanovich, et al., "Functional Improvement of Dystrophic Muscle by Myostatin Blockade", *Nature*, 420: 418-421 (2002).

Bong, et al., "Chemoselective Pd(0)-Catalyzed Peptide Coupling in Water", *Org. Lett.*, 3(16): 2509-2511 (2001).

Bourinet, et al., "Silencing of the $Ca_v3.2$ T-type Calcium Channel Gene in Sensory Neurons Demonstrates its Major Role in Nociception", *EMBO J*, 24(2): 315-324 (2005).

Bowlby, et al., "Modulation of the Kv1.3 Potassium Channel by Receptor Tyrosine Kinases", *J Gen. Physiol.*, 110: 601-610 (1997).

Braquet, et al., "Effect of Endothelin-1 on Blood Pressure and Bronchopulmonary System of the Guinea Pig", *J of Cardiovascular Pharmacol.*, 13(Suppl. 5): S143-S146 (1989).

Caliceti, et al., "Pharmacokinetic and Biodistribution Properties of Poly(ethylene glycol)-Protein Conjugates", *Advanced Drug Delivery Reviews*, 55: 1261-1277 (2003).

Castle, et al., "Maurotoxin: A Potent Inhibitor of Intermediate Conductance $Ca^{2+}$-Activated Potassium Channels", *Mol. Pharmacol.*, 63(2): 409-418 (2003).

Catterall, et al., "International Union of Pharmacology: Approaches to the Nomenclature of Voltage-Gated Ion Channels", *Pharmacol. Rev.*, 55(4): 573-574 (2003).

Catterall, et al., "International Union of Pharmacology. XXXIX. Compendium of Voltage-Gated Ion Channels: Sodium Channels", *Pharmacol. Rev.*, 55(4): 575-578 (2003).

Catterall, et al., "International Union of Pharmacology. XL. Compendium of Voltage-Gated Ion Channels: Calcium Channels", *Pharmacol. Rev.*, 55(4): 579-581 (2003).

Chan, W. C. and White, P. D., Eds., "Fmoc Solid Phase Peptide Synthesis: A Practical Approach", *Oxford University Press*, (2000) (Provided Table of Contents only).

Chandy, "Simplified Gene Nomenclature", *Nature*, 352: pp. 26 (1991).

Chandy, et al., "$K^+$ Channels as Targets for Specific Immunomodulation", *Trends in Pharmacol. Sciences*, 25(5): 280-289 (2004).

Chaubert, et al., "Simultaneous Double Immunoenzymatic Labeling: A New Procedure for the Histopathologic Routine", *Modern Pathology*, 10(6): 585-591 (1997).

Chen, et al., "MMDB: Entrez's 3D-Structure Database", *Nucleic Acids Res.*, 31(1), 474-477 (2003).

Clapham, et al., "International Union of Pharmacology. XLIII. Compendium of Voltage-Gated Ion Channels: Transient Receptor Potential Channels", *Pharmacol. Rev.*, 55(4): 591-596 (2003).

Connelly, et al., "Neutral Endopeptidase 24.11 in Human Neutrophils: Cleavage of Chemotactic Peptide", *Proc. Natl. Acad. Sci. USA*, 82: 8737-8741 (1985).

Creighton, "Proteins: Structures and Molecular Principles", W. H. Freeman & Co., San Francisco, pp. 70-86 (1983) (Provided Title/Versa Pages and Table of Contents as well).

Cwirla, et al., "Peptide Agonist of the Thrombopoietin Receptor as Potent as the Natural Cytokine", *Science*, 276: 1696-1699 (1997).

Davis, et al., "Preparation and Characterization of Antibodies with Specificity for the Amino-Terminal Tetrapeptide Sequence of the Platelet-Derived Connective Tissue Activating Peptide-III", *Biochem Intl.*, 10(3): 395-404 (1985).

Debs, et al., "Lung-Specific Delivery of Cytokines Induces Sustained Pulmonary and Systemic Immunomodulation in Rats", *J Immunol.*, 140(10): 3482-3488 (1988).

Dedman, et al., Selection of Targeted Biological Modifiers from a Bacteriophage Library of Random Peptides', *J Biol. Chem.*, 268(31): 23025-23030 (1993).

del Rio-Portilla, et al., "NMR Solution Structure of Cn12, a Novel Peptide from the Mexican Scorpion *Centruroides noxius* with a Typical β-Toxin Sequence but with α-Like Physiological Activity", *Eur. J Biochem.*, 271: 2504-2516 (2004).

Delgado, et al., "The Uses and Properties of PEG-Linked Proteins", *Critical Ref. Therap. Drug Carrier Sys.*, 9(3,4): 249-304 (1992).

DeVasher, et al., "Aqueous-Phase, Palladium-Catalyzed Cross-Coupling of Aryl Bromides Under Mild Conditions, Using Water-Soluble, Sterically Demanding Alkylphosphines", *J Org. Chem.*, 69: 7919-7927 (2004).

Dibowski, et al., "Bioconjugation of Peptides by Palladium-Catalyzed C—C Cross-Coupling in Water", *Angew. Chem. Int. Ed.*, 37(4): 476-478 (1998).

Doering, et al., "Cysteine Scanning Mutagenesis at 40 of 76 Positions in Villin Headpiece Maps the F-Actin Binding Site and Structural Features of the Domain", *Biochemistry*, 35: 12677-12685 (1996).

Dogrul, et al., "Reversal of Experimental Neuropathic Pain by T-Type Calcium Channel Blockers", *Pain*, 105: 159-168 (2003).

Duffy, et al., The $K^+$ Channel $iK_{Ca}1$ Potentiates $Ca^{2+}$ Influx and Degranulation in Human Lung Mast Cells, *J Allergy Clin. Immunol.*, 114(1): 66-72 (2004).

Earnshaw, et al., "Mammalian Caspases: Structure, Activation, Substrates, and Functions During Apoptosis", *Annu. Rev. Biochem.*, 68: 383-424 (1999). (Table of Contents included).

Ellison, et al., "The Nucleotide Sequence of a Human Immunoglobulin $C\gamma_1$ Gene", *Nucleic Acids Res.*, 10(13): 4071-4079 (1982).

Engel, et al., "Insertion of Carrier Proteins into Hydrophilic Loops of the *Escherichia coli* Lactose Permease", *Biochimica et Biophysica Acta*, 1564: 38-46 (2002).

Erickson, et al., "Solid-Phase Peptide Synthesis", *The Proteins*, ($3^{rd}$ ed.), Chapter 3, pp. 257-517 (1976). [Submitting as 1 of 3: pp. 257-346; 2 of 3: pp. 347-431; 3 of 3: pp. 432-517].

Ertel, et al., "Nomenclature of Voltage-Gated Calcium Channels", *Neuron* 25: 533-535 (2000).

Felix, A.M., "Site-Specific Poly(ethylene glycol)ylation of Peptides", *American Chem. Soc.*, Chapter 16, pp. 218-238 (1997).

Felix, A.M., "Pegylated Peptides IV: Enhanced Biological Activity of Site-Directed Pegylated GRF Analogs", *Int. J Peptide Protein Res.*, 46: 253-264 (1995).

Feske, et al., "A Severe Defect in CRAC $Ca^{2+}$ Channel Activation and Altered $K^+$ Channel Gating in T Cells from Immunodeficient Patients", *J Exp. Med*. 202(5): 651-662 (2005).

Fields, et al., "Principles and Practice of Solid-Phase Peptide Synthesis", *Synthetic Peptides: A User's Guide*, Chapter 3, pp. 77-183, [G. Grant, ed., W.H. Freeman and Co, NY] (1992) [Also providing Table of Contents and title page].

Fields, et al., "Synthetic Peptides: A User's Guide", *Oxford University Press*, Grant, G.A. (ed.), ($2^{nd}$ ed.), Chapter 3, pp. 93-219 (2002). [Submitting as 4 pdfs: 1 of 4:pp. 93-149; 2 of 4: pp. 150-173; 3 of 4: pp. 174-213; 4 of 4: pp. 214-219].

Finn, et al., *The Proteins*, "The Synthesis of Peptides by Solution Methods with Emphasis on Peptide Hormones", ($3^{rd}$ ed.), vol. II, pp. 105-253 (1976).

Flatters, et al., "Ethosuximide Reverses Paclitaxel- and Vincristine-Induced Painful Peripheral Neuropathy", *Pain*, 109: 150-161 (2004).

Flint, et al., "Glucagon-like Peptide 1 Promotes Satiety and Suppresses Energy Intake in Humans", *J Clin Invest*, 101(3): 515-520 (1998).

Fraser, et al., "Predominant Expression of Kv1.3 Voltage-Gated $K^+$ Channel Subunit in Rat Prostate Cancer Cell Lines: Electrophysiological, Pharmacological and Molecular Characterisation", *Pflugers Arch—Eur. J Physiol.*, 446: 559-571 (2003).

Gaffen, et al., "Overview of Interleukin-2 Function, Production and Clinical Applications", *Cytokine*, 28; 109-123 (2004).

Gennaro, A. R. (ed.), *Remington's Pharmaceutical Sciences*, $18^{th}$ Ed., Mack Publishing Co., Easton, PA, (1990). [Provided Table of Contents only].

Glazebrook, et al., "Potassium Channels Kv1.1, Kv1.2 and Kv1.6 Influence Excitablity of Rat Visceral Sensory Neurons", *J Physiology*, 541.2: 467-482 (2002).

Goldin, et al, "Nomenclature of Voltage-Gated Sodium Channels", *Neuron*, 28: 365-368 (2000).

Gonzalez-Cadavid, et al., "Organization of the Human Myostatin Gene and Expression in Healthy Men and HIV-Infected Men With Muscle Wasting", *PNAS USA*, 95: 14938-14943 (1998).

González-Pinto, et al., "Five-Year Follow-Up of a Trial Comparing Tacrolimus and Cyclosporine Microemulsion in Liver Transplantation", *Transplan. Proc.*, 37: 1713-1715 (2005).

Goodson, RJ and Katre, NV, "Site-Directed Pegylation of Recombinant Interleukin-2 at its Glycosylation Site", *Biotechnology*, 8: 343-346 (1990).

Greene, et al., *Protective Groups in Organic Synthesis*, $3^{rd}$. Ed., John Wiley & Sons, Inc., (1999) (Provided Table of Contents only).

Greenwald, et al., "Poly(ethylene glycol) Conjugated Drugs and Prodrugs: A Comprehensive Review", *Crit. Rev. in Therap. Drug Carrier Systems*, 17(2): 101-161 (2000).

Grgic, et al., "Selective Blockade of the Intermediate-Conductance $Ca^{2+}$-Activated $K^+$ Channel Suppresses Proliferation of Microvascular and Macrovascular Endothelial Cells and Angiogenesis In Vivo", *Arterioscler Thromb. Vasc. Biol.*, 25: 704-709 (2005).

Gutman, et al., "International Union of Pharmacology. XLI. Compendium of Voltage-Gated Ion Channels: Potassium Channels", *Pharmacol. Rev.*, 55(4): 583-586 (2003).

Gutniak, et al., "Antidiabetogenic Effect of Glucagon-Like Peptide-1 (7-36)Amide in Normal Subjects and Patients with Diabetes Mellitus", *New Eng J Med*, 326(20): 1316-1322 (1992).

Gutzwiller, et al., "Glucagon-like Peptide-1; A Potent Regulator of Food Intake in Humans", *Gut*, 44: 81-86 (1999).

Halaby, et al., "The Immunoglobin Fold Family: Sequence Analysis and 3D Structure Comparisons", *Prot. Engin.*, 12(7): 563-571 (1999).

Hamrick, et al., "Bone Mineral Content and Density in the Humerus of Adult Myostatin-Deficient Mice", *Calcif Tissue Int*, 71: 63-68 (2002).

Harte, et al., "Genome-wide Detection and Family Clustering of Ion Channels", *FEBS Letters*, 514: 129-134 (2002).

Hendrickson, et al., "Incorporation of Nonnatural Amino Acids into Proteins", *Annu. Rev. Biochem.*, 73: 147-176 (2004).

Herman, et al., Poly(Ethylene Glycol) with Reactive Endgroups: I. Modification of Proteins, *J. Bioactive and Comp. Polymers*, 10(2): 145-187 (1995).

Herz, et al., "Molecular Approaches to Receptors as Targets for Drug Discovery", *J of Receptor & Signal Transduction Research*, 17(5): 671-776 (1997).

Hofmann, et al., "International Union of Pharmacology. XLII. Compendium of Voltage-Gated Ion Channels: Cyclic Nucleotide-Modulated Channels", *Pharmacol. Rev.*, 55(4): 587-589 (2003).

Holick, et al., "A Parathyroid Hormone Antagonist Stimulates Epidermal Proliferation and Hair Growth in Mice", *Proc Natl Acad Sci USA*, 91: 8014-8016 (1994).

Hubbard, et al., "Anti-Neutrophil-Elastase Defenses of the Lower Respiratory Tract in $\alpha$1-Antitrypsin Deficiency Directly Augmented with an Aerosol of $\alpha$1-Antitrypsin", *Annals of Internal Med.*, 111(3): 206-212 (1989).

Irwin, DM & Wong, J, "Trout and Chicken Proglucagon: Alternative Splicing Generates mRNA Transcripts Encoding Glucagon-Like Peptide 2", *Mol. Endocrinol.*, 9(3): 267-277 (1995).

Jäger, et al., "Blockage of Intermediate-Conductance $Ca^{2+}$-Activated $K^+$ Channels Inhibit Human Pancreatic Cancer Cell Growth In Vitro", *Mol. Pharmacol.*, 65(3): 630-638 (2004).

Jaravine, et al., "Three-Dimensional Structure of Toxin OSK1 from *Orthochirus scrobiculosus* Scorpion Venom", *Biochemistry*, 36: 1223-1232 (1997). [7 drawing-related pages included after p. 1232].

Jensen, et al., "The $Ca^{2+}$-Activated K+ Channel of Intermediate Conductance: A Molecular Target for Novel Treatments?" *Current Drug Targets*, 2: 401-422 (2001).

Jeppesen, P.B., "Growth Factors in Short-Bowel Syndrome Patients", *Gastroenterol Clin N Am*, 36: 109-121 (2007).

Judge, et al., "Potassium Channel Blockers in Multiple Sclerosis: Neuronal Kv Channels and Effects of Symptomatic Treatment", *Pharmacology & Therapeutics, Elsevier, GB*, 111(1): 224-259 (2006). [Sent as 1 of 2; pp. 224-240 and 2 of 2; pp. 241-259].

Kalman, et al., "ShK-Dap$^{22}$, a Potent Kv1.3-Specific Immunosuppressive Polypeptide", *J Biol. Chem.*, 273(49): 32697-32707 (1998).

Kay, et al., "From Peptides to Drugs Via Phage Display", *Drug Disc. Today*, 3(8): 370-378 (1998).

Keil, B., *Specificity of Proteolysis*, Springer-Verlag, (Berlin/Heidelberg/New York) (1992). (Provided Table of Contents only).

Kho, et al., "A Tagging-Via-Substrate Technology for Detection and Proteomics of Farnesylated Proteins", *PNAS*, 101(34): 12479-12484 (2004).

Kocienski, P.J., "Protecting Groups", *Georg Thieme Verlag*, (Stuttgart/New York) (1994) (Provided Table of Contents only).

Köhler, et al., "Blockade of the Intermediate-Conductance Calcium-Activated Potassium Channel as a New Therapeutic Strategy for Restenosis", *Circulation*, 108: 1119-1125 (2003).

Koo, J., "A Randomized, Double-Blind Study Comparing the Efficacy, Safety and Optional Dose of Two Formulations of Cyclosporin, Neoral and Sandimmun, in Patients with Severe Psoriasis", *British J Derm.*, 139: 88-95 (1998).

Koo, et al., "Correolide and Derivatives Are Novel Immunosuppressants Blocking the Lymphocyte Kv1.3 Potassium Channels", *Cell. Immunol.*, 197: 99-107 (1999).

Koo, et al., "Blockade of the Voltage-Gated Potassium Channel Kv1.3 Inhibits Immune Responses In Vivo", *J Immunol.*, 158: 5120-5128 (1997).

Korner, et al., "GLP-1 Receptor Expression in Human Tumors and Human Normal Tissues: Potential for In Vivo Targeting", *J Nucl. Med.*, 48(5): 736-743 (2007).

Krysan, et al., "Quantitative Characterization of Furin Specificity", *J of Biol. Chem.*, 274(33): 23229-23234 (1999).

Kuai, et al., "Plasminogen Activator Inhibitor-1 Fused with Erythropoietin (EPO) Mimetic Peptide (EMP) Enhances the EPO Activity of EMP", *J Peptide Res.*, 56: 59-62 (2000).

Kuypers, D.R. J., "Immunosuppressive Drug Monitoring—What to Use in Clinical Practice Today to Improve Renal Graft Outcome", *Transplant Internat.*, 18: 140-150 (2005).

Kyte, et al., "A Simple Method for Displaying the Hydropathic Character of a Protein", *J Mol. Biol.*, 157: 105-132 (1982).

Lalani, et al., "Myostatin and Insulin-like Growth Factor-I and -II Expression in the Muscle of Rats Exposed to the Microgravity Environment of the NeuroLab Space Shuttle Flight", *J Endocrin.*, 167: 417-428 (2000).

Legros, et al., "Influence of a $NH_2$-Terminal Extension on the Activity of KTX2, a $K^+$ Channel Blocker Purified From *Androctonus australis* Scorpion Venom", *FEBS Letters, Elsvier, Amsterdam, NL*, 417(1): 123-129 (1997).

Lehmann-Horn, F and Jurkat-Rott, K, "Voltage-Gated Ion Channels and Hereditary Disease", *Physiol. Reviews*, 79(4): 1317-1372 (1999).

Lewis, et al., "Therapeutic Potential of Venom Peptides", *Nature Reviews/Drug Dis.*, 2: 790-802 (2003).

Lin, et al., "Myostatin Knockout in Mice Increases Myogenesis and Decreases Adipogenesis", *Biochemical and Biophysical Research Communications*, 291(3): 701-706 (2002).

Link, et al., "Non-Canonical Amino Acids in Protein Engineering", *Curr. Opn. in Biotech.*, 14: 603-609 (2003).

Lu, Y-A and Felix, AM, "Pegylated Peptides, III. Solid-Phase Synthesis with Pegylating Reagents of Varying Molecular Weight: Synthesis of Multiply Peglylated Peptides", *Reactive Polymers*, 22: 221-229 (1994).

Macian, F., "NFAT Proteins: Key Regulators of T-Cell Development and Function", *Nature Reviews/Immunol.*, 5: 472-484 (2005).

MacLennan, et al., "Structure-Function Relationships in the $Ca^{2+}$-Binding and Translocation Domain of SERCA1: Physiological Correlates in Brody Disease", *Acta. Physiol. Scand.*, 163(Suppl 643): 55-67 (1998).

Maniatis, et al., "Regulation of Inducible and Tissue-Specific Gene Expression", *Science*, 236: 1237-1245 (1987).

Mannstadt, et al., "Receptors for PTH and PTHrP: Their Biological Importance and Functional Properties" *Am J Physiol-Renal Physiol*, 277: 665-675 (1999).

Marshall, K., "Solid Oral Dosage Forms", *Modern Pharmaceutics*, Chapter 10: 359-427 (1979).

Mauler, et al., "Selective Intermediate-/Small Conductance Calcium-Activated Potassium Channel (KCNN4) Blockers are Potent and Effective Therapeutics in Experimental Brain Oedema and Traumatic Brain Injury Caused by Acute Subdural Haematoma", *European J Neuroscience*, 20: 1761-1768 (2004).

McKnight, et al., "A Thermostable 35-Residue Subdomain within Villin Headpiece", *J Mol Biol*, 260: 126-134 (1996).

McKnight, et al., "NMR Structure of the 35-Residue Villin Headpiece Subdomain", *Nature Structural Biology*, 4(3): 180-184 (1997).

Means, et al., "Selected Techniques for the Modification of Protein Side Chains", in *Chemical Modification of Proteins* published by Holden Day, Inc., 214-230 (1971). [also included Table of Contents].

Merrifield, R.B., "Solid-Phase Peptide Synthesis", *The Chemistry of Polypeptides—Essays in Honor of Dr. Leonidas Zervas*, Chapter 16, pp. 335-361 (1973). (also providing title page and Table of Contents).

Merrifield, R.B., "Solid-Phase Peptide Synthesis. I. The Synthesis of a Tetrapeptide", *J. Am. Chem. Soc.*, 85: 2149-2154 (1963).

Mojsov, S., "Structural Requirements for Biological Activity of Glucagon-like Peptide-I", *Int J Peptide Protein Res*, 40: 333-343 (1992).

Morpurgo, et al., "Preparation and Characterization of Poly(ethylene glycol) Vinyl Sulfone", *Bioconjugate Chem.*, 7: 363-368 (1996).

Mouhat, et al., "K+ Channel Types Targeted by Synthetic OSK1, a Toxin from *Orthochirus scrobiculosus* Scorpion Venom", *Biochem J*, 385: 95-104 (2005).

Mouhat, et al., "Pharmacological Profiling of *Orthochirus scrobiculosus* Toxin 1 Analogs with a Trimmed N-Terminal Domain", *Mol. Pharmacol.*, 69(1): 354-362 (2006).

Mouhat, et al., "Pharmacological Profiling of *Orthochirus scrobiculosus* Toxin 1 Analogues with a Trimmed N-terminal Domain", *Mol. Pharmacol. Fast Forward*, [doi:10.1124/mol.105.017210], pp. 1-30 (2005).

Multiple Sclerosis Study Group, "Efficacy and Toxicity of Cyclosporine in Chronic Progressive Multiple Sclerosis: A Randomized, Double-Blinded, Placebo-Controlled Clinical Trial", *Annals Neurol.*, 27(6): 591-605 (1990).

Naranda, et al., "Activation of Erythropoietin Receptor in the Absence of Hormone by a Peptide that Binds to a Domain Different from the Hormone Binding Site", *Proc Natl Acad Sci USA*, 96: 7569-7574 (1999).

Nelson, et al., "The Endogenous Redox Agent L-Cysteine Induces T-Type $Ca^{2+}$ Channel-Dependent Sensitization of a Novel Subpopulation of Rat Peripheral Nociceptors", *J of Neurosci.*, 25(38): 8766-8775 (2005).

Newmark, et al., "Preparation and Properties of Adducts of Streptokinase and Streptokinase-Plasmin Complex with Polyethylene Glycol and Pluronic Polyol F38", *J Appl. Biochem.*, 4: 185-189 (1982).

Nicke, et al., "α-Conotoxins as Tools for the Elucidation of Structure and Function of Neuronal Nicotinic Acetylcholine Receptor Subtypes", *Eur J Biochem.*, 271: 2305-2319 (2004).

Niemeyer, et al., "Ion Channels in Health and Disease", *EMBO Reports*, 2(7): 568-573 (2001).

"Nomenclature and Symbolism for Amino Acids and Peptides, Recommendations 1983"—(by IUPAC Joint Commission on Biochemical Nomenclature (JCBN)), *FEBS 1984, Eur. J. Biochem*, 138: 9-37 (1984).

"Nomenclature and Symbolism for Amino Acids and Peptides, Enzyme Nomenclature 1984 Announcement, Corrections to Recommendations 1983", *FEBS 1985, Eur. J. Biochem*, 152: 1 (1985).

"Nomenclature and Symbolism for Amino Acids and Peptides, Biochemical Nomenclature, and Enzyme Nomenclature Announcements: Symbolism and Terminology in Enzyme Kinetics, Correction to Recommendations 1981, Nomenclature and Symbolism for Amino Acids and Peptides, Corrections to Recommendations 1983, The nomenclature of Steroids, Corrections to Recommendations 1989, Nomenclature of Electron-Transfer Proteins, Corrections to Recommendations 1989", *FEBS 1993, Eur. J Biochem.*, 213: 1-3 (1993).

Norton, et al., "Potassium Channel Blockade by the Sea Anemone Toxin ShK for the Treatment of Multiple Sclerosis and Other Autoimmune Diseases", *Curr. Med. Chem.*, 11: 3041-3052 (2004).

Nova Biochem, "Channel Blockers", Calbiochem, 10294 Pacific Ctr. Ct., San Diego, CA 92121 (2000).

Oeswein, et al., "Aerosolization of Protein Pharmaceuticals", Proc. Symp. Resp. Drug Delivery II, Keystone, CO, pp. 14-34 (1990). [Also included are additional 14 pgs. of figures].

Pathirathna, et al., "New Evidence that Both T-Type Calcium Channels and $GABA_A$ Channels are Responsible for the Potent Peripheral Analgesic Effects of 5α-Reduced Neuroactive Steroids", *Pain*, 114: 429-443 (2005).
Pennington, et al., "Role of Disulfide Bonds in the Structure and Potassium Channel Blocking Activity of ShK Toxin", *Biochem.*, 38: 14549-14558 (1999).
Perfetti, R and Merkel, P, "Glucagon-like Peptide-1: A Major Regulator of Pancreatic β-cell Function", *Eur J Endocrinol*, 143: 717-725 (2000).
Prasad, et al., "Glucagonlike Peptide-2 Analogue Enhances Intestinal Mucosal Mass After Ischemia and Reperfusion", *J Pediatr Surg*, 35(2): 357-359 (2000).
Prescher, et al., "Chemistry in Living Systems", *Nature Chem. Biol.*, 1(1): 13-21 (2005).
Prochnicka-Chalufour, "Solution of Discrepin, a New K+-Channel Blocking Peptide from the α-KTx15 Subfamily", *Biochemistry*, 45: 1795-1804 (2006).
Ptacek, LJ and Fu, Y-H, "Channels and Disease—Past, Present, and Future", *Arch. Neurol.*, 61: 1665-1668 (2004).
Quezada, et al., "CD40/CD154 Interactions at the Interface of Tolerance and Immunity", *Annu. Rev. Immunol.*, 22: 307-328 (2004). [Also providing 2 Figure Pages and Table of Contents].
Quintana, et al., "Calcium-Dependent Activation of T-Lymphocytes", *Pflugers Arch—Eur. J Physiol.*, 450: 1-12 (2005).
Rauer, et al., "Structure-Guided Transformation of Charybdotoxin Yields an Analog that Selectively Targets $Ca^{2+}$-Activated Over Voltage-Gated $K^+$ Channels", *J Biol. Chem.*, 275(2): 1201-1208 (2000).
Ravin, et al., "Preformulation", *Remington's Pharmaceutical Sciences*, 18th Ed., Mack Publishing Co., Easton, PA, (1990), Chapter 75, pp. 1435-1450 (1990). [Also providing Title/versa pages and Table of Contents].
Reich, et al., "Blocking Ion Channel KCNN4 Alleviates the Symptoms of Experimental Autoimmune Encephalomyelitis in Mice", *Eur. J. Immunol.*, 35: 1027-1036 (2005).
Rodríguez de la Vega, et al., "Novel Interactions Between $K^+$ Channels and Scorpion Toxins", *TRENDS in Pharmacol. Sciences*, 24(5): 222-227 (2003).
Rohatagi, et al., "Pharmacokinetics, Pharmacodynamics, and Safety of Inhaled Cyclosporin A (ADI628) after Single and Repeated Administration in Healthy Male and Female Subjects and Asthmatic Patients", *J Clin. Pharmacol.*, 40: 1211-1226 (2000).
Rudnic, "Oral Solid Dosage Forms", *Remington's Pharmaceutical Sciences*, 18th Ed., A.R. Gennaro (ed) Mack Publishing Co., Easton, PA, Chapter 89, pp. 1633-1665 (1990). [Also providing Title/versa pages and Table of Contents].
Rus, et al., "The Voltage-Gated Potassium Channel Kv1.3 is Highly Expressed on Inflammatory Infiltrates in Multiple Sclerosis Brain", *PNAS*, 102: 11094-11099 (2005).
Sandler,SR and Karo, W, "Polyoxyalkylation of Hydroxy Compounds", Polymer Synthesis, Academic Press, vol. III, Chapter 5, pp. 138-161 (1980). [also including Table of Contents].
Sarmay, et al., "Mapping and Comparison of the Interaction Sites on the Fc Region of IgG Responsible for Triggering Antibody Dependent Cellular Cytotoxicity (ADCC) Through Different Types of Human Fcγ Receptor", *Molecular Immun.*, 29(5): 633-639 (1992).
Sasaki, et al., "Structure-Mutation Analysis of the ATPase Site of *Dictyostelium discoideum* Myosin II", *Adv. Biophys.*, 35: 1-24 (1998).
Schechter, et al., "On the Size of the Active Site in Proteases. I. Papain", *Biochem. and Biophys. Res. Communications.*, 27(2): 157-162 (1967).
Schechter, et al., "On the Active Site of Proteases. III. Mapping the Active Site of Papain; Specific Peptide Inhibitors of Papain", *Biochem. and Biophys. Res. Communications.*, 32(5): 898-902 (1968).
Schilli, et al., "Control of Hair Growth with Parathyroid Hormone (7-34)", *J Investigative Dermatology*, 108(6): 928-932 (1997).
Schmitz, et al., "Design of PAP-1, a Selective Small Molecule Kv1.3 Blocker, for the Suppression of Effector Memory T Cells in Autoimmune Diseases", *Mol. Pharmacol.*, 68(5): 1254-1270 (2005).
Schroder, et al., "Interferon-γ: An Overview of Signals, Mechanisms and Functions", *J Leukocyte Biol.*, 75: 163-189 (2004).

Shakkottai, et al., "Design and Characterization of a Highly Selective Peptide Inhibitor of the Small Conductance Calcium-Activated $K^+$ Channel, SkCa2", *J Biol. Chem.*, 276(46): 43145-43151 (2001).
Sharma, et al., "Myostatin, A Transforming Growth Factor-β Superfamily Member, Is Expressed in Heart Muscle and Is Upregulated in Cardiomyocytes After Infarct", *J Cell Physiol*, 180(1): 1-9 (1999).
Shin, et al., "A T-Type Calcium Channel Required for Normal Function of a Mammalian Mechanoreceptor", *Nature Neuroscience*, 6(7): 724-730 (2003).
Shinmei, et al., "Quantitation of Chondroitin 4-Sulfate and Chondroitin 6-Sulfate in Pathologic Joint Fluid", *Arthritis Rheum*, 35(11): 1304-1308 (1992).
Silberberg, Ruth, "Diseases of Joints", *Anderson's Pathology—vol. II*, Eighth Edition, J.M.Kissane (ed)., publ. By C.V. Mosby Company, Chapter 42: pp. 1817-1852 (1985). [Also including Title page and Table of Contents].
Smith, et al., "Pulmonary Deposition and Clearance of Aerosolized Alpha-1-Proteinase Inhibitor Administered to Dogs and to Sheep" *J Clin. Invest.*, 84: 1145-1154 (1989).
Smith, et al., "Modifications to the N-Terminus but Not the C-Terminus of Calcitonin Gene-Related Peptide(8-37) Produce Antagonists with Increased Affinity", *J Med Chem*, 46(12): 2427-2435 (2003).
Speers, et al., "Profiling Enzyme Activities In Vivo Using Click Chemistry Methods", *Chem. & Biol.*, 11: 535-546 (2004).
Speers, et al., "Activity-Based Protein Profiling In Vivo Using a Copper(I)-Catalyzed Azide-Alkyne [3 + 2] Cycloaddition", *J Am. Chem. Soc.*, 125: 4686-4687 (2003).
Steiner, D.F., "The Proprotein Convertases", *Curr. Opinion Chem. Biology*, 2: 31-39 (1998).
Stewart, et al., Solid Phase Peptide Synthesis, *W.H. Freeman and Co.*, San Francisco, (1969) (Provided Table of Contents only).
Stocker, et al., "ICA-17043, a Novel Gardos Channel Blocker, Prevents Sickled Red Blood Cell Dehydration In Vitro and In Vivo in SAD Mice", *Blood*, 101(6): 2412-2418 (2003).
Tang, et al., "Metabolic Regulation of Potassium Channels", *Annu. Rev. Physiol.*, 66: 131-159 (2004). [Also including Table of Contents].
Thonar, et al., "Body Fluid Markers of Cartilage Changes in Osteoarthritis", *Rheumatic Disease Clinics of North America*, Moskowitz (ed)., 19(3): 635-657 (1993).
Todorovic, et al., "Redox Modulation of Peripheral T-type $Ca^{2+}$ Channels In Vivo: Alteration of Nerve Injury-Induced Thermal Hyperalgesia", *Pain*, 109: 328-339 (2004).
Toft-Nielsen, et al., "Continuous Subcutaneous Infusion of Glucagon-Like Peptide 1 Lowers Plasma Glucose and Reduces Appetite in Type 2 Diabetic Patients", *Diabetes Care*, 22(7): 1137-1143. (1999).
Tolessa, "Inhibitory Effect of Glucagon-like Peptide-1 on Small Bowel Motility—Fasting But Not Fed Motility Inhibited Via Nitric Oxide Independently of Insulin and Somatostatin", *J Clin Invest*, 102(4): 764-774 (1998).
Tudor, et al., "Ionisation Behaviour and Solution Properties of the Potassium-Channel Blocker ShK Toxin", *Eur. J Biochem.*, 251: 133-141 (1998).
Turk, et al., "Determination of Protease Cleavage Site Motifs Using Mixture-Based Oriented Peptide Libraries", *Nature Biotechnology*, 19: 661-667 (2001).
Tytgat, et al., "A Unified Nomenclature for Short-Chain Peptides Isolated from Scorpion Venoms: Alpha-KTx Molecular Subfamilies", *Trends in Pharmacological Sciences, Elsevier, Hayworth, GB*, 20(11): 444-447 (1999).
Valverde, et al., "Selective Blockage of Voltage-Gated Potassium Channels Reduces Inflammatory Bone Resorption in Experimental Periodontal Disease", *J of Bone and Mineral Res.*, 19(1): 155-164 (2004).
Van den Ouweland, et al., "Structural Homology Between the Human *Fur* Gene Product and the Subtilisin-Like Protease Encoded by Yeast *KEX2*", *Nucleic Acids Res.*, 18(3): 664 (1990).
Vardar, et al., "NMR Structure of an F-Actin-binding "Headpiece" Motif from Villin", *J Mol Biol*, 294: 1299-1310 (1999).

Venkatesh, et al., "Chemical Genetics to Identify NFAT Inhibitors: Potential of Targeting Calcium Moblization in Immunosuppression", *PNAS*, 101(24): 8969-8974 (2004).

Voss, et al., "The Role of Enhancers in the Regulation of Cell-Type-Specific Transcriptional Control", *TIBS*, 11: 287-289 (1986).

Vrang, et al., "Characterization of Brainstem Preproglucagon Projections to the Paraventricular and Dorsomedial Hypothalamic Nuclei", Brain Research, 1149: 118-126 (2007).

Wang, LX and Wang, ZJ, "Animal and Cellular Models of Chronic Pain", *Adv Drug Del Reviews*, 55: 949-965 (2003).

Wang, et al., "Polyethylene Glycol-Modified Chimeric Toxin Composed of Transforming Growth Factor α and *Pseudomonas* Exotoxin", *Cancer Res.*, 53: 4588-4594 (1993).

Wang, et al., "Glucagon-like Peptide-1 Can Reverse the Age-related Decline in Glucose Tolerance in Rats", *J Clin Invest*, 99(12): 2883-2889 (1997).

Wilson, et al., "Phage Display: Applications, Innovations, and Issues in Phage and Host Biology", *Can. J Microbiol.*, 44: 313-329 (1998).

Winslow, et al., "Calcium Signalling in Lymphocytes", *Curr. Opn. Immun.*, 15: 299-307 (2003).

Winzell, et al., "Glucagon Receptor Antagonism Improves Islet Function in Mice with Insulin Resistance Induced by a High-Fat Diet", *Diabetologia*, 50: 1453-1462 (2007).

Wright, et al., "The Importance of Loop Length in the Folding of an Immunoglobulin Domain", *Prot. Eng. Des. & Sel.*, 17(5): 443-453 (2004).

Wrighton, et al., "Small Peptides as Potent Mimetics of the Protein Hormone Erythropoietin", *Science*, 273: 458-463 (1996).

Wulff, et al., "Delineation of the Clotrimazole/TRAM-34 Binding Site on the Intermediate Conductance Calcium-Activated Potassium Channel, IKCa1", *J of Biological Chem.*, 276(34): 32040-32045 (2001).

Wulff, et al., "The Voltage-Gated Kv1.3 $K^+$ Channel in Effector Memory T Cells as New Target for MS", *J of Clin. Investigation*, 111(11): 1703-1713 (2003).

Wulff, et al., "$K^+$ Channel Expression During B Cell Differentiation: Implications for Immunomodulation and Autoimmunity[1]", *J of Immunology*, 173: 776-786 (2004).

Xu, et al., "Exendin-4 Stimulates Both β-Cell Replication and Neogenesis, Resulting in Increased β-Cell Mass and Improved Glucose Tolerance in Diabetic Rats", Diabetes, 48: 2270-2276 (1999).

Xu, et al., "The Voltage-Gated Potassium Channel Kv1.3 Regulates Energy Homeostasis and Body Weight", *Human Molecular Genetics*, 12(5): 551-559 (2003).

Xu, et al., "The Voltage-Gated Potassium Channel Kv1.3 Regulates Peripheral Insulin Sensitivity", *PNAS*, 101(9): 3112-3117 (2004).

Yarasheski, et al., "Serum Myostatin-Immunoreactive Protein is Increased in 60-92 Year Old Women and Men with Muscle Wasting", *J Nutr Health Aging*, 6(5): 343-348 (2002).

Yazdany, et al., "The Role of CD40 Ligand in Systemic Lupus Erythematosus", *Lupus*, 13: 377-380 (2004).

Yen, et al., "Obesity, Diabetes, and Neoplasia in Yellow A$^{vy}$/-Mice: Ectopic Expression of the *Agouti* Gene", *FASEB J.*, 8: 479 (1994).

Yocum, et al., "Microemulsion Formulation of Cyclosporin (Sandimmun Neoral®) vs Sandimmun®: Comparative Safety, Tolerability and Efficacy in Severe Active Rheumatoid Arthritis", *Rheumatology*, 39: 156-164 (2000).

Yusta, et al., "Glucagon-like Peptide-2 Receptor Activation Engages Bad and Glycogen Synthase Kinase-3 in a Protein Kinase A-dependent Manner and Prevents Apoptosis following Inhibition of Phosphatidylinositol 3-Kinase", *J Biol Chem*, 277(28): 24896-24906 (2002).

Zachwieja, et al., "Plasma Myostatin-Immunoreactive Protein is Increased after Prolonged Bed Rest with Low-Dose $T_3$ Administration", *J Gravitational Physiology*, 6(2): 11-15 (1999).

Zalipsky, S., "Chemistry of Polyethylene Glycol Conjugates with Biologically Active Molecules", *Advanced Drug Del. Rev.*, 16: 157-182 (1995).

Zalipsky, S and Lee, C, "Use of Functionalized Poly(Ethylene Glycol)s for Modification of Polypeptides", *Poly(Ethylene /Glycol) Chemistry: Biotechnical and Biomedical Applications*, J Harris, Ed., Plenum Press, New York, NY, Chapter 21, pp. 347-370 (1992).

Zhang, et al., "A New Strategy for the Site-Specific Modification of Proteins In Vivo", *Biochem.*, 42: 6735-6746 (2003).

Zimmers, et al., "Induction of Cachexia in Mice by Systemically Administered Myostatin", *Science*, 296: 1486-1488 (2002).

Zitt, et al., "Potent Inhibition of $Ca^{2+}$ Release-activated $Ca^{2+}$ Channels and T-Lymphocyte Activation by the Pyrazole Derivative BTP2", *J Biol. Chem.*, 279(13): 12427-12437 (2004).

\* cited by examiner

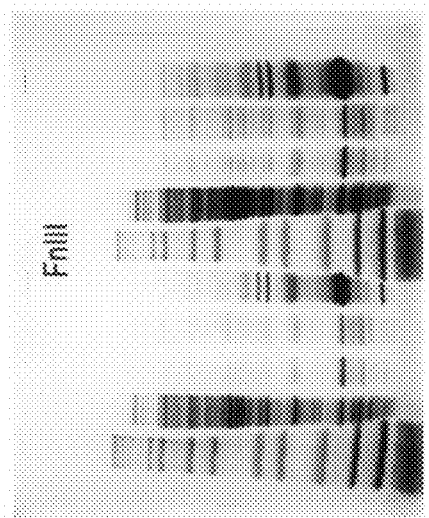
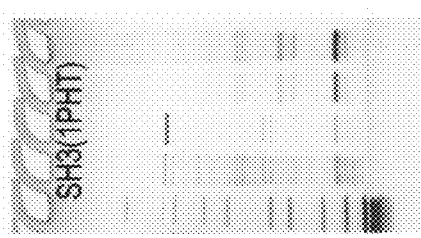
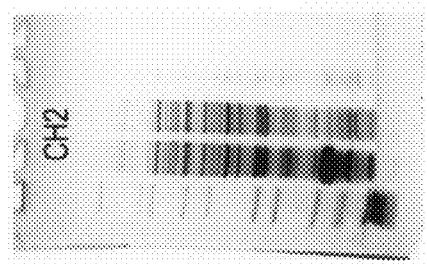

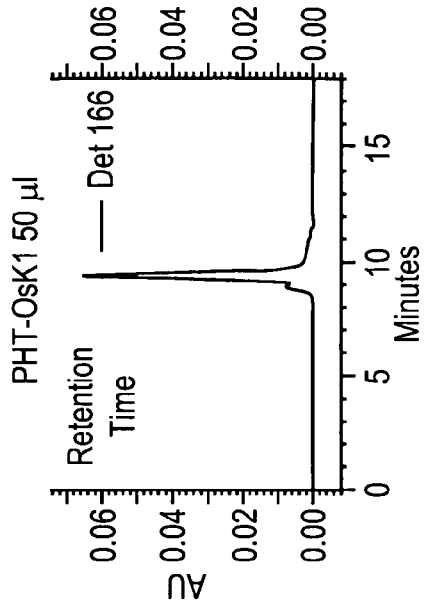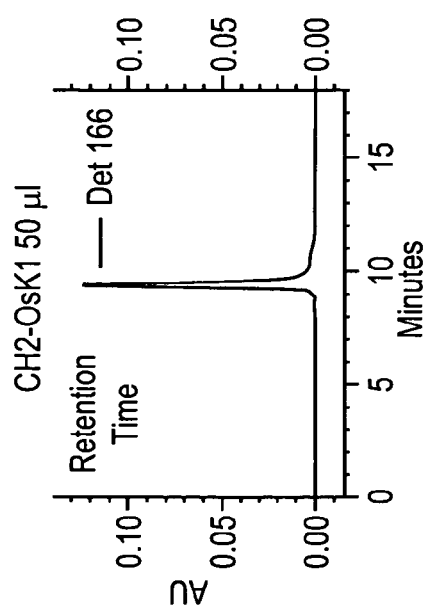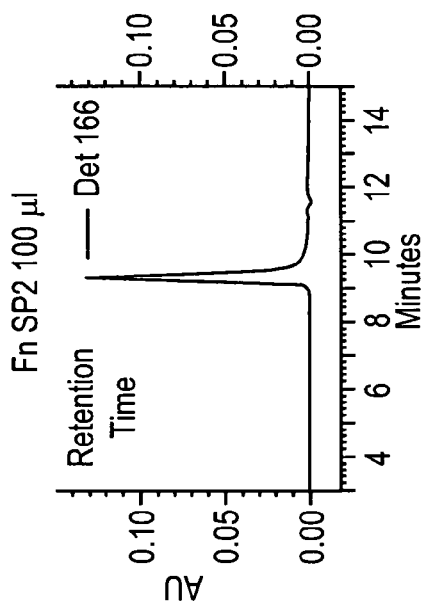

```
Ch: LSDED FKAVF GMTRS AFANL PLWKQ QNLKK EKGLF
Hu: LSIED FTQAF GMTPA AFSAL PRWKQ QNLKK EKGLF
```

COMPOSITIONS AND METHODS FOR PRODUCING BIOACTIVE FUSION PROTEINS

This application claims the benefit of U.S. Provisional Application No. 60/931,344, filed May 22, 2007, which is hereby incorporated by reference in its entirety.

Throughout this application various publications are referenced within parentheses or brackets. The disclosures of these publications in their entireties are hereby incorporated by reference in this application in order to more fully describe the state of the art to which this invention pertains.

BACKGROUND OF THE INVENTION

1. Field of Art

The present invention relates to the biochemical arts, particularly to recombinant expression of polypeptides.

2. Discussion of Related Art

Bioactive or therapeutic peptides can be potent drugs which specifically target and modulate unique signaling and metabolic pathways. Their relatively small size and simple composition makes these peptides amenable to molecular engineering to refine and enhance desirable activities. Subtle changes to the peptide sequence can discriminate between linked activities or help prevent degradation in vivo. Similarly, well placed linker sites can permit conjugation of large molecules, such as poly(ethylene glycol) PEG, to enhance circulating half-lives. However, these same properties also present special challenges to peptide production and delivery.

Artificial synthetic techniques are not cost-effective for producing many peptides, particularly the larger peptides (15-40 amino acid residues or more). As an alternative, the use of recombinant host cells is well known for recombinant production of bioactive peptides or proteins. Commonly used recombinant host cells include bacteria (such as *E. coli* sp.), yeast (such as *Saccharomyces* sp.) and other fungi, insect cells, plant cells, and mammalian cells in culture. However, recombinant expression is often difficult. One reason for the low expression of recombinant peptides or proteins is likely due to their poor refolding potential, owing to marginally stable secondary and tertiary structures in solution.

To overcome this, many peptides have been expressed as chimeric fusions with proteins such as immunoglobulin Fc domains, ubiquitin, an albumin (e.g., human serum albumin (HSA)), a transthyretin (TTR), or a thyroxine-binding globulin (TBG). (See, e.g., Sullivan et al., Toxin Peptide therapeutic agents, WO 2006/116156 A2; Gegg et al., Modified Fc molecules, WO 2006/036834 A2; Gegg et al., Modified Fc molecules, PCT/US2006/031609; Feige et al., Modified peptides as therapeutic agents, WO 2000/024782; Rosen et al., Albumin fusion proteins, U.S. Pat. No. 6,926,898 and US 2005/0054051; Bridon et al., Protection of endogenous therapeutic peptides from peptidase activity through conjugation to blood components, U.S. Pat. No. 6,887,470); Walker et al., Use of transthyretin peptide/protein fusions to increase the serum half-life of pharmacologically active peptides/proteins, US 2003/0195154A1; 2003/0191056A1). Such large fusion proteins have made possible the commercial expression of therapeutic peptides and provided the added advantage of dramatically extending the circulating half-lives of their peptide partners, thereby rendering them more efficacious in vivo.

While these fusion proteins often facilitate peptide expression at much higher levels, they can also present difficult refolding challenges that can affect their bioactivity. Protein recovery can be further complicated by undesirable domain-domain interactions between the fusion partners and disulphide bond isomerizations. In addition, the cost of producing a fusion protein with a large protein carrier moiety can affect the commercial viability of such a therapeutic agent.

Consequently, compositions and methods for high yield recombinant expression of bioactive fusion proteins with a relatively low mass ratio of carrier component to bioactive component are desirable. These and other benefits are provided by the present invention.

SUMMARY OF THE INVENTION

The present invention relates to compositions of matter involving recombinant fusion proteins. The inventive recombinant fusion protein includes: (a) a small pharmacologically inactive protein domain of human origin as described herein; and (b) a pharmacologically active protein. The present invention is also directed to nucleic acids (e.g., DNA constructs) encoding the fusion protein, and expression vectors and recombinant host cells for expression of the fusion protein.

Optionally, for modulation of the pharmacokinetic profile of the inventive recombinant fusion protein molecule to fit a particular therapeutic need by attaching or conjugating covalently one or more half-life extending moieties of various masses and configurations to the fusion protein. Thus, the invention encompasses a composition of matter of the formula:

$$(F^1)_a\text{—}(X^2)_b \qquad (I)$$

and multimers thereof, wherein:

$F^1$ is a half-life extending moiety, a is 0 or 1, and b is 1;

$X^2$ is D-$(L)_c$-$(P^5)_d$-$(X^3)_e$-$(X^4)_f$-$(P^5)_d$-$(L)_c$-D, or $(X^4)_f$-$(P^5)_d$-$(L)_c$-D-$(L)_g$-$(P^6)_h$-$(X^3)_i$, wherein c and g are each independently 0 or 1, d and h are 1, and e, f, and i are each independently is 0, 1, 2, 3, or 4;

$X^3$ is -$(L)_j$-$(P^7)$, j is 0 or 1;

$X^4$ is $(P^8)$-$(L)_k$-, k is 0 or 1;

D is small pharmacologically inactive protein domain of human origin;

$P^5$, $P^6$, $P^7$ and $P^8$ are each independently a pharmacologically active protein; and L is in each instance a peptidyl linker. Within the meaning of Formula I, the pharmaceutically active protein, "P" (i.e., $P^5$, $P^6$, $P^7$ and $P^8$), if more than one is present, can be independently the same or different from, any other P also present in the inventive composition; this includes a $P^7$ and/or a $P^8$, if more than one is present, which can be the same or different from any other $P^7$ and/or $P^8$. Similarly, the peptidyl linker moiety, "L" (i.e., $(L)_c$, $(L)_g$, $(L)_j$, and/or $(L)_k$), if present, can be independently the same or different from any other linker, or linkers, that may be present in the inventive composition.

The present invention also provides a high efficiency method of producing a pharmacologically active fusion protein in a host cell. The recombinant host cell of the invention is placed in a growth medium under physiologically suitable conditions such that the recombinant fusion protein is expressed; and the fusion protein is then isolated or purified from the cells. This can involve separation from the cell by conventional biochemical techniques involving cell lysis and separation of the fusion protein from the cell extract. It may involve solubilization of the fusion protein released from inclusion bodies, after refolding, if necessary. Alternatively, if expression of the fusion protein involves its secretion from the recombinant host cell, isolating the fusion protein from the cell can simply be accomplished with centrifugation or filtration to separate the cells from the medium containing the secreted fusion protein, without lysing the cells, the recombinant fusion protein being in the supernatant or filtrate growth medium.

Typically, the method does not require post-expression cleavage of the pharmacologically active protein component from the small pharmacologically inactive protein domain in order to use the inventive recombinant fusion protein as a therapeutic, since the small pharmacologically inactive protein domain component has a human amino acid sequence posing a low immunogenic risk to a human patient to whom the therapeutic is administered. The present invention provides a useful alternative to the costly in vitro syntheses of large therapeutic peptides or proteins.

BRIEF DESCRIPTION OF THE DRAWINGS

FIGS. 6A-E illustrates shaker flask expression of small domain OsK1 fusions with Coomassie stained 4-20% tris-glycine SDS-PAGE. Lane contents in FIGS. 6A-C were (left to right): Novex Mark 12 standards, soluble fraction, deoxycholic acid wash, water wash, insoluble fraction, Novex Mark 12 standards, soluble fraction, deoxycholic acid wash, water wash, and insoluble fraction. In FIG. 6A, in lanes 2-5, the small domain fused with OsK1 was PDZ(1WFV), i.e., construct encoded by SEQ ID NO:65; in lanes 7-10, the small domain fused with OsK1 was SH3(1×2K), i.e., construct SEQ ID NO:84. In FIG. 6B, in lanes 2-5, the small domain fused with OsK1 was PDZ(1N7F), i.e., construct SEQ ID NO:83; in lanes 7-10, the small domain fused with OsK1 was PDZ(1UEZ), i.e., construct SEQ ID NO:85. In FIG. 6C, in lanes 2-5 and 7-10, the small domain fused with OsK1 was FnIII, i.e., construct SEQ ID NO:81. Lane contents in FIGS. 6D-E were (left to right): Novex Mark 12 standards, soluble fraction, deoxycholic acid wash, water wash, and insoluble fraction. Preparation of samples for loading into wells for electrophoresis was as described in Example 2 (protein purification section) herein, and the material for each well was diluted with ½ volume of reducing 3×SDS-PAGE sample buffer (167 mM Tris pH 6.8, 26.7% glycerol, 5.3% SDS, and 13.3% 2-mercaptoethanol); 2-4, aliquots of sample were loaded per well. In FIG. 6D, in lanes 2-5, the small domain fused with OsK1 was CH2, i.e., construct SEQ ID NO:80. In FIG. 6E, in lanes 2-5, the small domain fused with OsK1 was SH3(1PHT), i.e., construct SEQ ID NO:82.

FIGS. 7A-F shows analytical SEC of various small domain OsK1 fusions SE-HPLC of OsK1 fusion proteins after refolding and purification using a Phenomenex BioSep-SEC 3000 column with 50 mM NaH2PO4, 250 mM NaCl, pH 6.9 as the running buffer observing the absorbence at 280 nm. In FIG. 7A, the small domain fused with OsK1 was CH2, i.e., construct SEQ ID NO:80. In FIG. 7B, the small domain fused with OsK1 was SH3(1PHT), i.e., construct SEQ ID NO:82. In FIG. 7C, the small domain fused with OsK1 was FnIII, i.e., construct SEQ ID NO:81. In FIG. 7D, the small domain fused with OsK1 was PDZ(1UEZ), i.e., construct SEQ ID NO:85. In FIG. 7E, the small domain fused with OsK1 was PDZ(1N7F), i.e., construct SEQ ID NO:83. In FIG. 7F, the small domain fused with OsK1 was SH3(1×2K), i.e., construct SEQ ID NO:84.

In FIG. 8A, in lanes 2, 4, 6, the small domain fused with OsK1 was FnIII, i.e., construct SEQ ID NO:81; in lanes 8, 10, 12, the small domain fused with OsK1 was SH3(1×2K), i.e., construct SEQ ID NO:84. In FIG. 8B, in lanes 2, 4, 6, the small domain fused with OsK1 was PDZ(1UEZ), i.e., construct SEQ ID NO:85; in lanes 8, 10, 12, the small domain fused with OsK1 was PDZ(1N7F), i.e., construct SEQ ID NO:83. In FIG. 8C, in lanes 2, 4, 6, the small domain fused with OsK1 was CH2, i.e., construct SEQ ID NO:80; in lanes 8, 10, 12, the small domain fused with OsK1 was SH3 (1PHT), i.e., construct SEQ ID NO:82.

In FIG. 9A, the small domain fused with OsK1 was PDZ(1UEZ), i.e., construct SEQ ID NO:85. In FIG. 9B, the small domain fused with OsK1 was PDZ(1N7F), i.e., construct SEQ ID NO:83. In FIG. 9C, the small domain fused with OsK1 was FnIII, i.e., construct SEQ ID NO:81. In FIG. 9D, the small domain fused with OsK1 was CH2, i.e., construct SEQ ID NO:80. In FIG. 9E, the small domain fused with OsK1 was SH3(1PHT), i.e., construct SEQ ID NO:82.

FIG. 11A (left to right): lanes #1 and 7 were molecular weight (MW) markers; lanes #2, 3, 8 and 9 were non-reduced, and lanes #5, 6, 11 and 12 were reduced. Lanes #2 and 5 were unconjugated 1UEZ-OSK1 fusion protein and lanes #3 and 6 were the purified 20 kD PEG-1UEZ-OSK1 conjugate. Lanes #8 and 11 were unconjugated 1N7F-OSK1 fusion protein and lanes #9 and 12 were the purified 20 kD PEG-1N7F-OSK1 conjugate. FIG. 11B (left to right): Lanes #1 and 7 were MW markers. Lanes #2, 3, 8 and 9 were non-reduced, and lanes #5, 6, 11 and 12 were reduced. Lanes #2 and 5 were unconjugated Fn3-OSK1 fusion protein and lanes #3 and 6 were the purified 20 kD PEG-Fn3-OSK1 conjugate. Lanes #8 and 11 were unconjugated 1X2K-OSK1 fusion protein and lanes #8 and 12 were the purified 20 kD PEG-1X2K-OSK1 conjugate.

DETAILED DESCRIPTION

Figure 1:
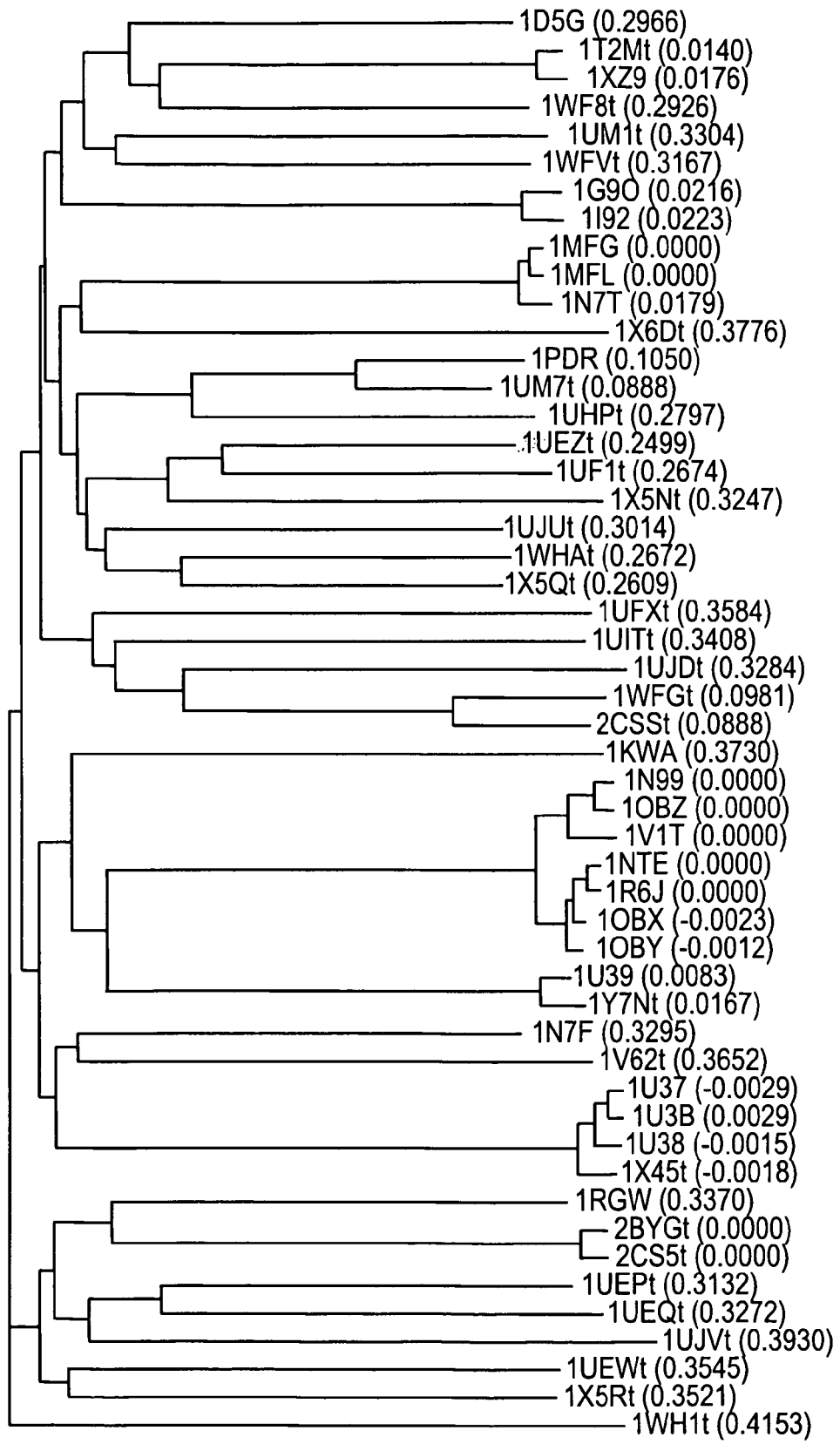
FIG. 1 shows a tree diagram that illustrates the amino acid sequence relatedness of various human PDZ domains that were identified in the Brookhaven Protein Databank. The four digit code is the accession number from the Brookhaven Protein Databank. Alignment was completed using Vector NTI Align-X.

As used in this specification and the appended claims, the singular forms "a", "an" and "the" include plural referents unless the context clearly indicates otherwise. Thus, for example, reference to "a protein" includes a plurality of proteins; reference to "a cell" includes populations of a plurality of cells.

"Polypeptide" and "protein" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be expressed recombinantly using known protein engineering techniques. In addition, inventive fusion proteins can be derivatized as described herein by well-known organic chemistry techniques.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

A "domain" of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

As used herein "soluble" when in reference to a protein produced by recombinant DNA technology in a host cell is a protein that exists in aqueous solution; if the protein contains a twin-arginine signal amino acid sequence the soluble protein is exported to the periplasmic space in gram negative bacterial hosts, or is secreted into the culture medium by eukaryotic host cells capable of secretion, or by bacterial host possessing the appropriate genes (e.g., the kil gene). Thus, a soluble protein is a protein which is not found in an inclusion body inside the host cell. Alternatively, depending on the context, a soluble protein is a protein which is not found integrated in cellular membranes; in contrast, an insoluble protein is one which exists in denatured form inside cytoplasmic granules (called an inclusion body) in the host cell, or again depending on the context, an insoluble protein is one which is present in cell membranes, including but not limited to, cytoplasmic membranes, mitochondrial membranes, chloroplast membranes, endoplasmic reticulum membranes, etc.

A distinction is also drawn between proteins which are "soluble" (i.e., dissolved or capable of being dissolved) in an aqueous solution devoid of significant amounts of ionic detergents (e.g., SDS) or denaturants (e.g., urea, guanidine hydrochloride) and proteins which exist as a suspension of insoluble protein molecules dispersed within the solution. A "soluble" protein will not be removed from a solution containing the protein by centrifugation using conditions sufficient to remove cells present in a liquid medium (e.g., centrifugation at 5,000×g for 4-5 minutes). In some embodiments of the inventive composition, the recombinant fusion protein is synthesized by the host cell and segregated in an insoluble form within cellular inclusion bodies, which can then be purified from other cellular components in a cell extract with relative ease, and the recombinant fusion protein can in turn be solubilized, refolded and/or further purified.

A distinction is drawn between a "soluble" protein (i.e., a protein which when expressed in a host cell is produced in a soluble form) and a "solubilized" protein. An insoluble recombinant protein found inside an inclusion body or found integrated in a cell membrane may be solubilized (i.e., rendered into a soluble form) by treating purified inclusion bodies or cell membranes with denaturants such as guanidine hydrochloride, urea or sodium dodecyl sulfate (SDS). These denaturants must then be removed from the solubilized protein preparation to allow the recovered protein to renature (refold). Although the inventive compositions can be refolded in active form, not all proteins will refold into an active conformation after solubilization in a denaturant and removal of the denaturant. Many proteins precipitate upon removal of the denaturant. SDS may be used to solubilize inclusion bodies and cell membranes and will maintain the proteins in solution at low concentration. However, dialysis will not always remove all of the SDS (SDS can form micelles which do not dialyze out); therefore, SDS-solubilized inclusion body protein and SDS-solubilized cell membrane protein is soluble but not refolded.

A "secreted" protein refers to those proteins capable of being directed to the ER, secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage. In some other embodiments of the inventive composition, the recombinant fusion protein can be synthesized by the host cell as a secreted protein, which can then be further purified from the extracellular space and/or medium.

The term "recombinant" indicates that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well known molecular biological procedures. A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

A "polynucleotide sequence" or "nucleotide sequence" or "nucleic acid sequence," as used interchangeably herein, is a polymer of nucleotides, including an oligonucleotide, a DNA, and RNA, a nucleic acid, or a character string representing a nucleotide polymer, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. A "fusion gene" contains a coding region that encodes a fusion protein. Genes also include non-expressed nucleic acid segments that, for example, form recognition sequences for other proteins. Non-expressed regulatory sequences including transcriptional control elements to which regulatory proteins, such as transcription factors, bind, resulting in transcription of adjacent or nearby sequences.

As used herein the term "coding region" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986) and Maniatis, et al., Science 236:1237 (1987)).

The term "expression vector" as used herein refers to a recombinant DNA molecule containing a desired coding sequence and appropriate nucleic acid sequences necessary for the expression of the operably linked coding sequence in a particular host cell. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence for the inventive recombinant fusion protein, so that the expressed fusion protein can be secreted by the recombinant host cell, for more facile isolation of the fusion protein from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. No. 6,022,952 and U.S. Pat. No. 6,335,178; Uemura et al., Protein expression vector and utilization thereof, U.S. Pat. No. 7,029,909; Ruben et al., 27 human secreted proteins, US 2003/0104400 A1).

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

Recombinant DNA- and/or RNA-mediated protein expression techniques, or any other methods of preparing peptides or, are applicable to the making of the inventive recombinant fusion proteins. For example, the peptides can be made in transformed host cells. Briefly, a recombinant DNA molecule, or construct, coding for the peptide is prepared. Methods of preparing such DNA molecules are well known in the art. For instance, sequences encoding the peptides can be excised from DNA using suitable restriction enzymes. Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, insect cells, plant cells, mammalian (including human) cells, e.g., CHO cells and HEK293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art.

In further describing the fusion proteins herein, a one-letter abbreviation system is frequently applied to designate the identities of the twenty "canonical" amino acid residues generally incorporated into naturally occurring peptides and proteins (Table 1). Such one-letter abbreviations are entirely interchangeable in meaning with three-letter abbreviations, or non-abbreviated amino acid names. Within the one-letter abbreviation system used herein, an upper case letter indicates a L-amino acid, and a lower case letter indicates a D-amino acid. For example, the abbreviation "R" designates L-arginine and the abbreviation "r" designates D-arginine.

TABLE 1

One-letter abbreviations for the canonical amino acids.
Three-letter abbreviations are in parentheses.

| | |
|---|---|
| Alanine (Ala) | A |
| Glutamine (Gln) | Q |
| Leucine (Leu) | L |
| Serine (Ser) | S |
| Arginine (Arg) | R |
| Glutamic Acid (Glu) | E |
| Lysine (Lys) | K |
| Threonine (Thr) | T |
| Asparagine (Asn) | N |

TABLE 1-continued

One-letter abbreviations for the canonical amino acids.
Three-letter abbreviations are in parentheses.

| | |
|---|---|
| Glycine (Gly) | G |
| Methionine (Met) | M |
| Tryptophan (Trp) | W |
| Aspartic Acid (Asp) | D |
| Histidine (His) | H |
| Phenylalanine (Phe) | F |
| Tyrosine (Tyr) | Y |
| Cysteine (Cys) | C |
| Isoleucine (Ile) | I |
| Proline (Pro) | P |
| Valine (Val) | V |

An amino acid substitution in an amino acid sequence is typically designated herein with a one-letter abbreviation for the amino acid residue in a particular position, followed by the numerical amino acid position relative to a native sequence of interest, which is then followed by the one-letter symbol for the amino acid residue substituted in. For example, "T30D" symbolizes a substitution of a threonine residue by an aspartate residue at amino acid position 30, relative to the native sequence of interest.

Non-canonical amino acid residues can be incorporated into a peptide within the scope of the invention by employing known techniques of protein engineering that use recombinantly expressing cells. (See, e.g., Link et al., Non-canonical amino acids in protein engineering, Current Opinion in Biotechnology, 14(6):603-609 (2003)). The term "non-canonical amino acid residue" refers to amino acid residues in D- or L-form that are not among the 20 canonical amino acids generally incorporated into naturally occurring proteins, for example, β-amino acids, homoamino acids, cyclic amino acids and amino acids with derivatized side chains. Examples include (in the L-form or D-form; abbreviated as in parentheses): citrulline (Cit), homocitrulline (hCit), $N^\alpha$-methylcitrulline (NMeCit), $N^\alpha$-methylhomocitrulline ($N^\alpha$-MeHoCit), ornithine (Orn), $N^\alpha$-Methylornithine ($N^\alpha$-MeOrn or NMeOrn), sarcosine (Sar), homolysine (hLys or hK), homoarginine (hArg or hR), homoglutamine (hQ), $N^\alpha$-methylarginine (NMeR), $N^\alpha$-methylleucine ($N^\alpha$-MeL or NMeL), N-methylhomolysine (NMeHoK), $N^\alpha$-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl)alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α,β-diaminopropionoic acid (Dpr), α,γ-diaminobutyric acid (Dab), diaminoproprionic acid (Dap), cyclohexylalanine (Cha), 4-methyl-phenylalanine (MePhe), β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, and other similar amino acids, and derivatized forms of any of these as described herein. Table 2 contains some exemplary non-canonical amino acid residues that are useful in accordance with the present invention and associated abbreviations as typically used herein, although the skilled practitioner will understand that different abbreviations and nomenclatures may be applicable to the same substance and my appear interchangeably herein.

TABLE 2

Useful non-canonical amino acids for amino acid addition, insertion, or substitution into peptide sequences in accordance with the present invention. In the event an abbreviation listed in Table 2 differs from another abbreviation for the same substance disclosed elsewhere herein, both abbreviations are understood to be applicable.

| Abbreviation | Amino Acid |
| --- | --- |
| Sar | Sarcosine |
| Nle | Norleucine |
| Ile | isoleucine |
| 1-Nal | 3-(1-naphthyl)alanine |
| 2-Nal | 3-(2-naphthyl)alanine |
| Bip | 4,4'-biphenyl alanine |
| Dip | 3,3-diphenylalanine |
| Nvl | norvaline |
| NMe-Val | Nα-methyl valine |
| NMe-Leu | Nα-methyl leucine |
| NMe-Nle | Nα-methyl norleucine |
| Cpg | cyclopentyl glycine |
| Chg | cyclohexyl glycine |
| Hyp | hydroxy praline |
| Oic | Octahydroindole-2-Carboxylic Acid |
| Igl | Indanyl glycine |
| Aib | aminoisobutyric acid |
| Aic | 2-aminoindane-2-carboxylic acid |
| Pip | pipecolic acid |
| BhTic | β-homo Tic |
| BhPro | β-homo praline |
| Tiq | 1,2,3,4-L-Tetrahydroisoquinoline-1-Carboxylic acid |
| Nip | Nipecotic Acid |
| Thz | Thiazolidine-4-carboxylic acid |
| Thi | 3-thienyl alanine |
| 4GuaPr | 4-guanidino proline |
| 4Pip | 4-Amino-1-piperidine-4-carboxylic acid |
| Idc | indoline-2-carboxylic acid |
| Hydroxyl-Tic | 1,2,3,4-Tetrahydroisoquinoline-7-hydroxy-3-carboxylic acid |
| Bip | 4,4'-biphenyl alanine |
| Ome-Tyr | O-methyl tyrosine |
| I-Tyr | Iodotyrosine |
| Tic | 1,2,3,4-L-Tetrahydroisoquinoline-3-Carboxylic acid |
| Igl | Indanyl glycine |
| BhTic | β-homo Tic |
| BhPhe | β-homo phenylalanine |
| AMeF | α-methyl Phenylalanine |
| BPhe | β-phenylalanine |
| Phg | Phenylglycine |
| Anc | 3-amino-2-naphthoic acid |
| Atc | 2-aminotetraline-2-carboxylic acid |
| NMe-Phe | Nα-methyl phenylalanine |
| NMe-Lys | Nα-methyl lysine |
| Tpi | 1,2,3,4-Tetrahydronorharman-3-Carboxylic acid |
| Cpg | cyclopentyl glycine |
| Dip | 3,3-diphenylalanine |
| 4Pal | 4-pyridinylalanine |
| 3Pal | 3-pyridinylalanine |
| 2Pal | 2-pyridinylalanine |
| Idc | indoline-2-carboxylic acid |
| Chg | cyclohexyl glycine |
| hPhe | homophenylalanine |

TABLE 2-continued

Useful non-canonical amino acids for amino acid addition, insertion, or substitution into peptide sequences in accordance with the present invention. In the event an abbreviation listed in Table 2 differs from another abbreviation for the same substance disclosed elsewhere herein, both abbreviations are understood to be applicable.

| Abbreviation | Amino Acid |
| --- | --- |
| BhTrp | β-homotryptophan |
| pI-Phe | 4-iodophenylalanine |
| Orn | ornithine |
| Dpr | 2,3-Diaminopropionic acid |
| Dbu | 2,4-Diaminobutyric acid |
| homoLys | homolysine |
| N-εMe-K | Nε-methyl-lysine |
| N-εEt-K | Nε-ethyl-lysine |
| N-εIPr-K | Nε-isopropyl-lysine |
| bhomoK | β-homolysine |
| rLys | Lys ψ(CH2NH)-reduced amide bond |
| rOrn | Orn ψ(CH2NH)-reduced amide bond |
| Acm | acetamidomethyl |
| Ahx | 6-aminohexanoic acid |
| ε Ahx | 6-aminohexanoic acid |
| K(NPeg11) | Nε-(O-(aminoethyl)-O'-(2-propanoyl)-undecaethyleneglycol)-Lysine |
| K(NPeg27) | Nε-(O-(aminoethyl)-O'-(2-propanoyl)-(ethyleneglycol)27-Lysine |
| Cit | Citrulline |
| hArg | homoarginine |
| hCit | homocitrulline |
| NMe-Arg | Nα-methyl arginine (NMeR) |
| Guf | 4-guanidinyl phenylalanine |
| bhArg | β-homoarginine |
| 3G-Dpr | 2-amino-3-guanidinopropanoic acid |
| 4AmP | 4-amino-phenylalanine |
| 4AmPhe | 4-amidino-phenylalanine |
| 4AmPig | 2-amino-2-(1-carbamimidoylpiperidin-4-yl)acetic acid |
| 4GuaPr | 4-guanidino proline |
| N-Arg | Nα-[(CH$_2$)$_3$ NHCH(NH)NH$_2$] substituted glycine |
| rArg | Arg ψ(CH2NH)-reduced amide bond |
| 4PipA | 4-Piperidinyl alanine |
| NMe-Thr | Nα-methyl threonine(or NMeThr) |

Nomenclature and Symbolism for Amino Acids and Peptides by the UPAC-IUB Joint Commission on Biochemical Nomenclature (JCBN) have been published in the following documents: Biochem. J., 1984, 219, 345-373; Eur. J. Biochem., 1984, 138, 9-37; 1985, 152, 1; 1993, 213, 2; Internat. J. Pept. Prot. Res., 1984, 24, following p 84; J. Biol. Chem., 1985, 260, 14-42; Pure Appl. Chem., 1984, 56, 595-624; Amino Acids and Peptides, 1985, 16, 387-410; Biochemical Nomenclature and Related Documents, 2nd edition, Portland Press, 1992, pages 39-69.

The one or more useful modifications to peptide domains of the inventive recombinant fusion protein can include amino acid additions or insertions, amino acid deletions, peptide truncations, amino acid substitutions, and/or chemical derivatization of amino acid residues, accomplished by known chemical techniques. For example, the thusly modified amino acid sequence includes at least one amino acid residue inserted or substituted therein, relative to the amino acid sequence of the native sequence of interest, in which the inserted or substituted amino acid residue has a side chain comprising a nucleophilic or electrophilic reactive functional group by which the peptide is conjugated to a linker and/or half-life extending moiety. In accordance with the invention, useful examples of such a nucleophilic or electrophilic reactive functional group include, but are not limited to, a thiol, a primary amine, a seleno, a hydrazide, an aldehyde, a carboxylic acid, a ketone, an aminooxy, a masked (protected) aldehyde, or a masked (protected) keto functional group. Examples of amino acid residues having a side chain comprising a nucleophilic reactive functional group include, but are not limited to, a lysine residue, a homolysine, an α,β-diaminoproprionic acid residue, an α,γ-diaminobutyric acid residue, an ornithine residue, a cysteine, a homocysteine, a glutamic acid residue, an aspartic acid residue, or a selenocysteine residue.

Amino acid residues are commonly categorized according to different chemical and/or physical characteristics. The term "acidic amino acid residue" refers to amino acid residues in D- or L-form having side chains comprising acidic groups. Exemplary acidic residues include aspartatic acid and glutamatic acid residues. The term "aromatic amino acid residue" refers to amino acid residues in D- or L-form having side chains comprising aromatic groups. Exemplary aromatic residues include tryptophan, tyrosine, 3-(1-naphthyl)alanine, or phenylalanine residues. The term "basic amino acid residue" refers to amino acid residues in D- or L-form having side chains comprising basic groups. Exemplary basic amino acid residues include histidine, lysine, homolysine, ornithine, arginine, N-methyl-arginine, ω-aminoarginine, ω-methyl-arginine, 1-methyl-histidine, 3-methyl-histidine, and homoarginine (hR) residues. The term "hydrophilic amino acid residue" refers to amino acid residues in D- or L-form having side chains comprising polar groups. Exemplary hydrophilic residues include cysteine, serine, threonine, histidine, lysine, asparagine, aspartate, glutamate, glutamine, and citrulline (Cit) residues. The terms "lipophilic amino acid residue" refers to amino acid residues in D- or L-form having sidechains comprising uncharged, aliphatic or aromatic groups. Exemplary lipophilic sidechains include phenylalanine, isoleucine, leucine, methionine, valine, tryptophan, and tyrosine. Alanine (A) is amphiphilic—it is capable of acting as a hydrophilic or lipophilic residue. Alanine, therefore, is included within the definition of both "lipophilic residue" and "hydrophilic residue." The term "nonfunctional amino acid residue" refers to amino acid residues in D- or L-form having side chains that lack acidic, basic, or aromatic groups. Exemplary neutral amino acid residues include methionine, glycine, alanine, valine, isoleucine, leucine, and norleucine (Nle) residues.

Additional useful embodiments of conjugated recombinant fusion proteins can result from conservative modifications of the amino acid sequences of the polypeptides disclosed herein. Conservative modifications will produce half-life extending moiety-conjugated peptides having functional, physical, and chemical characteristics similar to those of the conjugated (e.g., PEG-conjugated) peptide from which such modifications are made. Such conservatively modified forms of the vehicle- or PEG-conjugated peptides disclosed herein are also contemplated as being an embodiment of the present invention.

In contrast, substantial modifications in the functional and/or chemical characteristics of the fusion proteins may be accomplished by selecting substitutions in the amino acid sequence that differ significantly in their effect on maintaining (a) the structure of the molecular backbone in the region of the substitution, for example, as an α-helical conformation, (b) the charge or hydrophobicity of the molecule at the target site, or (c) the size of the molecule.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., Acta Physiol. Scand. Suppl., 643:55-67 (1998); Sasaki et al., 1998, Adv. Biophys. 35:1-24 (1998), which discuss alanine scanning mutagenesis).

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-conjugated peptide molecules described herein.

Naturally occurring residues may be divided into classes based on common side chain properties:
 1) hydrophobic: norleucine (Nor), Met, Ala, Val, Leu, Ile;
 2) neutral hydrophilic: Cys, Ser, Thr, Asn, Gln;
 3) acidic: Asp, Glu;
 4) basic: His, Lys, Arg;
 5) residues that influence chain orientation: Gly, Pro; and
 6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of the fusion protein.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Examples of conservative substitutions include the substitution of one non-polar (hydrophobic) amino acid residue such as isoleucine, valine, leucine norleucine, alanine, or methionine for another, the substitution of one polar (hydrophilic) amino acid residue for another such as between arginine and lysine, between glutamine and asparagine, between glycine and serine, the substitution of one basic amino acid residue such as lysine, arginine or histidine for another, or the substitution of one acidic residue, such as aspartic acid or glutamic acid for another. The phrase "conservative amino acid substitution" also includes the use of a chemically derivatized residue in place of a non-derivatized residue, provided that such polypeptide displays the requisite bioactivity. Other exemplary amino acid substitutions that can be useful in accordance with the present invention are set forth in Table 2.

TABLE 2

Some Useful Amino Acid Substitutions.

| Original Residues | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4-Diamino-butyric Acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

As stated herein above, in accordance with the present invention, the peptide portions of the inventive fusion protein can also be chemically derivatized at one or more amino acid residues by known organic chemistry techniques. "Chemical derivative" or "chemically derivatized" refers to a subject peptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty canonical amino acids, whether in L- or D-form. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Useful derivatizations include, in some embodiments, those in which the amino terminal of the peptide is chemically blocked so that conjugation with the vehicle will be prevented from taking place at an N-terminal free amino group. There may also be other beneficial effects of such a modification, for example a reduction in the fusion protein's susceptibility to enzymatic proteolysis. The N-terminus can be acylated or modified to a substituted amine, or derivatized with another functional group, such as an aromatic moiety (e.g., an indole acid, benzyl (Bzl or Bn), dibenzyl (DiBzl or $Bn_2$), or benzyloxycarbonyl (Cbz or Z)), N,N-dimethylglycine or creatine. For example, in some embodiments, an acyl moiety, such as, but not limited to, a formyl, acetyl (Ac), propanoyl, butanyl, heptanyl, hexanoyl, octanoyl, or nonanoyl, can be covalently linked to the N-terminal end of the peptide, which can prevent undesired side reactions during conjugation of the vehicle to the peptide. Other exemplary N-terminal derivative groups include —$NRR^1$ (other than —$NH_2$), —$NRC(O)R^1$, —$NRC(O)OR^1$, —$NRS(O)_2R^1$, —$NHC(O)NHR^1$, succinimide, or benzyloxycarbonyl-NH— (Cbz-NH—), wherein R and $R^1$ are each independently hydrogen or lower alkyl and wherein the phenyl ring may be substituted with 1 to 3 substituents selected from $C_1$-$C_4$ alkyl, $C_1$-$C_4$ alkoxy, chloro, and bromo.

In some embodiments, one or more peptidyl [—C(O)NR—] linkages (bonds) between amino acid residues can be replaced by a non-peptidyl linkage. Exemplary non-peptidyl linkages are —$CH_2$-carbamate [—$CH_2$—OC(O)NR—], phosphonate, —$CH_2$-sulfonamide [—$CH_2$—S(O)$_2$NR—], urea [—NHC(O)NH—], —$CH_2$-secondary amine, and alkylated peptide [—C(O)$NR^6$— wherein $R^6$ is lower alkyl].

In some embodiments, one or more individual amino acid residues can be derivatized. Various derivatizing agents are known to react specifically with selected sidechains or terminal residues, as described in detail below by way of example.

Lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl sidechain groups (aspartyl or glutamyl) may be selectively modified by reaction with carbodiimides (R'—N═C═N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Cysteinyl residues can be replaced by amino acid residues or other moieties either to eliminate disulfide bonding or, conversely, to stabilize cross-linking. (See, e.g., Bhatnagar et al., J. Med. Chem., 39:3814-3819 (1996)).

Derivatization with bifunctional agents is useful for cross-linking the peptides or their functional derivatives to a water-insoluble support matrix, if desired, or to other macromolecular vehicles. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates, e.g., as described in U.S. Pat. Nos. 3,969,287; 3,691,016; 4,195,128; 4,247,642; 4,229,537; and 4,330,440, are employed for protein immobilization.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains. Creighton, Proteins: Structure and Molecule Properties (W.H. Freeman & Co., San Francisco), 79-86 (1983).

The above examples of derivatizations are not intended to be an exhaustive treatment, but merely illustrative.

The production of the recombinant fusion protein can also involve suitable protein purification techniques, when applicable. In some embodiments of the fusion proteins of the invention, the molecule can be prepared to include a suitable isotopic label (e.g., $^{125}I$, $^{14}C$, $^{13}C$, $^{35}S$, $^{3}H$, $^{2}H$, $^{13}N$, $^{15}N$, $^{18}O$, $^{17}O$, etc.), for ease of quantification or detection.

The placement of the small pharmacologically inactive protein domain ("D") within the inventive recombinant fusion protein can be closer to the N-terminal end of the fusion protein than the pharmacologically active protein ("P") part of the fusion protein. Alternatively, other useful embodiments of the inventive recombinant fusion protein have the pharmacologically active protein situated closer to the N-terminal end of the fusion protein than the small pharmacologically inactive protein domain. Optionally, there can be a peptidyl linker between the two fusion partners, as described herein, or there can be additional peptide domains, or "tails", fused on either, or both, of the N-terminal and C-terminal ends of the fusion protein.

The small pharmacologically inactive protein domain is of human origin, but also encompassed is an amino acid sequence of human origin that is modified in one or more ways relative to the native human sequence of interest to facilitate covalent conjugation to a linker or half-life extending moiety, such as an activated PEG. For example, a nucleophilic or electrophilic reactive functional group can be added to a side chain and/or a terminus, such as, but not limited to, a thiol, a primary amine, a seleno, a hydrazide, an aldehyde, a carboxylic acid, a ketone, an aminooxy, a masked (protected) aldehyde, or a masked (protected) keto functional group. For example, a cysteine residue, or a residue that provides a reactive primary or secondary amino group, can be inserted into the sequence or can be substituted for another residue in the native human sequence.

Small pharmacologically inactive protein domains suitable for use within the present invention are selected for their small size, which can range from about 3 to about 20 kDa, and typically is about 4 to about 12 kDa, which can aid in high level expression in prokaryotic hosts. In addition, such a useful small pharmacologically inactive protein domain is of human origin. This has the advantage of minimizing immunogenicity when the inventive composition is employed as part of a therapeutic molecule for administration to humans. The small pharmacologically inactive protein domain is characterized by forming a stable "stand-alone" protein domain, i.e., a domain that maintains its ability to fold into its native, or near-native, secondary and/or tertiary structure in a pharmaceutically acceptable aqueous formulation buffer of interest, and is soluble in such a buffer when folded (or refolded, if necessary). Thus, a small pharmacologically inactive protein domain suitable for use in the present invention should be one that forms insignificant amounts of insoluble aggregates (aggregates less than about 10%, and typically less than about 5%, of total protein) when it is suspended without other proteins (at physiologically compatible temperature) in a pharmaceutically acceptable aqueous formulation buffer of interest, not containing a detergent or chaotropic agent, such as urea, guanidinium hydrochloride, or lithium perchlorate. Such a formulation buffer is one that is suitable for administration to a mammal by injection or other drug delivery route (if need be, after sterile re-hydration or thawing of the lyophilized or frozen formulation buffer). Such pharmaceutically acceptable formulation buffers, suitable for the administration of protein therapeutic agents, are well known in the biopharmaceutical art and can be selected from various compositions and pH (e.g., between about pH 5.0 to about pH 8.2), involving, for example, but not limited to, acetate, citrate, tris(hydroxymethyl)aminomethane, or phosphate buffer systems, and optionally containing various other excipient, cryoprotectant, surfactant, tonicifying and/or stabilizing components (e.g., polysorbate 20, polysorbate 80) known in the biopharmaceutical art. (See, e.g., Lam et al., U.S. Pat. No. 6,171,586; Pearlman et al., U.S. Pat. No. 5,096,885; O'Connor et al. U.S. Pat. No. 5,981,485; Castensson et al. U.S. Pat. No. 5,567,677; Brych et al. US20070190047A1, all of which foregoing are incorporated by reference in their entireties.) Other examples of pharmaceutically acceptable formulation buffers that may be of interest include: 10 mM acetic acid, 9% sucrose, pH 5.0; 10 mM Tris, 150 mM NaCl, pH 8.0; and 10 mM $NaH_2PO_4$, 140 mM NaCl, pH 7.2.

Within the present invention, useful embodiments of the small pharmacologically inactive protein domain include fragments or modifications of the native sequence of human origin, including amino acid additions or insertions, amino acid deletions, peptide truncations, amino acid substitutions, or chemical derivatization of amino acid residues (accomplished by known chemical techniques), as long as the preceding characteristics of a stable stand-alone domain are maintained.

Useful examples of the small pharmacologically inactive protein domain include a $10^{th}$ fibronectin III domain, a SH3 domain, a SH2 domain, a CH2 domain of IgG1, a PDZ domain, a thrombospondin repeat domain, an ubiquitin domain, a leucine-rich repeat domain a villin headpiece HP35 domain, or a villin headpiece HP76 domain, or a fragment or a modification of any of these that is soluble and maintains its native, or near-native, secondary or tertiary structure, in a biologically compatible aqueous buffer at physiological pH (i.e., about pH 6.8-7.4) and temperature. Amino acid sequences for some of these include the following:

```
1. CH2 Domain of Human IgG1 sequence:
GPSVFLFPPKPKDTLMISRTPEVTCVVVDVSHEDPEVKFNWYVDGVEVHNAKTKPREEQ       SEQ ID NO: 1

YNSTYRVVSVLTVLHQDWLNGKEYKCKVSNKALPAPIEKTISKAKG//;

or a truncated fragment of CH2 Domain of Human IgG1, such as:
GPSVFLFPPKPKDTLMISRTPEVTCVVVDVSHEDPEVKFNWYVDGVEVHNAKTKPREEQ       SEQ ID NO: 107

YNSTYRVVSVLTVLHQDWLNGKEYKCKVSNKALPAPIEKTIS//
or

PSVFLFPPKPKDTLMISRTPEVTCVVVDVSHEDPEVKFNWYVDGVEVHNAKTKPREEQY       SEQ ID NO: 108

NSTYRVVSVLTVLHQDWLNGKEYKCKVSNKALPAPIEKTIS//;
or

2. Human Tenth Fibronectin III Domain (also designated "FN3" or "FnIII" or
"10thFn3") sequences:
VSDVPRDLEVVAATPTSLLISWDAPAVTVRYYRITYGETGGNSPVQEFTVPGSKSTATIS     SEQ ID NO: 2

GLKPGVDYTITVYAVTGRGDSPASSKPISINYRTEIDKPSQ// or a truncated fragment thereof, such as:
VSDVPRDLEVVAATPTSLLISWDAPAVTVRYYRITYGETGGNSPVQEFTVPGSKSTATIS     SEQ ID NO: 13

GLKPGVDYTITVYAVTGRGDSPASSKPISINYRTE// or an extension, such as:
TVSDVPRDLEVVAATPTSLLISWDAPAVTVRYYRITYGETGGNSPVQEFTVPGSKSTATIS    SEQ ID NO: 50

GLKPGVDYTITVYAVTGRGDSPASSKPISINYRTE//;
or

3. Human PDZ Domain (Erbin):
GSMEIRVRVEKDPELGFSISGGVGGRGNPFRPDDDGIFVTRVQPEGPASKLLQPGDKIIQA     SEQ ID NO: 3

NGYSFINIEHGQAVSLLKTFQNTVELIIVREVSS//,
or

PDZ(1N7F):
SSGAIIYTVELKRYGGPLGITISGTEEPFDPIIISSLTKGGLAERTGAIHIGDRILAINSSSLKG  SEQ ID NO: 102

KPLSEAIHLLQMAGETVTLKIKKQTDAQSASSP//,

PDZ(1UEZ):
PGEVRLVSLRRAKAHEGLGFSIRGGSEHGVGIYVSLVEPGSLAEKEGLRVGDQILRVNDK      SEQ ID NO: 103

SLARVTHAEAVKALKGSKKLVLSVYSAGRIP//,

PDZ(1WFV):
PQDFDYFTVD MEKGAKGFGF SIRGGREYKM DLYVLRLAED GPAIRNGRMR            SEQ ID NO: 104

VGDQIIEING ESTRDMTHAR AIELIKSGGR RVRLLLKRGT GQVP//;

4. Human SH3 Domain (Fyn):
VTLFVALYDYEARTEDDLSFHKGEKFQILNSSEGDWWEARSLTTGETGYIPSNYVAPV//;     SEQ ID NO: 4

SH3(1PHT):
SAEGYQYRALYDYKKEREEDIDLHLGDILTVNKGSLVALGFSDGQEARPEEIGWLNGYN      SEQ ID NO: 105

ETTGERGDFPGTYVEYIGRKKISP//,

SH3(1WA7):
PEEQGDIVVA LYPYDGIHPD DLSFKKGEKM KVLEEHGEWW KAKSLLTKKE             SEQ ID NO: 106

GFIPSNYVAK LNT//

SH3(1X2K):
KVFRALYTFE PRTPDELYFE EGDIIYITDM SDTNWWKGTS KGRTGLIPSN YVAEQ//     SEQ ID NO: 94

5. Human SH2 Domain (Grb2):
GSMAWFFGKIPRAKAEEMLSKQRHDGAFLIRESESAPGDFSLSVKFGNDVQHFKVLRDG      SEQ ID NO: 5
```

-continued
```
AGKYFLWVVKFNSLNELVDYHRSTSVSRNQQIFLRDI//

SH2(1AB2):
NSLEKHSWYH GPVSRNAAEY LLSSGINGSF LVRESESSPG QRSISLRYEG        SEQ ID NO: 109

RVYHYRINTA SDGKLYVSSE SRFNTLAELV HHHSTVADGL ITTLHYPAP//;

SH2(1JYQ):
PWFFGKIPRA KAEEMLSKQR HDGAFLIRES ESAPGDFSLS VKFGNDVQHF        SEQ ID NO: 110

KVLRDGAGKY FLWVVKFNSL NELVDYHRST SVSRNQQIFL RDIEQ//;

Ubiquitin:
MQIFVKTLTGKTITLEVEPSDTIENVKAKIQDKEGIPPDQQRLIFAGKQLEDGRTLSDYNI   SEQ ID NO: 6

QKESTLHLVLRLRGG//;

Thrombospondin repeat domain:
QDGGWSHWSPWSSCSVTCGDGVITRIRLCNSPSPQMNGKPCEGEARETKACKKDACP//;   SEQ ID NO: 7

Leucine-rich repeat domain:
LHLSENLLYTFSLATLMPYTRLTQLNLDRCELTKLQVDGTLPVLGTLDLSHNQLQSLPLL   SEQ ID NO: 8

GQTLPALTVLDVSFNRLTSLPLGALRGLGELQELYLKGNELKTLPPGLLTPTPKLEKLSL

ANNNLTELPAGLLNGLENLDTLLLQENSLYTIPKGFFGSHLLPFA//;
and

Figures 12, 13:
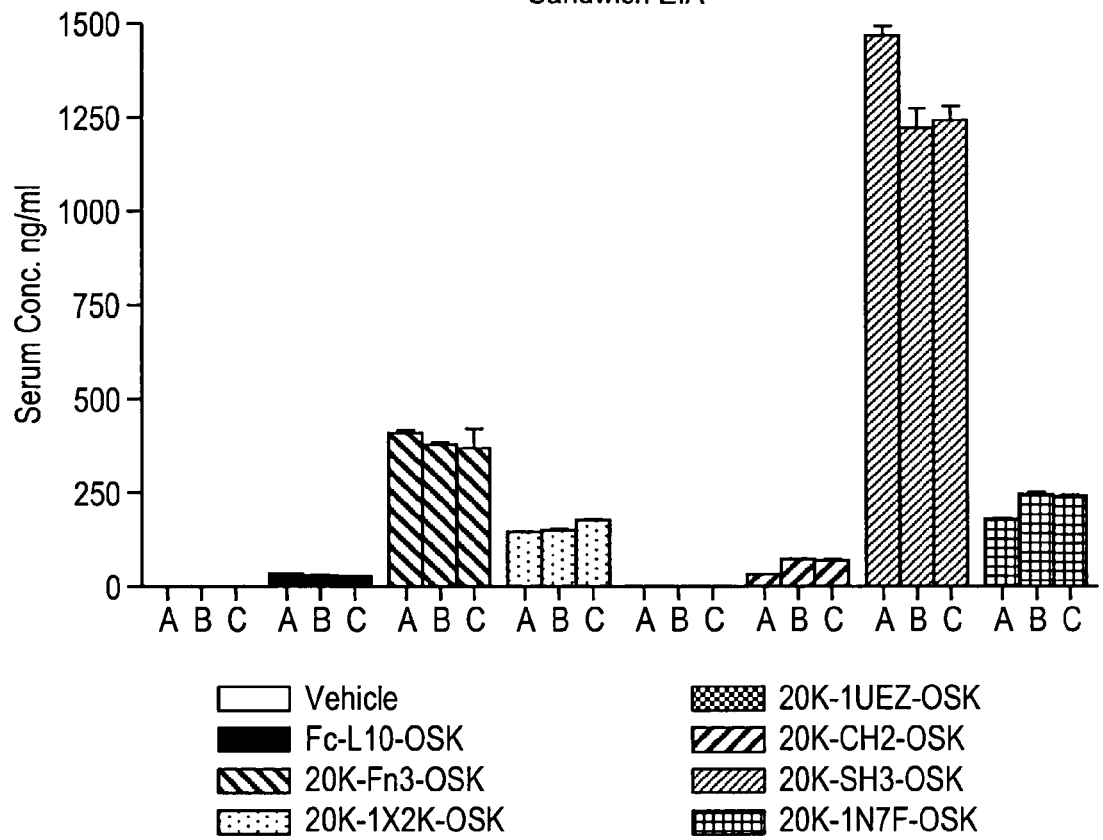
FIG. 12 illustrates the serum levels of the various OsK1 constructs 24 hours post-i.v. injection (2 mg/kg) in mice, as determined by ELISA using polyclonal rabbit anti-OsK1 antibodies for detection.
FIG. 13 shows an alignment of chicken (ch; SEQ ID NO:60) and human (hu; SEQ ID NO:61) HP-35 sequences. Numbering is based on intact villin headpiece sequence: Leu42>>Phe76. Helical sequences are underlined based on NMR structure.

Villin headpiece domain, such as the HP-35 subdomain (FIG. 13; SEQ ID NO: 61)

or HP-76 subdomain, which is the following sequence:
VFNANSNLSS GPLPIFPLEQ LVNKPVEELP EGVDPSRKEE HLSIEDFTQA        SEQ ID NO: 89

FGMTPAAFSA LPRWKQQNLK KEKGLF//;

or a modified sequence for facilitating PEGylation, e.g:,
VFNANSNLSS GPLPIFPLEQ LVNKPVEELP EGVDPSRKEE HLSIEDFTQA FGMTPAAFSA   SEQ ID NO: 90

LPRWKQQCLK KEKGLF//.
```

The four digit code following a domain family name herein is the coordinate dataset identifier for that particular protein deposited in the RCSB Protein Databank (www.rcsb.org/pdb/). For example, PDZ (1N7F) refers to the sixth PDZ domain of GRIP1; PDZ (1UEZ) refers to the first PDZ domain of human KIAA1526 protein; PDZ(1WFV) refers to the fifth PDZ domain of human membrane associated guanylate kinase inverted-2; SH2(1AB2) refers to the SRC homology 2 domain of C-ABL; SH2(1JYQ) refers to the Grb2 SRC homology 2 domain; SH3(1PHT) refers to the phosphatidylinositol 3-kinase P85-alpha subunit SH3 domain; SH3 (1WA7) refers to SH3 domain of human LYN tyrosine kinase; and SH3(1X2K) refers to SH3 domain of human osteoclast stimulating factor 1.

The inventive compositions involve a pharmacologically active protein ("P") part of the recombinant fusion protein. The term "pharmacologically active" means that a substance so described is determined to have activity that affects a medical parameter (e.g., blood pressure, blood cell count, cholesterol level, pain perception) or disease state (e.g., cancer, autoimmune disorders, chronic pain). Conversely, the term "pharmacologically inactive" means that no activity affecting a medical parameter or disease state can be determined for that substance. Thus, pharmacologically active peptides or proteins comprise agonistic or mimetic and antagonistic peptides as defined below. The present invention encompasses the use of any pharmacologically active protein, which has an amino acid sequence ranging from about 5 to about 80 amino acid residues in length, and which is amenable to recombinant expression. In some useful embodiments of the invention, the pharmacologically active protein is modified in one or more ways relative to a native sequence of interest, including amino acid additions or insertions, amino acid deletions, peptide truncations, amino acid substitutions, or chemical derivatization of amino acid residues (accomplished by known chemical techniques), so long as the requisite bioactivity is maintained.

The terms "-mimetic peptide," "peptide mimetic," and "-agonist peptide" refer to a peptide or protein having biological activity comparable to a naturally occurring protein of interest, for example, but not limited to, a toxin peptide molecule, e.g., naturally occurring OSK1 toxin peptide. These terms further include peptides that indirectly mimic the activity of a naturally occurring peptide molecule, such as by potentiating the effects of the naturally occurring molecule.

The term "-antagonist peptide," "peptide antagonist," and "inhibitor peptide" refer to a peptide that blocks or in some way interferes with the biological activity of a receptor of interest, or has biological activity comparable to a known antagonist or inhibitor of a receptor of interest (such as, but not limited to, an ion channel or a G-Protein Coupled Receptor (GPCR)).

Examples of pharmacologically active proteins that can be used within the present invention include, but are not limited to, a toxin peptide (e.g., OSK1 or an OSK1 peptide analog; ShK or an ShK peptide analog), a CGRP peptide antagonist, a bradykinin B1 receptor peptide antagonist, a parathyroid hormone (PTH) agonist peptide, a parathyroid hormone (PTH) antagonist peptide, an ang-2 binding peptide, a myostatin binding peptide, an erythropoietin-mimetic (EPO-mimetic) peptide, a thrombopoietin-mimetic (TPO-mimetic) peptide, a nerve growth factor (NGF) binding peptide, a B cell activating factor (BAFF) binding peptide, and a glucagon-like peptide (GLP)-1 or a peptide mimetic thereof or GLP-2 or a peptide mimetic thereof.

Glucagon-like peptide 1 (GLP-1) and the related peptide glucagon are produced via differential processing of proglucagon and have opposing biological activities. Proglucagon itself is produced in α-cells of the pancreas and in the enteroendocrine L-cells, which are located primarily in the distal small intestine and colon. In the pancreas, glucagon is selectively cleaved from proglucagon. In the intestine, in contrast, proglucagon is processed to form GLP-1 and glucagon-like peptide 2 (GLP-2), which correspond to amino acid residues 78-107 and 126-158 of proglucagon, respectively (see, e.g., Irwin and Wong, 1995, *Mol. Endocrinol.* 9:267-277 and Bell et al., 1983, *Nature* 304:368-371). By convention, the numbering of the amino acids of GLP-1 is based on the GLP-1 (1-37) formed from cleavage of proglucagon. The biologically active forms are generated from further processing of this peptide, which, in one numbering convention, yields GLP-1 (7-37)-OH and GLP-1 (7-36)-NH$_2$. Both GLP-1 (7-37)-OH (or simply GLP-1 (7-37)) and GLP-1 (7-36)-NH$_2$ have the same activities. For convenience, the term "GLP-1", is used to refer to both of these forms. The first amino acid of these processed peptides is His7 in this numbering convention. Another numbering convention recognized in the art, however, assumes that the numbering of the processed peptide begins with His as position 1 rather than position 7. Thus, in this numbering scheme, GLP-1(1-31) is the same as GLP-1 (7-37), and GLP-1 (1-30) is the same as GLP-1 (7-36). Examples of GLP-1 mimetic polypeptide sequences include:

```
                                          (SEQ ID NO: 45)
HGEGTFTSDQSSYLEGQAAKEFIAWLVKGRG//;

(SEQ ID NO: 46)
HGEGTFTSDQSSYLEGQAAKEFIAWLQKGRG//;

(SEQ ID NO: 47)
HGEGTFTSDVSSYQEGQAAKEFIAWLVKGRG//;

(SEQ ID NO: 48)
HGEGTFTSDVSSYLEGQAAKEFIAQLVKGRG//;

(SEQ ID NO: 91)
HGEGTFTSDVSSYLEGQAAKEFIAQLQKGRG//;

(SEQ ID NO: 92)
HGEGTFTSDVSSYLEGQAAKEFIAWLQKGRG//;

(SEQ ID NO: 93)
HNETTFTSDVSSYLEGQAAKEFIAWLVKGRG//;

(SEQ ID NO: 95)
HGEGTFTSDVSSYLENQTAKEFIAWLVKGRG//;

(SEQ ID NO: 96)
HGEGTFTSDVSSYLEGNATKEFIAWLVKGRG//;

(SEQ ID NO: 97)
HGEGTFTSDVSSYLEGQAAKEFIAWLVNGTG//;

(SEQ ID NO: 98)
HGEGTFTSDVSSYLEGQAAKEFIAWLVKNRT//;

(SEQ ID NO: 99)
HGEGTFTSDVSSYLEGQAAKEFIAWLVKGRNGT//;

(SEQ ID NO: 100)
HGEGTFTSDVSSYLEGQAAKEFIAWLVKGRGGTGNGT//;
and (SEQ ID NO: 101)
HGEGTFTSDVSSYLEGQAAKEFIAWLVKGRGGSGNGT//.
```

Human GLP-2 and GLP-2-mimetic analogs are also known in the art. (See, e.g., Prasad et al., Glucagonlike peptide-2 analogue enhances intestinal mucosal mass after ischemia and reperfusion, J. Pediatr. Surg. 2000 February; 35(2):357-59 (2000); Yusta et al., Glucagon-like peptide-2 receptor activation engages bad and glycogen synthase kinase-3 in a protein kinase A-dependent manner and prevents apoptosis following inhibition of phosphatidylinositol 3-kinase, J. Biol. Chem. 277(28):24896-906 (2002)).

"Toxin peptides" include peptides and polypeptides having the same amino acid sequence of a naturally occurring pharmacologically active peptide or polypeptide that can be isolated from a venom, and also include modified peptide analogs of such naturally occurring molecules. (See, e.g., Kalman et al., ShK-Dap22, a potent Kv1.3-specific immunosuppressive polypeptide, J. Biol. Chem. 273(49):32697-707 (1998); Kem et al., U.S. Pat. No. 6,077,680; Mouhat et al., OsK1 derivatives, WO 2006/002850 A2; Chandy et al., Analogs of SHK toxin and their uses in selective inhibition of Kv1.3 potassium channels, WO 2006/042151; Sullivan et al., Toxin Peptide therapeutic agents, WO 2006/116156A2, all of which are incorporated herein by reference in their entirety). Snakes, scorpions, spiders, bees, snails and sea anemone are a few examples of organisms that produce venom that can serve as a rich source of small bioactive toxin peptides or "toxins" that potently and selectively target ion channels and receptors. An example of a toxin peptide is OSK1 (also known as OsK1), a toxin peptide isolated from *Orthochirus scrobiculosus* scorpion venom. (e.g., Mouhat et al., K+ channel types targeted by synthetic OSK1, a toxin from *Orthochirus scrobiculosus* scorpion venom, Biochem. J. 385:95-104 (2005); Mouhat et al., Pharmacological profiling of *Orthochirus scrobiculosus* toxin 1 analogs with a trimmed N-terminal domain, Molec. Pharmacol. 69:354-62 (2006); Mouhat et al., OsK1 derivatives, WO 2006/002850 A2). Another example is ShK, isolated from the venom of the sea anemone *Stichodactyla helianthus*. (E.g., Tudor et al., Ionisation behaviour and solution properties of the potassium-channel blocker ShK toxin, Eur. J. Biochem. 251(1-2):133-41 (1998); Pennington et al., Role of disulfide bonds in the structure and potassium channel blocking activity of ShK toxin, Biochem. 38(44): 14549-58 (1999); Kem et al., ShK toxin compositions and methods of use, U.S. Pat. No. 6,077,680; Lebrun et al., Neuropeptides originating in scorpion, U.S. Pat. No. 6,689,749; Beeton et al., Targeting effector memory T cells with a selective peptide inhibitor of Kv1.3 channels for therapy of autoimmune diseases, Molec. Pharmacol. 67(4):1369-81 (2005)).

The toxin peptides are usually between about 20 and about 80 amino acids in length, contain 2-5 disulfide linkages and form a very compact structure. Toxin peptides (e.g., from the venom of scorpions, sea anemones and cone snails) have been isolated and characterized for their impact on ion channels. Such peptides appear to have evolved from a relatively small number of structural frameworks that are particularly well suited to addressing the critical issues of potency and stability. The majority of scorpion and Conus toxin peptides, for example, contain 10-40 amino acids and up to five disulfide bonds, forming extremely compact and constrained structure (microproteins) often resistant to proteolysis. The conotoxin and scorpion toxin peptides can be divided into a number of superfamilies based on their disulfide connections and peptide folds. The solution structure of many of these has been determined by NMR spectroscopy, illustrating their compact structure and verifying conservation of their family fold. (E.g., Tudor et al., Ionisation behaviour and solution properties of the potassium-channel blocker ShK toxin, Eur. J. Biochem. 251(1-2): 133-41 (1998); Pennington et al., Role of disulfide bonds in the structure and potassium channel blocking activity of ShK toxin, Biochem. 38(44): 14549-58 (1999);

Jaravine et al., Three-dimensional structure of toxin OSK1 from *Orthochirus scrobiculosus* scorpion venom, Biochem. 36(6):1223-32 (1997); del Rio-Portillo et al.; NMR solution structure of Cn12, a novel peptide from the Mexican scorpion *Centruroides noxius* with a typical beta-toxin sequence but with alpha-like physiological activity, Eur. J. Biochem. 271 (12): 2504-16 (2004); Prochnicka-Chalufour et al., Solution structure of discrepin, a new K+-channel blocking peptide from the alpha-KTx15 subfamily, Biochem. 45(6):1795-1804 (2006)). Examples of pharmacologically active toxin peptides for which the practice of the present invention can be useful include, but are not limited to ShK, OSK1, charybdotoxin (ChTx), kaliotoxin1 KTX1), or maurotoxin, or toxin peptide analogs of any of these, modified from the native sequences at one or more amino acid residues. Other examples are known in the art, or can be found in Sullivan et al., WO06116156 A2 or U.S. patent application Ser. No. 11/406,454 (titled: Toxin Peptide Therapeutic Agents, published as US 2007/0071764); Mouhat et al., OsK1 derivatives, WO 2006/002850 A2; Sullivan et al., U.S. patent application Ser. No. 11/978,076 (titled: Conjugated Toxin Peptide Therapeutic Agents, filed 25 Oct. 2007), Lebrun et al., U.S. Pat. No. 6,689,749, which are each incorporated by reference in their entireties.

The term "peptide analog" refers to a peptide having a sequence that differs from a peptide sequence existing in nature by at least one amino acid residue substitution, internal addition, or internal deletion of at least one amino acid, and/or amino- or carboxy-terminal end truncations, or additions). An "internal deletion" refers to absence of an amino acid from a sequence existing in nature at a position other than the N- or C-terminus. Likewise, an "internal addition" refers to presence of an amino acid in a sequence existing in nature at a position other than the N- or C-terminus. "Toxin peptide analogs", such as, but not limited to, an OSK1 peptide analog, ShK peptide analog, or ChTx peptide analog, contain modifications of a native toxin peptide sequence of interest (e.g., amino acid residue substitutions, internal additions or insertions, internal deletions, and/or amino- or carboxy-terminal end truncations, or additions as previously described above) relative to a native toxin peptide sequence of interest, which is in the case of OSK1: GVIINVKCKISRQCLEPCKKAGMRFGKCMNGKCHCTPK// SEQ ID NO: 111; and in the case of ShK is RSCIDTIPKSRCTAFQCKHSMKYRLSFCRKTCGTC// SEQ ID NO:112.

A "CGRP peptide antagonist" is a peptide that preferentially binds the CGRP, receptor, such as, but not limited to, a CGRP peptide analog, and that antagonizes, blocks, decreases, reduces, impedes, or inhibits CGRP, receptor activation by full length native human αCGRP or βCGRP under physiological conditions of temperature, pH, and ionic strength. CGRP peptide antagonists include full and partial antagonists. Such antagonist activity can be detected by known in vitro methods or in vivo functional assay methods. (See, e.g., Smith et al., Modifications to the N-terminus but not the C-terminus of calcitonin gene-related peptide(8-37) produce antagonists with increased affinity, J. Med. Chem., 46:2427-2435 (2003)). Examples of useful CGRP peptide antagonists are disclosed in Gegg et al., CGRP peptide antagonists and conjugates, WO 2007/048026 A2 and U.S. Ser. No. 11/584,177, filed on Oct. 19, 2006, published as US 2008/0020978 A1, which is incorporated herein by reference in its entirety.

The terms "parathyroid hormone (PTH) agonist" and "PTH agonist" refer to a molecule that binds to PTH-1 or PTH-2 receptor and increases or decreases one or more PTH activity assay parameters as does full-length native human parathyroid hormone. Examples of useful PTH agonist peptides are disclosed in Table 1 of U.S. Pat. No. 6,756,480, titled Modulators of receptors for parathyroid hormone and parathyroid hormone-related protein, which is incorporated herein by reference in its entirety. An exemplary PTH activity assay is disclosed in Example 1 of U.S. Pat. No. 6,756,480.

The term "parathyroid hormone (PTH) antagonist" refers to a molecule that binds to PTH-1 or PTH-2 receptor and blocks or prevents the normal effect on those parameters by full length native human parathyroid hormone. Examples of useful PTH antagonist peptides are disclosed in Table 2 of U.S. Pat. No. 6,756,480, which is incorporated herein by reference in its entirety. An exemplary PTH activity assay is disclosed in Example 2 of U.S. Pat. No. 6,756,480.

The terms "bradykinin B1 receptor antagonist peptide" and "bradykinin B1 receptor peptide antagonist" mean a peptide with antagonist activity with respect to human bradykinin B1 receptor (hB1). Useful bradykinin B1 receptor antagonist peptides can be identified or derived as described in Ng et al., Antagonist of the bradykinin B1 receptor, US 2005/0215470 A1, published Sep. 29, 2005, or U.S. Pat. No. 5,834,431 or 5,849,863. An exemplary B1 receptor activity assays are disclosed in Examples 6-8 of US 2005/0215470 A1.

The terms "thrombopoietin (TPO)-mimetic peptide" and "TPO-mimetic peptide" refer to peptides that can be identified or derived as described in Cwirla et al. (1997), Science 276: 1696-9, U.S. Pat. Nos. 5,869,451 and 5,932,946, which are incorporated by reference in their entireties; U.S. Pat. App. No. 2003/0176352, published Sep. 18, 2003, which is incorporated by reference in its entirety; WO 03/031589, published Apr. 17, 2003; WO 00/24770, published May 4, 2000; and any peptides appearing in Table 5 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that each of these references enables one to select different peptides than actually disclosed therein by following the disclosed procedures with different peptide libraries.

The terms "EPO-mimetic peptide" and "erythropoietin-mimetic peptide" refers to peptides that can be identified or derived as described in Wrighton et al. (1996), Science 273: 458-63, and Naranda et al. (1999), Proc. Natl. Acad. Sci. USA 96: 7569-74, both of which are incorporated herein by reference in their entireties. Useful EPO-mimetic peptides include EPO-mimetic peptides listed in Table 5 of published U.S. patent application US 2007/0269369 A1 and in U.S. Pat. No. 6,660,843, which are both hereby incorporated by reference in their entireties.

The term "ang-2-binding peptide" comprises peptides that can be identified or derived as described in U.S. Pat. App. No. 2003/0229023, published Dec. 11, 2003; WO 03/057134, published Jul. 17, 2003; U.S. 2003/0236193, published Dec. 25, 2003 (each of which is incorporated herein by reference in its entirety); and any peptides appearing in Table 6 of published application US 2006/0140934 (U.S. Ser. No. 11/234, 731, filed Sep. 23, 2005, titled Modified Fc Molecules, which is incorporated herein by reference in its entirety). Those of ordinary skill in the art appreciate that each of these references enables one to select different peptides than actually disclosed therein by following the disclosed procedures with different peptide libraries.

The terms "nerve growth factor (NGF) binding peptide" and "NGF-binding peptide" comprise peptides that can be identified or derived as described in WO 04/026329, published Apr. 1, 2004 and any peptides identified in Table 7 of published application US 2006/0140934 (U.S. Ser. No.

11/234,731, filed Sep. 23, 2005, titled Modified Fc Molecules, which is incorporated herein by reference in its entirety). Those of ordinary skill in the art appreciate that this reference enables one to select different peptides than actually disclosed therein by following the disclosed procedures with different peptide libraries.

The term "myostatin-binding peptide" comprises peptides that can be identified or derived as described in U.S. Ser. No. 10/742,379, filed Dec. 19, 2003, which is incorporated herein by reference in its entirety, and peptides appearing in Table 8 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that each of these references enables one to select different peptides than actually disclosed therein by following the disclosed procedures with different peptide libraries.

The terms "BAFF-antagonist peptide" and "BAFF binding peptide" comprise peptides that can be identified or derived as described in U.S. Pat. Appln. No. 2003/0195156 A1, which is incorporated herein by reference in its entirety and those peptides appearing in Table 9 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that the foregoing references enable one to select different peptides than actually disclosed therein by following the disclosed procedures with different peptide libraries.

The small size of the small pharmacologically inactive protein domain (D) selected typically results in a short serum half-life for the fusion protein molecule, which can allow, optionally, for modulation of the pharmacokinetic profile of the molecule to fit the therapeutic need by attaching or conjugating covalently one or more half-life extending moieties of various masses and configurations to the fusion protein. A "half-life extending moiety" (or "$F^1$") refers to a molecule that prevents or mitigates in vivo degradation by proteolysis or other activity-diminishing chemical modification, increases in vivo half-life or other pharmacokinetic properties such as but not limited to increasing the rate of absorption, reduces toxicity, reduces immunogenicity, improves solubility, increases biological activity and/or target selectivity of the fusion protein with respect to a target of interest, and/or increases manufacturability, compared to an unconjugated form of the fusion protein. In accordance with the invention, the half-life extending moiety is one that is pharmaceutically acceptable. The half-life extending moiety should be selected such that the conjugated fusion protein (i.e., fusion protein with half-life extending moiety covalently attached thereto) achieves a sufficient hydrodynamic size to reduce clearance by renal filtration in vivo. For example, a half-life extending moiety can be selected that is a polymeric macromolecule, which is substantially straight chain, branched-chain, or dendritic in form. Alternatively, a half-life extending moiety can be selected such that, in vivo, the inventive composition of matter will bind to a plasma protein to form a complex, such that the complex thus formed avoids or reduces substantial renal clearance.

Exemplary half-life extending moiety that can be used, in accordance with the present invention, include a polyalkylene glycol compound, such as a polyethylene glycol (PEG) or a polypropylene glycol. Other appropriate polyalkylene glycol compounds include, but are not limited to, charged or neutral polymers of the following types: dextran, colominic acids or other carbohydrate based polymers, polymers of amino acids, and biotin derivatives.

Other examples of the half-life extending moiety, in accordance with the invention, include a copolymer of ethylene glycol, a copolymer of propylene glycol, a carboxymethylcellulose, a polyvinyl pyrrolidone, a poly-1,3-dioxolane, a poly-1,3,6-trioxane, an ethylene maleic anhydride copolymer, a polyaminoacid (e.g., polylysine or polyornithine), a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group.

Other embodiments of the half-life extending moiety, in accordance with the invention, include peptide ligands or small (organic) molecule ligands that have binding affinity for a long half-life plasma protein under physiological conditions of temperature, pH, and ionic strength. Examples include an albumin-binding peptide or small molecule (i.e., organic non-peptidyl) ligand, a transthyretin-binding peptide or small molecule ligand, a thyroxine-binding globulin-binding peptide or small molecule ligand, an antibody-binding peptide or small molecule ligand, or another peptide or small molecule that has an affinity for a long half-life plasma protein. (See, e.g., Blaney et al., Method and compositions for increasing the serum half-life of pharmacologically active agents by binding to transthyretin-selective ligands, U.S. Pat. No. 5,714,142; Sato et al., Serum albumin binding moieties, US 2003/0069395 A1; Jones et al., Pharmaceutical active conjugates, U.S. Pat. No. 6,342,225). A "long half-life plasma protein" is one of the hundreds of different proteins dissolved in mammalian blood plasma, including so-called "carrier proteins" (such as albumin, transferrin and haptoglobin), fibrinogen and other blood coagulation factors, complement components, immunoglobulins, enzyme inhibitors, precursors of substances such as angiotensin and bradykinin and many other types of proteins.

The invention encompasses the use of any single species of pharmaceutically acceptable half-life extending moiety, such as, but not limited to, those described herein, in conjugation with the fusion protein, or the use of a combination of two or more like or different half-life extending moieties.

In being conjugated, the half-life extending moiety, as described herein, is covalently bound directly to an amino acid residue of the fusion protein itself, or optionally, to a peptidyl or non-peptidyl linker (including but not limited to aromatic or aryl linkers) that is covalently bound to an amino acid residue of the fusion protein. Any "linker" group is optional. When present, its chemical structure is not critical, since it serves primarily as a spacer, which can be useful in optimizing pharmacological activity of some embodiments of the inventive composition. The linker is preferably made up of amino acids linked together by peptide bonds. The linker moiety, if present, can be independently the same or different from any other linker, or linkers, that may be present in the inventive composition.

As stated above, the linker, if present (whether within the primary amino acid sequence of the recombinant fusion protein, or as a linker for attaching a half-life extending moiety to the fusion protein), can be peptidyl in nature (i.e., made up of amino acids linked together by peptide bonds) and made up in length, preferably, of from 1 up to about 40 amino acid residues, more preferably, of from 1 up to about 20 amino acid residues, and most preferably of from 1 to about 10 amino acid residues. Preferably, but not necessarily, the amino acid residues in the linker are from among the twenty canonical amino acids, more preferably, cysteine, glycine, alanine, proline, asparagine, glutamine, and/or serine. Even more preferably, a peptidyl linker is made up of a majority of amino acids that are sterically unhindered, such as glycine, serine, and alanine linked by a peptide bond. It is also desirable that, if present, a peptidyl linker be selected that avoids rapid proteolytic turnover in circulation in vivo. Some of these amino acids may be glycosylated, as is well understood by those in the art. For example, a useful linker sequence constituting a sialylation site is $X_1X_2NX_4X_5G$ (SEQ ID NO:9), wherein $X_1$, $X_2$, $X_4$ and $X_5$ are each independently any amino acid residue.

In other embodiments, the 1 to 40 amino acids are selected from glycine, alanine, proline, asparagine, glutamine, and lysine. Preferably, a linker is made up of a majority of amino acids that are sterically unhindered, such as glycine and alanine. Thus, preferred linkers include polyglycines, polyserines, and polyalanines, or combinations of any of these. Some exemplary peptidyl linkers are poly(Gly)$_{1-8}$, particularly (Gly)$_3$, (Gly)$_4$ (SEQ ID NO:10), (Gly)$_5$ (SEQ ID NO:11) and (Gly)$_7$ (SEQ ID NO:12), as well as, poly(Gly)$_4$Ser (SEQ ID NO:21), poly(Gly-Ala)$_{2-4}$ and poly(Ala)$_{1-8}$. Other specific examples of peptidyl linkers include (Gly)$_5$Lys (SEQ ID NO:14), and (Gly)$_5$LysArg (SEQ ID NO:15). Other specific examples of linkers are: Other examples of useful peptidyl linkers are:

```
(Gly)3Lys(Gly)4;          (SEQ ID NO: 16)

(Gly)3AsnGlySer(Gly)2;    (SEQ ID NO: 17)

(Gly)3Cys(Gly)4;          (SEQ ID NO: 18)
and

GlyProAsnGlyGly.          (SEQ ID NO: 19)
```

To explain the above nomenclature, for example, (Gly)$_3$Lys(Gly)$_4$ means Gly-Gly-Gly-Lys-Gly-Gly-Gly-Gly (SEQ ID NO:20). Other combinations of Gly and Ala are also useful.

Other preferred linkers are those identified herein as "L5" (GGGGS; SEQ ID NO:21), "L10" (GGGGSGGGGS; SEQ ID NO:22), "L25" (GGGGSGGGGSGGGGSGGGGSGGGGS; SEQ ID NO:23) and any linkers used in the working examples hereinafter.

In some embodiments of the compositions of this invention, which comprise a peptide linker moiety ("L"), acidic residues, for example, glutamate or aspartate residues, are placed in the amino acid sequence of the linker moiety (L). Examples include the following peptide linker sequences:

```
GGEGGG;                   (SEQ ID NO: 24)

GGEEEGGG;                 (SEQ ID NO: 25)

GEEEG;                    (SEQ ID NO: 26)

GEEE;                     (SEQ ID NO: 27)

GGDGGG;                   (SEQ ID NO: 28)

GGDDDGG;                  (SEQ ID NO: 29)

GDDDG;                    (SEQ ID NO: 30)

GDDD;                     (SEQ ID NO: 31)

GGGGSDDSDEGSDGEDGGGGS;    (SEQ ID NO: 32)

WEWEW;                    (SEQ ID NO: 33)

FEFEF;                    (SEQ ID NO: 34)

EEEWWW;                   (SEQ ID NO: 35)

EEEFFF;                   (SEQ ID NO: 36)

WWEEEWW;                  (SEQ ID NO: 37)
or

FFEEEFF.                  (SEQ ID NO: 38)
```

In other embodiments, the linker constitutes a phosphorylation site, e.g., $X_1X_2YX_4X_5G$ (SEQ ID NO:39), wherein $X_1$, $X_2$, $X_4$, and $X_5$ are each independently any amino acid residue; $X_1X_2SX_4X_5G$ (SEQ ID NO:40), wherein $X_1$, $X_2$, $X_4$ and $X_5$ are each independently any amino acid residue; or $X_1X_2TX_4X_5G$ (SEQ ID NO:41), wherein $X_1$, $X_2$, $X_4$ and $X_5$ are each independently any amino acid residue.

The linkers shown here are exemplary; peptidyl linkers within the scope of this invention may be much longer and may include other residues. A peptidyl linker can contain, e.g., a cysteine, another thiol, or nucleophile for conjugation with a half-life extending moiety. In another embodiment, the linker contains a cysteine or homocysteine residue, or other 2-amino-ethanethiol or 3-amino-propanethiol moiety for conjugation to maleimide, iodoacetamide or thioester, functionalized half-life extending moiety.

Another useful peptidyl linker is a large, flexible linker comprising a random Gly/Ser/Thr sequence, for example: GSGSATGGSGSTASSGSGSATH (SEQ ID NO:42) or HGSGSATGGSGSTASSGSGSAT (SEQ ID NO:43), that is estimated to be about the size of a 1 kDa PEG molecule. Alternatively, a useful peptidyl linker may be comprised of amino acid sequences known in the art to form rigid helical structures (e.g., Rigid linker: -AEAAAKEAAAKEAAAK-AGG-) (SEQ ID NO:44). Additionally, a peptidyl linker can also comprise a non-peptidyl segment such as a 6 carbon aliphatic molecule of the formula —CH$_2$—CH$_2$—CH$_2$—CH$_2$—CH$_2$—CH$_2$—. The peptidyl linkers can be altered to form derivatives as described herein.

Optionally, non-peptidyl linkers are also useful for conjugating the half-life extending moiety to the peptide portion of the half-life extending moiety-conjugated fusion protein. For example, alkyl linkers such as —NH—(CH$_2$)$_s$—C(O)—, wherein s=2-20 can be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. Exemplary non-peptidyl linkers are PEG linkers (e.g., shown below):

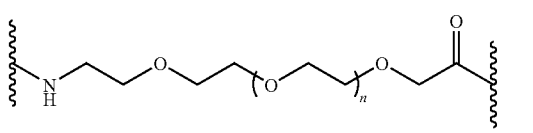

(II)

wherein n is such that the linker has a molecular weight of about 100 to about 5000 kilodaltons (kDa), preferably about 100 to about 500 kDa.

In one embodiment, the non-peptidyl linker is aryl. The linkers may be altered to form derivatives in the same manner as described herein. In addition, PEG moieties may be attached to the N-terminal amine or selected side chain amines by either reductive alkylation using PEG aldehydes or acylation using hydroxysuccinimido or carbonate esters of PEG, or by thiol conjugation.

"Aryl" is phenyl or phenyl vicinally-fused with a saturated, partially-saturated, or unsaturated 3-, 4-, or 5 membered carbon bridge, the phenyl or bridge being substituted by 0, 1, 2 or 3 substituents selected from $C_{18}$ alkyl, $C_{14}$ haloalkyl or halo.

"Heteroaryl" is an unsaturated 5, 6 or 7 membered monocyclic or partially-saturated or unsaturated 6-, 7-, 8-, 9-, 10- or 11 membered bicyclic ring, wherein at least one ring is unsaturated, the monocyclic and the bicyclic rings containing 1, 2, 3 or 4 atoms selected from N, O and S, wherein the ring is substituted by 0, 1, 2 or 3 substituents selected from $C_{18}$ alkyl, $C_{14}$ haloalkyl and halo.

Non-peptide portions of the inventive composition of matter, such as non-peptidyl linkers or non-peptide half-life extending moieties can be synthesized by conventional organic chemistry reactions.

The above is merely illustrative and not an exhaustive treatment of the kinds of linkers that can optionally be employed in accordance with the present invention.

In another useful embodiment of the inventive composition of matter and/or the method of producing a composition of matter, involving an inventive half-life extending moiety-conjugated fusion protein, the fusion protein is conjugated at the amino acid residue at the peptide's amino terminal end to the half-life extending moiety. (See, e.g., Kinstler et al., N-terminally chemically modified protein compositions and methods, U.S. Pat. Nos. 5,985,265, and 5,824,784).

It will be appreciated that "multimers" of Formula I, $(F^1)_a$—$(X^2)_b$, can be made, since the half-life extending moiety, $F^1$, employed for conjugation to the fusion protein can be multivalent (e.g., bivalent, trivalent, tetravalent or a higher order valency), as to the number of amino acid residues at which the half-life extending moiety can be conjugated. In some embodiments the peptide portion of the inventive composition of matter can be multivalent (e.g., bivalent, trivalent, tetravalent or a higher order valency), and, thus, some "multimers" of the inventive composition may have more that one $F^1$. Consequently, it is possible by the inventive method of producing a composition of matter to produce a variety of conjugated half-life extending moiety:peptide structures. By way of example, a univalent half-life extending moiety and a univalent peptide will produce a 1:1 conjugate; a bivalent peptide and a univalent half-life extending moiety may form conjugates wherein the peptide conjugates bear two half-life extending moiety moieties, whereas a bivalent half-life extending moiety and a univalent peptide may produce species where two peptide entities are linked to a single half-life extending moiety; use of higher-valence half-life extending moiety can lead to the formation of clusters of peptide entities bound to a single half-life extending moiety, whereas higher-valence peptides may become encrusted with a plurality of half-life extending moiety moieties. By way of further example, if the site of conjugation of a multivalent half-life extending moiety to the fusion protein is a cysteine or other aminothiol the methods disclosed by D'Amico et al. may be employed (U.S. Ser. No. 60/646,685, Method of conjugating aminothiol containing molecules to water-soluble polymers, which application is incorporated herein by reference in its entirety).

The peptide moieties may have more than one reactive group which will react with the activated half-life extending moiety and the possibility of forming complex structures must always be considered; when it is desired to form simple structures such as 1:1 adducts of half-life extending moiety and peptide, or to use bivalent half-life extending moiety to form peptide:half-life extending moiety:peptide adducts, it will be beneficial to use predetermined ratios of activated half-life extending moiety and peptide material, predetermined concentrations thereof and to conduct the reaction under predetermined conditions (such as duration, temperature, pH, etc.) so as to form a proportion of the described product and then to separate the described product from the other reaction products. The reaction conditions, proportions and concentrations of the reagents can be obtained by relatively simple trial-and-error experiments which are within the ability of an ordinarily skilled artisan with appropriate scaling-up as necessary. Purification and separation of the products is similarly achieved by conventional techniques well known to those skilled in the art.

Additionally, physiologically acceptable salts of the half-life extending moiety-conjugated or unconjugated fusion proteins of this invention are also encompassed within the present invention. By "physiologically acceptable salts" is meant any salts that are known or later discovered to be pharmaceutically acceptable. Some specific examples are: acetate; trifluoroacetate; hydrohalides, such as hydrochloride and hydrobromide; sulfate; citrate; maleate; tartrate; glycolate; gluconate; succinate; mesylate; besylate; pamoate, tannate, gallic acid ester, cholesteryl sulfate, and oxalate salts.

As an illustration, in some embodiments of the inventive composition of matter and/or the method of producing a composition of matter, the half-life extending moiety is poly (ethylene glycol) (PEG). Covalent conjugation of proteins with poly(ethylene glycol) (PEG) has been widely recognized as an approach to significantly extend the in vivo circulating half-lives of therapeutic proteins. PEGylation achieves this effect predominately by retarding renal clearance, since the PEG moiety adds considerable hydrodynamic radius to the protein. (Zalipsky, S., et al., Use of functionalized poly(ethylene glycol)s for modification of polypeptides, in poly(ethylene glycol) chemistry: Biotechnical and biomedical applications, J. M. Harris, Ed., Plenum Press: New York, 347-370 (1992)). Additional benefits often conferred by PEGylation of proteins include increased solubility, resistance to proteolytic degradation, and reduced immunogenicity of the therapeutic polypeptide. The merits of protein PEGylation are evidenced by the commercialization of several PEGylated proteins including PEG-Adenosine deaminase (Adagen™/Enzon Corp.), PEG-L-asparaginase (Oncaspar™/Enzon Corp.), PEG-Interferon α-2b (PEG-Intron™/Schering/Enzon), PEG-Interferon α-2a (PEGASYS™/Roche) and PEG-G-CSF (Neulasta™/Amgen) as well as many others in clinical trials.

By "PEGylated peptide" or "PEGylated protein" is meant a peptide having a polyethylene glycol (PEG) moiety covalently bound to an amino acid residue of the peptide itself or to a peptidyl or non-peptidyl linker that is covalently bound to a residue of the peptide.

By "polyethylene glycol" or "PEG" is meant a polyalkylene glycol compound or a derivative thereof, with or without coupling agents or derivatization with coupling or activating moieties (e.g., with aldehyde, hydroxysuccinimidyl, hydrazide, thiol, triflate, tresylate, azirdine, oxirane, orthopyridyl disulphide, vinylsulfone, iodoacetamide or a maleimide moiety). In accordance with the present invention, useful PEG includes substantially linear, straight chain PEG, branched PEG, or dendritic PEG. (See, e.g., Merrill, U.S. Pat. No. 5,171,264; Harris et al., Multiarmed, monofunctional, polymer for coupling to molecules and surfaces, U.S. Pat. No. 5,932,462; Shen, N-maleimidyl polymer derivatives, U.S. Pat. No. 6,602,498).

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). In the present application, the term "PEG" is used broadly to encompass any polyethylene glycol molecule, in mono-, bi-, or polyfunctional form, without regard to size or to modification at an end of the PEG, and can be represented by the formula:

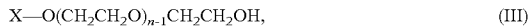
$$X-O(CH_2CH_2O)_{n-1}CH_2CH_2OH, \quad (III)$$

where n is 20 to 2300 and X is H or a terminal modification, e.g., a $C_{1-4}$ alkyl.

In some useful embodiments, a PEG used in the invention terminates on one end with hydroxy or methoxy, i.e., X is H or $CH_3$ ("methoxy PEG"). It is noted that the other end of the PEG, which is shown in formula (II) terminating in OH, covalently attaches to an activating moiety via an ether oxygen bond, an amine linkage, or amide linkage. When used in a chemical structure, the term "PEG" includes the formula (II) above without the hydrogen of the hydroxyl group shown, leaving the oxygen available to react with a free carbon atom of a linker to form an ether bond. More specifically, in order to conjugate PEG to a peptide, the peptide must be reacted with PEG in an "activated" form. Activated PEG can be represented by the formula:

$$(PEG)-(A) \quad (IV)$$

where PEG (defined supra) covalently attaches to a carbon atom of the activation moiety (A) to form an ether bond, an amine linkage, or amide linkage, and (A) contains a reactive group which can react with an amino, imino, or thiol group on an amino acid residue of a peptide or a linker moiety covalently attached to the peptide.

Techniques for the preparation of activated PEG and its conjugation to biologically active peptides are well known in the art. (E.g., see U.S. Pat. Nos. 5,643,575, 5,919,455, 5,932, 462, and 5,990,237; Thompson et al., PEGylation of polypeptides, EP 0575545 B1; Petit, Site specific protein modification, U.S. Pat. Nos. 6,451,986, and 6,548,644; S. Herman et al., Poly(ethylene glycol) with reactive endgroups: I. Modification of proteins, J. Bioactive Compatible Polymers, 10:145-187 (1995); Y. Lu et al., Pegylated peptides III: Solid-phase synthesis with PEGylating reagents of varying molecular weight: synthesis of multiply PEGylated peptides, Reactive Polymers, 22:221-229 (1994); A. M. Felix et al., PEGylated Peptides IV: Enhanced biological activity of site-directed PEGylated GRF analogs, Int. J. Peptide Protein Res., 46:253-264 (1995); A. M. Felix, Site-specific poly(ethylene glycol)ylation of peptides, ACS Symposium Series 680(poly (ethylene glycol)): 218-238 (1997); Y. Ikeda et al., Polyethylene glycol derivatives, their modified peptides, methods for producing them and use of the modified peptides, EP 0473084 B1; G. E. Means et al., Selected techniques for the modification of protein side chains, in: Chemical modification of proteins, Holden Day, Inc., 219 (1971)).

Activated PEG, such as PEG-aldehydes or PEG-aldehyde hydrates, can be chemically synthesized by known means or obtained from commercial sources, e.g., Shearwater Polymers, (Huntsville, Ala.) or Enzon, Inc. (Piscataway, N.J.).

An example of a useful activated PEG for purposes of the present invention is a PEG-aldehyde compound (e.g., a methoxy PEG-aldehyde), such as PEG-propionaldehyde, which is commercially available from Shearwater Polymers (Huntsville, Ala.). PEG-propionaldehyde is represented by the formula $PEG-CH_2CH_2CHO$. (See, e.g., U.S. Pat. No. 5,252, 714). Also included within the meaning of "PEG aldehyde compound" are PEG aldehyde hydrates, e.g., PEG acetaldehyde hydrate and PEG bis aldehyde hydrate, which latter yields a bifunctionally activated structure. (See, e.g., Bentley et al., Poly(ethylene glycol) aldehyde hydrates and related polymers and applications in modifying amines, U.S. Pat. No. 5,990,237) (See, e.g., Bentley et al., Poly(ethylene glycol) aldehyde hydrates and related polymers and applications in modifying amines, U.S. Pat. No. 5,990,237). An activated multi-branched PEG-aldehyde compound can be used (PEG derivatives comprising multiple arms to give divalent, trivalent, tetravalent, octavalent constructs). Using a 4-arm PEG derivative four (4) fusion proteins are attached to each PEG molecule. For example, in accordance with the present invention, the recombinant fusion protein can be conjugated to a polyethylene glycol (PEG) at 1, 2, 3 or 4 amino functionalized sites of the PEG.

In being conjugated in accordance with the inventive method, the polyethylene glycol (PEG), as described herein, is covalently bound by reductive amination directly to at least one solvent-exposed free amine moiety of an amino acid residue of the fusion protein itself. In some embodiments of the inventive method, the fusion protein is conjugated to a PEG at one or more primary or secondary amines on the recombinant fusion protein, or to two PEG groups at a single primary amine site on the fusion protein (e.g., this can occur when the reductive amination reaction involves the presence of excess PEG-aldehyde compound). We have observed that when PEGylation by reductive amination is at a primary amine on the peptide, it is not uncommon to have amounts (1 to 100% range) of reaction product that have two or more PEGs present per molecule, and if the desired PEGylation product is one with only one PEG per molecule, then this "over-PEGylation" may be undesirable. When PEGylated product with a single PEG per PEGylation product molecule is desired, an embodiment of the inventive method can be employed that involves PEGylation using secondary amines of the pharmacologically active peptide, because only one PEG group per molecule will be transferred in the reductive amination reaction.

Amino acid residues that can provide a primary amine moiety include residues of lysine, homolysine, ornithine, α,β-diaminoproprionic acid (Dap), α,β-diaminopropionoic acid (Dpr), and α,γ-diaminobutyric acid (Dab), aminobutyric acid (Abu), and α-amino-isobutyric acid (Aib). The polypeptide N-terminus also provides a useful α-amino group for PEGylation. Amino acid residues that can provide a secondary amine moiety include ε-N-alkyl lysine, α-N-alkyl lysine, δ-N-alkyl ornithine, α-N-alkyl ornithine, or an N-terminal proline, where the alkyl is $C_1$ to $C_6$.

Another useful activated PEG for generating the PEGylated recombinant fusion proteins of the present invention is a PEG-maleimide compound, such as, but not limited to, a methoxy PEG-maleimide, such as maleimido monomethoxy PEG, are particularly useful for generating the PEG-conjugated peptides of the invention. (E.g., Shen, N-maleimidyl polymer derivatives, U.S. Pat. No. 6,602,498; C. Delgado et al., The uses and properties of PEG-linked proteins, Crit. Rev. Therap. Drug Carrier Systems, 9:249-304 (1992); S. Zalipsky et al., Use of functionalized poly(ethylene glycol)s for modification of polypeptides, in: Poly(ethylene glycol) chemistry: Biotechnical and biomedical applications (J. M. Harris, Editor, Plenum Press: New York, 347-370 (1992); S. Herman et al., Poly(ethylene glycol) with reactive endgroups: I. Modification of proteins, J. Bioactive Compatible Polymers, 10:145-187 (1995); P. J. Shadle et al., Conjugation of polymer to colony stimulating factor-1, U.S. Pat. No. 4,847,325; G. Shaw et al., Cysteine added variants IL-3 and chemical modifications thereof, U.S. Pat. No. 5,166,322 and EP 0469074 B1; G. Shaw et al., Cysteine added variants of EPO and chemical modifications thereof, EP 0668353 A1; G. Shaw et al., Cysteine added variants G-CSF and chemical modifications thereof, EP 0668354 A1; N. V. Katre et al., Interleukin-2 muteins and polymer conjugation thereof, U.S. Pat. No. 5,206,344; R. J. Goodson and N. V. Katre, Site-directed pegylation of recombinant interleukin-2 at its glycosylation site, Biotechnology, 8:343-346 (1990)).

A poly(ethylene glycol) vinyl sulfone is another useful activated PEG for generating the PEG-conjugated fusion proteins of the present invention by conjugation at thiolated amino acid residues, e.g., at C residues. (E.g., M. Morpurgo et al., Preparation and characterization of poly(ethylene glycol) vinyl sulfone, Bioconj. Chem., 7:363-368 (1996); see also Harris, Functionalization of polyethylene glycol for formation of active sulfone-terminated PEG derivatives for binding to proteins and biologically compatible materials, U.S. Pat. Nos. 5,446,090; 5,739,208; 5,900,461; 6,610,281 and 6,894,025; and Harris, Water soluble active sulfones of poly(ethylene glycol), WO 95/13312 A1).

Another activated form of PEG that is useful in accordance with the present invention, is a PEG-N-hydroxysuccinimide ester compound, for example, methoxy PEG-N-hydroxysuccinimidyl (NHS) ester.

Heterobifunctionally activated forms of PEG are also useful. (See, e.g., Thompson et al., PEGylation reagents and biologically active compounds formed therewith, U.S. Pat. No. 6,552,170).

In still other embodiments of the inventive method of producing a composition of matter, the recombinant fusion protein is reacted by known chemical techniques with an activated PEG compound, such as but not limited to, a thiol-activated PEG compound, a diol-activated PEG compound, a PEG-hydrazide compound, a PEG-oxyamine compound, or a PEG-bromoacetyl compound. (See, e.g., S. Herman, Poly (ethylene glycol) with Reactive Endgroups: I. Modification of Proteins, J. Bioactive and Compatible Polymers, 10:145-187 (1995); S. Zalipsky, Chemistry of Polyethylene Glycol Conjugates with Biologically Active Molecules, Advanced Drug Delivery Reviews, 16:157-182 (1995); R. Greenwald et al., Poly(ethylene glycol) conjugated drugs and prodrugs: a comprehensive review, Critical Reviews in Therapeutic Drug Carrier Systems, 17:101-161 (2000)).

An even more preferred activated PEG for generating the PEG-conjugated fusion proteins of the present invention is a multivalent PEG having more than one activated residues. Preferred multivalent PEG moieties include, but are not limited to, those shown below:

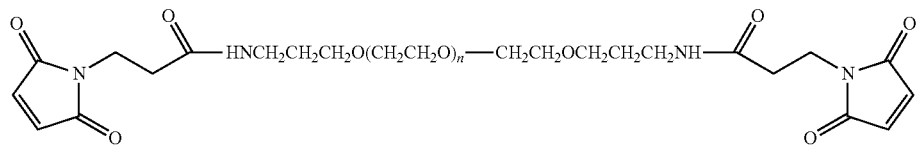

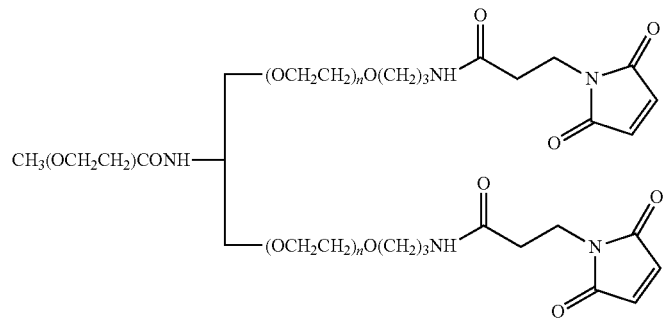

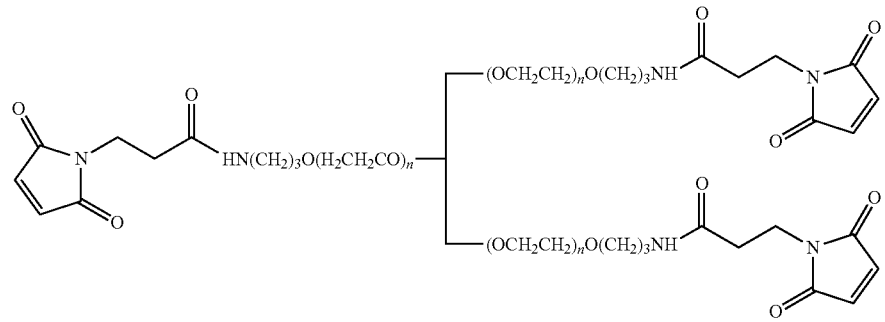

-continued

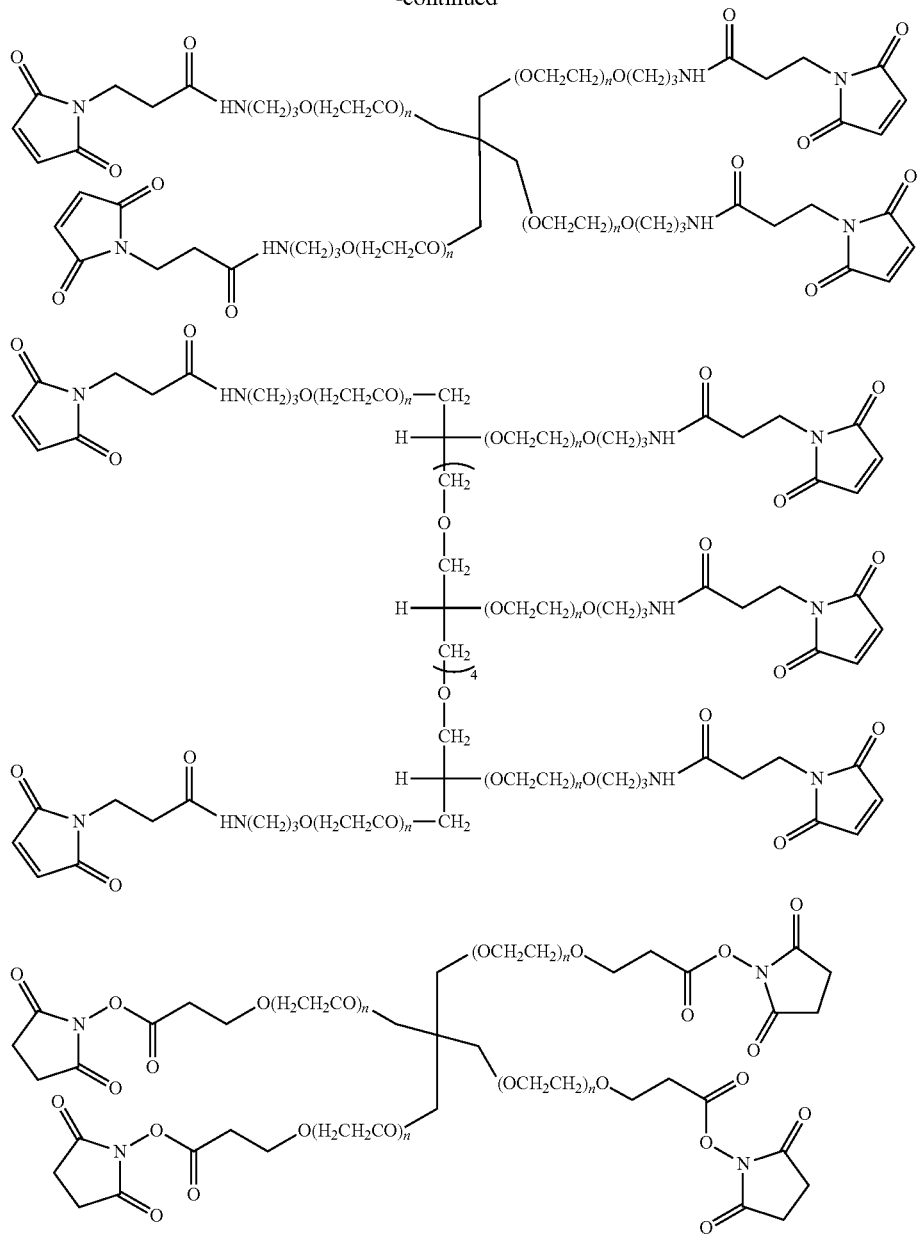

The smallest practical size of PEG is about 500 Daltons (Da), below which PEG becomes toxic. Above about 500 Da, any molecular mass for a PEG can be used as practically desired, e.g., from about 1,000 Daltons (Da) to 100,000 Da (n is 20 to 2300). The number of PEG monomers (n) is approximated from the average molecular mass using a MW=44Da for each monomer. It is preferred that the combined molecular mass of PEG on an activated linker is suitable for pharmaceutical use. Thus, the combined molecular mass of the PEG molecule should not exceed about 100,000 Da.

In still other embodiments of the inventive method of producing a composition of matter, the inventive recombinant fusion protein is reacted by known chemical techniques with an activated multi-branched PEG compound (PEG derivatives comprising multiple arms to give divalent, trivalent, tetravalent, octavalent constructs), such as but not limited to, pentaerythritol tetra-polyethyleneglycol ether. Functionalization and activated derivatives, such as, but not limited to, N-succinimidyloxycarbonyl)propyl, p-nitrophenyloxycarbonyl, ($-CO_2$-p-$C_6H_4NO_2$), 3-(N-maleimido)propanamido, 2-sulfanylethyl, and 3-aminopropyl. Using a 4-arm PEG derivative, four recombinant fusion proteins are attached to each PEG molecule. For example, in accordance with the present invention, the fusion protein can be conjugated to a polyethylene glycol (PEG) at:

(a) 1, 2, 3 or 4 amino functionalized sites of the PEG;
(b) 1, 2, 3 or 4 thiol functionalized sites of the PEG;
(c) 1, 2, 3 or 4 maleimido functionalized sites of the PEG;
(d) 1, 2, 3 or 4 N-succinimidyl functionalized sites of the PEG;
(e) 1, 2, 3 or 4 carboxyl functionalized sites of the PEG; or
(f) 1, 2, 3 or 4 p-nitrophenyloxycarbonyl functionalized sites of the PEG.

Preferably, the combined or total average molecular mass of PEG used in a PEG-conjugated recombinant fusion protein of the present invention is from about 3,000 Da to 60,000 Da (total n is from 70 to 1,400), more preferably from about 10,000 Da to 40,000 Da (total n is about 230 to about 910). The most preferred combined mass for PEG is from about 20,000 Da to 30,000 Da (total n is about 450 to about 680).

Uses of the Inventive Compounds

In General.

The fusion protein compounds of this invention have pharmacologic activity resulting from their ability to bind to proteins of interest as agonists, mimetics or antagonists of the native ligands of such proteins of interest. The activity of these compounds can be measured by assays known in the art.

In addition to therapeutic uses, the compounds of the present invention are useful in diagnosing diseases characterized by dysfunction of their associated protein of interest. For some of these diagnostic embodiments and for other detection (including semi-quantitative and quantitative) purposes, covalent conjugation of the active fusion protein to an immobilized substrate as an additional functional moiety, such as but not limited to, a plate surface, a chip, a bead, a matrix or a particle, can be useful. Also a moiety detectably labeled with a radioisotope, an enzyme (e.g., a peroxidase or a kinase), a biotinyl moiety, a fluorophore, or a chromophore can be useful for such purposes.

In one embodiment, a method of detecting in a biological sample a protein of interest (e.g., a receptor) that is capable of being activated comprising the steps of: (a) contacting the sample with a compound of this invention; and (b) detecting activation of the protein of interest by the compound. The biological samples include tissue specimens, intact cells, or extracts thereof. The compounds of this invention may be used as part of a kit to detect the presence of their associated proteins of interest in a biological sample. Such kits employ the compounds of the invention having an attached label to allow for detection. The compounds are useful for identifying normal or abnormal proteins of interest. For the EPO-mimetic compounds, for example, presence of abnormal protein of interest in a biological sample may be indicative of such disorders as Diamond Blackfan anemia, where it is believed that the EPO receptor is dysfunctional.

In addition, embodiments of the compositions of matter of the present invention, including the fusion proteins and pharmaceutical compositions or medicaments containing them are also useful in treating, alleviating, preventing or mitigating symptoms of a wide variety of diseases, disorders, or medical conditions in a patient. "Alleviated" with respect to a symptom means to be lessened, lightened, diminished, softened, mitigated (i.e., made more mild or gentle), quieted, assuaged, abated, relieved, nullified, or allayed, regardless of whether the symptom is entirely erased, eradicated, eliminated, or prevented in a particular patient.

Therapeutic Uses of CGRP Antagonist Molecules

The CGRP antagonist compounds of the invention are useful for treating migraine, and preventing or mitigating migraine and are of benefit in preventing, alleviating and/or mitigating symptoms of migraine. (See, e.g., Gegg et al., CGRP peptide antagonists and conjugates, WO 2007/048026 A2).

If desired, the therapeutic or prophylactic efficacy of CGRP antagonists may be tested preclinically, prior to clinical use in humans, using any appropriate animal model known to those skilled in the art related to a particular condition of interest. (See, e.g., Wang and Wang, Animal and cellular models of chronic pain, Advanced Drug Delivery Reviews 55:949-965 (2003)). An appropriate animal model for migraine can be selected from numerous methods, as described, for example, in Bergerot et al., Review Article: Animal models of migraine: looking at the component parts of a complex disorder, European Journal of Neuroscience 24:1517-1534 (2006); and Akerman, S and Goadsby P J, The role of dopamine in a model of trigeminovascular nociception, Pharmacol. Exp. Ther. 314(1):162-169 (2005), which are both incorporated by reference in their entireties.

A patient in need of treatment for migraine, or a patient who has previously experienced a migraine, are well-recognizable and/or diagnosed by the skilled practitioner, such as a physician, familiar with migraine and its symptoms.

There are several types of migraine, each with unique features or symptoms well known to those of skill in the art, but the present invention is not limited to any one type and can be useful in treating, alleviating, preventing or mitigating symptoms of any type of migraine. Classic migraine and common migraine are the two major varieties. Common migraine (without aura) is the most frequent type, accounting for about 80-85% of migraines. Unlike other headaches, migraines usually occur on one side of the head, although the side that is affected can shift with each new attack. Migraines are also often accompanied by symptoms of abnormal sensitivity to light and/or sound. The pain symptoms of a migraine headache are often described as an intense throbbing or pounding felt in the forehead/temple, ear/jaw or around the eyes. Although migraine pain usually appears on one side of the head, 30-40% of migraines occur on both sides. A migraine attack typically lasts about 4 to 72 hours. Migraine symptoms may also include speech difficulty, nausea, vomiting, confusion, weakness of an arm or leg and tingling of face or hands.

The basic difference between common and classic types of migraine is the appearance of an "aura." The aura is the occurrence of neurological symptoms 10-30 minutes before the classic migraine attack. During migraine aura, the migraineur may see flashing or shimmering lights, zigzag lines, geometric shapes, or may temporarily lose vision (e.g., hemianopsia), or experience blind spots called scotomas, experience speech disturbances, or experience other sensory phenomena, such as gustatory and/or olfactory hallucinations. Other symptoms of migraine aura may include numbness, tingling, speech difficulties and muscle weakness on one side of the body.

Another type of migraine is basilar migraine, which is accompanied by transient brainstem signs thought to be due to vasospastic narrowing of the basilar artery. In basilar-type migraine, the migraine sufferer meets the general criteria for migraine with aura and has two or more of the following symptoms: dysarthria, vertigo, tinnitus, hypacusia, double vision (diplopia), bilateral visual symptoms, ataxia, perioral numbness, decreased level of consciousness, and/or simultaneously bilateral paraesthesias.

The above-described symptoms of migraine are merely illustrative and are not intended to be an exhaustive description of all possible migraine symptoms experienced by a single patient or by several migraine sufferers in composite, and to which the present invention is directed. Those skilled in the art are aware of various other migraine symptoms and constellations of migraine symptoms suffered by individual patients, and to those migraine symptoms are also directed the present inventive methods of treating migraine, or preventing or mitigating migraine.

In addition, CGRP antagonists can be useful in the treatment, amelioration, and prevention of sleep disorders, such as sleep apneas and other sleep-related breathing disorders. (e.g., Carley et al., Pharmacological treatments for sleep disorders, WO 2007/047577 A2).

Therapeutic Uses of Molecules Comprising GLP-1 and GLP-2 and Mimetics Thereof

Glucagon is secreted from the α-cells of the pancreas in response to low blood sugar, with the main target organ for glucagon being the liver. Glucagon stimulates glycogen breakdown and inhibits glycogen biosynthesis. It also inhibits fatty acid synthesis, but enhances gluconeogenesis. The net result of these actions is to significantly increase the release of glucose to the liver. GLP-1, in contrast, lowers glucagon secretion, while stimulating insulin secretion, glucose uptake and cyclic-AMP (cAMP) formation in response to absorption of nutrients by the gut. Various clinical data provide evidence of these activities. The administration of GLP, for example, to poorly controlled type 2 diabetics normalized their fasting blood glucose levels (see, e.g., Gutniak, et al., 1992, *New Eng. J. Med.* 326:1316-1322).

GLP-1 has a number of other important activities. For instance, GLP-1 also inhibits gastric motility and gastric secretion (see, e.g., Tolessa, 1998, *J. Clin. Invest.* 102:764-774). This effect, sometimes referred to as the ileal brake effect, results in a lag phase in the availability of nutrients, thus significantly reducing the need for rapid insulin response.

Studies also indicate that GLP-1 can promote cell differentiation and replication, which in turn aids in the preservation of pancreatic islet cells and an increase in β-cell mass (See, e.g., Andreasen et al., 1994, *Digestion* 55:221-228; Wang, et al., 1997, *J. Clin. Invest.* 99:2883-2889; Mojsov, 1992, *Int. J. Pep. Prot. Res.* 40:333-343; and Xu et al., 1999, *Diabetes* 48:2270-2276). Evidence also indicates that GLP-1 can increase satiety and decrease food intake (see, e.g., Toft-Nielsen et al., 1999, *Diabetes Care* 22:1137-1143; Flint et al., 1998, *J. Clin. Invest.* 101:515-520; Gutswiller et al., 1999 *Gut* 44:81-86). Other research indicates that GLP-1 induces β-cell-specific genes, including GLUT-1 transporter, insulin receptor and hexokinase-1 (see, e.g., Perfetti and Merkel, 2000, *Eur. J. Endocrinol.* 143:717-725). Such induction could reverse glucose intolerance often associated with aging. Because it plays a key role in regulating metabolic homeostasis, GLP-1 is an attractive target for treating a variety of metabolic disorders, including diabetes, obesity and metabolic syndrome.

Glucagon-like peptide-1 (GLP-1) is a hormone that stimulates insulin secretion and simultaneously decreases glucagon secretion. The insulinotropic effect is glucose dependent. Because GLP-1 stimulates insulin secretion primarily at elevated glucose levels, GLP-1 therapy of type 2 diabetes may present a low risk of hypoglycemia. GLP-1 can also decrease hepatic glucose production indirectly, delay gastric emptying, and suppress appetite in type 2 diabetic patients. This array of effects gives GLP-1 the potential to be an efficacious and safe glucose-lowering agent for type 2 diabetes. In addition, GLP-1 has been shown to stimulate the differentiation of islet progenitor cells into insulin-producing cells and may be important for β-cell neogenesis. Short-term (12-h) infusion of GLP-1 as well as 6-week continuous subcutaneous infusion of GLP-1 has been shown to significantly improve insulin secretion in type 2 diabetic patients. While the main target of action of GLP-1 is the islet, where the hormone stimulates insulin secretion, promotes beta cell proliferation and neogenesis, and inhibits glucagon secretion, GLP-1 receptors are also expressed outside the islets, increasing the likelihood that GLP-1 also plays a role in other organs. These functions are mainly the inhibition of gastric emptying, gastric acid secretion and exocrine pancreatic secretion, indicating that the hormone acts as an enterogastrone—a hormone released from the distal portion of the small intestine that inhibits proximal gastrointestinal events. Another important action of GLP-1 is to induce satiety. Other effects of the hormone include cardioprotection, neuroprotection, induction of learning and memory, stimulation of afferent, sensory nerves, stimulation of surfactant production in the lung, dilatation of pulmonary vessels, induction of diuresis, and also under some conditions, induction of antidiabetic actions unrelated to islet function. Thus, GLP-1 clearly has several manifestations of pharmacologic activity. (See, e.g., Vrang et al., Characterization of brainstem preproglucagon progections to the paraventricular and dorsomedial hypothalamic nuclei, Brain Res. 1149:118-26 (2007); Korner et al., GLP-1 receptor expression in human tumors and human normal tissues:potential for in vivo targeting, J. Nucl. Med. 48(5):736-43 (2007)).

Glucagonlike peptide-2 (GLP-2), a product of the posttranslational processing of proglucagon, has been shown to enhance mucosal mass and function in both normal intestine and in the residual intestine after massive small bowel resection. Activation of glucagon-like peptide-2 receptor (GLP-2R) signaling by GLP-2 and GLP-2 mimetic protein analogs promotes expansion of the mucosal epithelium indirectly via activation of growth and anti-apoptotic pathways. GLP-2 and GLP-2 (GLP-2alpha)-mimetic analogs can enhance mucosal mass in small intestine after ischemia and reperfusion (I/R) injury. (See, e.g., Prasad et al., Glucagonlike peptide-2 analogue enhances intestinal mucosal mass after ischemia and reperfusion, J. Pediatr. Surg. 2000 February; 35(2):357-59 (2000).

Therapeutic Uses of Bradykinin B1 Receptor Antagonist Molecules

Bradykinin B1 receptor antagonist compounds of the present invention are useful in the treatment, amelioration and/or prevention of diseases, disorders, medical conditions and symptoms mediated by the B1 receptor, e.g., in the prevention or treatment of inflammation and chronic pain (including, but not limited to, inflammatory pain and associated hyperalgesia and allodynia). The fusion proteins and/or conjugated fusion proteins of the invention also have therapeutic value for the prevention or treatment of other painful conditions associated with or mediated by B1 activation, including, but not limited to, thalamic pain syndrome, diabetes, toxins and chemotherapy, septic shock, arthritis, mixed-vascular and non-vascular syndromes, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, inflammatory bowel disease, dermatitis, myositis, neuritis, collagen vascular diseases, chronic inflammatory conditions, epithelial tissue damage or dysfunction, herpes simplex, diabetic neuropathy pain, post-herpetic neuralgia, causalgia, sympathetically maintained pain, deafferentation syndromes, tension headache, angina, migraine, surgical pain, disturbances of visceral motility at respiratory, genitourinary, gastrointestinal or vascular regions, wounds, burns, allergic rhinitis, asthma, allergic skin reactions, pruritis, vitiligo, general gastrointestinal disorders, colitis, gastric ulceration, duodenal ulcers, or vasomotor or allergic rhinitis.

The invention also provides for the use of the inventive bradykinin B1 receptor antagonist fusion proteins and/or conjugated recombinant fusion proteins of the present invention for the prevention or treatment of acute pain, dental pain, back pain, lower back pain, pain from trauma, surgical pain, pain resulting from amputation or abscess, causalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, and bronchial disorders.

Therapeutic Uses of PTH Antagonist or Agonist Molecules.

PTH agonist fusion proteins of this invention have pharmacologic activity resulting from their interaction with PTH-1 receptor or PTH-2 receptor. Mannstadt et al. (1999), Am. J. Physiol. 277. 5Pt 2. F665-75. PTH and agonists thereof increase bone resorption, increase renal calcium reabsorption, decrease epidermal proliferation, and decrease hair growth. Holick et al. (1994) Proc. Natl. Sci. USA 91 (17): 8014-6; Schilli et al. (1997), J. Invest. Dermatol. 108(6): 928-32. Thus, antagonists of PTH-1 receptor and/or PTH-2 receptor are useful in treating:

primary and secondary hyperparathyroidism;
hypercalcemia, including hypercalcemia resulting from solid tumors (breast, lung and kidney) and hematologic malignancies (multiple myeloma, lymphoma and leukemia); idiopathic hypercalcemia, and hypercalcemia associated with hyperthyroidism and renal function disorders;
tumor metastases, particularly metastases to bone, and particularly related to breast and prostate cancer;
cachexia and anorexia, particularly as associated with cancer;
osteopenia that is related to or aggravated by aberrant PTH receptor signaling, including various forms of osteoporosis, such as:
primary osteoporosis;
post-menopausal and age-related osteoporosis;
endocrine osteoporosis (hyperthyroidism, hyperparathyroidism, Cushing's syndrome, and acromegaly);
hereditary and congenital forms of osteoporosis (e.g., osteogenesis imperfecta, homocystinuria, Menkes' syndrome, and Riley-Day syndrome);
osteoporosis due to immobilization of extremities;
osteoporosis secondary to other disorders, such as hemochromatosis, hyperprolactinemia, anorexia nervosa, thyrotoxicosis, diabetes mellitus, celiac disease, inflammatory bowel disease, primary biliary cirrhosis, rheumatoid arthritis, ankylosing spondylitis, multiple myeloma, lymphoproliferative diseases, and systemic mastocytosis;
osteoporosis secondary to surgery (e.g., gastrectomy) or to drug therapy, such as chemotherapy, anticonvulsant therapy, immunosuppressive therapy, and anticoagulant therapy;
osteoporosis secondary to glucocorticosteroid treatment for such diseases as rheumatoid arthritis (RA), systemic lupus erythematosus (SLE), asthma, temporal arteritis, vasculitis, chronic obstructive pulmonary disease, polymyalgia rheumatica, polymyositis, chronic interstitial lung disease;
osteoporosis secondary to glucocorticosteroid and/or immunomodulatory treatment to prevent organ rejection following organ transplant such as kidney, liver, lung, heart transplants;
osteoporosis due to submission to microgravity, such as observed during space travel;
osteoporosis associated with malignant disease, such as breast cancer, prostate cancer;
Paget's disease of bone (osteitis deformans) in adults and juveniles;
osteomyelitis, or an infectious lesion in bone, leading to bone loss;
osteopenia following surgery, induced by steroid administration, and associated with disorders of the small and large intestine and with chronic hepatic and renal diseases.
Osteonecrosis, or bone cell death, associated with traumatic injury or nontraumatic necrosis associated with Gaucher's disease, sickle cell anemia, systemic lupus erythematosus, rheumatoid arthritis, periodontal disease, osteolytic metastasis, and other conditions;
alopecia (deficient hair growth or partial or complete hair loss), including androgenic alopecia (male pattern baldness), toxic alopecia, alopecia senilis, alopecia greata, alopecia pelada, and trichotillomania;
and the like.

There are other conditions wherein a patient would benefit from the activity of PTH or PTHrP. For those indications, PTH receptor agonists are useful as a therapeutic treatment. In particular, such indications include fracture repair (including healing of non-union fractures), osteopenia, including various forms of osteoporosis, such as:
primary osteoporosis;
post-menopausal and age-related osteoporosis;
endocrine osteoporosis (hyperthyroidism, Cushing's syndrome, and acromegaly);
hereditary and congenital forms of osteoporosis (e.g., osteogenesis imperfecta, homocystinuria, Menkes' syndrome, and Riley-Day syndrome);
osteoporosis due to immobilization of extremities;
osteoporosis secondary to other disorders, such as hemochromatosis, hyperprolactinemia, anorexia nervosa, thyrotoxicosis, diabetes mellitus, celiac disease, inflammatory bowel disease, primary biliary cirrhosis, rheumatoid arthritis, ankylosing spondylitis, multiple myeloma, lymphoproliferative diseases, and systemic mastocytosis;
osteoporosis secondary to surgery (e.g., gastrectomy) or to drug therapy, such as chemotherapy, anticonvulsant therapy, immunosuppressive therapy, and anticoagulant therapy;
osteoporosis secondary to glucocorticosteroid treatment for diseases such as RA, SLE, asthma, temporal arteritis, vasculitis, chronic obstructive pulmonary disease, polymyalgia rheumatica, polymyositis, chronic interstitial lung disease;
osteoporosis secondary to glucocorticosteroid and/or immunomodulatory treatment to prevent organ rejection following organ transplant such as kidney, liver, lung, heart transplants;
osteoporosis due to submission to microgravity, such as observed during space travel;
osteoporosis associated with malignant disease, such as breast cancer, prostate cancer;
PTH agonists with extended half-life (e.g., those linked to Fc domains) may be used with an inhibitor of bone resorption. Inhibitors of bone resorption include OPG and OPG derivatives, OPG-L (RANKL) antibody, calcitonin (e.g., Miacalcin®, Calcimar®), bisphosphonates (e.g., APD, alendronate, risedronate, etidronate, pamidronate, tiludronate, clodronate, neridronate, ibandronate, zoledronate), estrogens (e.g., Premarin®, Estraderm®, Prempro®, Alora®, Climara®, Vivelle®, Estratab® Ogen®), selective estrogen receptor modulators (e.g., raloxifene, droloxifene, lasofoxifene), tibolone, and the like. Exemplary bone resorption inhibitors are described in WO98/46751 and WO97/23614, which are hereby incorporated by reference in their entireties.

Therapeutic Uses of EPO-Mimetic Molecules

The EPO-mimetic compounds of the invention are useful for treating disorders characterized by low red blood cell levels. Included in the invention are methods of modulating the endogenous activity of an EPO receptor in a mammal, preferably methods of increasing the activity of an EPO receptor. In general, any condition treatable by erythropoietin, such as anemia, may also be treated by the EPO-mimetic compounds of the invention. These compounds are administered by an amount and route of delivery that is appropriate for the nature and severity of the condition being treated and may be ascertained by one skilled in the art. Preferably, administration is by injection, either subcutaneous, intramuscular, or intravenous.

Therapeutic Uses of TPO-Mimetic Compounds

For the TPO-mimetic compounds, one can utilize such standard assays as those described in WO95/26746 entitled "Compositions and Methods for Stimulating Megakaryocyte Growth and Differentiation." The conditions to be treated are generally those that involve an existing megakaryocyte/platelet deficiency or an expected megakaryocyte/platelet deficiency (e.g., because of planned surgery or platelet donation). Such conditions will usually be the result of a deficiency (temporary or permanent) of active Mpl ligand in vivo. The generic term for platelet deficiency is thrombocytopenia, and hence the methods and compositions of the present invention are generally available for treating thrombocytopenia in patients in need thereof.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: aplastic anemia, idiopathic thrombocytopenia, metastatic tumors which result in thrombocytopenia, systemic lupus erythematosus, splenomegaly, Fanconi's syndrome, vitamin B12 deficiency, folic acid deficiency, May-Hegglin anomaly, Wiskott-Aldrich syndrome, and paroxysmal nocturnal hemoglobinuria. Also, certain treatments for AIDS result in thrombocytopenia (e.g., AZT). Certain wound healing disorders might also benefit from an increase in platelet numbers.

With regard to anticipated platelet deficiencies, e.g., due to future surgery, a compound of the present invention could be administered several days to several hours prior to the need for platelets. With regard to acute situations, e.g., accidental and massive blood loss, a compound of this invention could be administered along with blood or purified platelets.

The TPO-mimetic compounds of this invention may also be useful in stimulating certain cell types other than megakaryocytes if such cells are found to express Mpl receptor. Conditions associated with such cells that express the Mpl receptor, which are responsive to stimulation by the Mpl ligand, are also within the scope of this invention.

The TPO-mimetic compounds of this invention may be used in any situation in which production of platelets or platelet precursor cells is desired, or in which stimulation of the c-Mpl receptor is desired. Thus, for example, the compounds of this invention may be used to treat any condition in a mammal wherein there is a need of platelets, megakaryocytes, and the like. Such conditions are described in detail in the following exemplary sources: WO95/26746; WO95/21919; WO95/18858; WO95/21920 and are incorporated herein by reference in their entireties.

The TPO-mimetic compounds of this invention may also be useful in maintaining the viability or storage life of platelets and/or megakaryocytes and related cells. Accordingly, it could be useful to include an effective amount of one or more such compounds in a composition containing such cells.

Therapeutic Uses of Ang-2 Binding Molecules

Agents that modulate Ang-2 binding activity, or other cellular activity, may be used in combination with other therapeutic agents to enhance their therapeutic effects or decrease potential side effects.

In one aspect, the present invention provides reagents and methods useful for treating diseases and conditions characterized by undesirable or aberrant levels of Ang-2 activity in a cell. These diseases include cancers, and other hyperproliferative conditions, such as hyperplasia, psoriasis, contact dermatitis, immunological disorders, and infertility.

The present invention also provides methods of treating cancer in an animal, including humans, comprising administering to the animal an effective amount of a specific binding agent, such as a peptibody, that inhibits or decreases Ang-2 activity. The invention is further directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. Methods of the invention are also readily adaptable for use in assay systems, e.g., assaying cancer cell growth and properties thereof, as well as identifying compounds that affect cancer cell growth.

The cancers treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

Tumors or neoplasms include growths of tissue cells in which the multiplication of the cells is uncontrolled and progressive. Some such growths are benign, but others are termed malignant and may lead to death of the organism. Malignant neoplasms or cancers are distinguished from benign growths in that, in addition to exhibiting aggressive cellular proliferation, they may invade surrounding tissues and metastasize. Moreover, malignant neoplasms are characterized in that they show a greater loss of differentiation (greater dedifferentiation), and of their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells that infiltrate (invade) the surrounding tissues and give rise to metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems.

The ang-2 binding molecules of this invention are thus useful for the treatment of a wide variety of cancers, including solid tumors and leukemias. Types of cancer or tumor cells amenable to treatment according to the invention include, for example, ACTH-producing tumor; acute lymphocytic leukemia; acute nonlymphocytic leukemia; adenoma; cancer of the adrenal cortex; adenocarcinoma of the breast, prostate, and colon; ameloblastoma; apudoma; bladder cancer; brain cancer; branchioma; breast cancer; all forms of bronchogenic carcinoma of the lung; carcinoid heart disease; carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); malignant carcinoid syndrome; immunoproliferative small lung cell carcinoma; cementoma; cervical cancer; chondroblastoma; chondroma; chondrosarcoma; choristoma; chronic lymphocytic leukemia; chronic myelocytic leukemia; colorectal cancer; chordoma; craniopharyngioma; cutaneous T-cell lymphoma; dysgerminoma; endometrial cancer; esophageal cancer; Ewing's sarcoma; fibroma; fibrosarcoma; gallbladder cancer; giant cell tumors; glioma; hairy cell leukemia; hamartoma; head and neck cancer; hepatoma; histiocytic disorders; histiocytosis; Hodgkin's lymphoma; Kaposi's sarcoma; kidney cancer; lipoma; liposarcoma; liver cancer; lung cancer (small and non-small cell); malignant peritoneal effusion; malignant pleural effusion; melanoma; mesenchymoma; mesonephroma; mesothelioma; multiple myeloma; myosarcoma; myxoma; myxosarcoma; neuroblastoma; non-Hodgkin's lymphoma; odontoma; osteoma; osteosarcoma; ovarian cancer; ovarian (germ cell) cancer; pancreatic cancer; papilloma; penile cancer; plasmacytoma; prostate cancer; reticuloendotheliosis; retinoblastoma; skin cancer; soft tissue sarcoma; squamous cell carcinomas; stomach cancer; teratoma; testicular cancer; thymoma; thyroid cancer; trophoblastic neoplasms; uterine cancer; vaginal cancer; cancer of the vulva; Wilms' tumor.

Further, the following types of cancers may also be treated: cholangioma; cholesteatoma; cyclindroma; cystadenocarcinoma; cystadenoma; granulosa cell tumor; gynandroblastoma; hidradenoma; islet cell tumor; Leydig cell tumor; papilloma; Sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Therapeutic Uses of NGF Binding Molecules

The NGF binding molecules may be used in the prevention or treatment of NGF-related diseases and disorders. Such indications include but are not limited to pain (including, but not limited to, inflammatory pain and associated hyperalgesia and allodynia, neuropathic pain and associated hyperalgesia and allodynia, diabetic neuropathy pain, causalgia, sympathetically maintained pain, deafferentation syndromes, acute pain, tension headache, migraine, dental pain, pain from trauma, surgical pain, pain resulting from amputation or abscess, causalgia, demyelinating diseases, and trigeminal neuralgia). The peptides and modified peptides of the invention have therapeutic value for the prevention or treatment of other diseases linked to NGF as a causative agent, including, but not limited to, asthma, urge incontinence (i.e., hyperactive bladder), psoriasis, cancer (especially, pancreatic cancer and melanoma), chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, vasomotor or allergic rhinitis, or bronchial disorders.

Therapeutic Uses of Myostatin Binding Molecules

The myostatin binding agents of the present invention bind to myostatin and block or inhibit myostatin signaling within targeted cells. The present invention provides methods and reagents for reducing the amount or activity of myostatin in an animal by administering an effective dosage of one or more myostatin binding agents to the animal. In one aspect, the present invention provides methods and reagents for treating myostatin-related disorders in an animal comprising administering an effective dosage of one or more binding agents to the animal. These myostatin-related disorders include but are not limited to various forms of muscle wasting, as well as metabolic disorders such as diabetes and related disorders, and bone degenerative diseases such as osteoporosis.

Muscle wasting disorders include dystrophies such as Duchenne's muscular dystrophy, progressive muscular dystrophy, Becker's type muscular dystrophy, Dejerine-Landouzy muscular dystrophy, Erb's muscular dystrophy, and infantile neuroaxonal muscular dystrophy. For example, blocking myostatin through use of antibodies in vivo improved the dystrophic phenotype of the mdx mouse model of Duchenne muscular dystrophy (Bogdanovich et al. (2002), *Nature* 420: 28).

Additional muscle wasting disorders arise from chronic disease such as amyotrophic lateral sclerosis, congestive obstructive pulmonary disease, cancer, AIDS, renal failure, and rheumatoid arthritis. For example, cachexia or muscle wasting and loss of body weight was induced in athymic nude mice by a systemically administered myostatin (Zimmers et al., supra). In another example, serum and intramuscular concentrations of myostatin-immunoreactive protein was found to be increased in men exhibiting AIDS-related muscle wasting and was inversely related to fat-free mass (Gonzalez-Cadavid et al. (1998), *PNAS USA* 95: 14938-14943). Additional conditions resulting in muscle wasting may arise from inactivity due to disability such as confinement in a wheelchair, prolonged bedrest due to stroke, illness, bone fracture or trauma, and muscular atrophy in a microgravity environment (space flight). For example, plasma myostatin immunoreactive protein was found to increase after prolonged bedrest (Zachwieja et al. *J Gravit Physiol.* 6(2):11 (1999). It was also found that the muscles of rats exposed to a microgravity environment during a space shuttle flight expressed an increased amount of myostatin compared with the muscles of rats which were not exposed (Lalani et al. (2000), *J. Endocrin.* 167(3):417-28).

In addition, age-related increases in fat to muscle ratios, and age-related muscular atrophy appear to be related to myostatin. For example, the average serum myostatin-immunoreactive protein increased with age in groups of young (19-35 yr old), middle-aged (36-75 yr old), and elderly (76-92 yr old) men and women, while the average muscle mass and fat-free mass declined with age in these groups (Yarasheski et al. *J Nutr Aging* 6(5):343-8 (2002)). It has also been shown that myostatin gene knockout in mice increased myogenesis and decreased adipogenesis (Lin et al. (2002), *Biochem Biophys Res Commun* 291(3):701-6, resulting in adults with increased muscle mass and decreased fat accumulation and leptin secretion.

In addition, myostatin has now been found to be expressed at low levels in heart muscle and expression is upregulated after cardiomyocytes after infarct (Sharma et al. (1999), *J Cell Physiol.* 180(1): 1-9). Therefore, reducing myostatin levels in the heart muscle may improve recovery of heart muscle after infarct.

Myostatin also appears to influence metabolic disorders including type 2 diabetes, noninsulin-dependent diabetes mellitus, hyperglycemia, and obesity. For example, lack of myostatin has been shown to improve the obese and diabetic phenotypes of two mouse models (Yen et al. supra). In addition, increasing muscle mass by reducing myostatin levels may improve bone strength and reduce osteoporosis and other degenerative bone diseases. It has been found, for example, that myostatin-deficient mice showed increased mineral content and density of the mouse humerus and increased mineral content of both trabecular and cortical bone at the regions where the muscles attach, as well as increased muscle mass (Hamrick et al. (2002), *Calcif Tissue Int* 71(1): 63-8).

The present invention also provides methods and reagents for increasing muscle mass in food animals by administering an effective dosage of the myostatin binding agent to the animal. Since the mature C-terminal myostatin polypeptide is identical in all species tested, myostatin binding agents would be expected to be effective for increasing muscle mass and reducing fat in any agriculturally important species including cattle, chicken, turkeys, and pigs.

The myostatin-binding molecules of the present invention may be used alone or in combination with other therapeutic agents to enhance their therapeutic effects or decrease potential side effects. The molecules of the present invention possess one or more desirable but unexpected combination of properties to improve the therapeutic value of the agents. These properties include increased activity, increased solubility, reduced degradation, increased half-life, reduced toxicity, and reduced immunogenicity. Thus the molecules of the present invention are useful for extended treatment regimes. In addition, the properties of hydrophilicity and hydrophobicity of the compounds of the invention are well balanced, thereby enhancing their utility for both in vitro and especially in vivo uses. Specifically, compounds of the invention have an appropriate degree of solubility in aqueous media that permits absorption and bioavailability in the body, while also having a degree of solubility in lipids that permits the compounds to traverse the cell membrane to a putative site of action, such as a particular muscle mass.

The myostatin-binding molecules of the present invention are useful for treating a "subject" or any animal, including humans, when administered in an effective dosages in a suitable composition.

In addition, the mystatin-binding molecules of the present invention are useful for detecting and quantitating myostatin in a number of assays. These assays are described in detail in U.S. Ser. No. 10/742,379, filed Dec. 19, 2003 (published as US 2004/0181033 A1).

In general, the myostatin-binding molecules of the present invention are useful as capture agents to bind and immobilize myostatin in a variety of assays, similar to those described, for example, in Asai, ed., *Methods in Cell Biology,* 37, *Antibodies in Cell Biology*, Academic Press, Inc., New York (1993). The myostatin-binding molecule may be labeled in some manner or may react with a third molecule such as an anti-binding molecule antibody which is labeled to enable myostatin to be detected and quantitated. For example, a myostatin-binding molecule or a third molecule can be modified with a detectable moiety, such as biotin, which can then be bound by a fourth molecule, such as enzyme-labeled streptavidin, or other proteins. (Akerstrom (1985), *J Immunol* 135:2589; Chaubert (1997), *Mod Pathol* 10:585).

Throughout any particular assay, incubation and/or washing steps may be required after each combination of reagents. Incubation steps can vary from about 5 seconds to several hours, preferably from about 5 minutes to about 24 hours. However, the incubation time will depend upon the assay format, volume of solution, concentrations, and the like. Usually, the assays will be carried out at ambient temperature, although they can be conducted over a range of temperatures.

Therapeutic Uses of BAFF-Binding Molecules.

BAFF-binding molecules of this invention may be particularly useful in treatment of B-cell mediated autoimmune diseases. In particular, they may be useful in treating, preventing, ameliorating, diagnosing or prognosing lupus, including systemic lupus erythematosus (SLE), and lupus-associated diseases and conditions. Other preferred indications include B-cell mediated cancers, including B-cell lymphoma.

The compounds of this invention can also be used to treat inflammatory conditions of the joints. Inflammatory conditions of a joint are chronic joint diseases that afflict and disable, to varying degrees, millions of people worldwide. Rheumatoid arthritis is a disease of articular joints in which the cartilage and bone are slowly eroded away by a proliferative, invasive connective tissue called pannus, which is derived from the synovial membrane. The disease may involve peri-articular structures such as bursae, tendon sheaths and tendons as well as extra-articular tissues such as the subcutis, cardiovascular system, lungs, spleen, lymph nodes, skeletal muscles, nervous system (central and peripheral) and eyes (Silberberg (1985), Anderson's Pathology, Kissane (ed.), II:1828). Osteoarthritis is a common joint disease characterized by degenerative changes in articular cartilage and reactive proliferation of bone and cartilage around the joint. Osteoarthritis is a cell-mediated active process that may result from the inappropriate response of chondrocytes to catabolic and anabolic stimuli. Changes in some matrix molecules of articular cartilage reportedly occur in early osteoarthritis (Thonar et al. (1993), Rheumatic disease clinics of North America, Moskowitz (ed.), 19:635-657 and Shinmei et al. (1992), *Arthritis Rheum.,* 35:1304-1308). TALL-1, TALL-1R and modulators thereof are believed to be useful in the treatment of these and related conditions.

BAFF-binding molecules may also be useful in treatment of a number of additional diseases and disorders, including acute pancreatitis; ALS; Alzheimer's disease; asthma; atherosclerosis; autoimmune hemolytic anemia; cancer, particularly cancers related to B cells; cachexia/anorexia; chronic fatigue syndrome; cirrhosis (e.g., primary biliary cirrhosis); diabetes (e.g., insulin diabetes); fever; glomerulonephritis, including IgA glomerulonephritis and primary glomerulonephritis; Goodpasture's syndrome; Guillain-Barre syndrome;

graft versus host disease; Hashimoto's thyroiditis; hemorrhagic shock; hyperalgesia; inflammatory bowel disease; inflammatory conditions of a joint, including osteoarthritis, psoriatic arthritis and rheumatoid arthritis; inflammatory conditions resulting from strain, sprain, cartilage damage, trauma, orthopedic surgery, infection or other disease processes; insulin-dependent diabetes mellitus; ischemic injury, including cerebral ischemia (e.g., brain injury as a result of trauma, epilepsy, hemorrhage or stroke, each of which may lead to neurodegeneration); learning impairment; lung diseases (e.g., ARDS); lupus, particularly systemic lupus erythematosus (SLE); multiple myeloma; multiple sclerosis; Myasthenia gravis; myelogenous (e.g., AML and CML) and other leukemias; myopathies (e.g., muscle protein metabolism, esp. in sepsis); neurotoxicity (e.g., as induced by HIV); osteoporosis; pain; Parkinson's disease; Pemphigus; polymyositis/dermatomyositis; pulmonary inflammation, including autoimmune pulmonary inflammation; pre-term labor; psoriasis; Reiter's disease; reperfusion injury; septic shock; side effects from radiation therapy; Sjogren's syndrome; sleep disturbance; temporal mandibular joint disease; thrombocytopenia, including idiopathic thrombocytopenia and autoimmune neonatal thrombocytopenia; tumor metastasis; uveitis; and vasculitis.

Combination Therapy.

The therapeutic methods, compositions and compounds of the present invention may also be employed, alone or in combination with other cytokines, soluble Mpl receptor, hematopoietic factors, interleukins, growth factors or antibodies in the treatment of disease states characterized by other symptoms as well as platelet deficiencies. It is anticipated that the inventive compound will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with Mpl ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), SCF, GM-CSF, granulocyte colony stimulating factor (G-CSF), EPO, interferon-alpha (IFN-alpha), consensus interferon, IFN-beta, or IFN-gamma. It may further be useful to administer, either simultaneously or sequentially, an effective amount of a soluble mammalian Mpl receptor, which appears to have an effect of causing megakaryocytes to fragment into platelets once the megakaryocytes have reached mature form. Thus, administration of an inventive compound (to enhance the number of mature megakaryocytes) followed by administration of the soluble Mpl receptor (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

In cases where the inventive compounds are added to compositions of platelets and/or megakaryocytes and related cells, the amount to be included will generally be ascertained experimentally by techniques and assays known in the art. An exemplary range of amounts is 0.1 µg-1 mg inventive compound per $10^6$ cells.

Therapeutics Incorporating Toxin Peptides.

Some embodiments of the inventive composition of matter incorporate toxin peptides as additional functional moieties, which toxin peptides can have pharmacologic activity resulting from the ability to bind to ion channels of interest as agonists, mimetics or antagonists of the native ligands of such ion channels of interest. Consequently such embodiments of the inventive composition of matter can have utility in the treatment of pathologies associated with ion channels. Heritable diseases that have a known linkage to ion channels ("channelopathies") cover various fields of medicine, some of which include neurology, nephrology, myology and cardiology. A list of inherited disorders attributed to ion channels (channel types in parentheses) includes:

cystic fibrosis (Cl⁻ channel; CFTR);
Dent's disease (proteinuria and hypercalciuria; Cl⁻ channel; CLCN5);
osteopetrosis (Cl⁻ channel; CLCN7); familial hyperinsulinemia (SUR1; KCNJ11; K channel);
diabetes (KATP/SUR channel);
Andersen syndrome (KCNJ2, Kir2.1 K channel);
Bartter syndrome (KCNJ1; Kir1.1/ROMK; K channel);
hereditary hearing loss (KCNQ4; K channel);
hereditary hypertension (Liddle's syndrome; SCNN1; epithelial Na channel);
dilated cardiomyopathy (SUR2, K channel);
long-QT syndrome or cardiac arrhythmias (cardiac potassium and sodium channels);
Thymothy syndrome (CACNA1C, Cav1.2);
myasthenic syndromes (CHRNA, CHRNB, CNRNE; nAChR), and a variety of other myopathies;
hyperkalemic periodic paralysis (Na and K channels);
epilepsy (Na⁺ and K⁺ channels);
hemiplegic migraine (CACNA1A, Cav2.1 Ca²⁺ channel and ATP1A2);
central core disease (RYR1, RyR1; Ca²⁺ channel), and paramyotonia and myotonia (Na⁺, Cl⁻ channels)
(See L. J. Ptacek and Y-H Fu (2004), *Arch. Neurol.* 61: 166-8; B. A. Niemeyer et al. (2001), *EMBO reports* 21: 568-73; F. Lehmann-Horn and K. Jurkat-Rott (1999), *Physiol. Rev.* 79: 1317-72.) Although the foregoing list concerned disorders of inherited origin, molecules targeting the channels cited in these disorders can also be useful in treating related disorders of other, or indeterminate, origin.

In addition to the aforementioned disorders, evidence has also been provided supporting ion channels as targets for treatment of:

sickle cell anemia (IKCa1)—in sickle cell anemia, water loss from erythrocytes leads to hemoglobin polymerization and subsequent hemolysis and vascular obstruction. The water loss is consequent to potassium efflux through the so-called Gardos channel i.e., IKCa1. Therefore, block of IKCa1 is a potential therapeutic treatment for sickle cell anemia.

glaucoma (BKCa)—in glaucoma the intraocular pressure is too high leading to optic nerve damage, abnormal eye function and possibly blindness. Block of BKCa potassium channels can reduce intraocular fluid secretion and increase smooth muscle contraction, possibly leading to lower intraocular pressure and neuroprotection in the eye;

multiple sclerosis (Kv, KCa);
psoriasis (Kv, KCa);
arthritis (Kv, KCa);
asthma (KCa, Kv);
allergy (KCa, Kv);
COPD (KCa, Kv, Ca);
allergic rhinitis (KCa, Kv);
pulmonary fibrosis;
lupus (IKCa1, Kv);
transplantation, GvHD (KCa, Kv);
inflammatory bone resorption (KCa, Kv);
periodontal disease (KCa, Kv);

diabetes, type I (Kv)—type I diabetes is an autoimmune disease that is characterized by abnormal glucose, protein and lipid metabolism and is associated with insulin deficiency or resistance. In this disease, Kv1.3-expressing T-lymphocytes attack and destroy pancreatic islets leading to loss of beta-cells. Block of Kv1.3 decreases inflammatory cytokines. In addition block of Kv1.3 facilitates the translocation of GLUT4 to the plasma membrane, thereby increasing insulin sensitivity;

obesity (Kv)—Kv1.3 appears to play a critical role in controlling energy homeostasis and in protecting against diet-induced obesity. Consequently, Kv1.3 blockers could increase metabolic rate, leading to greater energy utilization and decreased body weight;

restenosis (KCa, $Ca^{2+}$)—proliferation and migration of vascular smooth muscle cells can lead to neointimal thickening and vascular restenosis. Excessive neointimal vascular smooth muscle cell proliferation is associated with elevated expression of IKCa1. Therefore, block of IKCa1 could represent a therapeutic strategy to prevent restenosis after angioplasty;

ischaemia (KCa, $Ca^{2+}$)—in neuronal or cardiac ischemia, depolarization of cell membranes leads to opening of voltage-gated sodium and calcium channels. In turn this can lead to calcium overload, which is cytotoxic. Block of voltage-gated sodium and/or calcium channels can reduce calcium overload and provide cytoprotective effects. In addition, due to their critical role in controlling and stabilizing cell membrane potential, modulators of voltage- and calcium-activated potassium channels can also act to reduce calcium overload and protect cells; renal incontinence (KCa), renal incontinence is associated with overactive bladder smooth muscle cells. Calcium-activated potassium channels are expressed in bladder smooth muscle cells, where they control the membrane potential and indirectly control the force and frequency of cell contraction. Openers of calcium-activated potassium channels therefore provide a mechanism to dampen electrical and contractile activity in bladder, leading to reduced urge to urinate;

osteoporosis (Kv);

pain, including migraine ($Na_V$, TRP [transient receptor potential channels], P2X, $Ca^{2+}$), N-type voltage-gated calcium channels are key regulators of nociceptive neurotransmission in the spinal cord. Ziconotide, a peptide blocker of N-type calcium channels reduces nociceptive neurotransmission and is approved worldwide for the symptomatic alleviation of severe chronic pain in humans. Novel blockers of nociceptor-specific N-type calcium channels would be improved analgesics with reduced side-effect profiles;

hypertension ($Ca^{2+}$)—L-type and T-type voltage-gated calcium channels are expressed in vascular smooth muscle cells where they control excitation-contraction coupling and cellular proliferation. In particular, T-type calcium channel activity has been linked to neointima formation during hypertension. Blockers of L-type and T-type calcium channels are useful for the clinical treatment of hypertension because they reduce calcium influx and inhibit smooth muscle cell contraction;

wound healing, cell migration serves a key role in wound healing. Intracellular calcium gradients have been implicated as important regulators of cellular migration machinery in keratinocytes and fibroblasts. In addition, ion flux across cell membranes is associated with cell volume changes. By controlling cell volume, ion channels contribute to the intracellular environment that is required for operation of the cellular migration machinery. In particular, IKCa1 appears to be required universally for cell migration. In addition, Kv1.3, Kv3.1, NMDA receptors and N-type calcium channels are associated with the migration of lymphocytes and neurons;

stroke;

Alzheimer's Disease;

Parkinson's Disease (NACHR, Nav);

Bipolar Disorder (Nav, Cav);

cancer, many potassium channel genes are amplified and protein subunits are upregulated in many cancerous condition. Consistent with a pathophysiological role for potassium channel upregulation, potassium channel blockers have been shown to suppress proliferation of uterine cancer cells and hepatocarcinoma cells, presumably through inhibition of calcium influx and effects on calcium-dependent gene expression; and a variety of neurological, cardiovascular, metabolic and autoimmune diseases.

Both agonists and antagonists of ion channels can achieve therapeutic benefit. Therapeutic benefits can result, for example, from antagonizing Kv1.3, IKCa1, SKCa, BKCa, N-type or T-type $Ca^{2+}$ channels and the like. Small molecule and peptide antagonists of these channels have been shown to possess utility in vitro and in vivo.

Compositions of this invention incorporating peptide antagonists of the voltage-gated potassium channel Kv1.3, in particular recombinant fusion proteins comprising OSK1 peptide analogs, whether or not conjugated to a half-life extending moiety, are useful as immunosuppressive agents with therapeutic value for autoimmune diseases. For example, such molecules are useful in treating multiple sclerosis, type 1 diabetes, psoriasis, inflammatory bowel disease, and rheumatoid arthritis. (See, e.g., H. Wulff et al. (2003) J. Clin. Invest. 111, 1703-1713 and H. Rus et al. (2005) PNAS 102, 11094-11099; Beeton et al., Targeting effector memory T cells with a selective inhibitor peptide of Kv1.3 channels for therapy of autoimmune diseases, Molec. Pharmacol. 67(4): 1369-81 (2005); 1 Beeton et al. (2006), Kv1.3: therapeutic target for cell-mediated autoimmune disease, electronic pre-print at //webfiles.uci.edu/xythoswfs/webui/2670029.1). Inhibitors of the voltage-gated potassium channel Kv1.3 have been examined in a variety of preclinical animal models of inflammation. Small molecule and peptide inhibitors of Kv1.3 have been shown to block delayed type hypersensitivity responses to ovalbumin [C. Beeton et al. (2005) Mol. Pharmacol. 67, 1369] and tetanus toxoid [G. C. Koo et al. (1999) Clin. Immunol. 197, 99]. In addition to suppressing inflammation in the skin, inhibitors also reduced antibody production [G. C. Koo et al. (1997) J. Immunol. 158, 5120]. Kv1.3 antagonists have shown efficacy in a rat adoptive-transfer experimental autoimmune encephalomyelitis (AT-EAE) model of multiple sclerosis (MS). The Kv1.3 channel is overexpressed on myelin-specific T cells from MS patients, lending further support to the utility Kv1.3 inhibitors may provide in treating MS. Inflammatory bone resorption was also suppressed by Kv1.3 inhibitors in a preclinical adoptive-transfer model of periodontal disease [P. Valverde et al. (2004) J. Bone Mineral Res. 19, 155]. In this study, inhibitors additionally blocked antibody production to a bacterial outer membrane protein—one component of the bacteria used to induce gingival inflammation. Recently in preclinical rat models, efficacy of Kv1.3 inhibitors was shown in treating pristane-induced arthritis and diabetes [C. Beeton et al. (2006) preprint available at //webfiles.uci.edu/xythoswfs/webui/_xy-2670029_1]. The Kv1.3 channel is expressed on all subsets of T cells and B cells, but effector memory T cells and class-switched memory B cells are particularly dependent on Kv1.3 [H. Wulff et al. (2004) J. Immunol. 173, 776]. Gad5/insulin-specific T cells from patients with new onset type 1 diabetes, myelin-specific T cells from MS patients and T cells from the synovium of rheumatoid arthritis patients all overexpress Kv1.3 [C. Beeton et al. (2006) preprint at //webfiles.uci.edu/xythoswfs/webui/_xy-2670029__1]. Because mice deficient in Kv1.3 gained less weight when placed on a high fat diet [J. Xu et al. (2003) Human Mol. Genet. 12, 551] and showed altered glucose utilization [J. Xu et al. (2004) Proc. Natl. Acad. Sci. 101, 3112], Kv1.3 is also being investigated for the treatment of obesity and diabetes. Breast cancer specimens [M. Abdul et al. (2003) Anticancer Res. 23, 3347] and prostate cancer cell lines [S. P. Fraser et al. (2003) Pflugers Arch. 446, 559] have also been shown to express Kv1.3, and Kv1.3 blockade may be of utility for treatment of cancer. Disorders that can be treated with the inventive fusions proteins, involving Kv1.3 inhibitor toxin peptide(s), include multiple sclerosis, type 1 diabetes, psoriasis, inflammatory bowel disease, contact-mediated dermatitis, rheumatoid arthritis, psoriatic arthritis, asthma, allergy, restinosis, systemic sclerosis, fibrosis, scleroderma, glomerulonephritis, Sjogren syndrome, inflammatory bone resorption, transplant rejection, graft-versus-host disease, and systemic lupus erythematosus (SLE) and other forms of lupus.

Some of the cells that express the calcium-activated potassium of intermediate conductance IKCa1 include T cells, B cells, mast cells and red blood cells (RBCs). T cells and RBCs from mice deficient in IKCa1 show defects in volume regulation [T. Begenisich et al. (2004) J. Biol. Chem. 279, 47681]. Preclinical and clinical studies have demonstrated IKCa1 inhibitors utility in treating sickle cell anemia [J. W. Stocker et al. (2003) Blood 101, 2412; www.icagen.com]. Blockers of the IKCa1 channel have also been shown to block EAE, indicating they may possess utility in treatment of MS [E. P. Reich et al. (2005) Eur. J. Immunol. 35, 1027]. IgE-mediated histamine production from mast cells is also blocked by IKCa1 inhibitors [S. Mark Duffy et al. (2004) J. Allergy Clin. Immunol. 114, 66], therefore they may also be of benefit in treating asthma. The IKCa1 channel is overexpressed on activated T and B lymphocytes [H. Wulff et al. (2004) J. Immunol. 173, 776] and thus may show utility in treatment of a wide variety of immune disorders. Outside of the immune system, IKCa1 inhibitors have also shown efficacy in a rat model of vascular restinosis and thus might represent a new therapeutic strategy to prevent restenosis after angioplasty [R. Kohler et al. (2003) Circulation 108, 1119]. It is also thought that IKCa1 antagonists are of utility in treatment of tumor angiogenesis since inhibitors suppressed endothelial cell proliferation and angiogenesis in vivo [I. Grgic et al. (2005) Arterioscler. Thromb. Vasc. Biol. 25, 704]. The IKCa1 channel is upregulated in pancreatic tumors and inhibitors blocked proliferation of pancreatic tumor cell lines [H. Jager et al. (2004) Mol. Pharmacol. 65, 630]. IKCa1 antagonists may also represent an approach to attenuate acute brain damage caused by traumatic brain injury [F. Mauler (2004) Eur. J. Neurosci. 20, 1761]. Disorders that can be treated with the inventive recombinant fusion proteins comprising IKCa1 inhibitors include multiple sclerosis, asthma, allergy, psoriasis, contact-mediated dermatitis, rheumatoid arthritis, psoriatic arthritis, type 1 diabetes, inflammatory bowel disease, fibrosis, scleroderma, glomerulonephritis, Sjogren syndrome, inflammatory bone resorption, systemic sclerosis, transplant rejection, graft-versus-host disease, systemic lupus erythematosus (SLE) and other forms of lupus, restinosis, pancreatic cancer, tumor angiogenesis and traumatic brain injury.

Accordingly, molecules of this invention incorporating peptide antagonists of the calcium-activated potassium channel of intermediate conductance, IKCa can be used to treat, The diseases and pharmacologically active compositions described herein are merely exemplary and in no way limit the range of inventive pharmacologically active compounds and compositions that can be prepared using the inventive method or the diseases and disorders that can be treated with the benefit of the present invention.

Accordingly, the present invention also relates to the use of one or more of the inventive compositions of matter in the manufacture of a medicament for the treatment or prevention of a disease, disorder, or other medical condition described herein.

Such pharmaceutical compositions can be configured for administration to a patient by a wide variety of delivery routes, e.g., an intravascular delivery route such as by injection or infusion, subcutaneous, intramuscular, intraperitoneal, epidural, or intrathecal delivery routes, or for oral, enteral, pulmonary (e.g., inhalant), intranasal, transmucosal (e.g., sublingual administration), transdermal or other delivery routes and/or forms of administration known in the art. The inventive pharmaceutical compositions may be prepared in liquid form, or may be in dried powder form, such as lyophilized form. For oral or enteral use, the pharmaceutical compositions can be configured, for example, as tablets, troches, lozenges, aqueous or oily suspensions, dispersible powders or granules, emulsions, hard or soft capsules, syrups, elixirs or enteral formulas.

Pharmaceutical Compositions

In General.

The present invention also provides pharmaceutical compositions comprising the inventive composition of matter and a pharmaceutically acceptable carrier. Such pharmaceutical compositions can be configured for administration to a patient by a wide variety of delivery routes, e.g., an intravascular delivery route such as by injection or infusion, subcutaneous, intramuscular, intraperitoneal, epidural, or intrathecal delivery routes, or for oral, enteral, pulmonary (e.g., inhalant), intranasal, transmucosal (e.g., sublingual administration), transdermal or other delivery routes and/or forms of administration known in the art. The inventive pharmaceutical compositions may be prepared in liquid form, or may be in dried powder form, such as lyophilized form. For oral or enteral use, the pharmaceutical compositions can be configured, for example, as tablets, troches, lozenges, aqueous or oily suspensions, dispersible powders or granules, emulsions, hard or soft capsules, syrups, elixirs or enteral formulas.

In the practice of this invention the "pharmaceutically acceptable carrier" is any physiologically tolerated substance known to those of ordinary skill in the art useful in formulating pharmaceutical compositions, including, any pharmaceutically acceptable diluents, excipients, dispersants, binders, fillers, glidants, anti-frictional agents, compression aids, tablet-disintegrating agents (disintegrants), suspending agents, lubricants, flavorants, odorants, sweeteners, permeation or penetration enhancers, preservatives, surfactants, solubilizers, emulsifiers, thickeners, adjuvants, dyes, coatings, encapsulating material(s), and/or other additives singly or in combination. Such pharmaceutical compositions can include diluents of various buffer content (e.g., Tris-HCl, acetate, phosphate), pH and ionic strength; additives such as detergents and solubilizing agents (e.g., Tween® 80, Polysorbate 80), anti-oxidants (e.g., ascorbic acid, sodium metabisulfite), preservatives (e.g., Thimersol®, benzyl alcohol) and bulking substances (e.g., lactose, mannitol); incorporation of the material into particulate preparations of polymeric compounds such as polylactic acid, polyglycolic acid, etc. or into liposomes. Hyaluronic acid can also be used, and this can have the effect of promoting sustained duration in the circulation. Such compositions can influence the physical state, stability, rate of in vivo release, and rate of in vivo clearance of the present proteins and derivatives. See, e.g., *Remington's Pharmaceutical Sciences,* 18th Ed. (1990, Mack Publishing Co., Easton, Pa. 18042) pages 1435-1712, which are herein incorporated by reference in their entirety. The compositions can be prepared in liquid form, or can be in dried powder, such as lyophilized form. Implantable sustained release formulations are also useful, as are transdermal or transmucosal formulations. Additionally (or alternatively), the present invention provides compositions for use in any of the various slow or sustained release formulations or microparticle formulations known to the skilled artisan, for example, sustained release microparticle formulations, which can be administered via pulmonary, intranasal, or subcutaneous delivery routes. (See, e.g., Murthy et al., Injectable compositions for the controlled delivery of pharmacologically active compound, U.S. Pat. No. 6,887,487; Manning et al., Solubilization of pharmaceutical substances in an organic solvent and preparation of pharmaceutical powders using the same, U.S. Pat. Nos. 5,770,559 and 5,981,474; Lieberman et al., Lipophilic complexes of pharmacologically active inorganic mineral acid esters of organic compounds, U.S. Pat. No. 5,002, 936; Gen, Formative agent of protein complex, US 2002/0119946 A1; Goldenberg et al., Sustained release formulations, WO 2005/105057 A1).

One can dilute the inventive compositions or increase the volume of the pharmaceutical compositions of the invention with an inert material. Such diluents can include carbohydrates, especially, mannitol, α-lactose, anhydrous lactose, cellulose, sucrose, modified dextrans and starch. Certain inorganic salts may also be used as fillers, including calcium triphosphate, magnesium carbonate and sodium chloride. Some commercially available diluents are Fast-Flo, Emdex, STA-Rx 1500, Emcompress and Avicell.

A variety of conventional thickeners are useful in creams, ointments, suppository and gel configurations of the pharmaceutical composition, such as, but not limited to, alginate, xanthan gum, or petrolatum, may also be employed in such configurations of the pharmaceutical composition of the present invention. A permeation or penetration enhancer, such as polyethylene glycol monolaurate, dimethyl sulfoxide, N-vinyl-2-pyrrolidone, N-(2-hydroxyethyl)-pyrrolidone, or 3-hydroxy-N-methyl-2-pyrrolidone can also be employed. Useful techniques for producing hydrogel matrices are known. (E.g., Feijen, Biodegradable hydrogel matrices for the controlled release of pharmacologically active agents, U.S. Pat. No. 4,925,677; Shah et al., Biodegradable pH/thermosensitive hydrogels for sustained delivery of biologically active agents, WO 00/38651 A1). Such biodegradable gel matrices can be formed, for example, by crosslinking a proteinaceous component and a polysaccharide or mucopolysaccharide component, then loading with the inventive composition of matter to be delivered.

Liquid pharmaceutical compositions of the present invention that are sterile solutions or suspensions can be administered to a patient by injection, for example, intramuscularly, intrathecally, epidurally, intravascularly (e.g., intravenously or intraarterially), intraperitoneally or subcutaneously. (See, e.g., Goldenberg et al., Suspensions for the sustained release of proteins, U.S. Pat. No. 6,245,740 and WO 00/38652 A1). Sterile solutions can also be administered by intravenous infusion. The inventive composition can be included in a sterile solid pharmaceutical composition, such as a lyophilized powder, which can be dissolved or suspended at a convenient time before administration to a patient using sterile water, saline, buffered saline or other appropriate sterile injectable medium.

Implantable sustained release formulations are also useful embodiments of the inventive pharmaceutical compositions. For example, the pharmaceutically acceptable carrier, being a biodegradable matrix implanted within the body or under the skin of a human or non-human vertebrate, can be a hydrogel similar to those described above. Alternatively, it may be formed from a poly-alpha-amino acid component. (Sidman, Biodegradable, implantable drug delivery device, and process for preparing and using same, U.S. Pat. No. 4,351,337). Other techniques for making implants for delivery of drugs are also known and useful in accordance with the present invention.

In powder forms, the pharmaceutically acceptable carrier is a finely divided solid, which is in admixture with finely divided active ingredient(s), including the inventive composition. For example, in some embodiments, a powder form is useful when the pharmaceutical composition is configured as an inhalant. (See, e.g., Zeng et al., Method of preparing dry powder inhalation compositions, WO 2004/017918; Trunk et al., Salts of the CGRP antagonist BIBN4096 and inhalable powdered medicaments containing them, U.S. Pat. No. 6,900, 317).

One can dilute or increase the volume of the compound of the invention with an inert material. These diluents could include carbohydrates, especially mannitol, α-lactose, anhydrous lactose, cellulose, sucrose, modified dextrans and starch. Certain inorganic salts can also be used as fillers including calcium triphosphate, magnesium carbonate and sodium chloride. Some commercially available diluents are Fast-Flo™, Emdex™, STA-Rx™ 1500, Emcompress™ and Avicell™.

Disintegrants can be included in the formulation of the pharmaceutical composition into a solid dosage form. Materials used as disintegrants include but are not limited to starch including the commercial disintegrant based on starch, Explotab™. Sodium starch glycolate, Amberlite™, sodium carboxymethylcellulose, ultramylopectin, sodium alginate, gelatin, orange peel, acid carboxymethyl cellulose, natural sponge and bentonite can all be used. Insoluble cationic exchange resin is another form of disintegrant. Powdered gums can be used as disintegrants and as binders and these can include powdered gums such as agar, Karaya or tragacanth. Alginic acid and its sodium salt are also useful as disintegrants.

Binders can be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent can be included in the formulation of the therapeutic to prevent sticking during the formulation process. Lubricants can be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants can also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants can include starch, talc, pyrogenic silica and hydrated silicoaluminate.

To aid dissolution of the compound of this invention into the aqueous environment a surfactant might be added as a wetting agent. Surfactants can include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Oral Dosage Forms.

Also useful are oral dosage forms of the inventive compositions. If necessary, the composition can be chemically modified so that oral delivery is efficacious. Generally, the chemical modification contemplated is the attachment of at least one moiety to the molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached half-life extending moieties in this invention can also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis (1981), *Soluble Polymer-Enzyme Adducts, Enzymes as Drugs* (Hocenberg and Roberts, eds.), Wiley-Interscience, New York, N.Y., pp 367-83; Newmark, et al. (1982), *J. Appl. Biochem.* 4:185-9. Other polymers that could be used are poly-1,3-dioxolane and poly-1,3,6-tioxocane. Preferred for pharmaceutical usage, as indicated above, are PEG moieties.

For oral delivery dosage forms, it is also possible to use a salt of a modified aliphatic amino acid, such as sodium N-(8-[2-hydroxybenzoyl]amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods."

In one embodiment, the pharmaceutically acceptable carrier can be a liquid and the pharmaceutical composition is prepared in the form of a solution, suspension, emulsion, syrup, elixir or pressurized composition. The active ingredient(s) (e.g., the inventive composition of matter) can be dissolved, diluted or suspended in a pharmaceutically acceptable liquid carrier such as water, an organic solvent, a mixture of both, or pharmaceutically acceptable oils or fats. The liquid carrier can contain other suitable pharmaceutical additives such as detergents and/or solubilizers (e.g., Tween 80, Polysorbate 80), emulsifiers, buffers at appropriate pH (e.g., Tris-HCl, acetate, phosphate), adjuvants, anti-oxidants (e.g., ascorbic acid, sodium metabisulfite), preservatives (e.g., Thimersol, benzyl alcohol), sweeteners, flavoring agents, suspending agents, thickening agents, bulking substances (e.g., lactose, mannitol), colors, viscosity regulators, stabilizers, electrolytes, osmolutes or osmo-regulators. Additives can also be included in the formulation to enhance uptake of the inventive composition. Additives potentially having this property are for instance the fatty acids oleic acid, linoleic acid and linolenic acid.

Useful are oral solid dosage forms, which are described generally in *Remington's Pharmaceutical Sciences* (1990), supra, in Chapter 89, which is hereby incorporated by reference in its entirety. Solid dosage forms include tablets, capsules, pills, troches or lozenges, cachets or pellets. Also, liposomal or proteinoid encapsulation can be used to formulate the present compositions (as, for example, proteinoid microspheres reported in U.S. Pat. No. 4,925,673). Liposomal encapsulation can be used and the liposomes can be derivatized with various polymers (e.g., U.S. Pat. No. 5,013,556). A description of possible solid dosage forms for the therapeutic is given in Marshall, K., *Modern Pharmaceutics* (1979), edited by G. S. Banker and C. T. Rhodes, in Chapter 10, which is hereby incorporated by reference in its entirety. In general, the formulation will include the inventive compound, and inert ingredients that allow for protection against the stomach environment, and release of the biologically active material in the intestine.

The composition of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents can all be included. For example, the protein (or derivative) can be formulated (such as by liposome or microsphere encapsulation) and then further contained within an edible product, such as a refrigerated beverage containing colorants and flavoring agents.

In tablet form, the active ingredient(s) are mixed with a pharmaceutically acceptable carrier having the necessary compression properties in suitable proportions and compacted in the shape and size desired.

The powders and tablets preferably contain up to 99% of the active ingredient(s). Suitable solid carriers include, for example, calcium phosphate, magnesium stearate, talc, sugars, lactose, dextrin, starch, gelatin, cellulose, polyvinylpyrrolidine, low melting waxes and ion exchange resins.

Controlled release formulation can be desirable. The composition of this invention can be incorporated into an inert matrix that permits release by either diffusion or leaching mechanisms e.g., gums. Slowly degenerating matrices can also be incorporated into the formulation, e.g., alginates, polysaccharides. Another form of a controlled release of the compositions of this invention is by a method based on the Oros™ therapeutic system (Alza Corp.), i.e., the drug is enclosed in a semipermeable membrane which allows water to enter and push drug out through a single small opening due to osmotic effects. Some enteric coatings also have a delayed release effect.

Other coatings can be used for the formulation. These include a variety of sugars that could be applied in a coating pan. The therapeutic agent could also be given in a film-coated tablet and the materials used in this instance are divided into 2 groups. The first are the nonenteric materials and include methylcellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating can be carried out in a pan coater or in a fluidized bed or by compression coating.

Pulmonary Delivery Forms.

Pulmonary delivery of the inventive compositions is also useful. The protein (or derivative) is delivered to the lungs of a mammal while inhaling and traverses across the lung epithelial lining to the blood stream. (Other reports of this include Adjei et al., *Pharma. Res.* (1990) 7: 565-9; Adjei et al. (1990), *Internatl. J. Pharmaceutics* 63: 135-44 (leuprolide acetate); Braquet et al. (1989), *J. Cardiovasc. Pharmacol.* 13 (supp 1.5): s.143-146 (endothelin-1); Hubbard et al. (1989), *Annals Int. Med.* 3: 206-12 (α1-antitrypsin); Smith et al. (1989), *J. Clin. Invest.* 84: 1145-6 (α1-proteinase); Oswein et al. (March 1990), "Aerosolization of Proteins," *Proc. Symp. Resp. Drug Delivery II*, Keystone, Colo. (recombinant human growth hormone); Debs et al. (1988), *J. Immunol.* 140: 3482-8 (interferon-γ and tumor necrosis factor α) and Platz et al., U.S. Pat. No. 5,284,656 (granulocyte colony stimulating factor).

Useful in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass. (See, e.g., Helgesson et al., Inhalation device, U.S. Pat. No. 6,892,728; McDerment et al., Dry powder inhaler, WO 02/11801 A1; Ohki et al., Inhalant medicator, U.S. Pat. No. 6,273,086).

All such devices require the use of formulations suitable for the dispensing of the inventive compound. Typically, each formulation is specific to the type of device employed and can involve the use of an appropriate propellant material, in addition to diluents, adjuvants and/or carriers useful in therapy.

The inventive compound should most advantageously be prepared in particulate form with an average particle size of less than 10 μm (or microns), most preferably 0.5 to 5 μm, for most effective delivery to the distal lung.

Pharmaceutically acceptable excipients include carbohydrates such as trehalose, mannitol, xylitol, sucrose, lactose, and sorbitol. Other ingredients for use in formulations can include DPPC, DOPE, DSPC and DOPC. Natural or synthetic surfactants can be used. PEG can be used (even apart from its use in derivatizing the protein or analog). Dextrans, such as cyclodextran, can be used. Bile salts and other related enhancers can be used. Cellulose and cellulose derivatives can be used. Amino acids can be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation can also include a buffer and a simple sugar (e.g., for protein stabilization and regulation of osmotic pressure). The nebulizer formulation can also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid can also be useful as a surfactant. (See, e.g., Bäckström et al., Aerosol drug formulations containing hydrofluoroalkanes and alkyl saccharides, U.S. Pat. No. 6,932,962).

Formulations for dispensing from a powder inhaler device will comprise a finely divided dry powder containing the inventive compound and can also include a bulking agent, such as lactose, sorbitol, sucrose, mannitol, trehalose, or xylitol in amounts which facilitate dispersal of the powder from the device, e.g., 50 to 90% by weight of the formulation.

Nasal Delivery Forms.

In accordance with the present invention, intranasal delivery of the inventive composition of matter and/or pharmaceutical compositions is also useful, which allows passage thereof to the blood stream directly after administration to the inside of the nose, without the necessity for deposition of the product in the lung. Formulations suitable for intranasal administration include those with dextran or cyclodextran, and intranasal delivery devices are known. (See, e.g., Freezer, Inhaler, U.S. Pat. No. 4,083,368).

Transdermal and Transmucosal (e.g., Buccal) Delivery Forms).

In some embodiments, the inventive composition is configured as a part of a pharmaceutically acceptable transdermal or transmucosal patch or a troche. Transdermal patch drug delivery systems, for example, matrix type transdermal patches, are known and useful for practicing some embodiments of the present pharmaceutical compositions. (E.g., Chien et al., Transdermal estrogen/progestin dosage unit, system and process, U.S. Pat. Nos. 4,906,169 and 5,023,084; Cleary et al., Diffusion matrix for transdermal drug administration and transdermal drug delivery devices including same, U.S. Pat. No. 4,911,916; Teillaud et al., EVA-based transdermal matrix system for the administration of an estrogen and/or a progestogen, U.S. Pat. No. 5,605,702; Venkateshwaran et al., Transdermal drug delivery matrix for coadministering estradiol and another steroid, U.S. Pat. No. 5,783,208; Ebert et al., Methods for providing testosterone and optionally estrogen replacement therapy to women, U.S. Pat. No. 5,460,820). A variety of pharmaceutically acceptable systems for transmucosal delivery of therapeutic agents are also known in the art and are compatible with the practice of the present invention. (E.g., Heiber et al., Transmucosal delivery of macromolecular drugs, U.S. Pat. Nos. 5,346,701 and 5,516,523; Longenecker et al., Transmembrane formulations for drug administration, U.S. Pat. No. 4,994,439).

Buccal delivery of the inventive compositions is also useful. Buccal delivery formulations are known in the art for use with peptides. For example, known tablet or patch systems configured for drug delivery through the oral mucosa (e.g., sublingual mucosa), include some embodiments that comprise an inner layer containing the drug, a permeation enhancer, such as a bile salt or fusidate, and a hydrophilic polymer, such as hydroxypropyl cellulose, hydroxypropyl methylcellulose, hydroxyethyl cellulose, dextran, pectin, polyvinyl pyrrolidone, starch, gelatin, or any number of other polymers known to be useful for this purpose. This inner layer can have one surface adapted to contact and adhere to the moist mucosal tissue of the oral cavity and can have an opposing surface adhering to an overlying non-adhesive inert layer. Optionally, such a transmucosal delivery system can be in the form of a bilayer tablet, in which the inner layer also contains additional binding agents, flavoring agents, or fillers. Some useful systems employ a non-ionic detergent along with a permeation enhancer. Transmucosal delivery devices may be in free form, such as a cream, gel, or ointment, or may comprise a determinate form such as a tablet, patch or troche. For example, delivery of the inventive composition can be via a transmucosal delivery system comprising a laminated composite of, for example, an adhesive layer, a backing layer, a permeable membrane defining a reservoir containing the inventive composition, a peel seal disc underlying the membrane, one or more heat seals, and a removable release liner. (E.g., Ebert et al., Transdermal delivery system with adhesive overlay and peel seal disc, U.S. Pat. No. 5,662,925; Chang et al., Device for administering an active agent to the skin or mucosa, U.S. Pat. Nos. 4,849,224 and 4,983,395). These examples are merely illustrative of available transmucosal drug delivery technology and are not limiting of the present invention.

Dosages.

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1-1000 micrograms of the inventive compound per kilogram of body weight, preferably 0.1-150 micrograms per kilogram.

The following working examples are illustrative and not to be construed in any way as limiting the scope of the present invention.

EXAMPLES

Example 1

Expression and Bioactivity of Fusion Proteins

Human protein domains were selected for small size, in order to aid in high level expression in prokaryotic hosts, and also to provide an advantage to the mass ratio of active peptide to inactive carrier. The small size of the fusion protein is expected to result in a short serum half-life for the native molecule, which may allow for modulation of the pharmacokinetic profile of the molecule to fit the therapeutic need by attaching PEG moieties or other half-life extending moieties of various masses and configurations.

Selection of Small Pharmacologically Inactive Protein Domains.

Figure 2:
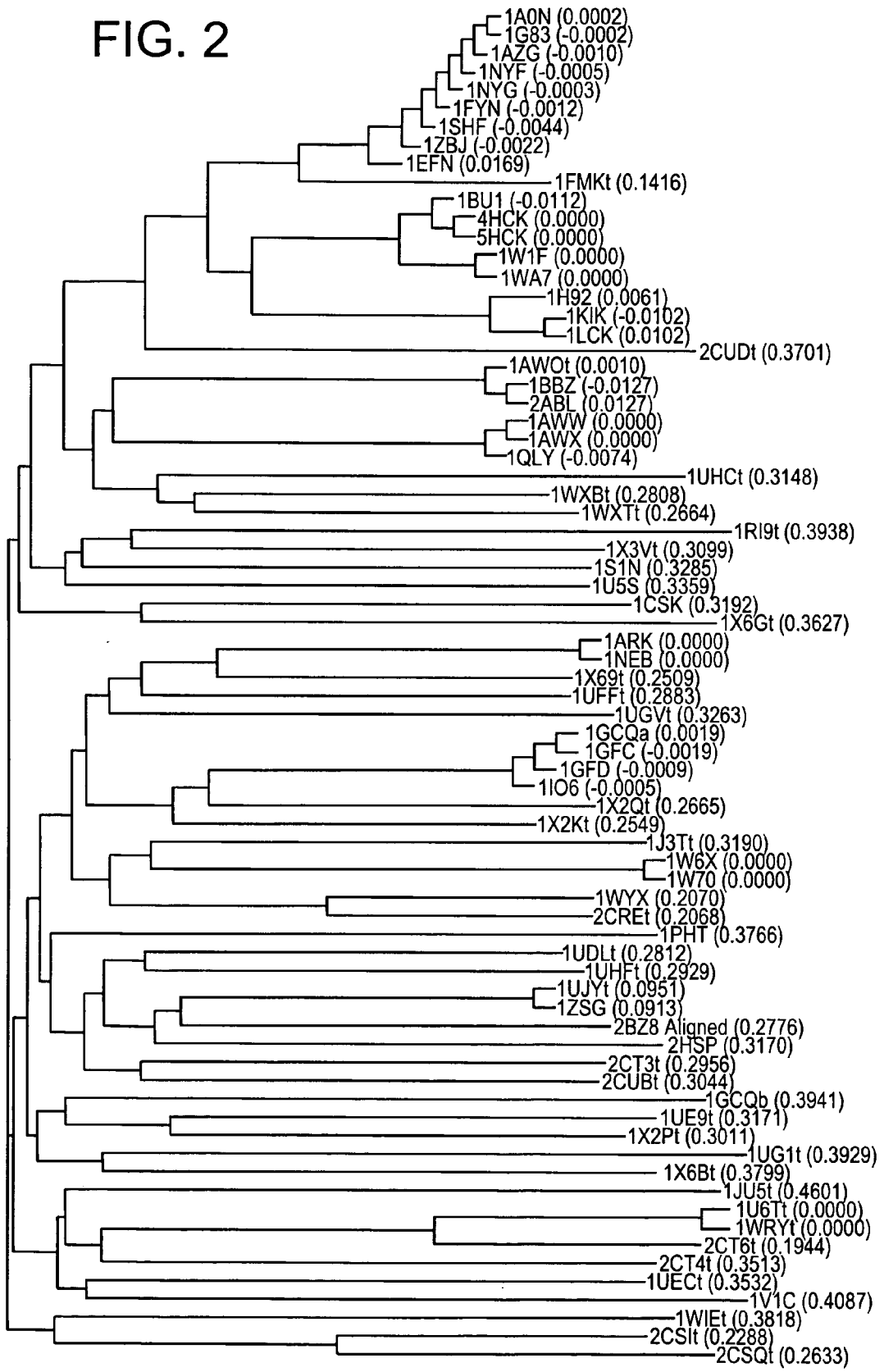
FIG. 2 shows a tree diagram that illustrates the amino acid sequence relatedness of various human SH3 domains that were identified in the Brookhaven Protein Databank. The four digit code is the accession number from the Brookhaven Protein Databank. Alignment was completed using Vector NTI Align-X.
Figure 3:
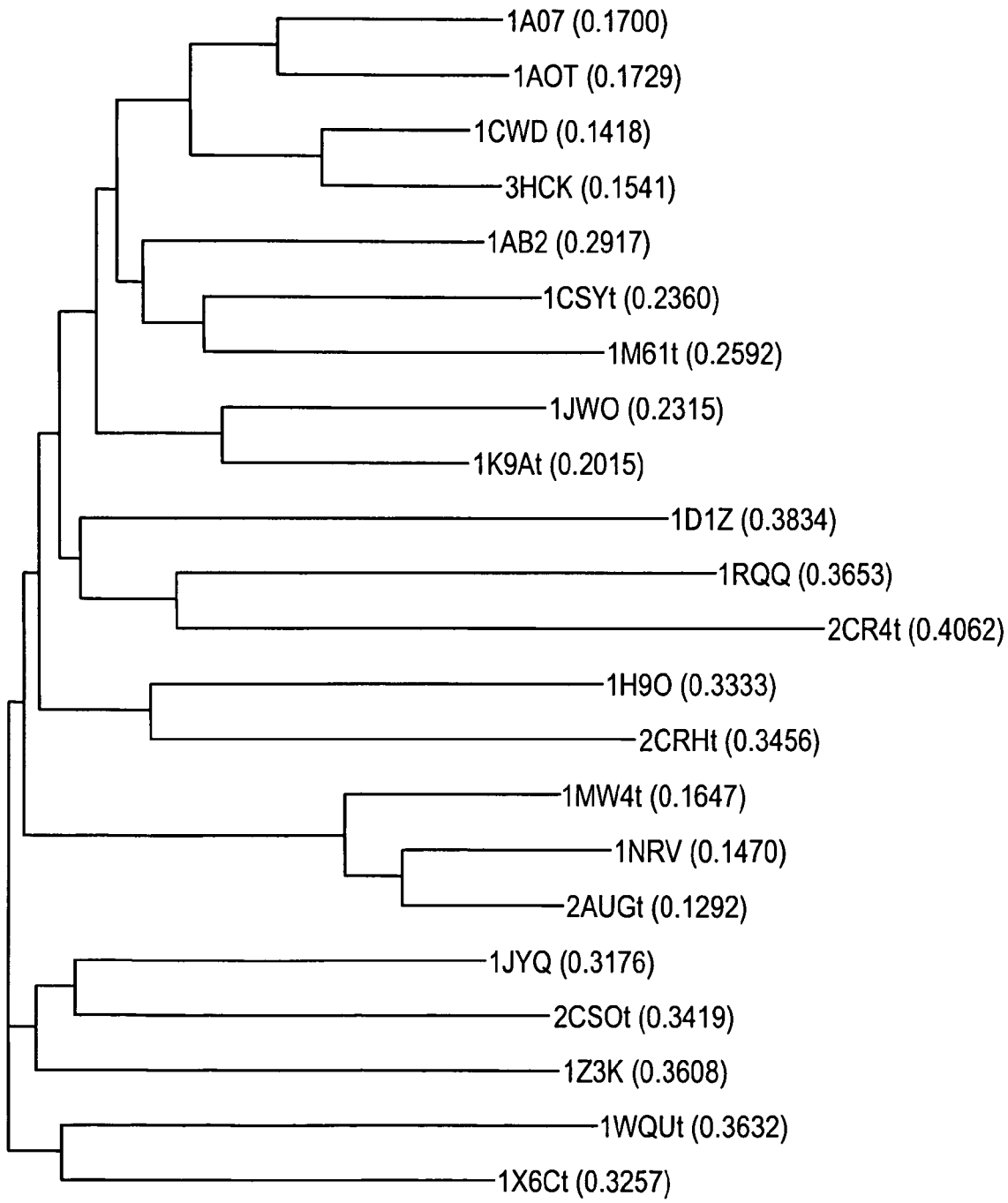
FIG. 3 shows a tree diagram that illustrates the amino acid sequence relatedness of various human SH2 domains that were identified in the Brookhaven Protein Databank. The four digit code is the accession number from the Brookhaven Protein Databank. Alignment was completed using Vector NTI Align-X.

Small protein domains from the following families were selected for further investigation: the CH2 domain of IgG1, the 10th fibronectin III domain, the villin headpiece domain, several SH3 domains, several PDZ domains, and several SH2 domains. The CH2 domain was chosen to represent the immunoglobulin fold superfamily, since it is the only domain in the ubiquitous IgG1 molecule that is not involved in dimerization. The 10th fibronectin III domain was also chosen to represent the immunoglobulin fold, since it is a stable domain and lacks the disulfide bonds found in most other members of this family. Fibronectins are extracellular proteins involved in cell adhesion, cell motility, opsonization, wound healing, and maintenance of cell shape. Three PDZ domains were chosen from divergent families of the 51 human PDZ domains for which structural coordinates were available at the Brookhaven Protein Databank (FIG. 1). PDZ domains are intracellular peptide binding domains that prefer C-terminal peptides and often form signal transduction complexes. Three SH3 domains were chosen from divergent families of the 74 human SH3 domains for which structural coordinates were available at the Brookhaven Protein Databank (FIG. 2). SH3 domains are intracellular proline motif (PxxP) recognition and binding domains. In addition, two SH2 domains were chosen from divergent families of the 22 human SH2 domains for which structural coordinates were available at the Brookhaven Protein Databank (FIG. 3). SH2 domains are intracellular phosphotyrosine recognition and binding domains. Taken together, these domains represent a wide array of protein structures with diverse biochemical properties.

Construct Assembly.

Two bacterial expression vectors were employed to express the fusion constructs (pAMG21 and pET30). The pAMG21(BamHI⁻) vector encodes resistance to kanamycin ("Kanr") and contains an R100-derived origin of replication as well as multiple unique restriction sites suitable for cloning. Expression in the pAMG21 constructs is driven by the inducible promoter luxPR from *Vibrio fischeri*. The pET30 vector (Novagen/EMD Biosciences, San Diego, Calif.) encodes Kanr and contains a pBR322-derived origin of replication. Expression in pET30 is driven by the inducible T7 promoter.

For OsK1 and ShK fusions, optimization, reduction of mRNA secondary structure and subsequent gene synthesis was carried out. Genes encoded (i) an affinity purification tag, for convenience, comprising an initiator methionine (M), two glycines ($G_2$), six histidines ($H_6$), and two or three glycines ($G_3$) ("M-$G_2$-$H_6$-$G_3$"; SEQ ID NO:49); (ii) the small pharmacologically inactive protein domain, (iii) a ten-residue linker composed of a repeat of four glycines and one serine ("$(G_4S)_2$" or "L10"; SEQ ID NO:22) and finally the bioactive peptide, examples of which were toxin peptides OSK1 and ShK. The following amino acid sequences are examples of the encoded fusion proteins:

```
CH2-OsK1:
GGHHHHHHGGGPSVFLFPPKPKDTLMISRTPEVTCVVVDVSHEDPEVKFNWYVDGVEVHNAKT         SEQ ID NO: 80

KPREEQYNSTYRVVSVLTVLHQDWLNGKEYKCKVSNKALPAPIEKTISGGGGSGGGGSGVIINV

KCKISRQCLEPCKKAGMRFGKCMNGKCHCTPK//;

FnIII-OsK1:
GGHHHHHHGGGTVSDVPRDLEVVAATPTSLLISWDAPAVTVRYYRITYGETGGNSPVQEFTVPG        SEQ ID NO: 81

SKSTATISGLKPGVDYTITVYAVTGRGDSPASSKPISINYRTEGGGGSGGGGSGVIINVKCKISRQC

LEPCKKAGMRFGKCMNGKCHCTPK//;

1PHT-OsK1:
GGHHHHHHGGGSAEGYQYRALYDYKKEREEDIDLHLGDILTVNKGSLVALGFSDGQEARPEEIG       SEQ ID NO: 82
```

```
WLNGYNETTGERGDFPGTYVEYIGRKKISPGGGGSGGGGSGVIINVKCKISRQCLEPCKKAGMRF

GKCMNGKCHCTPK//;

1N7F-OsK1:
GGHHHHHHGGGSSGAIIYTVELKRYGGPLGITISGTEEPFDPIIISSLTKGGLAERTGAIHIGDRILAI      SEQ ID NO: 83

NSSSLKGKPLSEAIHLLQMAGETVTLKIKKQTDAQSASSPGGGGSGGGGSGVIINVKCKISRQCLE

PCKKAGMRFGKCMNGKCHCTPK//;

1X2K-OsK1:
GGHHHHHHGGGKVFRALYTFEPRTPDELYFEEGDIIYITDMSDTNWWKGTSKGRTGLIPSNYVA         SEQ ID NO: 84

EQGGGGSGGGGSGVIINVKCKISRQCLEPCKKAGMRFGKCMNGKCHCTPK//;
and

1UEZ-OsK1:
GGHHHHHHGGGPGEVRLVSLRRAKAHEGLGFSIRGGSEHGVGIYVSLVEPGSLAEKEGL             SEQ ID NO: 85

RVGDQILRVNDKSLARVTHAEAVKALKGSKKLVLSVYSAGRIPGGGGSGGGGSGVIINV

KCKISRQCLEPCKKAGMRFGKCMNGKCHCTPK//.
```

Additional nucleotides were added to the 5' and 3' ends incorporating NdeI and EcoRI restriction sites. The final six nucleotides of the 10 residue linker, GAATTC, were designed to encode glycine and serine as well as providing a BamHI restriction site. Full nucleotide sequences of the genes are exemplified by the following.

```
M-G₂-H₆-G₃-10ᵗʰFn3-(G₄S)₂-OsK1 (coding region underlined)
                                                                           SEQ ID NO: 62
catatgggtggtcatcatcatcatcatcatggtggtggtaccgtaagcgatgtaccacgcgatctggaagtagtagctgccacaccaacctctt tgctgatctcttgggacgcacctgcagttacagtccgctatttatcgtattacgtatggagaaaccggtggcaacagtccagtacaagaatttac cgtgcctggttccaaaagtaccgcaacaatttcaggcctcaaaccaggtgttgattatacgattacagtttatgcggttaccggtcgtggcgatt cacccgcatcaagtaaaccaatttctattaactatcgtacagaaggcggggggaggtagcggcggaggaggatccggagtcattatcaatgtt aaatgtaaaatcagccgtcagtgtttagaaccatgtaaaaaagccggaatgcgctttggaaaatgtatgaatggtaaatgtcattgcaccccga aataatgaattc//;

M-G₂-H₆-G₃-PDZ(1N7F)-(G₄S)₂-OsK1 (coding region underlined)
                                                                           SEQ ID NO: 63
catatgggtggtcatcatcatcatcatcatggtggtggttccagcggtgcaattatctatacggtagaacttaaacgttacggtggtcctctgggt attacaatcagcggcacagaagaaccctttgatccaattattatttcatcgcttactaaaggtggtcttgctgaacgcacaggcgccattcatatt ggagatcgtattttagctatcaactcatcatcattaaaaggcaaaccgttatcagaagctattcacttattacaaatggcgggcgaaacagttac ccttaaaatcaaaaaacaaaccgacgcacaatctgcaagtagtccggggggaggcggctcaggaggaggaggatccggtgttattatcaa tgtcaaatgtaaaatttctcgtcagtgtttggaaccctgtaaaaaagccggtatgcgctttggaaaatgtatgaacggaaaatgtcactgtaccc caaaataatgaattc//;

M-G₂-H₆-G₃-PDZ(1UEZ)-(G₄S)₂-OsK1 (coding region underlined)
                                                                           SEQ ID NO: 64
catatgggtggtcatcatcatcatcatcatggtggtggtccgggcgaagttcgtcttgttagtttacgtcgcgcaaaagcacatgaaggcttag gtttctcaattcgtggcggcagcgaacatggtgttggaatttatgtatccttagtagaacctggtagtttagccgaaaaagaaggcctgcgtgtc ggcgatcaaatcttacgcgtcaacgataaatctttagcccgcgttactcatgccgaagccgttaaagcgttgaaaggtagcaaaaaattagttc tgtctgtttattccgcaggtcgtattcctggtggtggaggaagtggtggtggtggatccggagtaattattaacgttaaatgtaaaatcagtcgtc aatgtttggaaccctgtaaaaaagctggaatgcggtttggaaaatgtatgaatggtaaatgtcactgtaccccctaaataatgaattc//;

M-G₂-H₆-G₃-PDZ(1WFV)-(G₄S)₂-OsK1 (coding region underlined)
                                                                           SEQ ID NO: 65
catatgggtggtcatcatcatcatcatcatggtggtggtcctcaagacttcgattactttactgttgatatggaaaaaggtgcaaaaggttttggtt tctctattcgtggcggtcgtgaatataaaatggacttatatgtgttacgcttagctgaagacggaccgcaattcgtaacggacgtatgcgtgtt ggcgatcaaattattgaaattaatggcgaatcaactcgtgatatgacccatgcacgtgcgattgaacttattaaatctggaggacgtcgtgtac
```

-continued gcttactcttaaaacgtggtacaggtcaggttcccggtggcggcggcagtggtggtggtggatccggagttattatcaatgttaaatgtaaaat tagtcgtcaatgcttagaaccttgtaaaaaagctggaatgcgctttggaaaatgcatgaacgggaaatgtcactgcacacctaaataatgaatt c//;

M-G₂-H₆-G₃-SH2(1AB2)-(G₄S)₂-OsK1 (coding region underlined)

SEQ ID NO: 66 catatgggtggtcatcatcatcatcatcatggtggtggtaattctttagaaaaacattcatggtatcatggtcctgtatcacgtaacgcagccgaa tatctcttatcttctggcattaacggtagttttttagtccgcgaatccgaatcttctcctggccaacgcagtatcagtctccgttatgaaggtcgtgt gtatcattatcgcatcaataccgcttcagatggtaaattatatgtttcctcggaaagtcgtttcaataccctccgcgaactcgttcatcatcattcta ctgtggcagatggtctcattacaacgttacattatcctgcacccggcggtggtggctctggtggtggcggatccggtgttattattaatgttaaat gtaaaattagtcgccaatgtcttgaaccttgtaaaaaagctggcatgcgctttggtaaatgtatgaacggaaaatgtcattgtaccccgaaataa tgaattc//;

M-G₂-H₆-G₃-SH2(1JYQ)-(G₄S)₂-OsK1 (coding region underlined)

SEQ ID NO: 67 catatgggtggtcatcatcatcatcatcatggtggtggtccttggttttttggtaaaatcccacgtgcgaaagctgaagaaatgctctcaaaaca acgtcatgacggtgcattcttaattcgtgaaagtgaatctgctccaggtgattttagtttaagtgttaaatttggtaatgatgtccaacattttaaagt ccttcgtgatggtgcgggtaaatattttttatgggtagtcaaattcaatagtcttaacgaacttgtcgattatcatcgttccaccagtgttagccgta atcaacaaatttttctccgcgatattgaacaagtggtggtggttcaggaggggcggatccggcgtaatcatcaatgtaaaatgtaaaatctc tcgtcaatgtttagaaccgtgtaaaaaagcaggaatgcgtttcggtaaatgtatgaatggtaaatgtcattgtaccccaaaataatgaattc//;

M-G₂-H₆-G₃-SH3(1PHT)-(G₄S)₂-OsK1 (coding region underlined)

SEQ ID NO: 68 catatgggtggtcatcatcatcatcatcatggtggtggttcagcagaaggttatcaatatcgtgcattatatgattataaaaaagaacgtgaaga agatatcgacttacatctgggagacattttaactgttaataaaggaagcttagtcgctttaggatttagtgatgggcaagaggcacgccctgaa gaaattggatggttgaatggttataatgaaacaaccggcgaacgtggtgactttccgggtacctatgtagaatatatcggtcgtaaaaaatta gccctggaggagggggtctggaggtggtggatccggtgtaattatcaatgtaaaatgtaaaattagtcgtcaatgtttagaaccttgtaaaaa agcaggcatgcgctttggaaaatgtatgaacggtaaatgccattgcaccccaaaataatgaattc//;

M-G₂-H₆-G₃-SH3(1WA7)-(G₄S)₂-OsK1 (coding region underlined)

SEQ ID NO: 69 catatgggtggtcatcatcatcatcatcatggtggtggtccagaagaacaaggtgatattgtagttgctttatatccttatgatggtattcatccag acgatttaagttttaaaaaggtgaaaaaatgaaagtgttagaagaacatggagaatggtggaaggcaaaaagtttattaacgaaaaaagaa ggttttattccgtctaattatgtggcaaaattaaatacaggaggtggggtggtagtgggggggaggatccggtgtaattattaatgtaaaat gtaaaattagtcgtcaatgtttggaaccgtgtaaaaaagcaggtatgcgctttggtaaatgtatgaatggtaaatgtcattgcactccaaaataat gaattc//;

M-G₂-H₆-G₃-SH3(1X2K)-(G₄S)₂-OsK1 (coding region underlined)

SEQ ID NO: 70 catatgggtggtcatcatcatcatcatcatggtggtggtaaagttttcgcgcactttataccttgaaccccgtacccagatgaattatatttga agaaggcgacattatttatattacggacatgtcagatactaattggtggaaaggaacaagcaaaggccgtactggactgatcccaagtaatta cgtagcagaacaaggaggaggtggctcaggaggaggtggatccggtgtaattatcaatgtaaaatgtaaaatctctcgtcaatgcctggaac cctgtaaaaaagctggtatgcgctttggtaaatgtatgaatggtaaatgtcattgcaccccttaaataatgaattc//;

M-G₂-H₆-G₃-10ᵗʰFn3-(G₄S)₂-ShK (coding region underlined)

SEQ ID NO: 71 catatgggtggtcatcatcatcatcatcatggtggtggtaccgtaagcgatgttccccgtgacctggaagtggttgcagcgacccctacctcat tattaatcagttgggatgcacctgcagttacagtccggtattatcgtattacgtatggagagacaggcggcaactcaccagttcaagaatttacc gtccccgggctctaaatcaacagcaacaatttcaggcttaaaaccaggagtagattacacaattacagtatacgcagtaacaggtcgcggcga -continued ctccccagctagctcaaaacctatctctattaattatcgcaccgaaggtggcggaggttccggtggtggtggatcctgcatcgatacaatccct aagtcccgctgtactgcctttcaatgcaaacactcaatgaaataccgtctcagtttctgtcgtaaaactgtggcacctgttaatgaattc//;

M-$G_2$-$H_6$-$G_3$-PDZ(1N7F)-$(G_4S)_2$-ShK (coding region underlined)

SEQ ID NO: 72 catatgggtggtcatcatcatcatcatcatggtggtggttccagcggtgcaattatctatacggtagaacttaaacgttacggtggtcctctgggt attacaatcagcggcacagaagaaccctttgatccaattattatttcatcgcttactaaaggtggtcttgctgaacgcacaggcgccattcatatt ggagatcgtatttagctatcaactcatcatcattaaaaggcaaaccgttatcagaagctattcacttattacaaatggcgggcgaaacagttac ccttaaaatcaaaaaacaaaccgacgcacaatctgcaagtagtccgggggaggcggctcaggaggaggaggatcctgcatcgatacaa tccctaagtcccgctgtactgcctttcaatgcaaacactcaatgaaataccgtctcagtttctgtcgtaaaacctgtggcacctgttaatgaattc//;

M-$G_2$-$H_6$-$G_3$-PDZ(1UEZ)-$(G_4S)_2$- ShK (coding region underlined)

SEQ ID NO: 73 catatgggtggtcatcatcatcatcatcatggtggtggtccgggcgaagttcgtcttgttagtttacgtcgcgcaaaagcacatgaaggcttag gtttctcaattcgtggcggcagcgaacatggtgttggaatttatgtatccttagtagaacctggtagtttagccgaaaaagaaggctgcgtgtc ggcgatcaaatcttacgcgtcaacgataaatctttagcccgcgttactcatgccgaagccgttaaagcgttgaaaggtagcaaaaaattagttc tgtctgtttattccgcaggtcgtattcctggtggtggaggaagtggtggtggtggatcctgcatcgatacaatccctaagtcccgctgtactgcc tttcaatgcaaacactcaatgaaataccgtctcagtttctgtcgtaaaacctgtggcacctgttaatgaattc//;

M-$G_2$-$H_6$-$G_3$-PDZ(1WFV)-$(G_4S)_2$- ShK (coding region underlined)

SEQ ID NO: 74 catatgggtggtcatcatcatcatcatcatggtggtggtcctcaagacttcgattactttactgttgatatggaaaaaggtgcaaaaggttttggtt tctctattcgtggcggtcgtgaatataaaatggacttatatgtgttacgcttagctgaagacggacccgcaattcgtaacggacgtatgcgtgtt ggcgatcaaattattgaaattaatggcgaatcaaactcgtgatatgacccatgcacgtgcgattgaacttattaaatctggaggacgtcgtgtac gcttactcttaaaacgtggtacaggtcaggttcccggtggcggcggcagtggtggtggtggatcctgcatcgatacaatccctaagtcccgct gtactgcctttcaatgcaaacactcaatgaaataccgtctcagtttctgtcgtaaaacctgtggcacctgttaatgaattc//;

M-$G_2$-$H_6$-$G_3$-SH2(1AB2)-$(G_4S)_2$- ShK (coding region underlined)

SEQ ID NO: 75 catatgggtggtcatcatcatcatcatcatggtggtggtaattctttagaaaaacattcatggtatcatggtcctgtatcacgtaacgcagccgaa tatctcttatcttctggcattaacggtagtttttagtccgcgaatccgaatcttctcctggccaacgcagtatcagtctccgttatgaaggtcgtgt gtatcattatcgcatcaataccgcttcagatggtaaattatatgtttcctcggaaagtcgtttcaatacccttgcggaactcgttcatcatcattcta ctgtggcagatggtctcattacaacgttacattatcctgcacccggcggtggtggctctggtggtggcggatcctgcatcgatacaatccctaa gtcccgctgtactgcctttcaatgcaaacactcaatgaaataccgtctcagtttctgtcgtaaaacctgtggcacctgttaatgaattc//;

M-$G_2$-$H_6$-$G_3$-SH2(1JYQ)-$(G_4S)_2$- ShK (coding region underlined)

SEQ ID NO: 76 catatgggtggtcatcatcatcatcatcatggtggtggtccttggtttttggtaaaatcccacgtgcgaaagctgaagaaatgctctcaaaaca acgtcatgacggtgcattcttaattcgtgaaagtgaatctgctccaggtgattttagtttaagtgttaaatttggtaatgatgtccaacattttaaagt ccttcgtgatggtgcgggtaaatatttttttatgggtagtcaaattcaatagtcttaacgaacttgtcgattatcatcgttccaccagtgttagccgta atcaacaaattttctccgcgatattgaacaaggtggtggtggttcaggagggggcggatcctgcatcgatacaatccctaagtcccgctgta ctgcctttcaatgcaaacactcaatgaaataccgtctcagtttctgtcgtaaaacctgtggcacctgttaatgaattc//;

M-$G_2$-$H_6$-$G_3$-SH3(1PHT)-$(G_4S)_2$- ShK (coding region underlined)

SEQ ID NO: 77 catatgggtggtcatcatcatcatcatcatggtggtggttcagcagaaggttatcaatatcgtgcattatatgattataaaaaagaacgtgaaga agatatcgacttacatctgggagacattttaactgttaataaaggaagcttagtcgctttaggatttagtgatgggcaagaggcacgccctgaa gaaattggatggttgaatggttataatgaaacaaccggcgaacgtggtgactttccgggtacctatgtagaatatatcggtcgtaaaaaaatta -continued gccctggaggagggggtctggaggtggtggatcctgcatcgatacaatccctaagtcccgctgtactgcctttcaatgcaaacactcaatg aaataccgtctcagtttctgtcgtaaaaacctgtggcacctgttaatgaattc//;

M-G₂-H₆-G₃-SH3(1WA7)-(G₄S)₂-ShK (coding region underlined)

SEQ ID NO: 78 catatgggtggtcatcatcatcatcatcatggtggtggtccagaagaacaaggtgatattgtagttgctttatatccttatgatggtattcatccag acgatttaagttttaaaaaaggtgaaaaaatgaaagtgttagaagaacatggagaatggtggaaggcaaaaagtttattaacgaaaaagaa ggttttattccgtctaattatgtggcaaaattaaatacaggaggtggggtggtagtgggggggaggatcctgcatcgatacaatccctaag tcccgctgtactgcctttcaatgcaaacactcaatgaaataccgtctcagtttctgtcgtaaaaacctgtggcacctgttaatgaattc//;
and M-G₂-H₆-G₃-SH3(1X2K)-(G₄S)₂-ShK (coding region underlined)

SEQ ID NO: 79 catatgggtggtcatcatcatcatcatcatggtggtggtaaagttttcgcgcactttataccttttgaaccccgtacccagatgaattatattttga agaaggcgacattatttatattacggacatgtcagatactaattggtggaaaggaacaagcaaaggccgtactggactgatcccaagtaatta cgtagcagaacaaggaggaggtggctcaggaggaggtggatcctgcatcgatacaatccctaagtcccgctgtactgcctttcaatgcaaa cactcaatgaaataccgtctcagtttctgtcgtaaaaacctgtggcacctgttaatgaattc//.

The synthesized DNA was initially digested with NdeI and EcoRI, and then ligated into likewise treated pAMG21 (BamHI⁻; Table 3).

TABLE 3

Nucleotide sequence of pAMG21(BamHI⁻).

SEQ ID NO: 57 gatcagcagtccccggaacatcgtagctgacgccttcgcgttgctcagttgtccaacccccggaaacgggaaaaagcaagttttccccgctcc cggcgtttcaataactgaaaaccatactatttcacagtttaaatcacattaaacgacagtaatcccccgttgatttgtgcgccaacacagatcttcg tcacaattctcaagtcgctgatttcaaaaaactgtagtatcctctgcgaaacgatccctgtttgagtattgaggaggcgagatgtcgcagacag aaaatgcagtgacttcctcattgagtcaaaagcggtttgtgcgcagaggtaagcctatgactgactctgagaaacaaatggccgttgttgcaa gaaaacgtcttacacacaaagagataaaagttttttgtcaaaatcctctgaaggatctcatggttgagtactgcgagagagagggggataacac aggctcagttcgttgagaaaatcatcaaagatgaactgcaaagactggatatactaaagtaaagactttactttgtggcgtagcatgctagatta ctgatcgtttaaggaattttgtggctggccacgccgtaaggtggcaaggaactggttctgatgtggatttacaggagccagaaaagcaaaaa ccccgataatcttcttcaacttttgcgagtacgaaaagattaccggggcccacttaaaccgtatagccaacaattcagctatgcggggagtata gttatatgcccggaaaagttcaagacttctttctgtgctcgctccttctgcgcattgtaagtgcaggatggtgtgactgatcttcaccaaacgtatt accgccaggtaaagaacccgaatccggtgtttacaccccgtgaaggtgcaggaacgctgaagttctgcgaaaaactgatggaaaaggcg gtgggcttcacttcccgttttgatttcgccattcatgtggcgcacgcccgttcgcgtgatctgcgtcgccgtatgccaccagtgctgcgtcgtcg ggctattgatgcgctcttgcagggggctgtgtttccactatgacccgctggccaaccgcgtccagtgctccatcaccacgctggccattgagtg cggactggcgacggagtctgctgccggaaaactctccatcacccgtgccacccgtgccctgacgttcctgtcagagctgggactgattacct accagacggaatatgacccgcttatcgggtgctacattccgaccgatatcacgttcacatctgcactgtttgctgccctcgatgtatcagagga ggcagtggccgccgcgcgccgcagccgtgtggtatgggaaaacaaacaacgcaaaaagcaggggctggataccctgggcatggatga actgatagcgaaagcctggcgttttgttcgtgagcgttttcgcagttatcagacagagcttaagtcccgtggaataaagcgtgcccgtgcgcg tcgtgatgcggacagggaacgtcaggatattgtcaccctggtgaaacggcagctgacgcgcgaaatcgcggaagggcgcttcactgcca atcgtgaggcggtaaaacgcgaagttgagcgtcgtgtgaaggagcgcatgattctgtcacgtaaccgtaattacagccggctggccacagc ttcccctgaaagtgacctcctctgaataatccggcctgcgccggaggcttccgcacgtctgaagcccgacagcgcacaaaaaatcagcac cacatacaaaaaacaacctcatcatccagcttctggtgcatccggccccccctgttttcgatacaaaacacgcctcacagacggggaattttg cttatccacattaaactgcaagggacttccccataaggttacaaccgttcatgtcataaagcgccatccgccagcgttacagggtgcaatgtat ctttttaaacacctgtttatatctccttttaaactacttaattacattcatttaaaaagaaaacctattcactgcctgtccttggacagacagatatgcac TABLE 3-continued Nucleotide sequence of pAMG21(BamHI⁻).

```
ctcccaccgcaagcggcgggcccctaccggagccgctttagttacaacactcagacacaaccaccagaaaaaccccggtccagcgcaga actgaaaccacaaagcccctccctcataactgaaaagcggccccgccccggtccgaagggccggaacagagtcgcttttaattatgaatgt tgtaactacttcatcatcgctgtcagtcttctcgctggaagttctcagtacacgctcgtaagcggccctgacggcccgctaacgcggagatac gccccgacttcgggtaaaccctcgtcgggaccactccgaccgcgcacagaagctctctcatggctgaaagcgggtatggtctggcagggc tggggatgggtaaggtgaaatctatcaatcagtaccggcttacgccgggcttcggcggttttactcctgttttcatatatgaaacaacaggtcac cgccttccatgccgctgatgcggcatatcctggtaacgatatctgaattgttatacatgtgtatatacgtggtaatgacaaaaataggacaagtt aaaaatttacaggcgatgcaatgattcaaacacgtaatcaatatcggggtgggcgaagaactccagcatgagtccccgcgctggaggat catccagccggcgtcccggaaaacgattccgaagcccaacctttcatagaaggcggcggtggaatcgaaatctcgtgatggcaggttggg cgtcgcttggtcggtcatttcgaaccccagagtcccgctcagaagaactcgtcaagaaggcgatagaaggcgatgcgctgcgaatcggga gcggcgataccgtaaagcacgaggaagcggtcagcccattcgccgccaagctcttcagcaatatcacgggtagccaacgctatgtcctgat agcggtccgccacacccagccggcacagtcgatgaatccagaaaagcggccattttccaccatgatattcggcaagcaggcatcgccat gagtcacgacgagatcctcgccgtcgggcatgcgcgccttgagcctggcgaacagttcggctggcgcgagcccctgatgctcttcgtcca gatcatcctgatcgacaagaccggcttccatccgagtacgtgctcgctcgatgcgatgtttcgcttggtggtcgaatgggcaggtagccggat caagcgtatgcagccgccgcattgcatcagccatgatggatactttctcggcaggagcaaggtgagatgacaggagatcctgccccggca cttcgccaatagcagccagtcccttcccgcttcagtgacaacgtcgagcacagctgcgcaaggaacgcccgtcgtggccagccacgata gccgcgctgcctcgtcctgcaattcattcaggacaccggacaggtcggtcttgacaaaaagaaccgggcgcccctgcgctgacagccgga acacggcggcatcagagcagccgattgtctgttgtgcccagtcatagccgaatagcctctccacccaagcggccggagaacctgcgtgca atccatcttgttcaatcatgcgaaacgatcctcatcctgtctcttgatctgatcttgatccctgcgccatcagatccttggcggcaagaaagcca tccagtttactttgcagggcttcccaaccttaccagagggcgccccagctggcaattccggttcgcttgctgtccataaaaccgcccagtctag ctatcgccatgtaagcccactgcaagctacctgctttctctttgcgcttgcgttttcccttgtccagatagcccagtagctgacattcatccgggg tcagcaccgtttctgcggactggctttctacgtgttccgcttccttttagcagcccttgcgccctgagtgcttgcggcagcgtgaagctacatata tgtgatccgggcaaatcgctgaatattccttttgtctccgaccatcaggcacctgagtcgctgtcttttcgtgacattcagttcgctgcgctcac ggctctggcagtgaatgggggtaaatggcactacaggcgccttttatggattcatgcaaggaaactacccataatacaagaaaagcccgtca cgggcttctcagggcgtttttatggcgggtctgctatgtggtgctatctgacttttttgctgttcagcagttcctgccctctgattttccagtctgacca cttcggattatcccgtgacaggtcattcagactggctaatgcacccagtaaggcagcggtatcatcaacaggcttacccgtcttactgtcgaa gacgtgcgtaacgtatgcatggtctccccatgcgagagtagggaactgccaggcatcaaataaaacgaaaggctcagtcgaaagactggg cctttcgttttatctgttgtttgtcggtgaacgctctcctgagtaggacaaatccgccgggagcggatttgaacgttgcgaagcaacggcccgg agggtggcgggcaggacgcccgccataaactgccaggcatcaaattaagcagaaggccatcctgacggatggcctttttgcgtttctacaa actcttttgttttatttttctaaatacattcaaatatggacgtcgtacttaacttttaaagtatgggcaatcaattgctcctgttaaaattgcttagaaata ctttggcagcggtttgttgtattgagtttcatttgcgcattggttaaatggaaagtgaccgtgcgcttactacagcctaatattttgaaatatccca agagcttttccttcgcatgcccacgctaaacattcttttctcttttggttaaatcgttgtttgatttattatttgctatatttattttttcgataattatca actagagaaggaacaattaatggtatgttcatacacgcatgtaaaaataaactatctatatagttgtctttctctgaatgtgcaaaactaagcattccgaagc cattattagcagtatgaatagggaaactaaacccagtgataagacctgatgatttcgcttctttaattacatttggagatttttatttacagcattgttttc aaatatattccaattaatcggtgaatgattggagttagaataatctactataggatcatattttattaaattagcgtcatcataatattgcctccatttttta gggtaattatccagaattgaaatatcagatttaaccatagaatgaggataaatgatcgcgagtaaataatattcacaatgtaccattttagtcatatcagata agcattgattaatatcattattgcttctacaggctttaatttttattaattattctgtaagtgtcgtcggcatttatgtctttcatacccatctctttatcctt acctattgtttgtcgcaagttttgcgtgttatatatcattaaaaacggtaatagattgacatttgattctaataaattggattttttgtcacactattatatcgc ttgaaatacaattgtttaacataagtacctgtaggatcgtacaggtttacgcaagaaaatggttgttatagtcgattaatcgatttgattctagatttgttt taactaattaaaggaggaataacatatggttaacgcgttggaattcgagctcactagtgtcgacctgcagggtaccatggaagcttactcgaagatccgcgga
```

TABLE 3-continued

| Nucleotide sequence of pAMG21(BamHI$^-$). |
|---|
| aagaagaagaagaagaagaaagcccgaaaggaagctgagttggctgctgccaccgctgagcaataactagcataaccccttggggcctctaaacgggtcttga |
| ggggttttttgctgaaaggaggaaccgctcttcacgctcttcacgcggataaataagtaacgatccggtccagtaatgacctcagaactccatctggatttgt |
| tcagaacgctcggttgccgccgggcgttttttattggtgagaatcgcagcaacttgtcgcgccaatcgagccatgtcgtcgtcaacgacccccattcaagaa |
| cagcaagcagcattgagaactttggaatccagtccctcttccacctgctgaccg// |

This created the nine OSK1 fusions, as well as the first ShK fusion; to make the remaining ShK fusions (actually [desArg1]ShK fusions), the toxin DNA was first excised with BamHI and EcoRI digestion. Then the ShK (actually [desArg1]ShK peptide analog) coding sequence was ligated downstream of the small domain fusion partners. In addition, several of the ShK (actually [desArg1]ShK) fusions were excised with NdeI/EcoRI digestion and ligated to likewise digested pET30 DNA (Table 4).

TABLE 4

| Nucleotide sequence of pET30. |
|---|
| SEQ ID NO: 58 |
| atccggatatagttcctcctttcagcaaaaaacccctcaagacccgtttagaggccccaaggggttatgctagttattgctcagcggtggcag |
| cagccaactcagcttcctttcgggctttgttagcagccggatctcagtggtggtggtggtggtgctcgagtgcggccgcaagcttgtcgacg |
| gagctcgaattcggatccgatatcagccatggccttgtcgtcgtcgtcggtacccagatctgggctgtccatgtgctggcgttcgaatttagca |
| gcagcggtttctttcataccagaaccgcgtggcaccagaccagaagaatgatgatgatgatggtgcatatgtatatctccttcttaaagttaaac |
| aaaattatttctagaggggaattgttatccgctcacaattcccctatagtgagtcgtattaatttcgcgggatcgagatcgatctcgatcctctacg |
| ccggacgcatcgtggccggcatcaccggcgccacaggtgcggttgctggcgcctatatcgccgacatcaccgatggggaagatcgggct |
| cgccacttcgggctcatgagcgcttgtttcggcgtgggtatggtggcaggccccgtggccgggggactgttgggcgccatctccttgcatg |
| caccattccttgcggcggcggtgctcaacggcctcaacctactactgggctgcttcctaatgcaggagtcgcataagggagagcgtcgaga |
| tcccggacaccatcgaatggcgcaaaacctttcgcggtatggcatgatagcgcccggaagagagtcaattcagggtggtgaatgtgaaacc |
| agtaacgttatacgatgtcgcagagtatgccggtgtctcttatcagaccgtttcccgcgtggtgaaccaggccagccacgtttctgcgaaaac |
| gcgggaaaaagtggaagcggcgatggcggagctgaattacattcccaaccgcgtggcacaacaactggcgggcaaacagtcgttgctga |
| ttggcgttgccacctccagtctggccctgcacgcgccgtcgcaaattgtcgcggcgattaaatctcgcgccgatcaactgggtgccagcgtg |
| gtggtgtcgatggtagaacgaagcggcgtcgaagcctgtaaagcggcggtgcacatcttctcgcgcaacgcgtcagtgggctgatcatta |
| actatccgctggatgaccaggatgccattgctgtggaagctgcctgcactaatgttccggcgttatttcttgatgtctctgaccagacacccatc |
| aacagtattattttctcccatgaagacggtacgcgactgggcgtggagcatctggtcgcattgggtcaccagcaaatcgcgctgttagcggg |
| cccattaagttctgtctcggcgcgtctgcgtctggctggctggcataaatatctcactcgcaatcaaattcagccgatagcggaacgggaagg |
| cgactggagtgccatgtccggttttcaacaaaccatgcaaatgctgaatgagggcatcgttcccactgcgatgctggttgccaacgatcagat |
| ggcgctgggcgcaatgcgcgccattaccgagtccgggctgcgcgttggtgcggacatctcggtagtgggatacgacgataccgaagaca |
| gctcatgttatatcccgccgttaaccaccatcaaacaggattttcgcctgctggggcaaaccagcgtggaccgcttgctgcaactctctcagg |
| gccaggcggtgaagggcaatcagctgttgcccgtctcactggtgaaaagaaaaaccaccctggcgcccaatacgcaaaccgcctctcccc |
| gcgcgttggccgattcattaatgcagctggcacgacaggtttcccgactggaaagcgggcagtgagcgcaacgcaattaatgtaagttagct |
| cactcattaggcaccgggatctcgaccgatgcccttgagagccttcaacccagtcagctccttccggtgggcgcggggcatgactatcgtc |
| gccgcacttatgactgtcttctttatcatgcaactcgtaggacaggtgccggcagcgctctgggtcattttcggcgaggaccgctttcgctgga |
| gcgcgacgatgatcggcctgtcgcttgcggtattcggaatcttgcacgccctcgctcaagccttcgtcactggtcccgccaccaaacgtttcg |
| gcgagaagcaggccattatcgccggcatggcggccccacgggtgcgcatgatcgtgctcctgtcgttgaggacccggctaggctggcgg |

TABLE 4-continued

Nucleotide sequence of pET30.

ggttgccttactggttagcagaatgaatcaccgatacgcgagcgaacgtgaagcgactgctgctgcaaaacgtctgcgacctgagcaacaa
catgaatggtcttcggtttccgtgtttcgtaaagtctggaaacgcggaagtcagcgccctgcaccattatgttccggatctgcatcgcaggatg
ctgctggctaccctgtggaacacctacatctgtattaacgaagcgctggcattgaccctgagtgattttctctggtcccgccgcatccataccg
ccagttgtttaccctcacaacgttccagtaacccgggcatgttcatcatcagtaacccgtatcgtgagcatcctctctcgtttcatcggtatcattac
ccccatgaacagaaatcccccttacacggaggcatcagtgaccaaacaggaaaaaaccgcccttaacatggcccgctttatcagaagcca
gacattaacgcttctggagaaactcaacgagctggacgcggatgaacaggcagacatctgtgaatcgcttcacgaccacgctgatgagcttt
accgcagctgcctcgcgcgtttcggtgatgacggtgaaaacctctgacacatgcagctcccggagacggtcacagcttgtctgtaagcgga
tgccgggagcagacaagcccgtcagggcgcgtcagcgggtgttggcgggtgtcggggcgcagccatgacccagtcacgtagcgatagc
ggagtgtatactggcttaactatgcggcatcagagcagattgtactgagagtgcaccatatatgcggtgtgaaataccgcacagatgcgtaa
ggagaaaataccgcatcaggcgctcttccgcttcctcgctcactgactcgctgcgctcggtcgttcggctgcggcgagcggtatcagctcac
tcaaaggcggtaatacggttatccacagaatcaggggataacgcaggaaagaacatgtgagcaaaaggccagcaaaaggccaggaacc
gtaaaaaggccgcgttgctggcgtttttccataggctccgcccccctgacgagcatcacaaaaatcgacgctcaagtcagaggtggcgaaa
cccgacaggactataaagataccaggcgtttccccctggaagctccctcgtgcgctctcctgttccgaccctgccgcttaccggatacctgtc
cgcctttctcccttcgggaagcgtggcgctttctcatagctcacgctgtaggtatctcagttcggtgtaggtcgttcgctccaagctgggctgtg
tgcacgaaccccccgttcagcccgaccgctgcgccttatccggtaactatcgtcttgagtccaacccggtaagacacgacttatcgccactg
gcagcagccactggaacaggattagcagagcgaggtatgtaggcggtgctacagagttcttgaagtggtggcctaactacggctacacta
gaaggacagtatttggtatctgcgctctgctgaagccagttaccttcggaaaaagagttggtagctcttgatccggcaaacaaaccaccgctg
gtagcggtggtttttttgtttgcaagcagcagattacgcgcagaaaaaaaggatctcaagaagatcctttgatcttttctacggggtctgacgct
cagtggaacgaaaactcacgttaagggattttggtcatgaacaataaaactgtctgcttacataaacagtaatacaaggggtgttatgagccat
attcaacgggaaacgtcttgctctaggccgcgattaaattccaacatggatgctgatttatatgggtataaatgggctcgcgataatgtcgggc
aatcaggtgcgacaatctatcgattgtatgggaagcccgatgcgccagagttgtttctgaaacatggcaaaggtagcgttgccaatgatgtta
cagatgagatggtcagactaaactggctgacggaatttatgcctcttccgaccatcaagcattttatccgtactcctgatgatgcatggttactca
ccactgcgatccccgggaaaacagcattccaggtattagaagaatatcctgattcaggtgaaaatattgttgatgcgctggcagtgttcctgcg
ccggttgcattcgattcctgtttgtaattgtccttttaacagcgatcgcgtatttcgtctcgctcaggcgcaatcacgaatgaataacggtttggtt
gatgcgagtgattttgatgacgagcgtaatggctggcctgttgaacaagtctggaaagaatgcataaacttttgccattctcaccggattcagt
cgtcactcatggtgatttctcacttgataaccttatttttgacgaggggaaattaataggttgtattgatgttggacgagtcggaatcgcagaccg
ataccaggatcttgccatcctatggaactgcctcggtgagttttctccttcattacagaaacggcttttttcaaaaatatggtattgataatcctgata
tgaataaattgcagtttcatttgatgctcgatgagtttttctaagaattaattcatgagcggatacatatttgaatgtatttagaaaaataaacaaata
ggggttccgcgcacatttccccgaaaagtgccacctgaaattgtaaacgttaatattttgttaaaattcgcgttaaattttttgttaaatcagctcattt
tttaaccataggccgaaatcggcaaaatcccttataaatcaaaagaatagaccgagatagggttgagtgttgttccagtttggaacaagagtc
cactattaaagaacgtggactccaacgtcaaagggcgaaaaaccgtctatcagggcgatggcccactacgtgaaccatcaccctaatcaag
ttttttggggtcgaggtgccgtaaagcactaaatcggaaccctaaagggagcccccgatttagagcttgacggggaaagccggcgaacgtg
gcgagaaaggaagggaagaaagcgaaaggagcgggcgctagggcgctggcaagtgtagcggtcacgctgcgcgtaaccaccacacc
cgccgcgcttaatgcgccgctacagggcgcgtcccattcgcca//

The MK6H-G2-SH3-G5-2X(TMP22-7Q) fusion construct (Table 4A) was made as follows. A PCR fragment was amplified from strain 14066 harboring a plasmid encoding SH3 and MP22-7Q using the following two primers: GAG GAA TAA CAT ATG AAA CAT CAT CAT CAT CAT CAT GGT GGT AAA GTT TTT CGC GCA CTT TAT ACC TTT (SEQ ID NO:51), which encodes lysine, the 6 histidine tag, the glycine-glycine linker, the first 9 amino acids of SH3 plus a 15 nucleotides 5' extension including an NdeI site and GTT ATT GCT CAG CGG TGG CA (SEQ ID NO:52), which encodes a 20 nucleotides universal reverse primer for the pAMG21 vector. The PCR product was cloned in pAMG21 vector using NdeI and EcoRI sites, and the sequenced was confirmed.

TABLE 4A

| Amino acid sequence of MK6H-G2-SH3-G5-2X(TMP22-7Q). | |
|---|---|
| MKHHHHHHGGKVFRALYTFEPRTPDELYFEEGDIIYITDMSDTNWWKGTSKGRGLIPSNYVAEQ GGSGGQGCSSGGPTLREWQQCRRMQHSGGGGGGGGQGCSSGGPTLREWQQCRRMQHSGG// | SEQ ID NO: 86 |

The MK6H-G2-PDZ-G5-2X(TMP22-7Q) fusion construct (Table 4B) was made as follows. A PCR fragment was amplified from strain 14175 harboring a plasmid encoding PDZ and TMP22-7Q using the following two primers: AG GAA TAA CAT ATG AAA CAT CAT CAT CAT CAT CAT GGT GGT CCG GGC GAA GTT CGT CTT GTT AGT (SEQ ID NO:53), which encodes lysine, the 6 histidine tag, the glycine-glycine linker, the first 8 amino acids of PDZ plus a 15 nucleotides 5' extension including an NdeI site and GTT ATT GCT CAG CGG TGG CA (SEQ ID NO:54), which encodes a 20 nucleotides universal reverse primer for the pAMG21 vector. The PCR product was cloned in pAMG21 vector using NdeI and EcoRI sites, and the sequenced was confirmed.

TABLE 4B

| Amino acid sequence of MK6H-G2-PDZ-G5-2X(TMP22-7Q). | |
|---|---|
| MKHHHHHHGGPGEVRLVSLRRAKAHEGLGFSIRGGSEHGVGIYVSLVEPGSLAEKEGLRVGDQI LRVNDKSLARVTHAEAVKALKGSKKLVLSVYSAGRIPGGSGGQGCSSGGPTLREWQQCRRMQH SGGGGGGGGQGCSSGGPTLREWQQCRRMQHSGG// | SEQ ID NO: 87 |

The MK6H-G2-Fn3-G5-2X(TMP22-7Q) fusion construct (Table 4C) was made as follows. A PCR fragment was amplified from strain 14176 harboring a plasmid encoding Fn3 and TMP22-7Q using the following two primers: GAG GAA TAA CAT ATG AAA CAT CAT CAT CAT CAT CAT GGT GGT ACC GTA AGC GAT GTA CCA CGC GAT (SEQ ID NO:55), which encodes lysine, the 6 histidine tag, the glycine-glycine linker, the first 8 amino acids of Fn3 plus a 15 nucleotides 5' extension including an NdeI site and GTT ATT GCT CAG CGG TGG CA (SEQ ID NO:56), which encodes a 20 nucleotides universal reverse primer for the pAMG21 vector. The PCR product was cloned in pAMG21 vector using NdeI and EcoRI sites, and the sequenced was confirmed.

TABLE 4C

| Amino acid sequence of MK6H-G2-Fn3-G5-2X(TMP22-7Q). | |
|---|---|
| MKHHHHHHGGTVSDVPRDLEVVAATPTSLLISWDAPAVTVRYYRITYGETGGNSPVQE FTVPGSKSTATISGLKPGVDYTITVYAVTGRGDSPASSKPISINYRTEGGSGGQGCSSGGP TLREWQQCRRMQHSGGGGGGGGQGCSSGGPTLREWQQCRRMQHSGG// | SEQ ID NO: 88 |

Protein Expression.

Figure 4A:
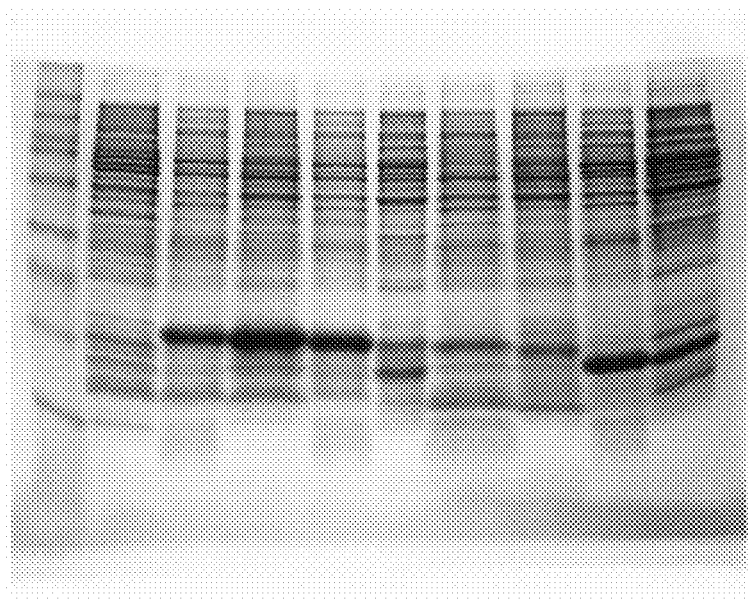
FIG. 4A illustrates the expression of various ShK (actually [desArg1]ShK) and OSK1 fusions with a Coomassie stained 18% Tris-Glycine SDS-PAGE. Lane contents were (left to right): Invitrogen Benchmark standards, uninduced lysate, 1N7F-OsK1, 1N7F-ShK, 1UEZ-OsK1, 1UEZ-ShK, 1WA7-OsK1, 1WA7-ShK, 1X2K-OsK1, 1X2K-ShK. Preparation of samples for electrophoresis involved measuring $OD_{600}$ of the cell culture, centrifugation of the cells, and resuspension in sufficient PBS (Dulbecco's Phosphate Buffered Saline (1×) (-Calcium Chloride, -Magnesium Chloride); GIBCO) to make a 10 $OD_{600}$/mL mixture. 15 µL of that was combined with 20 µL of loading buffer (80% Tris-Glycine SDS Sample Buffer (2×) [Novex] 20% β-mercaptoethanol), which was then heated at 99° C. for 5 minutes. Aliquots (10 µL) of this heated sample material were then loaded into the wells of the gel.
Figure 4B:
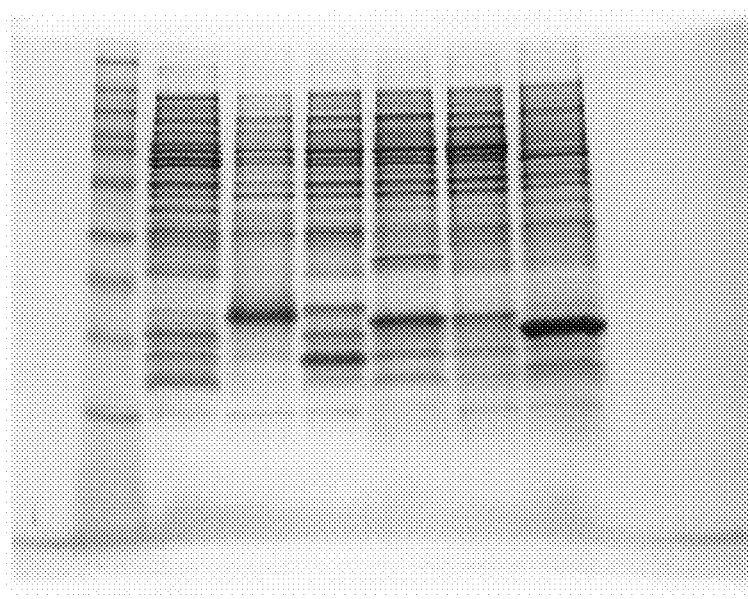
FIG. 4B illustrates the expression of various OSK1 fusions with a Coomassie stained 18% Tris-Glycine SDS-PAGE. Lane contents were (left to right): Invitrogen Benchmark standards, uninduced lysate, FN3-OsK1, 1WFV-OsK1, 1AB2-OsK1, 1JYQ-OsK1, 1PHT-OsK1. Preparation of samples for electrophoresis was as described above for FIG. 4A.

All the pAMG21 constructs were transformed into competent E. coli GM221 cells for expression (GM221 was derived from the K12 strain). Transformants were grown overnight (o/n) in TB media (1.2% Tryptone, 2.4% yeast extract, 0.4% glycerol, 72 mM K$_2$HPO$_4$, and 17 mM KH$_2$PO$_4$) supplemented with 40 μg/mL kanamycin. This o/n culture was diluted 1:100 into fresh media the following morning. The cells were then grown to an optical density (OD) at 600 nm of 0.4-0.6. Expression commenced upon addition of N-(3-oxo-hexanoyl) homoserine lactone (HSL) at a final concentration of 50 μg/mL. Harvesting by centrifugation was done 3 to 4 hours later. Expression levels were visualized and evaluated by Coomassie gel (see FIG. 4A-B and Table 5).

Figure 5A:
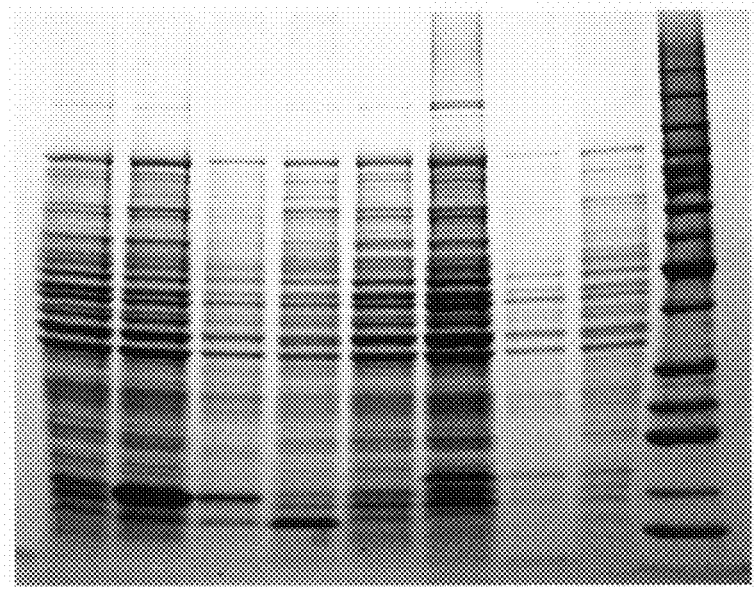
FIG. 5A illustrates expression of TMP(22-7Q) fusions with a Coomassie stained 18% Tris-Glycine SDS-PAGE. Lane contents were (left to right): uninduced lysate, SH3 lysate I+6, SH3 insoluble I+6, SH3 soluble I+6, uninduced lysate, SH2 lysate I+6, SH2 insoluble I+6, SH2 soluble I+6, Invitrogen Benchmark standards. Preparation of samples for electrophoresis involved measuring OD600 of the cell culture and centrifugation of the cells to get a 1 mg pellet using the formula 0.5291/OD. The pellet was resuspended in 50 µl of Tris-EDTA (pH 8.0) buffer and 50 µl of loading buffer (50% Tris-Glycine SDS Sample Buffer (2×) from Novex, 50% β-mercaptoethanol), which was then heated at 99° C. for 10 minutes. Aliquots (20 µL) of this heated sample material were then loaded into the wells of the gel.
Figure 5B:
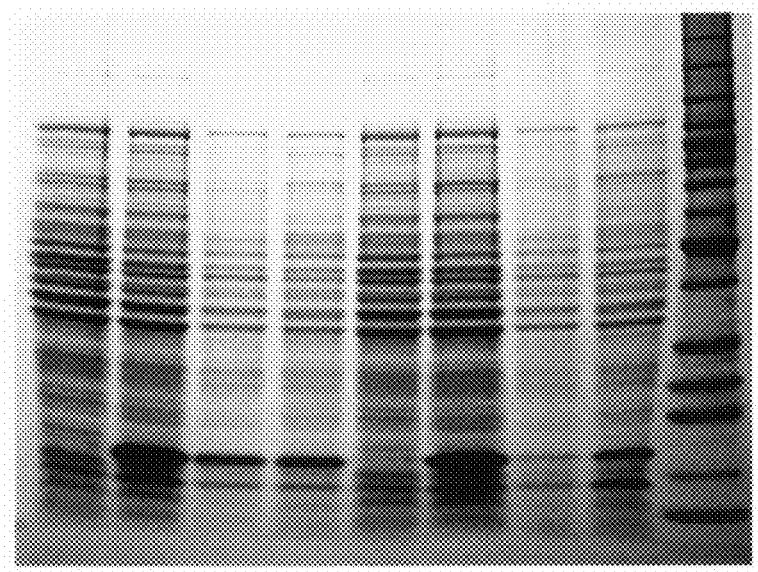
FIG. 5B illustrates expression of TMP(22-7Q) fusions with a Coomassie stained 18% Tris-Glycine SDS-PAGE. Lane contents were (left to right): uninduced lysate, PDZ lysate I+6, PDZ insoluble I+6, PDZ soluble I+6, uninduced lysate, Fn3 lysate I+6, Fn3 insoluble I+6, Fn3 soluble I+6, Invitrogen Benchmark standards. Preparation of samples for electrophoresis was as described above for FIG. 5A.
Figure 7D:
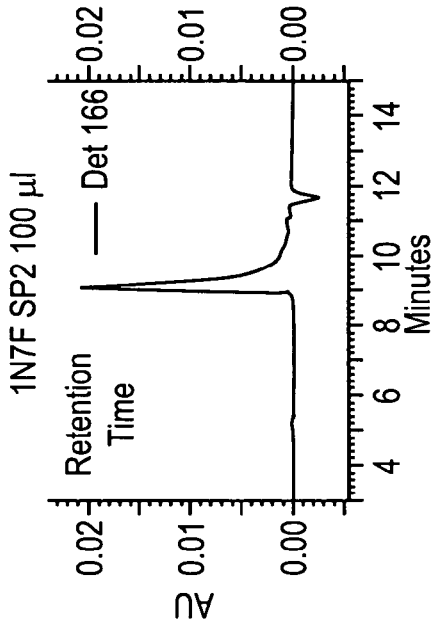
Figure 7E:
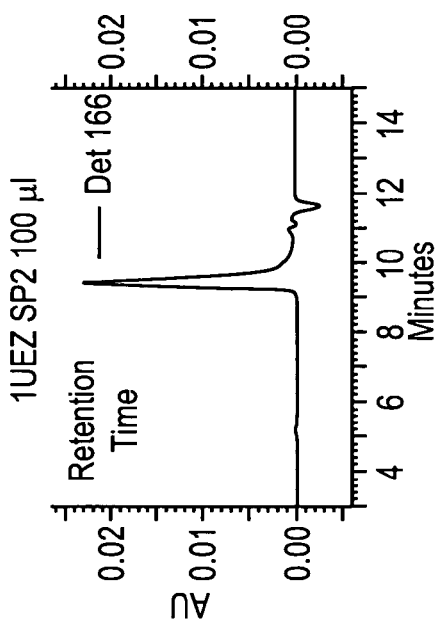
Figure 7F:
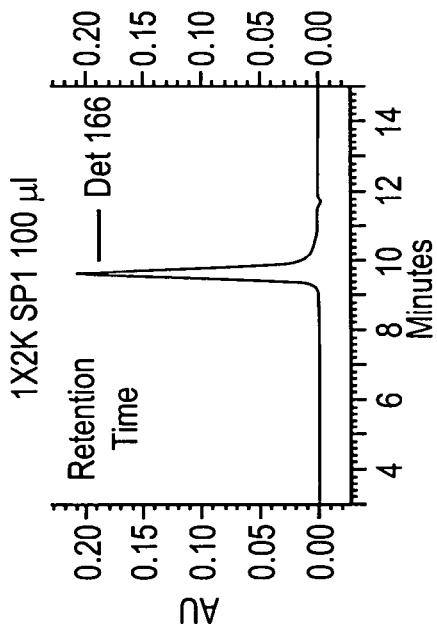

All the expression testing of the TMP fusion constructs was done with 5 ml test tubes using terrific broth. Cells were induced at 37° C. with N-(3-oxo-hexanoyl) homoserine lactone(HSL) for 6 hours. Whole cell extracts, soluble and insoluble fractions were analyzed using a 4-20% Tris-Glycine gel. The MK6H-G2-SH3-G5-2X(TMP22-7Q) construct showed good expression with about 25% of the recombinant protein insoluble and most of the soluble fraction is in the lower band (FIG. 5A-B). The MK6H-G2-PDZ-G5-2X (TMP22-7Q) construct showed very good expression with approximately 50% of the recombinant protein in the insoluble fraction and 50% of the recombinant protein in the soluble fraction. The MK6H-G2-Fn3-G5-2X(TMP22-7Q) also expressed well with about 15% of the recombinant protein in the insoluble fraction and the remainder in the soluble fraction.

TABLE 5

Relative expression levels of various ShK (actually [desArg1]ShK) fusion and OSK1 fusion constructs: "+/−" means a faint band was observed; "+" represents a weak band indicating definite low level expression of the recombinant fusion protein; "++" represents a moderately strong band indicating strong expression of the recombinant fusion protein; "+++" represents a strong band indicating high level expression of the recombinant fusion protein. The word "clipped" in the table refers to bands that ran significantly below their calculated mass; in some cases, two bands were apparent - one expected to be the full-length and another smaller product, for which protease-mediated clipping of the recombinant fusion protein is the most likely explanation.

| | pAMG21 | pET30 |
|---|---|---|
| M-G$_2$-H$_6$-G$_3$-10$^{th}$Fn3-(G$_4$S)$_2$-OsK1 | +++ | NA |
| M-G$_2$-H$_6$-G$_3$-PDZ(1N7F)-(G$_4$S)$_2$-OsK1 | ++ | NA |
| M-G$_2$-H$_6$-G$_3$-PDZ(1UEZ)-(G$_4$S)$_2$-OsK1 | +++ | NA |
| M-G$_2$-H$_6$-G$_3$-PDZ(1WFV)-(G$_4$S)$_2$-OsK1 | + | NA |
| M-G$_2$-H$_6$-G$_3$-SH2(1AB2)-(G$_4$S)$_2$-OsK1 | ++ | NA |
| M-G$_2$-H$_6$-G$_3$-SH2(1JYQ)-(G$_4$S)$_2$-OsK1 | +/− | NA |
| M-G$_2$-H$_6$-G$_3$-SH3(1PHT)-(G$_4$S)$_2$-OsK1 | ++ | NA |
| M-G$_2$-H$_6$-G$_3$-SH3(1WA7)-(G$_4$S)$_2$-OsK1$^b$ | ++ clipped | NA |
| M-G$_2$-H$_6$-G$_3$-SH3(1X2K)-(G$_4$S)$_2$-OsK1 | +++ | NA |
| M-G$_2$-H$_6$-G$_3$-CH2-(G$_4$S)$_2$-OsK1 | +++ | NA |
| M-G$_2$-H$_6$-G$_3$-10$^{th}$Fn3-(G$_4$S)$_2$-ShK | +/− | NA |
| M-G$_2$-H$_6$-G$_3$-PDZ(1N7F)-(G$_4$S)$_2$-ShK | + | ++ |
| M-G$_2$-H$_6$-G$_3$-PDZ(1UEZ)-(G$_4$S)$_2$-ShK | +/− | ++ |
| M-G$_2$-H$_6$-G$_3$-PDZ(1WFV)-(G$_4$S)$_2$-ShK | +/− | NA |
| M-G$_2$-H$_6$-G$_3$-SH2(1AB2)-(G$_4$S)$_2$-ShK | +/− | NA |
| M-G$_2$-H$_6$-G$_3$-SH2(1JYQ)-(G$_4$S)$_2$-ShK | +/− | NA |
| M-G$_2$-H$_6$-G$_3$-SH3(1PHT)-(G$_4$S)$_2$-ShK | +/− | NA |
| M-G$_2$-H$_6$-G$_3$-SH3(1WA7)-(G$_4$S)$_2$-ShK | +/− clipped | + clipped |
| M-G$_2$-H$_6$-G$_3$-SH3(1X2K)-(G$_4$S)$_2$-ShK | +/− | ++ |
| M-G$_2$-H$_6$-G$_3$-CH2-(G$_4$S)$_2$-ShK | ++ | NA |

Protein Purification.

Inclusion bodies were prepared by thawing frozen cell paste in 5 times the pellet mass (defined as 1 volume assuming 1 g=1 mL) of room temperature 50 mM tris HCl pH 8.0, 5 mM EDTA with approximately 0.1 mg/ml hen egg white lysozyme using a tissue grinder. The suspension was then passed through a microfluidizer twice at about 12,000 PSI to disrupt the cells. The homogenized suspension was then centrifuged at 11,300 g for 50 min at 4° C. and the supernatant was discarded. The pellet was resuspended in ½ volume of 1% deoxycholic acid using a tissue grinder and centrifuged at 15,300 g for 40 min at 4° C. discarding the supernatant. The pellet was then resuspended in ½ volume of water using a tissue grinder and centrifuged at 15,300 g for 40 min at 4° C. discarding the supernatant. The lysate and wash fractions were evaluated by SDS-PAGE (FIG. 6A-E).

The insoluble proteins were then subjected to protein refolding by first dissolving the washed inclusion bodies at a ratio of 9 ml of 8 M guanidine HCl with 50 mM tris pH 8.0 per gram of pellet mass using a tissue grinder followed by reduction using 10 mM DTT with gentle agitation for 30 min at room temperature. The refolding was then initiated by slowly adding 1 part by volume of the reduced denatured protein solution to 100 parts by volume of the refolding buffer cocktail (1 M urea, 50 mM ethanolamine, 160 mM arginine HCl, 5 mM EDTA, 0.02% NaN$_3$, pH 9.8, 4 mM cysteine, and 1.2 mM cystamine HCl) at 4° C. The refolding mixture was then incubated at 4° C. with gentle stirring typically from 2 to 4 days.

Purification of the refolding cocktail was then conducted by first filtering the refold mixture through a 0.45 μm cellulose acetate filter. The filtered solution was then concentrated and buffer exchanged using a Pall Omega 3 kDa UF/DF membrane and Ni-Buffer A (50 mM NaH$_2$PO$_4$, 300 mM NaCl, pH 7.5). After removing the retentate, the apparatus was flushed with Ni-Buffer A and combined this with the retentate, which was then filtered through a 0.45 μm cellulose acetate filter. The 1PHT and 1AB2 constructs were refolded in the absence of EDTA, hence, the diafiltration step was bypassed for these constructs. To the buffer exchanged material, 1/100 of a volume of 500 mM imidazole was added, then the protein was applied to a Qiagen Ni-NTA Superflow column in Ni-Buffer A at about 13° C. The column was washed with several column volumes of Ni-Buffer A followed by 8% Ni-Buffer B (250 mM Imidazole, 50 mM NaH$_2$PO$_4$, 300 mM NaCl, pH 7.5). The protein was eluted with 60% Ni-Buffer B. The eluted protein was then dialyzed against 10 mM NaH$_2$PO$_4$, pH 7.1 over night at 7° C. using a Pierce Slide-A-Lyzer with a 3.5 kDa membrane. The protein was further purified by loading on to a GE HiTrap SP-HP column in S-Buffer A (10 mM NaH$_2$PO$_4$, pH 7.1) at about 13° C. The column was washed with several column volumes of S-Buffer A, then eluted with a linear gradient to 60% S-Buffer B (1 M NaCl, 10 mM NaH$_2$PO$_4$, pH 7.1). The fractions were pooled based on SDS-PAGE analysis and concentrated to 2.47 to 5.44 mg/ml using a Pall Macrosep with a 3 kDa membrane at 4° C. The final product was then filtered through a 0.22 μm cellulose acetate filter.

Figure 8A:
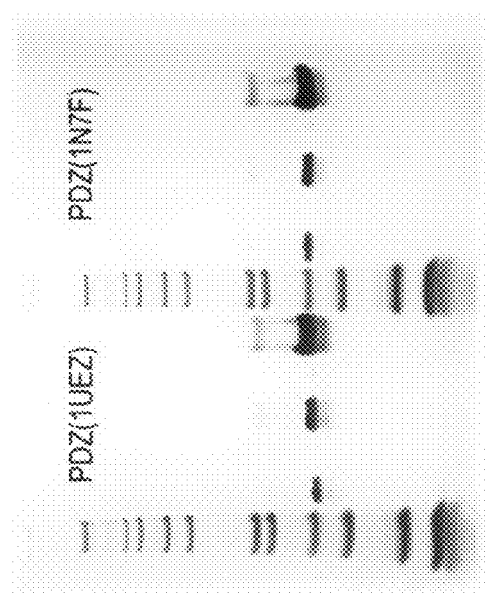
FIGS. 8A-C illustrates product of the refolded and purified small domain OsK1 fusions with Coomassie stained 4-20% tris-glycine SDS-PAGE. Lane contents in FIGS. 8A-C were (left to right): Novex Mark 12 standards, 0.5 µg protein; blank, 2.0 µg protein; blank, 10 µg protein; Novex Mark 12 standards, 0.5 µg protein; blank, 2.0 µg protein; blank, 10 µg protein.
Figure 8B:
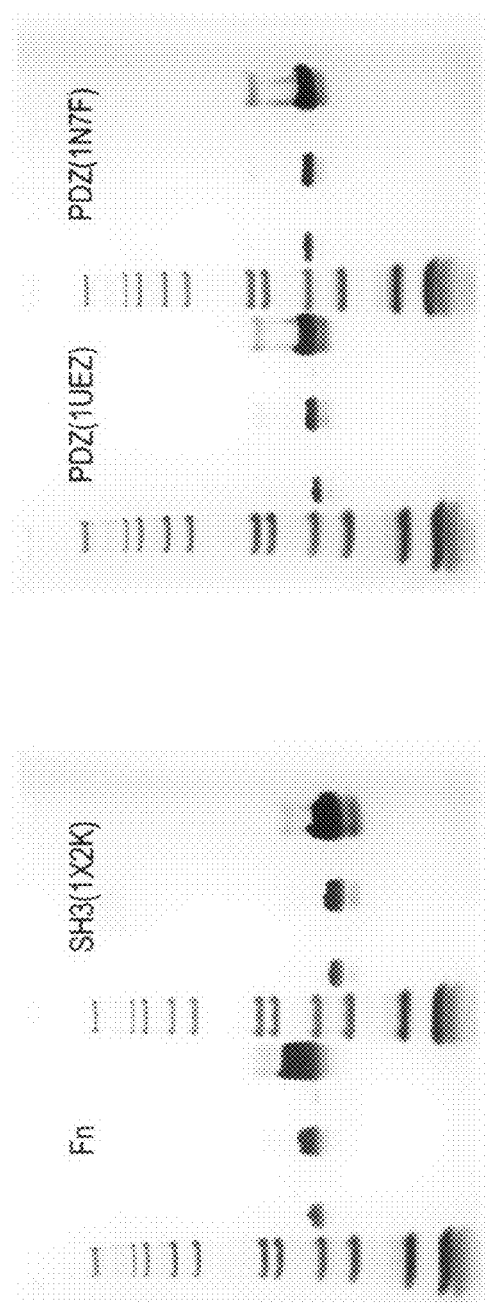
Figure 8C:
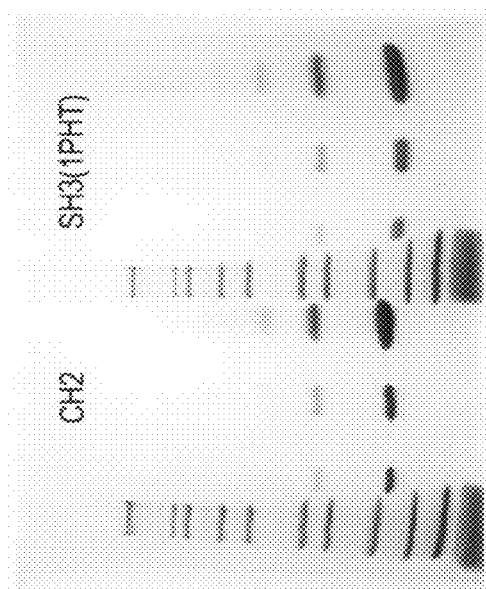
Figure 9A:
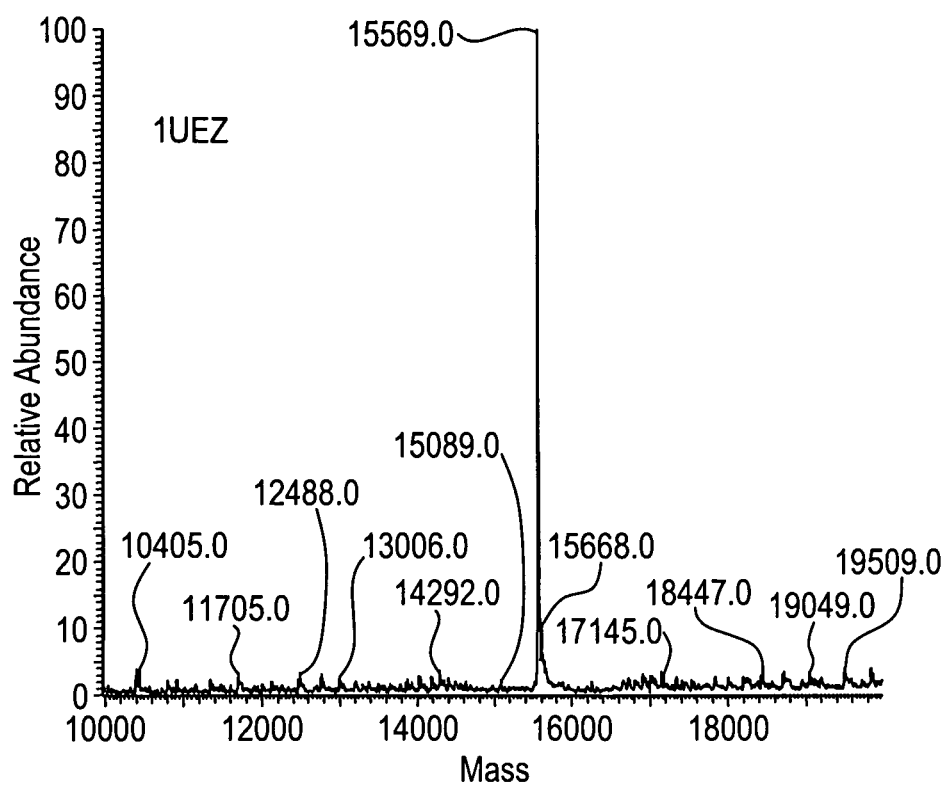
FIGS. 9A-E shows mass spectrometry of the refolded and purified small domain OsK1 fusions.
Figure 9B:
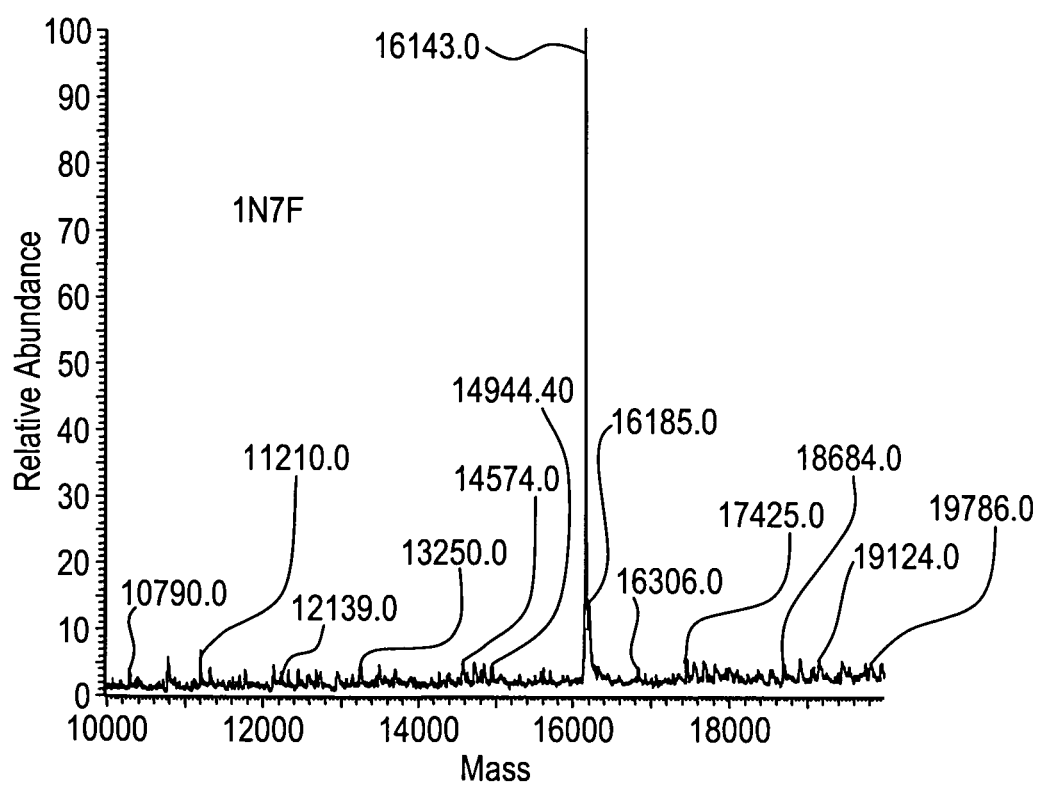
Figure 9C:
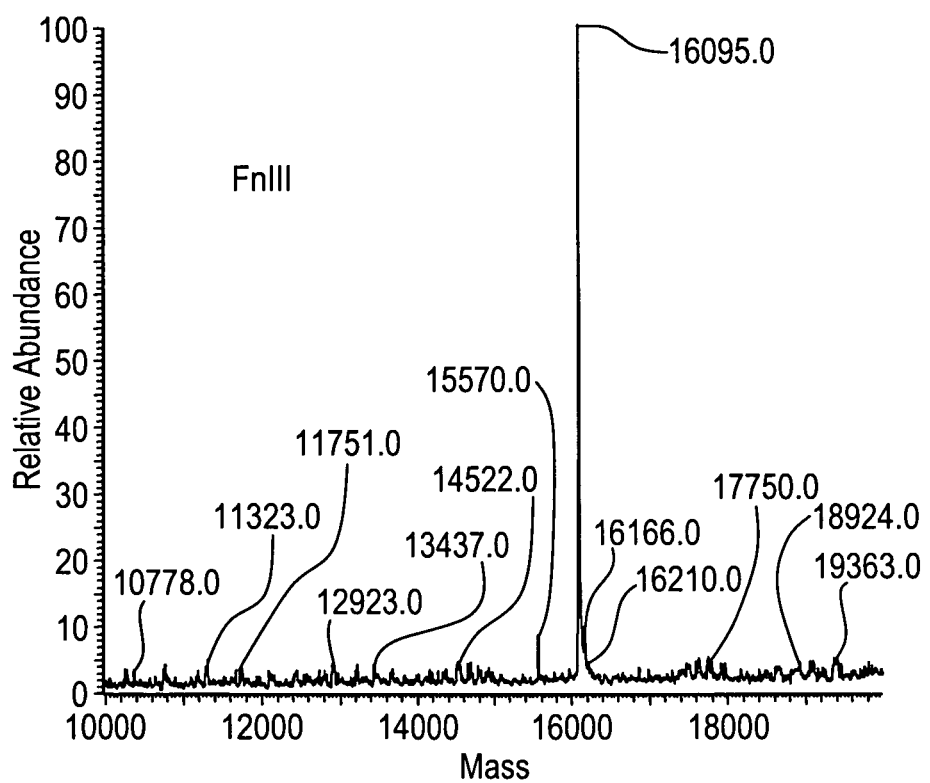
Figure 9D:
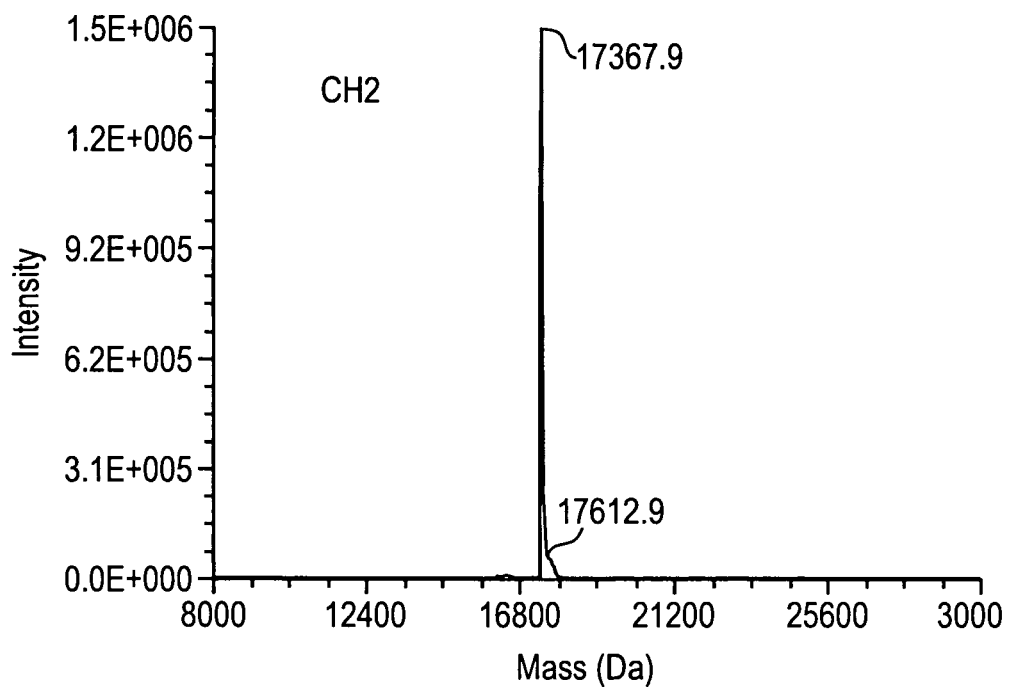
Figure 9E:
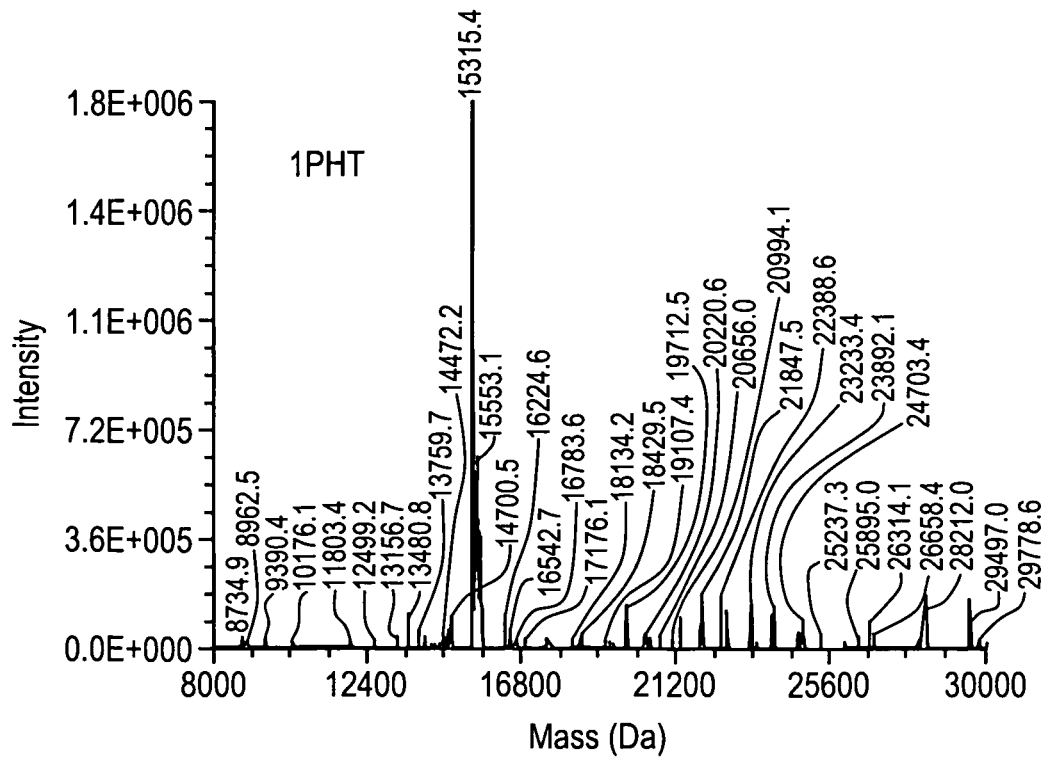

The concentration of the products was then analyzed by conducting a spectral scan from 250 to 340 nm, and concentrations were calculated using the molecular masses and extinction coefficients at 280 nm listed in Table 6 below. The pyrogen content was then determined using the Charles River Laboratories cartridge (0.05-5 EU/ml sensitivity) pyrogen assay diluting the samples to read between 1 and 100 EU/mg. The aggregation state was determined by injecting the protein solution on to a Phenomenex SEC 3000 column (7.8×300 mm) in SEC-Buffer (50 mM NaH$_2$PO$_4$ pH 6.9, 250 mM NaCl) at 1 m/min observing the absorbance at 280 nm (FIG. 7A-F). The purity of the proteins was assessed using a 1.0 mm 4-12% BisTris NuPAGE gel developing at 200V for 30 min in MES SDS running buffer and non-reducing NuPAGE loading buffer. The gels were stained with Boston Biologicals Quick-Blue stain (FIG. 8A-C). The molecular mass of the products was verified using mass spectroscopy (FIG. 9A-E).

TABLE 6

Product concentrations of OSK1 fusion proteins.

| Construct | $\epsilon$ ($M^{-1}$ $cm^{-1}$) | MW (Daltons) | Concentration (mg/ml) |
|---|---|---|---|
| CH2 SEQ ID NO: 80 | 17,460 | 17,373 | 3.35 |
| FnIII SEQ ID NO: 81 | 14,090 | 16,099 | 2.47 |
| 1X2K SEQ ID NO: 84 | 17,220 | 12,382 | 5.44 |
| 1UEZ SEQ ID NO: 85 | 3,280 | 15,574 | 2.70 |
| 1N7F SEQ ID NO: 83 | 3,280 | 16,148 | 4.01 |
| 1PHT SEQ ID NO: 82 | 15,390 | 15,324 | 3.90 |

Bioactivity Assay.

To determine the activity of the purified OsK1 fusions, test samples were serially diluted 1:3 eight times in 0.3% bovine serum albumin in PBS, with $Ca^{2+}$ and $Mg^{2+}$. CHO cells stably expressing the voltage-activated $K^+$ channel, $K_v1.3$, were plated in T-175 tissue culture flasks (at a density of $5 \times 10^6$) 2 days before experimentation and allowed to grow to around 95% confluence. Immediately prior to the experiment, the cells were washed with PBS and then detached with a mixture (2 ml) of trypsin (0.25%) and Versene (1:5000) (1:1 volume ratio) at 37° C. (for 3 minutes). Subsequently, the cells were re-suspended in the flask in 10 ml of tissue culture medium (HAM's F-12 with Glutamax, InVitrogen, #31765) with 10% FBS, 1×NEAA and 750 µg/ml of G418) and centrifuged at 1000 rpm for 1.5 minutes. The resultant cell pellet was re-suspended in PBS at $3-5 \times 10^6$ cells/ml. The ability of the peptides to inhibit $K^+$ currents in the CHO-$K_v1.3$ cells was investigated using the automated electrophysiology system IonWorks Quattro. Re-suspended cells, the assay plate, a population patch clamp (PPC) patch plate as well as appropriate intracellular (90 mM K-Gluconate, 20 mM KF, 2 mM NaCl, 1 mM MgCl2, 10 mM EGTA, 10 mM HEPES, pH 7.35) and extracellular (PBS, with $Ca^{2+}$ and $Mg^{2+}$) buffers and were positioned on the IonWorks Quattro. Electrophysiology recordings were made from the CHO-$K_v1.3$ cells using an amphotericin-based perforated patch-clamp method. Using the voltage-clamp circuitry of the IonWorks Quattro, cells were held at a membrane potential of −80 mV and voltage-activated $K^+$ currents were evoked by stepping the membrane potential to +30 mV for 400 ms. $K^+$ currents were evoked under control conditions (i.e. in the absence of inhibitor at the beginning of the experiment) and after a 10-15 minute incubation in the presence of the test solution. The mean $K^+$ current amplitude was measured between 430 and 440 ms. The amplitude of the $K^+$ current in the presence of each concentration of the test samples was expressed as a percentage of the $K^+$ current in control conditions in the same well. The data were then plotted as a function of peptide concentration in the test solution and the $IC_{50}$ value was estimated using the following logistic equation: $(Y=A+((B-A)/(1+((X/C)^D)))$, where A is min, B is max, C is IC50, D is slope, X is concn range, Y is POC range.

Example 2

PEGylation of Fusion Proteins

Six different OSK1 fusion proteins (SEQ ID NOS:80-85) were PEGylated with 20 kDa methoxy-PEG-aldehyde by reductive alkylation of their reactive amino groups similar to methods previously described in Kinstler et al., N-terminally chemically modified protein compositions and methods, U.S. Pat. No. 5,824,784. Briefly, the purified fusion proteins were diluted to 2 mg/ml in 50 mM NaOAc, pH 5.0 to which 20 kDa methoxy-PEG-propionaldehyde (Nektar, Huntsville, Ala.) was added in a 2-fold molar excess, followed by a sufficient volume of 1 M sodium cyanoborohydride to result in a final concentration of 10 mM. The reaction was sealed and mixed gently overnight at 4° C. Upon completion of the reaction period, the reactions were quenched by 4-fold dilution with 20 mM NaOAc, pH 4.0.

Figure 10:
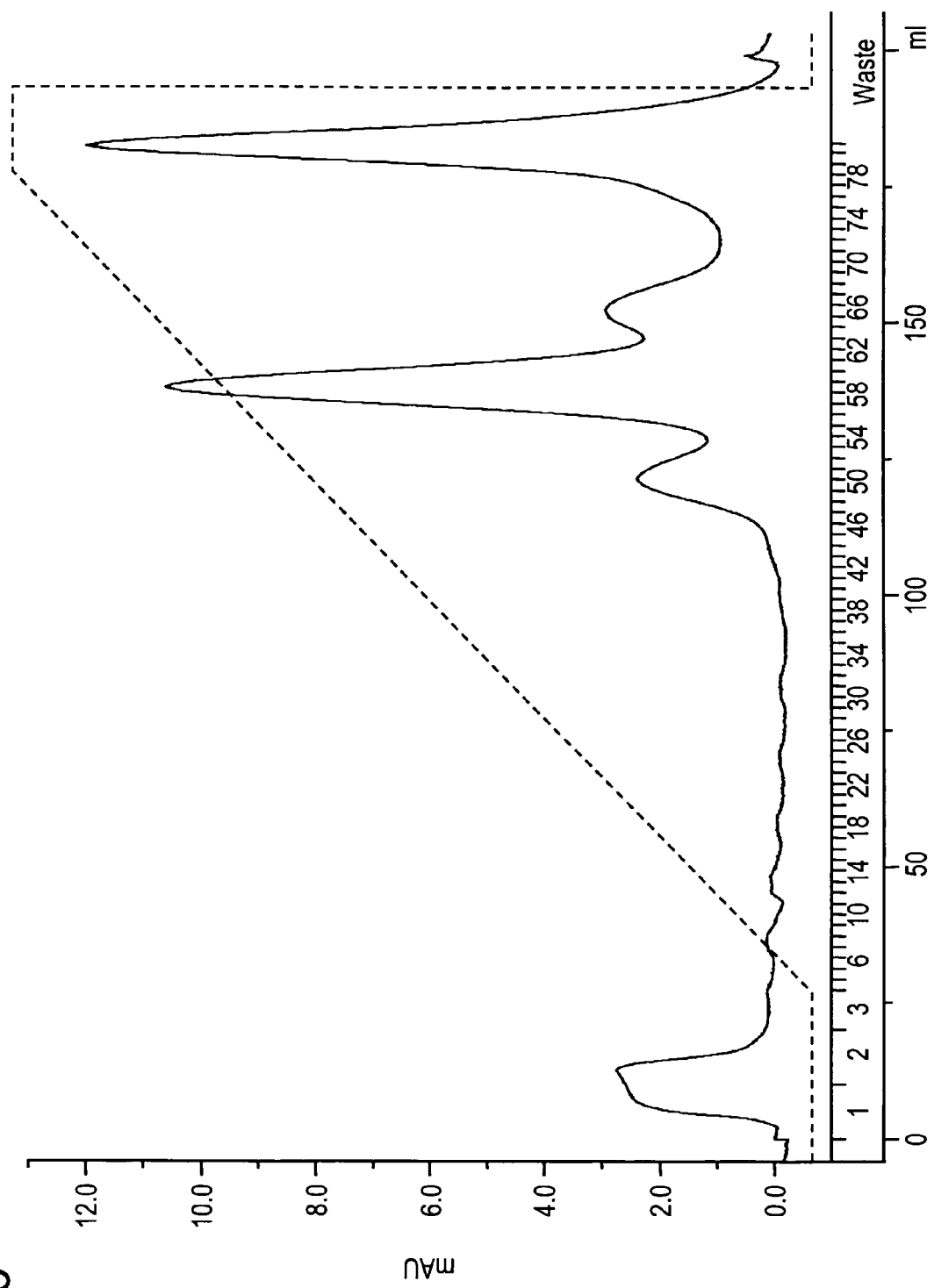
FIG. 10 shows cation exchange purification of the 1UEZ-OsK1 fusion construct after PEGylation using SP-HP sepharose, a 20 mM sodium acetate buffer pH 5.0, and a NaCl gradient from 0 to 1 M. The solid line traces the absorbance at 280 nm, while the broken line shows the conductivity.
Figure 11A:
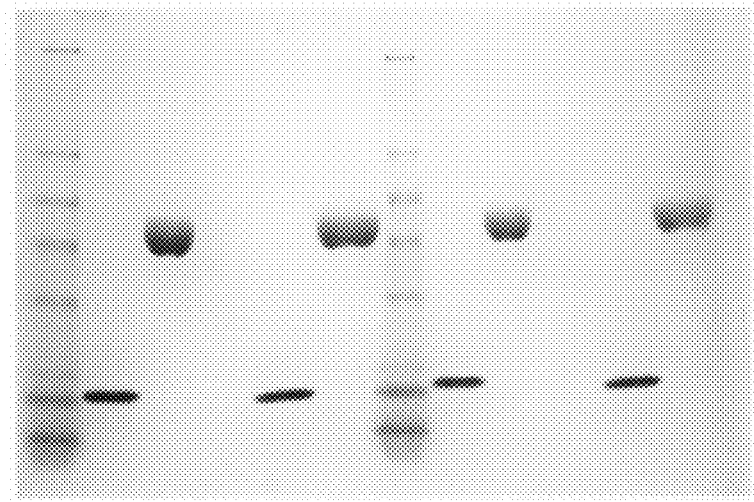
FIG. 11A-B shows SDS-PAGE of Purified PEGylated fusion proteins.
Figure 11B:
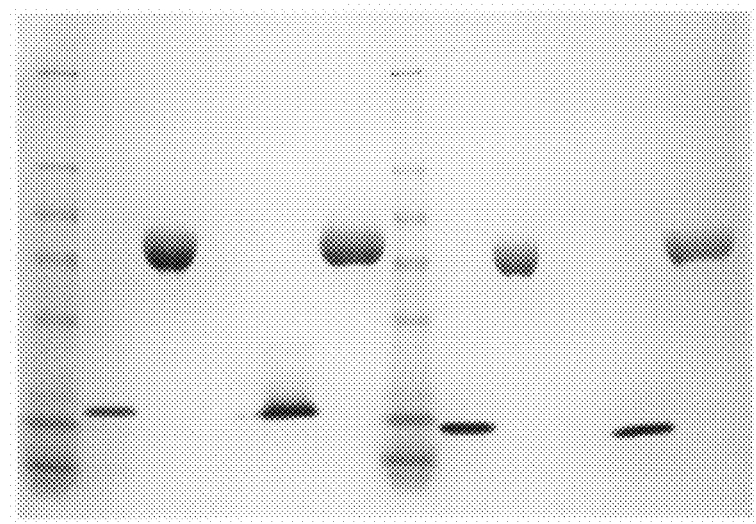

The mono-substituted PEG conjugates were purified from the poly-substituted conjugates and un-reacted fusion proteins by preparative FPLC (Akta, GE Healthcare, Piscataway, N.J.) using 5 ml SP Sepharose HP HiTrap columns in a 10 mM NaOAc, pH 4 buffer and eluted with a linear 0-0.5 M NaCl gradient over 25 column volumes. FIG. 10 shows a chromatogram from the purification of 20 kDa mPEG-1UEZ-OSK1 and is representative of the other purifications. Eluted peak fractions were evaluated by SDS-PAGE to identify fractions containing mono-substituted PEG-conjugates. These were pooled, concentrated and dialyzed into PBS. The final purified pools were characterized by SDS-PAGE (FIG. 11A-B) and submitted for further analyses.

Whole Blood Activity Assay.

For the in vitro whole blood activity assay of the compounds after PEGylation, the compounds were serially diluted 1:3 in DMSO (Sigma #D2650) and then diluted into Assay Medium (Iscoves DMEM (Gibco #2440-053)+0.1% Human Albumin (Human Serum Albumin 25% USP, Gemini #800-120)+1× Pen/Strep/Glu (Gibco #10378-016)+55 µM 2-mercaptoethanol (Gibco #21985-023)) to 4 times the working concentration in polypropylene 96 well plates (Corning #3365 or #3957). Samples were serially diluted 1:3 into Assay Medium to 4 times the working concentration.

Fifty microliters of samples were added to each well of 96 well flat bottom tissue culture plates (Falcon #35-3072). One hundred µl of heparinized human whole blood from healthy, non-medicated donors was then added. The plates were incubated for 1 hour at 37° C. After incubation, 50 µl per well of either 40 uM thapsigargin (Alomone Labs #T-650) for a final concentration of 10 µM or assay media (negative control) was added and plates were incubated at 37° C. for 48 hours. One hundred µl of the supernatant was then collected into round bottom polypropylene 96 well plates (Corning #3355) and either analyzed immediately or stored at −80° C.

Cytokines (human IL-2 and human IFN-γ) were measured on MSD MS6000 4 Spot Plates (#N41IB-1) per the manufacturer's recommendation. In brief, 20 µl of supernatant was added per well to MSD plates followed by 130 µl per well of detection antibody cocktail. The plate was then sealed and shaken in the dark at room temperature overnight. Plates were read the following morning on an MSD Sector HTS instrument (Meso Scale Discoveries, Gaithersburg, Md.). Data were then analyzed and IC$_{50}$ values generated using ActivityBase and Xlfit programs (IDBS, Guildford, UK). (Table 7 below).

TABLE 7

Bioactivity of PEGylated OSK1 fusion proteins.

| PEGylated Construct | IL-2 IC50 Donor 1 (µM) | IL-2 IC50 Donor 2 (µM) | IFN-γ IC50 Donor 1 (µM) | IFN-γ IC50 Donor 2 (µM) |
|---|---|---|---|---|
| CH2 SEQ ID NO: 80 | 0.007429 | 0.00922 | 0.088987 | 0.0113 |
| FnIII SEQ ID NO: 81 | 0.018726 | 0.03476 | 0.037399 | 0.003634 |
| 1X2K SEQ ID NO: 84 | 0.007057 | 0.020087 | 0.011178 | 0.013763 |
| 1UEZ SEQ ID NO: 85 | 0.00533 | >0.100000 | 0.004107 | 0.014324 |
| 1N7F SEQ ID NO: 83 | 0.033277 | 0.079462 | >0.100000 | >0.033333 |
| 1PHT SEQ ID NO: 82 | 0.017752 | >0.100000 | >0.100000 | >0.100000 |

Pharmacokinetics of Fusion Proteins.

The Swiss Webster mice used to determine the pharmacokinetic properties of the fusions were obtained from Taconic Inc. (nomenclature: Tac:SW). The mice were 8-10 weeks of age at the time of dosing and the average weight was 31 grams. The mice were maintained in groups of 5 in static filter top cages on Sani-Chip (Harlan-Teklad, Inc.) bedding. The mice were provided with irradiated rodent chow (Harlan-Teklad rodent diet 2919) and reverse osmosis water, ad libitum. The mice were maintained in a facility that is AAALAC accredited. Environmental conditions and sanitation practices meet or exceed standards set by the Guide for the Care and Use of Laboratory animals. The mice were exposed to a 12 hour light, 12 hour dark light cycle (6:30 AM-6:30 PM). The total volume injected per mouse was 150 µl at 2 mg/kg, intravenous. The animals were euthanized (CO$_2$ gas inhalation) 24 hours after injection with the test compounds, and blood was collected by cardiac puncture. The blood was placed in serum separator tubes (B.D.). The levels of the fusion proteins was determined by the whole blood activity assay described above (FIG. 12).

Example 3

Villin Headpiece Protein Fusions and PEGylation

In another embodiment of the present invention a small protein domain was selected that is an autonomously folding protein fragment from villin, which has an unusually thermostable structure and contains no cysteine. Several internal sites suitable for mutation to cysteine have been identified that allow PEGylation while not interfering with peptide fusions at either the N- or C-terminus of the small pharmacologically inactive protein domain. Provided herein is an example that the villin headpiece fusion platform permits recombinant expression of small, therapeutic peptides while allowing, optionally, facile PEGylation for enhanced pharmacokinetic properties.

Villin is a large (92.5 kDa) actin-binding protein involved in the maintenance and organization of actin filaments and implicated in the formation of microvilli in absorptive tissues. The protein is broadly expressed in a variety of tissues and the human sequence has been determined. (Arpin, M., et al., *Sequence of human villin: A large duplicated domain homologous with other actin-severing proteins and a unique small carboxy-terminal domain related to villin specificity*. J. Cell Biol., (1988). 107: p. 1759-1766). Villin activity is shared between two domains, a large core domain (84 kDa) and a much smaller, C-terminal domain (8 kDa) called the "headpiece". Both domains contain independent actin binding sites. An NMR structure of the villin headpiece domain has been determined and the actin-binding site and unique structural features mapped by cysteine scanning mutagenesis. (Vardar, D., et al., *NMR structure of an F-actin-binding "headpiece" motif from villin*. J. Mol. Biol., (1999). 294: p. 1299-1310; Doering, D. S. and P. T. Matsudaira, *Cysteine scanning mutagenesis at 40 of 76 positions in villin headpiece maps the F-actin binding site and structural features of the domain*. Biochemistry, (1996). 35: p. 12677-12685). These studies of the villin headpiece have lead to the identification of a headpiece subdomain called "HP-35" and consisting of the last 35 amino acids of the headpiece. The HP-35 polypeptide contains no cysteine and was readily expressed in *E. coli* independent of the remaining headpiece sequence. This fragment was found to fold autonomously into a stable, monomeric and well-organized structure. (McKnight, C. J., et al., A thermostable 35-residue subdomain within villin headpiece, J. Mol. Biol., (1996). 260: p. 126-134). HP-35 appears to be unique as the smallest known polypeptide with no disulphide bonds, which demonstrates reversible unfolding with unusually high thermostability (T$_m$=70° C.) and resistance to guanidine-HCl denaturation (>4 M GuHCl). Although the HP-35 subdomain contains some of the actin-binding site found in the headpiece domain, HP-35 does not bind actin. (See, Luna, E. J., et al., Actin-binding polypeptides and nucleic acids encoding the same, U.S. Pat. No. 5,985,608, (1999)). There has also been an NMR structure determined for HP-35 which indicates a very stable, well packed three-helix structure nearly identical to the equivalent sequence in the intact headpiece structure. (McKnight, J. C., P. T. Matsudaira, and P. S. Kim, *NMR structure of the 35-residue villin headpiece subdomain*. Nature Structural Biology, (1997). 4: p. 180-184). These studies conclude that most of the structural stability of the headpiece domain is derived from the HP-35 subdomain. Similarly, the larger extended villin headpiece domain consisting of the last 76 amino acids called HP-76 was also characterized as a fusion partner.

In order to facilitate subsequent PEGylation of the HP35-, or HP76-peptide fusion proteins three different positions for single cysteine substitutions were tested: T48C, A56C or N68C. These mutation sites are located on the solvent exposed surface of each of the three helices and are sufficiently distal to the polypeptide termini to minimize interference with the therapeutic peptide fusion partner once PEGylated. Each of these cysteine mutations has been shown to be well-tolerated and solvent exposed in expressed headpiece mutants. (Doering, D. S. and P. T. Matsudaira, *Cysteine scanning mutagenesis at 40 of 76 positions in villin headpiece maps the F-actin binding site and structural features of the domain*. Biochemistry, (1996). 35: p. 12677-12685). In fact, cysteine at position 68 was found to be stabilizing and increased the thermal stability of headpiece by 8° C. Although most of the HP-35 studies have been done with the chicken sequence, there is substantial homology with the equivalent human sequence (FIG. 13). The suggested cysteine mutation sites for the human sequence are conserved if not identical between the two species.

PTH-HP76 Fusion Protein.

In one embodiment of the inventive recombinant fusion protein, parathyroid hormone (PTH) was fused to the villin headpiece domain HP76 using conventional molecular biology techniques resulting in a polypeptide of the following sequence:

SVSEIQLMHN LGKHLNSMER VEWL-
RKKLQD VHNFGGGGGV FNANSNLSSG
PLPIFPLEQL VNKPVEELPE GVDPSR-
KEEH LSIEDFTQAF GMTPAAFSAL
PRWKQQ<u>C</u>LKK EKGLFHHHHH H//.

SEQ ID NO: 59

In this construct, the therapeutic peptide PTH represents the first 34 amino acids, the next 5 glycine residues represent a linker, followed by the 76 amino acids of the HP76 domain which includes the N68C mutation (underlined cysteine residue in SEQ ID NO:59) for conjugation to PEG and a six-histidine extension to facilitate IMAC purification.

Expressed in *E. coli*, the PTH-HP76 fusion was detected by western blot in both the soluble and insoluble fractions of the cell lysate. However, some degradation of the PTH-HP76 molecule was observed when the fusion protein was isolated from the soluble fraction. In contrast, PTH-HP76 isolated from the insoluble fraction appeared largely intact. Briefly, the cells were lysed, centrifuged and the insoluble pellet dissolved in 8 M urea, 10 mM NaHPO4, 50 mM NaCl, 10 mM DTT, pH7.5 by stirring 30 min. at 4 degrees C.

Figure 14:
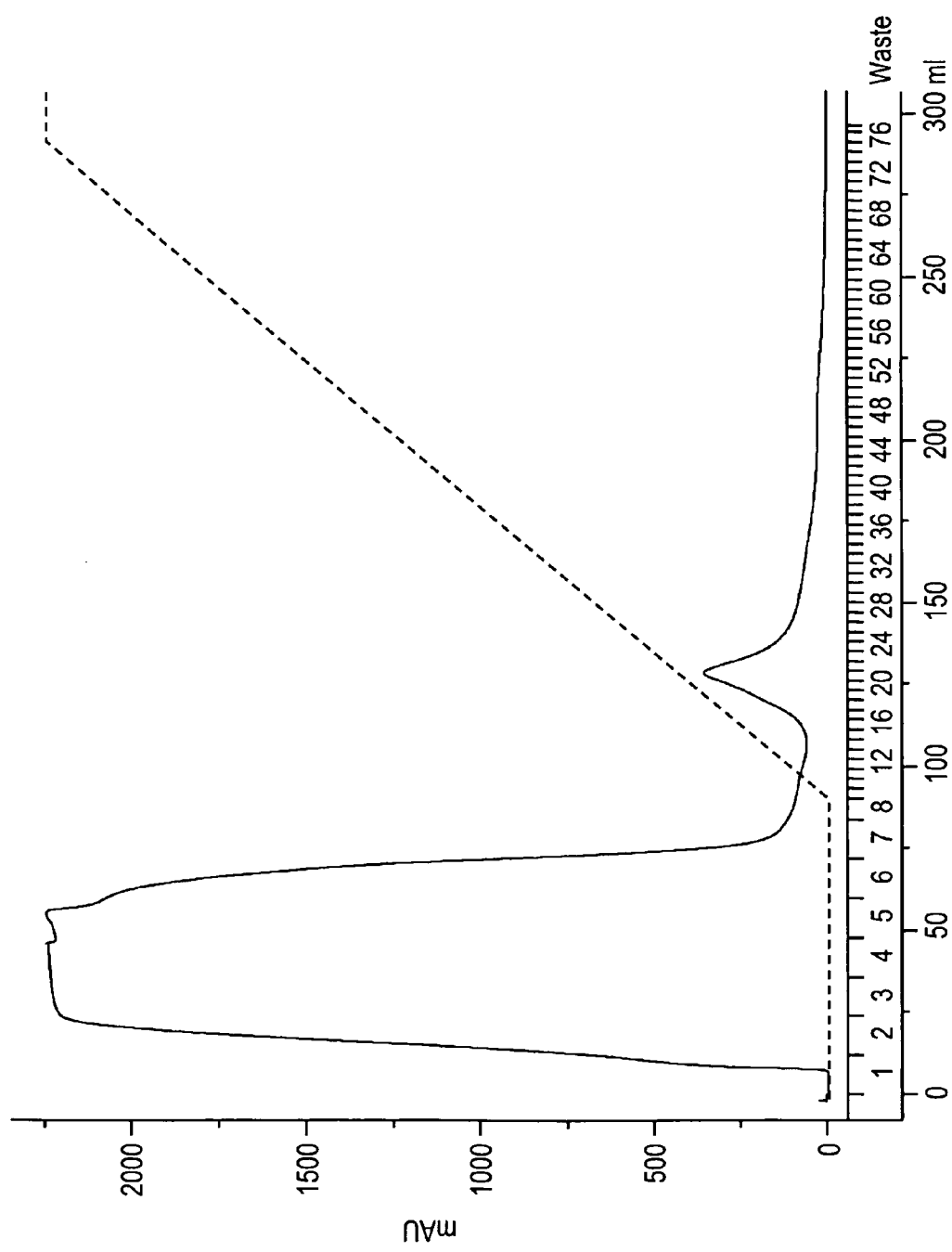
FIG. 14 shows a chromatogram from Ni-NTA purification of PTH-HP76 from *E. coli* lysate.
Figure 15:
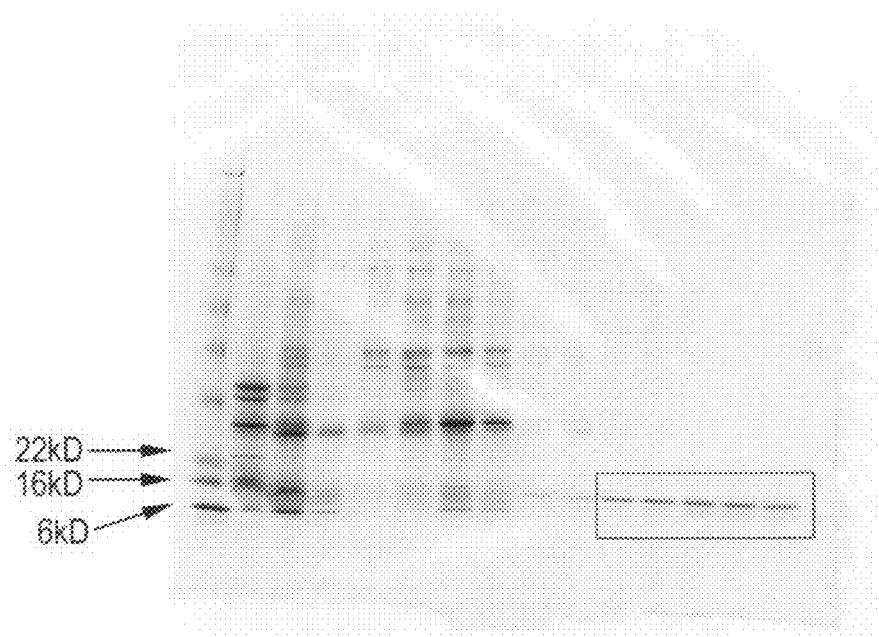
FIG. 15 shows a 4-20% SDS-PAGE gel of eluted peak fractions from Ni-NTA column (FIG. 14). Boxed fractions were confirmed as PTH-HP76 by western blot and were pooled.

The solubilized PTH-HP76 was clarified by centrifugation and the supernatant diluted 1:4 with 6 M urea, 10 mM NaHPO$_4$, 50 mM NaCl, 5 mM 2-mercaptoethanol, 5 mM imidazole, pH7. The diluted fusion protein was then loaded to a Ni-NTA column (Qiagen, Germany) and eluted with a linear 5-245 mM imidazole gradient (FIG. 14). Peak fractions were analyzed by SDS-PAGE gels (FIG. 15) and those containing PTH-HP76 pooled, concentrated and buffer exchanged into 50 mM NaHPO$_4$, 5 mM EDTA, pH6.5.

Figure 17:
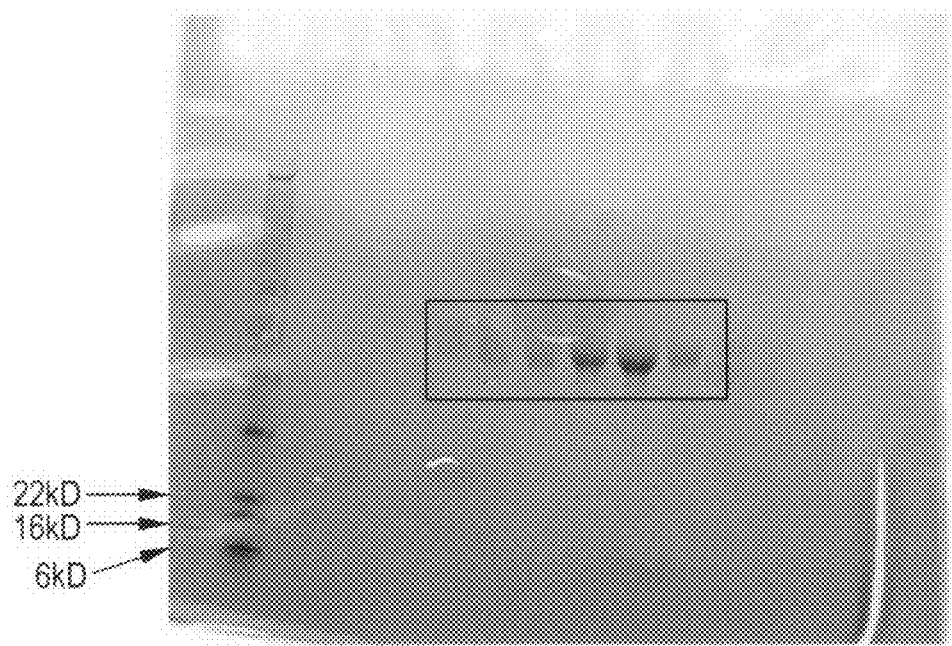
FIG. 17 shows 4-20% SDS-PAGE gel of eluted peak fractions from SP Sepharose column (FIG. 16). Boxed fractions representing purified PEG-PTH-HP76 were pooled.
Figure 16:
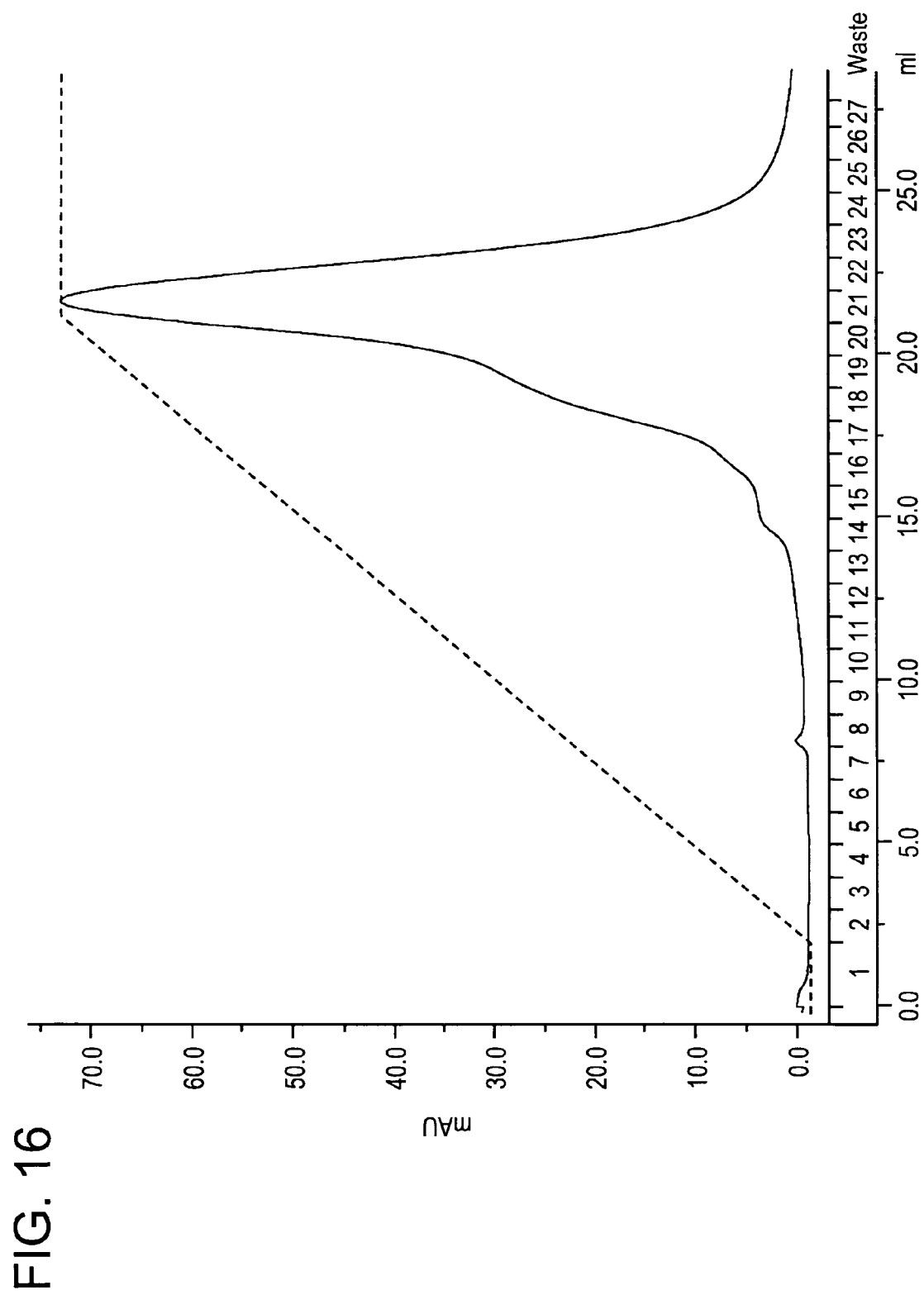
FIG. 16 shows a chromatogram from cation exchange purification of PEGylated PTH-HP76 using 1 ml SP Sepharose HP HiTrap column (GE Healthcare, Piscataway, N.J.).

The isolated PTH-HP76 fusion protein was then PEGylated by addition of 30 k mPEG-maleimide (Nektar, Huntsville, Ala.) in a 1.5-fold molar excess and allowed to react overnight at 4 degrees C. The conjugate was then purified by cation exchange chromatography (FIG. 16), analyzed by SDS-PAGE (FIG. 17), concentrated and dialyzed into PBS.

Figure 18:
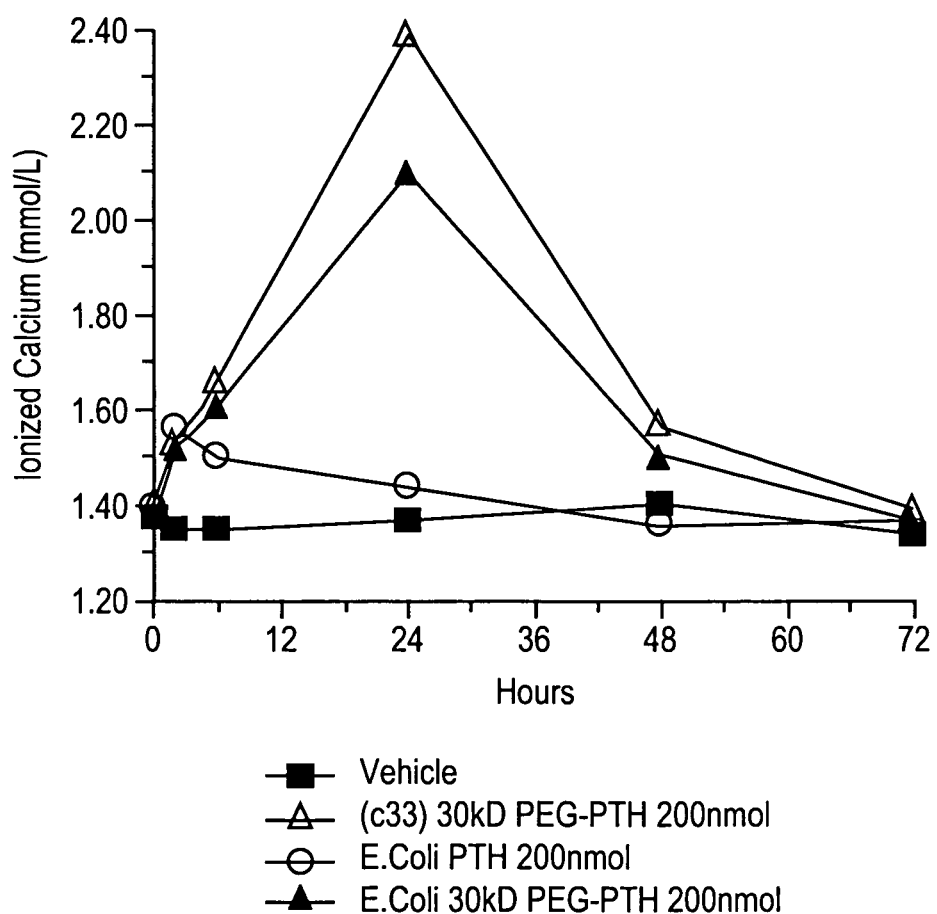
FIG. 18 shows the results of murine in vivo bioassay of the PTH-HP76 conjugates.

The PEG-PTH-HP76 was tested in a murine in vivo study measuring PTH induced hypercalcemia comparing a PEGylated synthetic PTH conjugate (designated "c33") and the *E. coli* derived PTH-HP76 and PEG-PTH-HP76 (FIG. 18). In this study, groups of 5 BDF 1 mice (4 weeks old, male) were given a single subcutaneous dose of either 200 nmoles synthetic PEG-PTH, 58.6 nmoles *E. coli*-derived PTH-HP76 or 58.6 nmoles *E. coli*-derived PEG-PTH-HP76 and ionized calcium measurements were taken at 0, 2, 6, 24, 48 and 72 hrs.

The data demonstrate that HP76 fusions with PTH enable expression of therapeutic peptides in a prokaryotic microbial host cell and incorporation of cysteine at position 68 allows facile site-directed PEGylation. The resultant conjugate was active and potent in vivo. The data presented in this Example further demonstrate that pharmacologically active peptides expressed as recombinant fusion proteins of the present invention can be optionally PEGylated and demonstrate prolonged efficacious half-lives.

The foregoing being illustrative but not an exhaustive description of the embodiments of the present invention, the following claims are presented.

---

We claim:

1. A composition of matter of the formula $$(F^1)_a\text{—}X^2$$

and multimers thereof, wherein:

F$^1$ is a half-life extending moiety, and a is 1;

X$^2$ is D-(L)$_c$-(P$^5$)$_d$—(X$^3$)$_e$, (X$^4$)$_f$—(P$^5$)$_d$-(L)$_c$-D, or (X$^4$)$_f$—(P$^5$)$_d$-(L)$_c$-D-(L)$_g$-(P$^6$)$_h$—(X$^3$)$_i$, wherein c and g are each independently 0 or 1, d and h are 1, and e, f, and i are each independently 0, 1, 2, 3, or 4;

X$^3$ is -(L)$_j$-(P$^7$), j is 0 or 1;

X$^4$ is (P$^8$)-(L)$_k$-, k is 0 or 1;

D is a pharmacologically inactive protein domain of human origin, wherein said pharmacologically inactive protein domain is a SH3 domain that comprises a native human amino acid sequence that is an intracellular proline motif (PxxP) recognition and binding domain, and (i) has a mass of 3 kDa to 20 kDa, and (ii) characteristically forms protein aggregates of less than 10 percent of total mass of protein when suspended without other proteins in a pharmaceutically acceptable formulation buffer of interest not comprising a detergent or chaotropic agent;

P$^5$, P$^6$, P$^7$ and P$^8$ are each independently a selected pharmacologically active protein of interest 5 to 80 amino acid residues in length; and L is in each instance a peptidyl linker.

2. The composition of matter of claim 1, wherein the pharmacologically inactive protein domain comprises an amino acid sequence selected from SEQ ID NOS: 4, 94, 105, and 106.

3. The composition of matter of claim 1, wherein the pharmacologically active protein is a toxin peptide, a CGRP peptide antagonist, a bradykinin B1 receptor peptide antagonist, a PTH agonist peptide, a PTH antagonist peptide, an ang-2 binding peptide, a myostatin binding peptide, an EPO-mimetic peptide, a TPO-mimetic peptide, a NGF binding peptide, a BAFF antagonist peptide, a GLP-1 or peptide mimetic thereof, or a GLP-2 or peptide mimetic thereof.

4. The composition of matter of claim 3, wherein the toxin peptide is selected from ShK, a ShK peptide analog, OSK1 and an OSK1 peptide analog, wherein the ShK peptide analog comprises a modification of the native ShK sequence by addition, deletion or substitution of one to nine amino acid residues, deletion of up to two amino acid residues at the N-terminus, or deletion of up to 5 amino acid residues at the C-terminus.

5. The composition of matter of claim 1, wherein F$^1$ is a polyethylene glycol, a copolymer of ethylene glycol, a polypropylene glycol, a copolymer of propylene glycol, a carboxymethylcellulose, a polyvinyl pyrrolidone, a poly-1,3-dioxolane, a poly-1,3,6-trioxane, an ethylene maleic anhydride copolymer, a polyaminoacid, a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group; or a combination of any of these members.

6. The composition of matter of claim 1, wherein F$^1$ is a polyethylene glycol.

7. A pharmaceutical composition, comprising the composition of matter of claim 1, and a pharmaceutically acceptable carrier.

8. The composition of matter of claim 1, wherein the pharmacologically inactive protein domain comprises the amino acid sequence of SEQ ID NO: 94.

9. A composition of matter comprising a recombinant fusion protein, wherein said fusion protein comprises:

(a) a pharmacologically inactive protein domain of human origin comprising the amino acid sequence of SEQ ID NO: 94; and (b) at least one pharmacologically active toxin peptide 20 to 80 amino acid residues in length comprising a selected ShK peptide analog of interest, wherein the ShK peptide analog comprises a modification of the native ShK sequence by addition, deletion or substitution of one to nine amino acid residues, deletion of up to two amino acid residues at the N-terminus, or deletion of up to 5 amino acid residues at the C-terminus.

10. The composition of matter of claim 9, wherein the composition of matter further comprises a half-life extending moiety comprising polyethylene glycol (PEG).

11. A nucleic acid comprising a polynucleotide sequence encoding a recombinant fusion protein comprising the composition of matter of claim 9.

12. The nucleic acid of claim 11, wherein the nucleic acid is a DNA.

13. An expression vector comprising the nucleic acid of claim 11.

14. The expression vector of claim 13, further comprising a coding sequence encoding a secretory signal peptide operably linked to the polynucleotide sequence encoding the recombinant fusion protein.

15. A cultured recombinant host cell comprising the expression vector of claim 13.

16. The cultured recombinant host cell of claim 15, wherein the host cell is a prokaryotic host cell.

17. The cultured recombinant host cell of claim 15, wherein the prokaryotic host cell is an *Escherichia coli*.

18. A method of producing a pharmacologically active recombinant fusion protein, comprising:
 (a) placing the recombinant host cell of claim 15 in a growth medium, such that the recombinant fusion protein is expressed; and
 (b) isolating the fusion protein from the cell or growth medium.

* * * * *

SEQUENCE LISTING

```
<160> NUMBER OF SEQ ID NOS: 112

<210> SEQ ID NO 1
<211> LENGTH: 105
<212> TYPE: PRT
<213> ORGANISM: Homo sapiens
<220> FEATURE:
<221> NAME/KEY: MISC_FEATURE
<223> OTHER INFORMATION: CH2 DOMAIN OF HUMAN IgG1

<400> SEQUENCE: 1

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly
            100                 105

<210> SEQ ID NO 2
<211> LENGTH: 101
```

```
<212> TYPE: PRT
<213> ORGANISM: Homo sapiens
<220> FEATURE:
<221> NAME/KEY: MISC_FEATURE
<223> OTHER INFORMATION: HUMAN TENTH FIBRONECTIN III DOMAIN

<400> SEQUENCE: 2

Val Ser Asp Val Pro Arg Asp Leu Glu Val Val Ala Ala Thr Pro Thr
1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 3
<211> LENGTH: 95
<212> TYPE: PRT
<213> ORGANISM: Homo sapiens
<220> FEATURE:
<221> NAME/KEY: MISC_FEATURE
<223> OTHER INFORMATION: HUMAN PDZ DOMAIN (ERBIN)

<400> SEQUENCE: 3

Gly Ser Met Glu Ile Arg Val Arg Val Glu Lys Asp Pro Glu Leu Gly
1               5                  10                  15

Phe Ser Ile Ser Gly Gly Val Gly Gly Arg Gly Asn Pro Phe Arg Pro
                20                  25                  30

Asp Asp Asp Gly Ile Phe Val Thr Arg Val Gln Pro Glu Gly Pro Ala
            35                  40                  45

Ser Lys Leu Leu Gln Pro Gly Asp Lys Ile Ile Gln Ala Asn Gly Tyr
    50                  55                  60

Ser Phe Ile Asn Ile Glu His Gly Gln Ala Val Ser Leu Leu Lys Thr
65                  70                  75                  80

Phe Gln Asn Thr Val Glu Leu Ile Ile Val Arg Glu Val Ser Ser
                85                  90                  95

<210> SEQ ID NO 4
<211> LENGTH: 58
<212> TYPE: PRT
<213> ORGANISM: Homo sapiens
<220> FEATURE:
<221> NAME/KEY: MISC_FEATURE
<223> OTHER INFORMATION: HUMAN SH3 DOMAIN (FYN)

<400> SEQUENCE: 4

Val Thr Leu Phe Val Ala Leu Tyr Asp Tyr Glu Ala Arg Thr Glu Asp
1               5                  10                  15

Asp Leu Ser Phe His Lys Gly Glu Lys Phe Gln Ile Leu Asn Ser Ser
                20                  25                  30

Glu Gly Asp Trp Trp Glu Ala Arg Ser Leu Thr Thr Gly Glu Thr Gly
            35                  40                  45

Tyr Ile Pro Ser Asn Tyr Val Ala Pro Val
    50                  55
```

-continued

```
<210> SEQ ID NO 5
<211> LENGTH: 96
<212> TYPE: PRT
<213> ORGANISM: Homo sapiens
<220> FEATURE:
<221> NAME/KEY: MISC_FEATURE
<223> OTHER INFORMATION: HUMAN SH2 DOMAIN (GRB2)

<400> SEQUENCE: 5

Gly Ser Met Ala Trp Phe Phe Gly Lys Ile Pro Arg Ala Lys Ala Glu
1               5                   10                  15

Glu Met Leu Ser Lys Gln Arg His Asp Gly Ala Phe Leu Ile Arg Glu
            20                  25                  30

Ser Glu Ser Ala Pro Gly Asp Phe Ser Leu Ser Val Lys Phe Gly Asn
        35                  40                  45

Asp Val Gln His Phe Lys Val Leu Arg Asp Gly Ala Gly Lys Tyr Phe
    50                  55                  60

Leu Trp Val Val Lys Phe Asn Ser Leu Asn Glu Leu Val Asp Tyr His
65                  70                  75                  80

Arg Ser Thr Ser Val Ser Arg Asn Gln Gln Ile Phe Leu Arg Asp Ile
                85                  90                  95

<210> SEQ ID NO 6
<211> LENGTH: 76
<212> TYPE: PRT
<213> ORGANISM: Homo sapiens
<220> FEATURE:
<221> NAME/KEY: MISC_FEATURE
<223> OTHER INFORMATION: UBIQUITIN

<400> SEQUENCE: 6

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 7
<211> LENGTH: 57
<212> TYPE: PRT
<213> ORGANISM: Homo sapiens
<220> FEATURE:
<221> NAME/KEY: MISC_FEATURE
<223> OTHER INFORMATION: THROMBOSPONDIN REPEAT DOMAIN

<400> SEQUENCE: 7

Gln Asp Gly Gly Trp Ser His Trp Ser Pro Trp Ser Ser Cys Ser Val
1               5                   10                  15

Thr Cys Gly Asp Gly Val Ile Thr Arg Ile Arg Leu Cys Asn Ser Pro
            20                  25                  30

Ser Pro Gln Met Asn Gly Lys Pro Cys Glu Gly Glu Ala Arg Glu Thr
        35                  40                  45

Lys Ala Cys Lys Lys Asp Ala Cys Pro
    50                  55
```

<210> SEQ ID NO 8
<211> LENGTH: 165
<212> TYPE: PRT
<213> ORGANISM: Homo sapiens
<220> FEATURE:
<221> NAME/KEY: MISC_FEATURE
<223> OTHER INFORMATION: LEUCINE-RICH REPEAT DOMAIN

<400> SEQUENCE: 8

Leu His Leu Ser Glu Asn Leu Leu Tyr Thr Phe Ser Leu Ala Thr Leu
1               5                   10                  15

Met Pro Tyr Thr Arg Leu Thr Gln Leu Asn Leu Asp Arg Cys Glu Leu
            20                  25                  30

Thr Lys Leu Gln Val Asp Gly Thr Leu Pro Val Leu Gly Thr Leu Asp
        35                  40                  45

Leu Ser His Asn Gln Leu Gln Ser Leu Pro Leu Gly Gln Thr Leu
    50                  55                  60

Pro Ala Leu Thr Val Leu Asp Val Ser Phe Asn Arg Leu Thr Ser Leu
65                  70                  75                  80

Pro Leu Gly Ala Leu Arg Gly Leu Gly Glu Leu Gln Glu Leu Tyr Leu
                85                  90                  95

Lys Gly Asn Glu Leu Lys Thr Leu Pro Pro Gly Leu Leu Thr Pro Thr
            100                 105                 110

Pro Lys Leu Glu Lys Leu Ser Leu Ala Asn Asn Asn Leu Thr Glu Leu
        115                 120                 125

Pro Ala Gly Leu Leu Asn Gly Leu Glu Asn Leu Asp Thr Leu Leu Leu
130                 135                 140

Gln Glu Asn Ser Leu Tyr Thr Ile Pro Lys Gly Phe Phe Gly Ser His
145                 150                 155                 160

Leu Leu Pro Phe Ala
                165

<210> SEQ ID NO 9
<211> LENGTH: 6
<212> TYPE: PRT
<213> ORGANISM: Artificial Sequence
<220> FEATURE:
<223> OTHER INFORMATION: LINKER SEQUENCE
<220> FEATURE:
<221> NAME/KEY: MISC_FEATURE
<222> LOCATION: (1)..(2)
<223> OTHER INFORMATION: X IS INDEPENDENTLY ANY AMINO ACID RESIDUE
<220> FEATURE:
<221> NAME/KEY: MISC_FEATURE
<222> LOCATION: (4)..(5)
<223> OTHER INFORMATION: X IS INDEPENDENTLY ANY AMINO ACID RESIDUE

<400> SEQUENCE: 9

Xaa Xaa Asn Xaa Xaa Gly
1               5

<210> SEQ ID NO 10
<211> LENGTH: 4
<212> TYPE: PRT
<213> ORGANISM: Artificial Sequence
<220> FEATURE:
<223> OTHER INFORMATION: PEPTIDYL LINKER

<400> SEQUENCE: 10

Gly Gly Gly Gly
1

<210> SEQ ID NO 11
<211> LENGTH: 5

```
<212> TYPE: PRT
<213> ORGANISM: Artificial Sequence
<220> FEATURE:
<223> OTHER INFORMATION: PEPTIDYL LINKER

<400> SEQUENCE: 11

Gly Gly Gly Gly Gly
1               5

<210> SEQ ID NO 12
<211> LENGTH: 7
<212> TYPE: PRT
<213> ORGANISM: Artificial Sequence
<220> FEATURE:
<223> OTHER INFORMATION: PEPTIDYL LINKER

<400> SEQUENCE: 12

Gly Gly Gly Gly Gly Gly Gly
1               5

<210> SEQ ID NO 13
<211> LENGTH: 95
<212> TYPE: PRT
<213> ORGANISM: Homo sapiens
<220> FEATURE:
<221> NAME/KEY: MISC_FEATURE
<223> OTHER INFORMATION: TRUNCATED FRAGMENT OF HUMAN TENTH FIBRONECTIN
      III DOMAIN

<400> SEQUENCE: 13

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu
                85                  90                  95

<210> SEQ ID NO 14
<211> LENGTH: 6
<212> TYPE: PRT
<213> ORGANISM: Artificial Sequence
<220> FEATURE:
<223> OTHER INFORMATION: PEPTIDYL LINKER

<400> SEQUENCE: 14

Gly Gly Gly Gly Gly Lys
1               5

<210> SEQ ID NO 15
<211> LENGTH: 7
<212> TYPE: PRT
<213> ORGANISM: Artificial Sequence
<220> FEATURE:
<223> OTHER INFORMATION: PEPTIDYL LINKER

<400> SEQUENCE: 15

Gly Gly Gly Gly Gly Lys Arg
1               5
```

```
<210> SEQ ID NO 16
<211> LENGTH: 8
<212> TYPE: PRT
<213> ORGANISM: Artificial Sequence
<220> FEATURE:
<223> OTHER INFORMATION: PEPTIDYL LINKER

<400> SEQUENCE: 16

Gly Gly Gly Lys Gly Gly Gly Gly
1               5

<210> SEQ ID NO 17
<211> LENGTH: 8
<212> TYPE: PRT
<213> ORGANISM: Artificial Sequence
<220> FEATURE:
<223> OTHER INFORMATION: PEPTIDYL LINKER

<400> SEQUENCE: 17

Gly Gly Gly Asn Gly Ser Gly Gly
1               5

<210> SEQ ID NO 18
<211> LENGTH: 8
<212> TYPE: PRT
<213> ORGANISM: Artificial Sequence
<220> FEATURE:
<223> OTHER INFORMATION: PEPTIDYL LINKER

<400> SEQUENCE: 18

Gly Gly Gly Cys Gly Gly Gly Gly
1               5

<210> SEQ ID NO 19
<211> LENGTH: 5
<212> TYPE: PRT
<213> ORGANISM: Artificial Sequence
<220> FEATURE:
<223> OTHER INFORMATION: PEPTIDYL LINKER

<400> SEQUENCE: 19

Gly Pro Asn Gly Gly
1               5

<210> SEQ ID NO 20
<211> LENGTH: 7
<212> TYPE: PRT
<213> ORGANISM: Artificial Sequence
<220> FEATURE:
<223> OTHER INFORMATION: PEPTIDYL LINKER

<400> SEQUENCE: 20

Gly Gly Lys Gly Gly Gly Gly
1               5

<210> SEQ ID NO 21
<211> LENGTH: 5
<212> TYPE: PRT
<213> ORGANISM: Artificial Sequence
<220> FEATURE:
<223> OTHER INFORMATION: L5 LINKER SEQUENCE

<400> SEQUENCE: 21

Gly Gly Gly Gly Ser
1               5

<210> SEQ ID NO 22
<211> LENGTH: 10
```

```
<212> TYPE: PRT
<213> ORGANISM: Artificial Sequence
<220> FEATURE:
<223> OTHER INFORMATION: L10 LINKER SEQUENCE

<400> SEQUENCE: 22

Gly Gly Gly Gly Ser Gly Gly Gly Gly Ser
1               5                   10

<210> SEQ ID NO 23
<211> LENGTH: 25
<212> TYPE: PRT
<213> ORGANISM: Artificial Sequence
<220> FEATURE:
<223> OTHER INFORMATION: L25 LINKER SEQUENCE

<400> SEQUENCE: 23

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 24
<211> LENGTH: 6
<212> TYPE: PRT
<213> ORGANISM: Artificial Sequence
<220> FEATURE:
<223> OTHER INFORMATION: PEPTIDE LINKER SEQUENCE

<400> SEQUENCE: 24

Gly Gly Glu Gly Gly Gly
1               5

<210> SEQ ID NO 25
<211> LENGTH: 8
<212> TYPE: PRT
<213> ORGANISM: Artificial Sequence
<220> FEATURE:
<223> OTHER INFORMATION: PEPTIDE LINKER SEQUENCE

<400> SEQUENCE: 25

Gly Gly Glu Glu Glu Gly Gly Gly
1               5

<210> SEQ ID NO 26
<211> LENGTH: 5
<212> TYPE: PRT
<213> ORGANISM: Artificial Sequence
<220> FEATURE:
<223> OTHER INFORMATION: PEPTIDE LINKER SEQUENCE

<400> SEQUENCE: 26

Gly Glu Glu Glu Gly
1               5

<210> SEQ ID NO 27
<211> LENGTH: 4
<212> TYPE: PRT
<213> ORGANISM: Artificial Sequence
<220> FEATURE:
<223> OTHER INFORMATION: PEPTIDE LINKER SEQUENCE

<400> SEQUENCE: 27

Gly Glu Glu Glu
1

<210> SEQ ID NO 28
```

```
<211> LENGTH: 6
<212> TYPE: PRT
<213> ORGANISM: Artificial Sequence
<220> FEATURE:
<223> OTHER INFORMATION: PEPTIDE LINKER SEQUENCE

<400> SEQUENCE: 28

Gly Gly Asp Gly Gly Gly
1               5

<210> SEQ ID NO 29
<211> LENGTH: 7
<212> TYPE: PRT
<213> ORGANISM: Artificial Sequence
<220> FEATURE:
<223> OTHER INFORMATION: PEPTIDE LINKER SEQUENCE

<400> SEQUENCE: 29

Gly Gly Asp Asp Asp Gly Gly
1               5

<210> SEQ ID NO 30
<211> LENGTH: 5
<212> TYPE: PRT
<213> ORGANISM: Artificial Sequence
<220> FEATURE:
<223> OTHER INFORMATION: PEPTIDE LINKER SEQUENCE

<400> SEQUENCE: 30

Gly Asp Asp Asp Gly
1               5

<210> SEQ ID NO 31
<211> LENGTH: 4
<212> TYPE: PRT
<213> ORGANISM: Artificial Sequence
<220> FEATURE:
<223> OTHER INFORMATION: PEPTIDE LINKER SEQUENCE

<400> SEQUENCE: 31

Gly Asp Asp Asp
1

<210> SEQ ID NO 32
<211> LENGTH: 21
<212> TYPE: PRT
<213> ORGANISM: Artificial Sequence
<220> FEATURE:
<223> OTHER INFORMATION: PEPTIDE LINKER SEQUENCE

<400> SEQUENCE: 32

Gly Gly Gly Gly Ser Asp Asp Ser Asp Glu Gly Ser Asp Glu Asp
1               5                   10                  15

Gly Gly Gly Gly Ser
            20

<210> SEQ ID NO 33
<211> LENGTH: 5
<212> TYPE: PRT
<213> ORGANISM: Artificial Sequence
<220> FEATURE:
<223> OTHER INFORMATION: PEPTIDE LINKER SEQUENCE

<400> SEQUENCE: 33

Trp Glu Trp Glu Trp
1               5
```

```
<210> SEQ ID NO 34
<211> LENGTH: 5
<212> TYPE: PRT
<213> ORGANISM: Artificial Sequence
<220> FEATURE:
<223> OTHER INFORMATION: PEPTIDE LINKER SEQUENCE

<400> SEQUENCE: 34

Phe Glu Phe Glu Phe
1               5

<210> SEQ ID NO 35
<211> LENGTH: 6
<212> TYPE: PRT
<213> ORGANISM: Artificial Sequence
<220> FEATURE:
<223> OTHER INFORMATION: PEPTIDE LINKER SEQUENCE

<400> SEQUENCE: 35

Glu Glu Glu Trp Trp Trp
1               5

<210> SEQ ID NO 36
<211> LENGTH: 6
<212> TYPE: PRT
<213> ORGANISM: Artificial Sequence
<220> FEATURE:
<223> OTHER INFORMATION: PEPTIDE LINKER SEQUENCE

<400> SEQUENCE: 36

Glu Glu Glu Phe Phe Phe
1               5

<210> SEQ ID NO 37
<211> LENGTH: 7
<212> TYPE: PRT
<213> ORGANISM: Artificial Sequence
<220> FEATURE:
<223> OTHER INFORMATION: PEPTIDE LINKER SEQUENCE

<400> SEQUENCE: 37

Trp Trp Glu Glu Glu Trp Trp
1               5

<210> SEQ ID NO 38
<211> LENGTH: 7
<212> TYPE: PRT
<213> ORGANISM: Artificial Sequence
<220> FEATURE:
<223> OTHER INFORMATION: PEPTIDE LINKER SEQUENCE

<400> SEQUENCE: 38

Phe Phe Glu Glu Glu Phe Phe
1               5

<210> SEQ ID NO 39
<211> LENGTH: 6
<212> TYPE: PRT
<213> ORGANISM: Artificial Sequence
<220> FEATURE:
<223> OTHER INFORMATION: PEPTIDE LINKER SEQUENCE
<220> FEATURE:
<221> NAME/KEY: MISC_FEATURE
<222> LOCATION: (1)..(2)
<223> OTHER INFORMATION: X IS INDEPENDENTLY ANY AMINO ACID RESIDUE
<220> FEATURE:
<221> NAME/KEY: MISC_FEATURE
<222> LOCATION: (4)..(5)
<223> OTHER INFORMATION: X IS INDEPENDENTLY ANY AMINO ACID RESIDUE
```

```
<400> SEQUENCE: 39

Xaa Xaa Tyr Xaa Xaa Gly
1               5

<210> SEQ ID NO 40
<211> LENGTH: 6
<212> TYPE: PRT
<213> ORGANISM: Artificial Sequence
<220> FEATURE:
<223> OTHER INFORMATION: PEPTIDE LINKER SEQUENCE
<220> FEATURE:
<221> NAME/KEY: MISC_FEATURE
<222> LOCATION: (1)..(2)
<223> OTHER INFORMATION: X IS INDEPENDENTLY ANY AMINO ACID RESIDUE
<220> FEATURE:
<221> NAME/KEY: MISC_FEATURE
<222> LOCATION: (4)..(5)
<223> OTHER INFORMATION: X IS INDEPENDENTLY ANY AMINO ACID RESIDUE

<400> SEQUENCE: 40

Xaa Xaa Ser Xaa Xaa Gly
1               5

<210> SEQ ID NO 41
<211> LENGTH: 6
<212> TYPE: PRT
<213> ORGANISM: Artificial Sequence
<220> FEATURE:
<223> OTHER INFORMATION: PEPTIDE LINKER SEQUENCE
<220> FEATURE:
<221> NAME/KEY: MISC_FEATURE
<222> LOCATION: (1)..(2)
<223> OTHER INFORMATION: X IS INDEPENDENTLY ANY AMINO ACID RESIDUE
<220> FEATURE:
<221> NAME/KEY: MISC_FEATURE
<222> LOCATION: (4)..(5)
<223> OTHER INFORMATION: X IS INDEPENDENTLY ANY AMINO ACID RESIDUE

<400> SEQUENCE: 41

Xaa Xaa Thr Xaa Xaa Gly
1               5

<210> SEQ ID NO 42
<211> LENGTH: 22
<212> TYPE: PRT
<213> ORGANISM: Artificial Sequence
<220> FEATURE:
<223> OTHER INFORMATION: PEPTIDE LINKER SEQUENCE

<400> SEQUENCE: 42

Gly Ser Gly Ser Ala Thr Gly Gly Ser Gly Ser Thr Ala Ser Ser Gly
1               5                   10                  15

Ser Gly Ser Ala Thr His
            20

<210> SEQ ID NO 43
<211> LENGTH: 22
<212> TYPE: PRT
<213> ORGANISM: Artificial Sequence
<220> FEATURE:
<223> OTHER INFORMATION: PEPTIDE LINKER SEQUENCE

<400> SEQUENCE: 43

His Gly Ser Gly Ser Ala Thr Gly Gly Ser Gly Ser Thr Ala Ser Ser
1               5                   10                  15

Gly Ser Gly Ser Ala Thr
            20
```

```
<210> SEQ ID NO 44
<211> LENGTH: 19
<212> TYPE: PRT
<213> ORGANISM: Artificial Sequence
<220> FEATURE:
<223> OTHER INFORMATION: RIDGID PEPTIDE LINKER SEQUENCE

<400> SEQUENCE: 44

Ala Glu Ala Ala Ala Lys Glu Ala Ala Ala Lys Glu Ala Ala Ala Lys
1               5                   10                  15

Ala Gly Gly

<210> SEQ ID NO 45
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 45

His Gly Glu Gly Thr Phe Thr Ser Asp Gln Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 46

His Gly Glu Gly Thr Phe Thr Ser Asp Gln Ser Ser Tyr Leu Glu Gly
1               5                   10                  15

Gln Ala Ala Lys Glu Phe Ile Ala Trp Leu Gln Lys Gly Arg Gly
            20                  25                  30

<210> SEQ ID NO 47
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 47

His Gly Glu Gly Thr Phe Thr Ser Asp Val Ser Ser Tyr Gln Glu Gly
1               5                   10                  15

Gln Ala Ala Lys Glu Phe Ile Ala Trp Leu Val Lys Gly Arg Gly
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 48

His Gly Glu Gly Thr Phe Thr Ser Asp Val Ser Ser Tyr Leu Glu Gly
1               5                   10                  15

Gln Ala Ala Lys Glu Phe Ile Ala Gln Leu Val Lys Gly Arg Gly
```

-continued

<210> SEQ ID NO 49
<211> LENGTH: 12
<212> TYPE: PRT
<213> ORGANISM: Artificial Sequence
<220> FEATURE:
<223> OTHER INFORMATION: AFFINITY PURIFICATION TAG
<220> FEATURE:
<221> NAME/KEY: MISC_FEATURE
<222> LOCATION: (12)..(12)
<223> OTHER INFORMATION: Xaa is glycine or absent

<400> SEQUENCE: 49

Met Gly Gly His His His His His His Gly Gly Xaa
1               5                   10

<210> SEQ ID NO 50
<211> LENGTH: 96
<212> TYPE: PRT
<213> ORGANISM: Homo sapiens
<220> FEATURE:
<221> NAME/KEY: MISC_FEATURE
<223> OTHER INFORMATION: HUMAN TENTH FIBRONECTIN III DOMAIN

<400> SEQUENCE: 50

Thr Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
                20                  25                  30

Tyr Arg Ile Thr Tyr Gly Glu Thr Gly Gly Asn Ser Pro Val Gln Glu
            35                  40                  45

Phe Thr Val Pro Gly Ser Lys Ser Thr Ala Thr Ile Ser Gly Leu Lys
50                  55                  60

Pro Gly Val Asp Tyr Thr Ile Thr Val Tyr Ala Val Thr Gly Arg Gly
65                  70                  75                  80

Asp Ser Pro Ala Ser Ser Lys Pro Ile Ser Ile Asn Tyr Arg Thr Glu
                85                  90                  95

<210> SEQ ID NO 51
<211> LENGTH: 69
<212> TYPE: DNA
<213> ORGANISM: Artificial Sequence
<220> FEATURE:
<223> OTHER INFORMATION: PRIMER SEQUENCE

<400> SEQUENCE: 51
gaggaataac atatgaaaca tcatcatcat catcatggtg gtaaagtttt tcgcgcactt     60
tatacctttt                                                           69

<210> SEQ ID NO 52
<211> LENGTH: 20
<212> TYPE: DNA
<213> ORGANISM: Artificial Sequence
<220> FEATURE:
<223> OTHER INFORMATION: PRIMER SEQUENCE

<400> SEQUENCE: 52
gttattgctc agcggtggca                                                20

<210> SEQ ID NO 53
<211> LENGTH: 65
<212> TYPE: DNA
<213> ORGANISM: Artificial Sequence
<220> FEATURE:

-continued

<223> OTHER INFORMATION: PRIMER SEQUENCE

<400> SEQUENCE: 53

```
aggaataaca tatgaaacat catcatcatc atcatggtgg tccgggcgaa gttcgtcttg    60
ttagt                                                                65
```

<210> SEQ ID NO 54
<211> LENGTH: 65
<212> TYPE: DNA
<213> ORGANISM: Artificial Sequence
<220> FEATURE:
<223> OTHER INFORMATION: PRIMER SEQUENCE

<400> SEQUENCE: 54

```
aggaataaca tatgaaacat catcatcatc atcatggtgg tccgggcgaa gttcgtcttg    60
ttagt                                                                65
```

<210> SEQ ID NO 55
<211> LENGTH: 66
<212> TYPE: DNA
<213> ORGANISM: Artificial Sequence
<220> FEATURE:
<223> OTHER INFORMATION: PRIMER SEQUENCE

<400> SEQUENCE: 55

```
gaggaataac atatgaaaca tcatcatcat catcatggtg gtaccgtaag cgatgtacca    60
cgcgat                                                               66
```

<210> SEQ ID NO 56
<211> LENGTH: 20
<212> TYPE: DNA
<213> ORGANISM: Artificial Sequence
<220> FEATURE:
<223> OTHER INFORMATION: PRIMER SEQUENCE

<400> SEQUENCE: 56

```
gttattgctc agcggtggca                                                20
```

<210> SEQ ID NO 57
<211> LENGTH: 6118
<212> TYPE: DNA
<213> ORGANISM: Artificial Sequence
<220> FEATURE:
<223> OTHER INFORMATION: pAMG21 (BamHI) Nucleotide Sequence

<400> SEQUENCE: 57

```
gatcagcagt ccccggaaca tcgtagctga cgccttcgcg ttgctcagtt gtccaacccc    60
ggaaacggga aaagcaagt tttccccgct cccggcgttt caataactga aaaccatact    120
atttcacagt ttaaatcaca ttaaacgaca gtaatccccg ttgatttgtg cgccaacaca    180
gatcttcgtc acaattctca agtcgctgat ttcaaaaaac tgtagtatcc tctgcgaaac    240
gatccctgtt tgagtattga ggaggcgaga tgtcgcagac agaaaatgca gtgacttcct    300
cattgagtca aaagcggttt gtgcgcagag gtaagcctat gactgactct gagaaacaaa    360
tggccgttgt tgcaagaaaa cgtcttacac acaaagagat aaaagttttt gtcaaaaatc    420
ctctgaagga tctcatggtt gagtactgcg agagagaggg gataacacag gctcagttcg    480
ttgagaaaat catcaaagat gaactgcaaa gactggatat actaaagtaa agactttact    540
ttgtggcgta gcatgctaga ttactgatcg tttaaggaat tttgtggctg gccacgccgt    600
aaggtggcaa ggaactggtt ctgatgtgga tttacaggag ccagaaaagc aaaaccccg    660
```

-continued

```
ataatcttct tcaacttttg cgagtacgaa aagattaccg gggcccactt aaaccgtata    720
gccaacaatt cagctatgcg gggagtatag ttatatgccc ggaaaagttc aagacttctt    780
tctgtgctcg ctccttctgc gcattgtaag tgcaggatgg tgtgactgat cttcaccaaa    840
cgtattaccg ccaggtaaag aacccgaatc cggtgtttac accccgtgaa ggtgcaggaa    900
cgctgaagtt ctgcgaaaaa ctgatggaaa aggcggtggg cttcacttcc cgttttgatt    960
tcgccattca tgtggcgcac gcccgttcgc gtgatctgcg tcgccgtatg ccaccagtgc   1020
tgcgtcgtcg ggctattgat gcgctcttgc aggggctgtg tttccactat gacccgctgg   1080
ccaaccgcgt ccagtgctcc atcaccacgc tggccattga gtgcggactg gcgacggagt   1140
ctgctgccgg aaaactctcc atcacccgtg ccacccgtgc cctgacgttc ctgtcagagc   1200
tgggactgat tacctaccag acggaatatg acccgcttat cgggtgctac attccgaccg   1260
atatcacgtt cacatctgca ctgtttgctg ccctcgatgt atcagaggag gcagtggccg   1320
ccgcgcgccg cagccgtgtg gtatgggaaa acaaacaacg caaaaagcag gggctggata   1380
ccctgggcat ggatgaactg atagcgaaag cctggcgttt tgttcgtgag cgttttcgca   1440
gttatcagac agagcttaag tcccgtggaa taaagcgtgc ccgtgcgcgt cgtgatgcgg   1500
acagggaacg tcaggatatt gtcaccctgg tgaaacggca gctgacgcgc gaaatcgcgg   1560
aagggcgctt cactgccaat cgtgaggcgg taaaacgcga agttgagcgt cgtgtgaagg   1620
agcgcatgat tctgtcacgt aaccgtaatt acagccggct ggccacagct tcccctgaa    1680
agtgacctcc tctgaataat ccggcctgcg ccggaggctt ccgcacgtct gaagcccgac   1740
agcgcacaaa aaatcagcac cacatacaaa aaacaacctc atcatccagc ttctggtgca   1800
tccggccccc cctgttttcg atacaaaaca cgcctcacag acggggaatt ttgcttatcc   1860
acattaaact gcaagggact tccccataag gttacaaccg ttcatgtcat aaagcgccat   1920
ccgccagcgt tacagggtgc aatgtatctt ttaaacacct gtttatatct cctttaaact   1980
acttaattac attcatttaa aaagaaaacc tattcactgc ctgtccttgg acagacagat   2040
atgcacctcc caccgcaagc ggcgggcccc taccggagcc gctttagtta caacactcag   2100
acacaaccac cagaaaaacc ccggtccagc gcagaactga aaccacaaag cccctccctc   2160
ataactgaaa agcggccccg ccccggtccg aagggccgga acagagtcgc ttttaattat   2220
gaatgttgta actacttcat catcgctgtc agtcttctcg ctggaagttc tcagtacacg   2280
ctcgtaagcg gccctgacgg cccgctaacg cggagatacg ccccgacttc gggtaaaccc   2340
tcgtcgggac cactccgacc gcgcacgaaa gctctctcat ggctgaaagc gggtatggtc   2400
tggcagggct ggggatgggt aaggtgaaat ctatcaatca gtaccggctt acgccgggct   2460
tcggcggttt tactcctgtt tcatatatga acaacaggt caccgccttc catgccgctg   2520
atgcggcata tcctggtaac gatatctgaa ttgttataca tgtgtatata cgtggtaatg   2580
acaaaaatag acaagttaa aaatttacag gcgatgcaat gattcaaaca cgtaatcaat   2640
atcggggtg ggcgaagaac tccagcatga atccccgcg ctggaggatc atccagccgg   2700
cgtcccggaa aacgattccg aagcccaacc tttcatagaa ggcggcggtg aatcgaaat   2760
ctcgtgatgg caggttgggc gtcgcttggt cggtcatttc gaaccccaga gtcccgctca   2820
gaagaactcg tcaagaaggc gatagaaggc gatgcgctgc gaatcgggag cggcgatacc   2880
gtaaagcacg aggaagcggt cagcccattc gccgccaagc tcttcagcaa tatcacgggt   2940
agccaacgct atgtcctgat agcggtccgc cacacccagc cggccacagt cgatgaatcc   3000
agaaaagcgg ccatttttcca ccatgatatt cggcaagcag gcatcgccat gagtcacgac   3060
```

```
gagatcctcg ccgtcgggca tgcgcgcctt gagcctggcg aacagttcgg ctggcgcgag    3120
cccctgatgc tcttcgtcca gatcatcctg atcgacaaga ccggcttcca tccgagtacg    3180
tgctcgctcg atgcgatgtt tcgcttggtg gtcgaatggg caggtagccg gatcaagcgt    3240
atgcagccgc cgcattgcat cagccatgat ggatactttc tcggcaggag caaggtgaga    3300
tgacaggaga tcctgccccg gcacttcgcc caatagcagc cagtcccttc ccgcttcagt    3360
gacaacgtcg agcacagctg cgcaaggaac gcccgtcgtg gccagccacg atagccgcgc    3420
tgcctcgtcc tgcaattcat tcaggacacc ggacaggtcg gtcttgacaa aaagaaccgg    3480
gcgcccctgc gctgacagcc ggaacacggc ggcatcagag cagccgattg tctgttgtgc    3540
ccagtcatag ccgaatagcc tctccaccca agcggccgga gaacctgcgt gcaatccatc    3600
ttgttcaatc atgcgaaacg atcctcatcc tgtctcttga tctgatcttg atcccctgcg    3660
ccatcagatc cttggcggca agaaagccat ccagtttact ttgcagggct tcccaacctt    3720
accagagggc gccccagctg gcaattccgg ttcgcttgct gtccataaaa ccgcccagtc    3780
tagctatcgc catgtaagcc cactgcaagc tacctgcttt ctctttgcgc ttgcgttttc    3840
ccttgtccag atagcccagt agctgacatt catccggggt cagcaccgtt tctgcggact    3900
ggctttctac gtgttccgct tccttttagca gcccttgcgc cctgagtgct gcggcagcg    3960
tgaagctaca tatatgtgat ccgggcaaat cgctgaatat tccttttgtc tccgaccatc    4020
aggcacctga gtcgctgtct ttttcgtgac attcagttcg ctgcgctcac ggctctggca    4080
gtgaatgggg gtaaatggca ctacaggcgc ctttttatgga ttcatgcaag gaaactaccc    4140
ataatacaag aaaagcccgt cacgggcttc tcagggcgtt ttatggcggg tctgctatgt    4200
ggtgctatct gacttttttgc tgttcagcag ttcctgccct ctgattttcc agtctgacca    4260
cttcggatta tcccgtgaca ggtcattcag actggctaat gcacccagta aggcagcggt    4320
atcatcaaca ggcttacccg tcttactgtc gaagacgtgc gtaacgtatg catggtctcc    4380
ccatgcgaga gtagggaact gccaggcatc aaataaaacg aaaggctcag tcgaaagact    4440
gggcctttcg ttttatctgt tgtttgtcgg tgaacgctct cctgagtagg acaaatccgc    4500
cgggagcgga tttgaacgtt gcgaagcaac ggcccgagg gtggcgggca ggacgcccgc    4560
cataaactgc caggcatcaa attaagcaga aggccatcct gacggatggc cttttttgcgt    4620
ttctacaaac tcttttgttt atttttctaa atacattcaa atatggacgt cgtacttaac    4680
ttttaaagta tgggcaatca attgctcctg ttaaaattgc tttagaaata ctttggcagc    4740
ggtttgttgt attgagtttc atttgcgcat tggttaaatg gaaagtgacc gtgcgcttac    4800
tacagcctaa tattttttgaa atatcccaag agcttttttcc ttcgcatgcc cacgctaaac    4860
attcttttttc tcttttggtt aaatcgttgt ttgatttatt atttgctata tttattttttc    4920
gataattatc aactagagaa ggaacaatta atggtatgtt catacacgca tgtaaaaata    4980
aactatctat atagttgtct ttctctgaat gtgcaaaact aagcattccg aagccattat    5040
tagcagtatg aatagggaaa ctaaacccag tgataagacc tgatgatttc gcttctttaa    5100
ttacatttgg agatttttta tttacagcat tgttttcaaa tatattccaa ttaatcggtg    5160
aatgattgga gttagaataa tctactatag gatcatattt tattaaatta gcgtcatcat    5220
aatattgcct ccatttttta gggtaattat ccagaattga aatatcagat ttaaccatag    5280
aatgaggata aatgatcgcg agtaaataat attcacaatg taccatttta gtcatatcag    5340
ataagcattg attaatatca ttattgcttc tacaggcttt aattttattta attattctgt    5400
aagtgtcgtc ggcatttatg tctttcatac ccatctcttt atccttacct attgtttgtc    5460
```

| | |
|---|---|
| gcaagttttg cgtgttatat atcattaaaa cggtaataga ttgacatttg attctaataa | 5520 |
| attggatttt tgtcacacta ttatatcgct tgaaatacaa ttgtttaaca taagtacctg | 5580 |
| taggatcgta caggtttacg caagaaaatg gtttgttata gtcgattaat cgatttgatt | 5640 |
| ctagatttgt tttaactaat taaaggagga ataacatatg gttaacgcgt tggaattcga | 5700 |
| gctcactagt gtcgacctgc agggtaccat ggaagcttac tcgaagatcc gcggaagaa | 5760 |
| gaagaagaag aagaaagccc gaaggaagc tgagttggct gctgccaccg ctgagcaata | 5820 |
| actagcataa cccccttgggg cctctaaacg ggtcttgagg ggttttttgc tgaaaggagg | 5880 |
| aaccgctctt cacgctcttc acgcggataa ataagtaacg atccggtcca gtaatgacct | 5940 |
| cagaactcca tctggatttg ttcagaacgc tcggttgccg ccgggcgttt tttattggtg | 6000 |
| agaatcgcag caacttgtcg cgccaatcga gccatgtcgt cgtcaacgac cccccattca | 6060 |
| agaacagcaa gcagcattga gaactttgga atccagtccc tcttccacct gctgaccg | 6118 |

<210> SEQ ID NO 58
<211> LENGTH: 5422
<212> TYPE: DNA
<213> ORGANISM: Artificial Sequence
<220> FEATURE:
<223> OTHER INFORMATION: pET30 Nucleotide Sequence

<400> SEQUENCE: 58

| | |
|---|---|
| atccggatat agttcctcct ttcagcaaaa aacccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gcaagcttgt | 180 |
| cgacggagct cgaattcgga tccgatatca gccatggcct tgtcgtcgtc gtcggtaccc | 240 |
| agatctgggc tgtccatgtg ctggcgttcg aatttagcag cagcggtttc tttcatacca | 300 |
| gaaccgcgtg gcaccagacc agaagaatga tgatgatgat ggtgcatatg tatatctcct | 360 |
| tcttaaagtt aaacaaaatt atttctagag gggaattgtt atccgctcac aattccccta | 420 |
| tagtgagtcg tattaatttc gcgggatcga gatcgatctc gatcctctac gccggacgca | 480 |
| tcgtggccgg catcaccggc gccacaggtg cggttgctgg cgcctatatc gccgacatca | 540 |
| ccgatgggga agatcgggct cgccacttcg ggctcatgag cgcttgtttc ggcgtgggta | 600 |
| tggtggcagg ccccgtggcc ggggactgt tgggcgccat ctccttgcat gcaccattcc | 660 |
| ttgcggcggc ggtgctcaac ggcctcaacc tactactggg ctgcttccta atgcaggagt | 720 |
| cgcataaggg agagcgtcga gatcccggac accatcgaat ggcgcaaaac ctttcgcggt | 780 |
| atggcatgat agcgcccgga agagagtcaa ttcagggtgg tgaatgtgaa accagtaacg | 840 |
| ttatacgatg tcgcagagta tgccggtgtc tcttatcaga ccgtttcccg cgtggtgaac | 900 |
| caggccagcc acgtttctgc gaaaacgcgg gaaaaagtgg aagcggcgat ggcggagctg | 960 |
| aattacattc ccaaccgcgt ggcacaacaa ctggcgggca aacagtcgtt gctgattggc | 1020 |
| gttgccacct ccagtctggc cctgcacgcg ccgtcgcaaa ttgtcgcggc gattaaatct | 1080 |
| cgcgccgatc aactgggtgc cagcgtggtg gtgtcgatgg tagaacgaag cggcgtcgaa | 1140 |
| gcctgtaaag cggcggtgca caatcttctc gcgcaacgcg tcagtgggct gatcattaac | 1200 |
| tatccgctgg atgaccagga tgccattgct gtggaagctg cctgcactaa tgttccggcg | 1260 |
| ttatttcttg atgtctctga ccagacaccc atcaacagta ttattttctc ccatgaagac | 1320 |
| ggtacgcgac tgggcgtgga gcatctggtc gcattgggtc accagcaaat cgcgctgtta | 1380 |
| gcgggcccat taagttctgt ctcggcgcgt ctgcgtctgg ctggctggca taaatatctc | 1440 |

-continued

```
actcgcaatc aaattcagcc gatagcggaa cgggaaggcg actggagtgc catgtccggt    1500
tttcaacaaa ccatgcaaat gctgaatgag ggcatcgttc ccactgcgat gctggttgcc    1560
aacgatcaga tggcgctggg cgcaatgcgc gccattaccg agtccgggct gcgcgttggt    1620
gcggacatct cggtagtggg atacgacgat accgaagaca gctcatgtta tatcccgccg    1680
ttaaccacca tcaaacagga ttttcgcctg ctggggcaaa ccagcgtgga ccgcttgctg    1740
caactctctc agggccaggc ggtgaagggc aatcagctgt tgcccgtctc actggtgaaa    1800
agaaaaacca ccctggcgcc caatacgcaa accgcctctc cccgcgcgtt ggccgattca    1860
ttaatgcagc tggcacgaca ggtttcccga ctggaaagcg ggcagtgagc gcaacgcaat    1920
taatgtaagt tagctcactc attaggcacc gggatctcga ccgatgccct tgagagcctt    1980
caacccagtc agctccttcc ggtgggcgcg ggcatgact atcgtcgccg cacttatgac     2040
tgtcttcttt atcatgcaac tcgtaggaca ggtgccggca gcgctctggg tcattttcgg    2100
cgaggaccgc tttcgctgga gcgcgacgat gatcggcctg tcgcttgcgg tattcggaat    2160
cttgcacgcc ctcgctcaag ccttcgtcac tggtcccgcc accaaacgtt tcggcgagaa    2220
gcaggccatt atcgccggca tggcggcccc acgggtgcgc atgatcgtgc tcctgtcgtt    2280
gaggacccgg ctaggctggc ggggttgcct tactggttag cagaatgaat caccgatacg    2340
cgagcgaacg tgaagcgact gctgctgcaa aacgtctgcg acctgagcaa caacatgaat    2400
ggtcttcggt ttccgtgttt cgtaaagtct ggaaacgcgg aagtcagcgc cctgcaccat    2460
tatgttccgg atctgcatcg caggatgctg ctggctaccc tgtggaacac ctacatctgt    2520
attaacgaag cgctggcatt gaccctgagt gattttctc tggtcccgcc gcatccatac     2580
cgccagttgt ttaccctcac aacgttccag taaccgggca tgttcatcat cagtaacccg    2640
tatcgtgagc atcctctctc gtttcatcgg tatcattacc cccatgaaca gaaatccccc    2700
ttacacggag gcatcagtga ccaaacagga aaaaaccgcc cttaacatgg cccgctttat    2760
cagaagccag acattaacgc ttctggagaa actcaacgag ctggacgcgg atgaacaggc    2820
agacatctgt gaatcgcttc acgaccacgc tgatgagctt taccgcagct gcctcgcgcg    2880
tttcggtgat gacggtgaaa acctctgaca catgcagctc ccggagacgg tcacagcttg    2940
tctgtaagcg gatgccggga gcagacaagc ccgtcagggc gcgtcagcgg gtgttggcgg    3000
gtgtcggggc gcagccatga cccagtcacg tagcgatagc ggagtgtata ctggcttaac    3060
tatgcggcat cagagcagat tgtactgaga gtgcaccata tatgcggtgt gaaataccgc    3120
acagatgcgt aaggagaaaa taccgcatca ggcgctcttc cgcttcctcg ctcactgact    3180
cgctgcgctc ggtcgttcgg ctgcggcgag cggtatcagc tcactcaaag gcggtaatac    3240
ggttatccac agaatcaggg gataacgcag gaaagaacat gtgagcaaaa ggccagcaaa    3300
aggccaggaa ccgtaaaaag gccgcgttgc tggcgttttt ccataggctc cgccccctg     3360 acgagcatca caaaaatcga cgctcaagtc agaggtggcg aaacccgaca ggactataaa    3420
gataccaggc gtttccccct ggaagctccc tcgtgcgctc tcctgttccg accctgccgc    3480
ttaccggata cctgtccgcc tttctccctt cgggaagcgt ggcgctttct catagctcac    3540
gctgtaggta tctcagttcg gtgtaggtcg ttcgctccaa gctgggctgt gtgcacgaac    3600
cccccgttca gcccgaccgc tgcgccttat ccggtaacta tcgtcttgag tccaacccgg    3660
taagacacga cttatcgcca ctggcagcag ccactggtaa caggattagc agagcgaggt    3720
atgtaggcgg tgctacagag ttcttgaagt ggtggcctaa ctacggctac actagaagga    3780
cagtatttgg tatctgcgct ctgctgaagc cagttacctt cggaaaaaga gttggtagct    3840
```

```
cttgatccgg caaacaaacc accgctggta gcggtggttt ttttgtttgc aagcagcaga    3900
ttacgcgcag aaaaaaagga tctcaagaag atcctttgat cttttctacg gggtctgacg    3960
ctcagtggaa cgaaaactca cgttaaggga ttttggtcat gaacaataaa actgtctgct    4020
tacataaaca gtaatacaag gggtgttatg agccatattc aacgggaaac gtcttgctct    4080
aggccgcgat taaattccaa catggatgct gatttatatg ggtataaatg gctcgcgat    4140 aatgtcgggc aatcaggtgc gacaatctat cgattgtatg ggaagcccga tgcgccagag    4200
ttgtttctga acatggcaa aggtagcgtt gccaatgatg ttacagatga gatggtcaga    4260
ctaaactggc tgacggaatt tatgcctctt ccgaccatca agcatttat ccgtactcct     4320 gatgatgcat ggttactcac cactgcgatc cccgggaaaa cagcattcca ggtattagaa    4380
gaatatcctg attcaggtga aaatattgtt gatgcgctgg cagtgttcct gcgccggttg    4440
cattcgattc ctgtttgtaa ttgtcctttt aacagcgatc gcgtatttcg tctcgctcag    4500
gcgcaatcac gaatgaataa cggtttggtt gatgcgagtg attttgatga cgagcgtaat    4560
ggctggcctg ttgaacaagt ctggaaagaa atgcataaac ttttgccatt ctcaccggat    4620
tcagtcgtca ctcatggtga tttctcactt gataaccta ttttttgacga ggggaaatta    4680 ataggttgta ttgatgttgg acgagtcgga atcgcagacc gataccagga tcttgccatc    4740
ctatggaact gcctcggtga gttttctcct tcattacaga aacggctttt tcaaaaatat    4800
ggtattgata atcctgatat gaataaattg cagtttcatt tgatgctcga tgagtttttc    4860
taagaattaa ttcatgagcg gatacatatt tgaatgtatt tagaaaaata acaaataggg    4920
ggttccgcgc acatttcccc gaaaagtgcc acctgaaatt gtaaacgtta atattttgtt    4980
aaaattcgcg ttaaattttt gttaaatcag ctcatttttt aaccaatagg ccgaaatcgg    5040
caaaatccct tataaatcaa aagaatagac cgagataggg ttgagtgttg ttccagtttg    5100
gaacaagagt ccactattaa agaacgtgga ctccaacgtc aaagggcgaa aaaccgtcta    5160
tcagggcgat ggcccactac gtgaaccatc accctaatca agttttttgg ggtcgaggtg    5220
ccgtaaagca ctaaatcgga acccctaaagg gagcccccga tttagagctt gacggggaaa    5280
gccggcgaac gtggcgagaa aggaagggaa gaaagcgaaa ggagcgggcg ctagggcgct    5340
ggcaagtgta gcggtcacgc tgcgcgtaac caccacaccc gccgcgctta atgcgccgct    5400
acagggcgcg tcccattcgc ca                                              5422
```

<210> SEQ ID NO 59
<211> LENGTH: 121
<212> TYPE: PRT
<213> ORGANISM: Artificial Sequence
<220> FEATURE:
<223> OTHER INFORMATION: PTH-HP76 Fusion Protein

<400> SEQUENCE: 59

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Gly Gly Gly Gly Val Phe Asn Ala Asn Ser Asn Leu Ser
            35                  40                  45

Ser Gly Pro Leu Pro Ile Phe Pro Leu Glu Gln Leu Val Asn Lys Pro
        50                  55                  60

Val Glu Glu Leu Pro Glu Gly Val Asp Pro Ser Arg Lys Glu Glu His
65                  70                  75                  80

Leu Ser Ile Glu Asp Phe Thr Gln Ala Phe Gly Met Thr Pro Ala Ala
```

```
                           85                  90                  95
Phe Ser Ala Leu Pro Arg Trp Lys Gln Gln Cys Leu Lys Lys Glu Lys
            100                 105                 110

Gly Leu Phe His His His His His His
        115                 120

<210> SEQ ID NO 60
<211> LENGTH: 35
<212> TYPE: PRT
<213> ORGANISM: Gallus domesticus
<220> FEATURE:
<221> NAME/KEY: MISC_FEATURE
<223> OTHER INFORMATION: HP-35 SUBDOMAIN OF VILLIN HEADPIECE DOMAIN

<400> SEQUENCE: 60

Leu Ser Asp Glu Asp Phe Lys Ala Val Phe Gly Met Thr Arg Ser Ala
1               5                   10                  15

Phe Ala Asn Leu Pro Leu Trp Lys Gln Gln Asn Leu Lys Lys Glu Lys
            20                  25                  30

Gly Leu Phe
        35

<210> SEQ ID NO 61
<211> LENGTH: 35
<212> TYPE: PRT
<213> ORGANISM: Homo sapiens
<220> FEATURE:
<221> NAME/KEY: MISC_FEATURE
<223> OTHER INFORMATION: HP-35 SUBDOMAIN OF VILLIN HEADPIECE DOMAIN

<400> SEQUENCE: 61

Leu Ser Ile Glu Asp Phe Thr Gln Ala Phe Gly Met Thr Pro Ala Ala
1               5                   10                  15

Phe Ser Ala Leu Pro Arg Trp Lys Gln Gln Asn Leu Lys Lys Glu Lys
            20                  25                  30

Gly Leu Phe
        35

<210> SEQ ID NO 62
<211> LENGTH: 481
<212> TYPE: DNA
<213> ORGANISM: Artificial Sequence
<220> FEATURE:
<223> OTHER INFORMATION: M-G2-H6-G3-10th Fn3-(G4S)2-OsK1
<220> FEATURE:
<221> NAME/KEY: exon
<222> LOCATION: (4)..(471)

<400> SEQUENCE: 62 cat atg ggt ggt cat cat cat cat cat cat ggt ggt ggt acc gta agc     48
    Met Gly Gly His His His His His His Gly Gly Gly Thr Val Ser
    1               5                   10                  15 gat gta cca cgc gat ctg gaa gta gta gct gcc aca cca acc tct ttg     96
Asp Val Pro Arg Asp Leu Glu Val Val Ala Ala Thr Pro Thr Ser Leu
            20                  25                  30 ctg atc tct tgg gac gca cct gca gtt aca gtc cgc tat tat cgt att    144
Leu Ile Ser Trp Asp Ala Pro Ala Val Thr Val Arg Tyr Tyr Arg Ile
        35                  40                  45 acg tat gga gaa acc ggt ggc aac agt cca gta caa gaa ttt acc gtg    192
Thr Tyr Gly Glu Thr Gly Gly Asn Ser Pro Val Gln Glu Phe Thr Val
    50                  55                  60 cct ggt tcc aaa agt acc gca aca att tca ggc ctc aaa cca ggt gtt    240
Pro Gly Ser Lys Ser Thr Ala Thr Ile Ser Gly Leu Lys Pro Gly Val
65                  70                  75
```

```
gat tat acg att aca gtt tat gcg gtt acc ggt cgt ggc gat tca ccc        288
Asp Tyr Thr Ile Thr Val Tyr Ala Val Thr Gly Arg Gly Asp Ser Pro
 80              85                  90                  95 gca tca agt aaa cca att tct att aac tat cgt aca gaa ggc ggg gga        336
Ala Ser Ser Lys Pro Ile Ser Ile Asn Tyr Arg Thr Glu Gly Gly Gly
            100                 105                 110 ggt agc ggc gga gga gga tcc gga gtc att atc aat gtt aaa tgt aaa        384
Gly Ser Gly Gly Gly Gly Ser Gly Val Ile Ile Asn Val Lys Cys Lys
        115                 120                 125 atc agc cgt cag tgt tta gaa cca tgt aaa aaa gcc gga atg cgc ttt        432
Ile Ser Arg Gln Cys Leu Glu Pro Cys Lys Lys Ala Gly Met Arg Phe
    130                 135                 140 gga aaa tgt atg aat ggt aaa tgt cat tgc acc ccg aaa taatgaattc         481
Gly Lys Cys Met Asn Gly Lys Cys His Cys Thr Pro Lys
145                 150                 155

<210> SEQ ID NO 63
<211> LENGTH: 487
<212> TYPE: DNA
<213> ORGANISM: Artificial Sequence
<220> FEATURE:
<223> OTHER INFORMATION: M-G2-H6-G3-PDZ(1N7F)-(G4S)2-OsK1
<220> FEATURE:
<221> NAME/KEY: exon
<222> LOCATION: (4)..(477)

<400> SEQUENCE: 63 cat atg ggt ggt cat cat cat cat cat cat ggt ggt ggt tcc agc ggt         48
    Met Gly Gly His His His His His His Gly Gly Gly Ser Ser Gly
     1               5                  10                  15 gca att atc tat acg gta gaa ctt aaa cgt tac ggt ggt cct ctg ggt         96
Ala Ile Ile Tyr Thr Val Glu Leu Lys Arg Tyr Gly Gly Pro Leu Gly
            20                  25                  30 att aca atc agc ggc aca gaa gaa ccc ttt gat cca att att att tca        144
Ile Thr Ile Ser Gly Thr Glu Glu Pro Phe Asp Pro Ile Ile Ile Ser
        35                  40                  45 tcg ctt act aaa ggt ggt ctt gct gaa cgc aca ggc gcc att cat att        192
Ser Leu Thr Lys Gly Gly Leu Ala Glu Arg Thr Gly Ala Ile His Ile
    50                  55                  60 gga gat cgt att tta gct atc aac tca tca tca tta aaa ggc aaa ccg        240
Gly Asp Arg Ile Leu Ala Ile Asn Ser Ser Ser Leu Lys Gly Lys Pro
 65                  70                  75 tta tca gaa gct att cac tta tta caa atg gcg ggc gaa aca gtt acc        288
Leu Ser Glu Ala Ile His Leu Leu Gln Met Ala Gly Glu Thr Val Thr
 80                  85                  90                  95 ctt aaa atc aaa aaa caa acc gac gca caa tct gca agt agt ccg ggg        336
Leu Lys Ile Lys Lys Gln Thr Asp Ala Gln Ser Ala Ser Ser Pro Gly
            100                 105                 110 gga ggc ggc tca gga gga gga gga tcc ggt gtt att atc aat gtc aaa        384
Gly Gly Gly Ser Gly Gly Gly Gly Ser Gly Val Ile Ile Asn Val Lys
        115                 120                 125 tgt aaa att tct cgt cag tgt ttg gaa ccc tgt aaa aaa gcc ggt atg        432
Cys Lys Ile Ser Arg Gln Cys Leu Glu Pro Cys Lys Lys Ala Gly Met
    130                 135                 140 cgc ttt gga aaa tgt atg aac gga aaa tgt cac tgt acc cca aaa            477
Arg Phe Gly Lys Cys Met Asn Gly Lys Cys His Cys Thr Pro Lys
145                 150                 155 taatgaattc                                                             487

<210> SEQ ID NO 64
<211> LENGTH: 466
<212> TYPE: DNA
```

-continued

```
<213> ORGANISM: Artificial Sequence
<220> FEATURE:
<223> OTHER INFORMATION: M-G2-H6-G3-PDZ(1UEZ)-(G4S)2-OsK1
<220> FEATURE:
<221> NAME/KEY: exon
<222> LOCATION: (4)..(456)

<400> SEQUENCE: 64 cat atg ggt ggt cat cat cat cat cat cat ggt ggt ggt ccg ggc gaa        48
    Met Gly Gly His His His His His His Gly Gly Gly Pro Gly Glu
    1               5                   10                  15 gtt cgt ctt gtt agt tta cgt cgc gca aaa gca cat gaa ggc tta ggt        96
Val Arg Leu Val Ser Leu Arg Arg Ala Lys Ala His Glu Gly Leu Gly
                20                  25                  30 ttc tca att cgt ggc ggc agc gaa cat ggt gtt gga att tat gta tcc       144
Phe Ser Ile Arg Gly Gly Ser Glu His Gly Val Gly Ile Tyr Val Ser
            35                  40                  45 tta gta gaa cct ggt agt tta gcc gaa aaa gaa ggc ctg cgt gtc ggc       192
Leu Val Glu Pro Gly Ser Leu Ala Glu Lys Glu Gly Leu Arg Val Gly
        50                  55                  60 gat caa atc tta cgc gtc aac gat aaa tct tta gcc cgc gtt act cat       240
Asp Gln Ile Leu Arg Val Asn Asp Lys Ser Leu Ala Arg Val Thr His
    65                  70                  75 gcc gaa gcc gtt aaa gcg ttg aaa ggc agc aaa aaa tta gtt ctg tct       288
Ala Glu Ala Val Lys Ala Leu Lys Gly Ser Lys Lys Leu Val Leu Ser
80                  85                  90                  95 gtt tat tcc gca ggt cgt att cct ggt ggt gga gga agt ggt ggt ggt       336
Val Tyr Ser Ala Gly Arg Ile Pro Gly Gly Gly Gly Ser Gly Gly Gly
                100                 105                 110 gga tcc gga gta att att aac gtt aaa tgt aaa atc agt cgt caa tgt       384
Gly Ser Gly Val Ile Ile Asn Val Lys Cys Lys Ile Ser Arg Gln Cys
            115                 120                 125 ttg gaa ccc tgt aaa aaa gct gga atg cgg ttt gga aaa tgt atg aat       432
Leu Glu Pro Cys Lys Lys Ala Gly Met Arg Phe Gly Lys Cys Met Asn
        130                 135                 140 ggt aaa tgt cac tgt acc cct aaa taatgaattc                            466
Gly Lys Cys His Cys Thr Pro Lys
    145                 150

<210> SEQ ID NO 65
<211> LENGTH: 475
<212> TYPE: DNA
<213> ORGANISM: Artificial Sequence
<220> FEATURE:
<223> OTHER INFORMATION: M-G2-H6-G3-PDZ(1WFV)-(G4S)2-OsK1
<220> FEATURE:
<221> NAME/KEY: exon
<222> LOCATION: (4)..(465)

<400> SEQUENCE: 65 cat atg ggt ggt cat cat cat cat cat cat ggt ggt ggt cct caa gac        48
    Met Gly Gly His His His His His His Gly Gly Gly Pro Gln Asp
    1               5                   10                  15 ttc gat tac ttt act gtt gat atg gaa aaa ggt gca aaa ggt ttt ggt        96
Phe Asp Tyr Phe Thr Val Asp Met Glu Lys Gly Ala Lys Gly Phe Gly
                20                  25                  30 ttc tct att cgt ggc ggt cgt gaa tat aaa atg gac tta tat gtg tta       144
Phe Ser Ile Arg Gly Gly Arg Glu Tyr Lys Met Asp Leu Tyr Val Leu
            35                  40                  45 cgc tta gct gaa gac gga ccc gca att cgt aac gga cgt atg cgt gtt       192
Arg Leu Ala Glu Asp Gly Pro Ala Ile Arg Asn Gly Arg Met Arg Val
        50                  55                  60 ggc gat caa att att gaa att aat ggc gaa tca act cgt gat atg acc       240
Gly Asp Gln Ile Ile Glu Ile Asn Gly Glu Ser Thr Arg Asp Met Thr
```

```
cat gca cgt gcg att gaa ctt att aaa tct gga gga cgt cgt gta cgc      288
His Ala Arg Ala Ile Glu Leu Ile Lys Ser Gly Gly Arg Arg Val Arg
 80                  85                  90                  95 tta ctc tta aaa cgt ggt aca ggt cag gtt ccc ggt ggc ggc ggc agt      336
Leu Leu Leu Lys Arg Gly Thr Gly Gln Val Pro Gly Gly Gly Gly Ser
                100                 105                 110 ggt ggt ggt gga tcc gga gtt att atc aat gtt aaa tgt aaa att agt      384
Gly Gly Gly Gly Ser Gly Val Ile Ile Asn Val Lys Cys Lys Ile Ser
            115                 120                 125 cgt caa tgc tta gaa cct tgt aaa aaa gct gga atg cgc ttt gga aaa      432
Arg Gln Cys Leu Glu Pro Cys Lys Lys Ala Gly Met Arg Phe Gly Lys
        130                 135                 140 tgc atg aac ggg aaa tgt cac tgc aca cct aaa taatgaattc                475
Cys Met Asn Gly Lys Cys His Cys Thr Pro Lys
145                 150
```

<210> SEQ ID NO 66
<211> LENGTH: 490
<212> TYPE: DNA
<213> ORGANISM: Artificial Sequence
<220> FEATURE:
<223> OTHER INFORMATION: M-G2-H6-G3-SH2(1AB2)-(G4S)2-OsK1
<220> FEATURE:
<221> NAME/KEY: exon
<222> LOCATION: (4)..(480)

<400> SEQUENCE: 66

```
cat atg ggt ggt cat cat cat cat cat cat ggt ggt ggt aat tct tta       48
    Met Gly Gly His His His His His His Gly Gly Gly Asn Ser Leu
    1               5                  10                  15 gaa aaa cat tca tgg tat cat ggt cct gta tca cgt aac gca gcc gaa       96
Glu Lys His Ser Trp Tyr His Gly Pro Val Ser Arg Asn Ala Ala Glu
                20                  25                  30 tat ctc tta tct tct ggc att aac ggt agt ttt tta gtc cgc gaa tcc      144
Tyr Leu Leu Ser Ser Gly Ile Asn Gly Ser Phe Leu Val Arg Glu Ser
            35                  40                  45 gaa tct tct cct ggc caa cgc agt atc agt ctc cgt tat gaa ggt cgt      192
Glu Ser Ser Pro Gly Gln Arg Ser Ile Ser Leu Arg Tyr Glu Gly Arg
        50                  55                  60 gtg tat cat tat cgc atc aat acc gct tca gat ggt aaa tta tat gtt      240
Val Tyr His Tyr Arg Ile Asn Thr Ala Ser Asp Gly Lys Leu Tyr Val
 65                  70                  75 tcc tcg gaa agt cgt ttc aat acc ctt gcg gaa ctc gtt cat cat cat      288
Ser Ser Glu Ser Arg Phe Asn Thr Leu Ala Glu Leu Val His His His
 80                  85                  90                  95 tct act gtg gca gat ggt ctc att aca acg tta cat tat cct gca ccc      336
Ser Thr Val Ala Asp Gly Leu Ile Thr Thr Leu His Tyr Pro Ala Pro
                100                 105                 110 ggc ggt ggt ggc tct ggt ggt ggc gga tcc ggt gtt att att aat gtt      384
Gly Gly Gly Gly Ser Gly Gly Gly Gly Ser Gly Val Ile Ile Asn Val
            115                 120                 125 aaa tgt aaa att agt cgc caa tgt ctt gaa cct tgt aaa aaa gct ggc      432
Lys Cys Lys Ile Ser Arg Gln Cys Leu Glu Pro Cys Lys Lys Ala Gly
        130                 135                 140 atg cgc ttt ggt aaa tgt atg aac gga aaa tgt cat tgt acc ccg aaa      480
Met Arg Phe Gly Lys Cys Met Asn Gly Lys Cys His Cys Thr Pro Lys
145                 150                 155 taatgaattc                                                            490
```

<210> SEQ ID NO 67
<211> LENGTH: 478

<212> TYPE: DNA
<213> ORGANISM: Artificial Sequence
<220> FEATURE:
<223> OTHER INFORMATION: M-G2-H6-G3-SH2(1JYQ)-(G4S)2-OsK1
<220> FEATURE:
<221> NAME/KEY: exon
<222> LOCATION: (4)..(468)

<400> SEQUENCE: 67

```
cat atg ggt ggt cat cat cat cat cat cat ggt ggt ggt cct tgg ttt        48
    Met Gly Gly His His His His His His Gly Gly Gly Pro Trp Phe
    1               5                   10                  15 ttt ggt aaa atc cca cgt gcg aaa gct gaa gaa atg ctc tca aaa caa        96
Phe Gly Lys Ile Pro Arg Ala Lys Ala Glu Glu Met Leu Ser Lys Gln
                20                  25                  30 cgt cat gac ggt gca ttc tta att cgt gaa agt gaa tct gct cca ggt       144
Arg His Asp Gly Ala Phe Leu Ile Arg Glu Ser Glu Ser Ala Pro Gly
            35                  40                  45 gat ttt agt tta agt gtt aaa ttt ggt aat gat gtc caa cat ttt aaa       192
Asp Phe Ser Leu Ser Val Lys Phe Gly Asn Asp Val Gln His Phe Lys
        50                  55                  60 gtc ctt cgt gat ggt gcg ggt aaa tat ttt tta tgg gta gtc aaa ttc       240
Val Leu Arg Asp Gly Ala Gly Lys Tyr Phe Leu Trp Val Val Lys Phe
65                  70                  75 aat agt ctt aac gaa ctt gtc gat tat cat cgt tcc acc agt gtt agc       288
Asn Ser Leu Asn Glu Leu Val Asp Tyr His Arg Ser Thr Ser Val Ser
80                  85                  90                  95 cgt aat caa caa att ttt ctc cgc gat att gaa caa ggt ggt ggt ggt       336
Arg Asn Gln Gln Ile Phe Leu Arg Asp Ile Glu Gln Gly Gly Gly Gly
                100                 105                 110 tca gga ggg ggc gga tcc ggc gta atc atc aat gta aaa tgt aaa atc       384
Ser Gly Gly Gly Gly Ser Gly Val Ile Ile Asn Val Lys Cys Lys Ile
            115                 120                 125 tct cgt caa tgt tta gaa ccg tgt aaa aaa gca gga atg cgt ttc ggt       432
Ser Arg Gln Cys Leu Glu Pro Cys Lys Lys Ala Gly Met Arg Phe Gly
        130                 135                 140 aaa tgt atg aat ggt aaa tgt cat tgt acc cca aaa taatgaattc            478
Lys Cys Met Asn Gly Lys Cys His Cys Thr Pro Lys
        145                 150                 155
```

<210> SEQ ID NO 68
<211> LENGTH: 442
<212> TYPE: DNA
<213> ORGANISM: Artificial Sequence
<220> FEATURE:
<223> OTHER INFORMATION: M-G2-H6-G3-SH3(1PHT)-(G4S)2-OsK1
<220> FEATURE:
<221> NAME/KEY: exon
<222> LOCATION: (4)..(432)

<400> SEQUENCE: 68

```
cat atg ggt ggt cat cat cat cat cat cat ggt ggt ggt tca gca gaa        48
    Met Gly Gly His His His His His His Gly Gly Gly Ser Ala Glu
    1               5                   10                  15 ggt tat caa tat cgt gca tta tat gat tat aaa aaa gaa cgt gaa gaa        96
Gly Tyr Gln Tyr Arg Ala Leu Tyr Asp Tyr Lys Lys Glu Arg Glu Glu
                20                  25                  30 gat atc gac tta cat ctg gga gac att tta act gtt aat aaa gga agc       144
Asp Ile Asp Leu His Leu Gly Asp Ile Leu Thr Val Asn Lys Gly Ser
            35                  40                  45 tta gtc gct tta gga ttt agt gat ggg caa gag gca cgc cct gaa gaa       192
Leu Val Ala Leu Gly Phe Ser Asp Gly Gln Glu Ala Arg Pro Glu Glu
        50                  55                  60 att gga tgg ttg aat ggt tat aat gaa aca acc ggc gaa cgt ggt gac       240
Ile Gly Trp Leu Asn Gly Tyr Asn Glu Thr Thr Gly Glu Arg Gly Asp
```

```
Ile Gly Trp Leu Asn Gly Tyr Asn Glu Thr Thr Gly Glu Arg Gly Asp
 65                  70                  75 ttt ccg ggt acc tat gta gaa tat atc ggt cgt aaa aaa att agc cct       288
Phe Pro Gly Thr Tyr Val Glu Tyr Ile Gly Arg Lys Lys Ile Ser Pro
 80                  85                  90                  95 gga gga ggg ggg tct gga ggt ggt gga tcc ggt gta att atc aat gta       336
Gly Gly Gly Gly Ser Gly Gly Gly Gly Ser Gly Val Ile Ile Asn Val
                    100                 105                 110 aaa tgt aaa att agt cgt caa tgt tta gaa cct tgt aaa aaa gca ggc       384
Lys Cys Lys Ile Ser Arg Gln Cys Leu Glu Pro Cys Lys Lys Ala Gly
                115                 120                 125 atg cgc ttt gga aaa tgt atg aac ggt aaa tgc cat tgc acc cca aaa       432
Met Arg Phe Gly Lys Cys Met Asn Gly Lys Cys His Cys Thr Pro Lys
        130                 135                 140 taatgaattc                                                            442

<210> SEQ ID NO 69
<211> LENGTH: 385
<212> TYPE: DNA
<213> ORGANISM: Artificial Sequence
<220> FEATURE:
<223> OTHER INFORMATION: M-G2-H6-G3-SH3(1WA7)-(G4S)S-OsK1
<220> FEATURE:
<221> NAME/KEY: exon
<222> LOCATION: (4)..(375)

<400> SEQUENCE: 69 cat atg ggt ggt cat cat cat cat cat cat ggt ggt gga cca gaa gaa        48
    Met Gly Gly His His His His His His Gly Gly Gly Pro Glu Glu
     1               5                  10                  15 caa ggt gat att gta gtt gct tta tat cct tat gat ggt att cat cca        96
Gln Gly Asp Ile Val Val Ala Leu Tyr Pro Tyr Asp Gly Ile His Pro
                20                  25                  30 gac gat tta agt ttt aaa aaa ggt gaa aaa atg aaa gtg tta gaa gaa       144
Asp Asp Leu Ser Phe Lys Lys Gly Glu Lys Met Lys Val Leu Glu Glu
            35                  40                  45 cat gga gaa tgg tgg aag gca aaa agt tta tta acg aaa aaa gaa ggt       192
His Gly Glu Trp Trp Lys Ala Lys Ser Leu Leu Thr Lys Lys Glu Gly
         50                 55                  60 ttt att ccg tct aat tat gtg gca aaa tta aat aca gga ggt ggg ggt       240
Phe Ile Pro Ser Asn Tyr Val Ala Lys Leu Asn Thr Gly Gly Gly Gly
 65                  70                  75 ggt agt ggg ggg gga gga tcc ggt gta att att aat gta aaa tgt aaa       288
Gly Ser Gly Gly Gly Gly Ser Gly Val Ile Ile Asn Val Lys Cys Lys
 80                  85                  90                  95 att agt cgt caa tgt ttg gaa ccg tgt aaa aaa gca ggt atg cgc ttt       336
Ile Ser Arg Gln Cys Leu Glu Pro Cys Lys Lys Ala Gly Met Arg Phe
                100                 105                 110 ggt aaa tgt atg aat ggt aaa tgt cat tgc act cca aaa taatgaattc         385
Gly Lys Cys Met Asn Gly Lys Cys His Cys Thr Pro Lys
            115                 120

<210> SEQ ID NO 70
<211> LENGTH: 358
<212> TYPE: DNA
<213> ORGANISM: Artificial Sequence
<220> FEATURE:
<223> OTHER INFORMATION: M-G2-H6-G3-SH3(1X2K)-(G4S)2-OsK1
<220> FEATURE:
<221> NAME/KEY: exon
<222> LOCATION: (4)..(348)

<400> SEQUENCE: 70 cat atg ggt ggt cat cat cat cat cat cat ggt ggt gga aaa gtt ttt        48
```

```
        Met Gly Gly His His His His His His Gly Gly Lys Val Phe
        1               5                   10              15 cgc gca ctt tat acc ttt gaa ccc cgt acc cca gat gaa tta tat ttt        96
Arg Ala Leu Tyr Thr Phe Glu Pro Arg Thr Pro Asp Glu Leu Tyr Phe
                20                  25                  30 gaa gaa ggc gac att att tat att acg gac atg tca gat act aat tgg       144
Glu Glu Gly Asp Ile Ile Tyr Ile Thr Asp Met Ser Asp Thr Asn Trp
            35                  40                  45 tgg aaa gga aca agc aaa ggc cgt act gga ctg atc cca agt aat tac       192
Trp Lys Gly Thr Ser Lys Gly Arg Thr Gly Leu Ile Pro Ser Asn Tyr
        50                  55                  60 gta gca gaa caa gga gga ggt ggc tca gga gga ggt gga tcc ggt gta       240
Val Ala Glu Gln Gly Gly Gly Gly Ser Gly Gly Gly Gly Ser Gly Val
    65                  70                  75 att atc aat gta aaa tgt aaa atc tct cgt caa tgc ctg gaa ccc tgt       288
Ile Ile Asn Val Lys Cys Lys Ile Ser Arg Gln Cys Leu Glu Pro Cys
80                  85                  90                  95 aaa aaa gct ggt atg cgc ttt ggt aaa tgt atg aat ggt aaa tgt cat       336
Lys Lys Ala Gly Met Arg Phe Gly Lys Cys Met Asn Gly Lys Cys His
                100                 105                 110 tgc acc cct aaa taatgaattc                                            358
Cys Thr Pro Lys
            115

<210> SEQ ID NO 71
<211> LENGTH: 466
<212> TYPE: DNA
<213> ORGANISM: Artificial Sequence
<220> FEATURE:
<223> OTHER INFORMATION: M-G2-H6-G3-10TH Fn3-(G4S)2-ShK
<220> FEATURE:
<221> NAME/KEY: exon
<222> LOCATION: (4)..(456)

<400> SEQUENCE: 71 cat atg ggt ggt cat cat cat cat cat cat ggt ggt ggt acc gta agc        48
    Met Gly Gly His His His His His His Gly Gly Gly Thr Val Ser
    1               5                   10                  15 gat gtt ccc cgt gac ctg gaa gtg gtt gca gcg acc cct acc tca tta        96
Asp Val Pro Arg Asp Leu Glu Val Val Ala Ala Thr Pro Thr Ser Leu
                20                  25                  30 tta atc agt tgg gat gca cct gca gtt aca gtt cgg tat tat cgt att       144
Leu Ile Ser Trp Asp Ala Pro Ala Val Thr Val Arg Tyr Tyr Arg Ile
            35                  40                  45 acg tat gga gag aca ggc ggc aac tca cca gtt caa gaa ttt acc gtc       192
Thr Tyr Gly Glu Thr Gly Gly Asn Ser Pro Val Gln Glu Phe Thr Val
        50                  55                  60 ccg ggc tct aaa tca aca gca aca att tca ggc tta aaa cca gga gta       240
Pro Gly Ser Lys Ser Thr Ala Thr Ile Ser Gly Leu Lys Pro Gly Val
    65                  70                  75 gat tac aca att aca gta tac gca gta aca ggt cgc ggc gac tcc cca       288
Asp Tyr Thr Ile Thr Val Tyr Ala Val Thr Gly Arg Gly Asp Ser Pro
80                  85                  90                  95 gct agc tca aaa cct atc tct att aat tat cgc acc gaa ggt ggc gga       336
Ala Ser Ser Lys Pro Ile Ser Ile Asn Tyr Arg Thr Glu Gly Gly Gly
                100                 105                 110 ggt tcc ggt ggt ggt gga tcc tgc atc gat aca atc cct aag tcc cgc       384
Gly Ser Gly Gly Gly Gly Ser Cys Ile Asp Thr Ile Pro Lys Ser Arg
            115                 120                 125 tgt act gcc ttt caa tgc aaa cac tca atg aaa tac cgt ctc agt ttc       432
Cys Thr Ala Phe Gln Cys Lys His Ser Met Lys Tyr Arg Leu Ser Phe
        130                 135                 140
```

```
tgt cgt aaa acc tgt ggc acc tgt taatgaattc                          466
Cys Arg Lys Thr Cys Gly Thr Cys
    145                 150

<210> SEQ ID NO 72
<211> LENGTH: 472
<212> TYPE: DNA
<213> ORGANISM: Artificial Sequence
<220> FEATURE:
<223> OTHER INFORMATION: M-G2-H6-G3-PDZ(1N7F)-(G4S)2-ShK
<220> FEATURE:
<221> NAME/KEY: exon
<222> LOCATION: (4)..(462)

<400> SEQUENCE: 72 cat atg ggt ggt cat cat cat cat cat cat ggt ggt ggt tcc agc ggt     48
    Met Gly Gly His His His His His His Gly Gly Gly Ser Ser Gly
    1               5                   10                  15 gca att atc tat acg gta gaa ctt aaa cgt tac ggt ggt cct ctg ggt     96
Ala Ile Ile Tyr Thr Val Glu Leu Lys Arg Tyr Gly Gly Pro Leu Gly
                20                  25                  30 att aca atc agc ggc aca gaa gaa ccc ttt gat cca att att att tca    144
Ile Thr Ile Ser Gly Thr Glu Glu Pro Phe Asp Pro Ile Ile Ile Ser
            35                  40                  45 tcg ctt act aaa ggt ggt ctt gct gaa cgc aca ggc gcc att cat att    192
Ser Leu Thr Lys Gly Gly Leu Ala Glu Arg Thr Gly Ala Ile His Ile
        50                  55                  60 gga gat cgt att tta gct atc aac tca tca tca tta aaa ggc aaa ccg    240
Gly Asp Arg Ile Leu Ala Ile Asn Ser Ser Ser Leu Lys Gly Lys Pro
65                  70                  75                  80 tta tca gaa gct att cac tta tta caa atg gcg ggc gaa aca gtt acc    288
Leu Ser Glu Ala Ile His Leu Leu Gln Met Ala Gly Glu Thr Val Thr
                85                  90                  95 ctt aaa atc aaa aaa caa acc gac gca caa tct gca agt agt ccg ggg    336
Leu Lys Ile Lys Lys Gln Thr Asp Ala Gln Ser Ala Ser Ser Pro Gly
            100                 105                 110 gga ggc ggc tca gga gga gga gga tcc tgc atc gat aca atc cct aag    384
Gly Gly Gly Ser Gly Gly Gly Gly Ser Cys Ile Asp Thr Ile Pro Lys
        115                 120                 125 tcc cgc tgt act gcc ttt caa tgc aaa cac tca atg aaa tac cgt ctc    432
Ser Arg Cys Thr Ala Phe Gln Cys Lys His Ser Met Lys Tyr Arg Leu
    130                 135                 140 agt ttc tgt cgt aaa acc tgt ggc acc tgt taatgaattc                 472
Ser Phe Cys Arg Lys Thr Cys Gly Thr Cys
    145                 150

<210> SEQ ID NO 73
<211> LENGTH: 451
<212> TYPE: DNA
<213> ORGANISM: Artificial Sequence
<220> FEATURE:
<223> OTHER INFORMATION: M-G2-H6-G3-PDZ(1UEZ)-(G4S)2-ShK
<220> FEATURE:
<221> NAME/KEY: exon
<222> LOCATION: (4)..(441)

<400> SEQUENCE: 73 cat atg ggt ggt cat cat cat cat cat cat ggt ggt ggt ccg ggc gaa     48
    Met Gly Gly His His His His His His Gly Gly Gly Pro Gly Glu
    1               5                   10                  15 gtt cgt ctt gtt agt tta cgt cgc gca aaa gca cat gaa ggc tta ggt     96
Val Arg Leu Val Ser Leu Arg Arg Ala Lys Ala His Glu Gly Leu Gly
                20                  25                  30 ttc tca att cgt ggc ggc agc gaa cat ggt gtt gga att tat gta tcc    144
Phe Ser Ile Arg Gly Gly Ser Glu His Gly Val Gly Ile Tyr Val Ser
```

```
                    35                  40                  45
tta gta gaa cct ggt agt tta gcc gaa aaa gaa ggc ctg cgt gtc ggc         192
Leu Val Glu Pro Gly Ser Leu Ala Glu Lys Glu Gly Leu Arg Val Gly
             50                  55                  60 gat caa atc tta cgc gtc aac gat aaa tct tta gcc cgc gtt act cat         240
Asp Gln Ile Leu Arg Val Asn Asp Lys Ser Leu Ala Arg Val Thr His
 65                  70                  75 gcc gaa gcc gtt aaa gcg ttg aaa ggt agc aaa aaa tta gtt ctg tct         288
Ala Glu Ala Val Lys Ala Leu Lys Gly Ser Lys Lys Leu Val Leu Ser
 80                  85                  90                  95 gtt tat tcc gca ggt cgt att cct ggt ggt gga agt ggt ggt ggt             336
Val Tyr Ser Ala Gly Arg Ile Pro Gly Gly Gly Ser Gly Gly Gly
                    100                 105                 110 gga tcc tgc atc gat aca atc cct aag tcc cgc tgt act gcc ttt caa         384
Gly Ser Cys Ile Asp Thr Ile Pro Lys Ser Arg Cys Thr Ala Phe Gln
             115                 120                 125 tgc aaa cac tca atg aaa tac cgt ctc agt ttc tgt cgt aaa acc tgt         432
Cys Lys His Ser Met Lys Tyr Arg Leu Ser Phe Cys Arg Lys Thr Cys
         130                 135                 140 ggc acc tgt taatgaattc                                                  451
Gly Thr Cys
    145

<210> SEQ ID NO 74
<211> LENGTH: 460
<212> TYPE: DNA
<213> ORGANISM: Artificial Sequence
<220> FEATURE:
<223> OTHER INFORMATION: M-G2-H6-G3-PDZ(1WFV)-(G4S)2-ShK
<220> FEATURE:
<221> NAME/KEY: exon
<222> LOCATION: (4)..(450)

<400> SEQUENCE: 74 cat atg ggt ggt cat cat cat cat cat cat ggt ggt ggt cct caa gac          48
    Met Gly Gly His His His His His His Gly Gly Gly Pro Gln Asp
     1               5                  10                  15 ttc gat tac ttt act gtt gat atg gaa aaa ggt gca aaa ggt ttt ggt          96
Phe Asp Tyr Phe Thr Val Asp Met Glu Lys Gly Ala Lys Gly Phe Gly
                 20                  25                  30 ttc tct att cgt ggc ggt cgt gaa tat aaa atg gac tta tat gtg tta         144
Phe Ser Ile Arg Gly Gly Arg Glu Tyr Lys Met Asp Leu Tyr Val Leu
             35                  40                  45 cgc tta gct gaa gac gga ccc gca att cgt aac gga cgt atg cgt gtt         192
Arg Leu Ala Glu Asp Gly Pro Ala Ile Arg Asn Gly Arg Met Arg Val
         50                  55                  60 ggc gat caa att att gaa att aat ggc gaa tca act cgt gat atg acc         240
Gly Asp Gln Ile Ile Glu Ile Asn Gly Glu Ser Thr Arg Asp Met Thr
 65                  70                  75 cat gca cgt gcg att gaa ctt att aaa tct gga gga cgt cgt gta cgc         288
His Ala Arg Ala Ile Glu Leu Ile Lys Ser Gly Gly Arg Arg Val Arg
 80                  85                  90                  95 tta ctc tta aaa cgt ggt aca ggt cag gtt ccc ggt ggc ggc agt             336
Leu Leu Leu Lys Arg Gly Thr Gly Gln Val Pro Gly Gly Gly Ser
                    100                 105                 110 ggt ggt ggt gga tcc tgc atc gat aca atc cct aag tcc cgc tgt act         384
Gly Gly Gly Gly Ser Cys Ile Asp Thr Ile Pro Lys Ser Arg Cys Thr
             115                 120                 125 gcc ttt caa tgc aaa cac tca atg aaa tac cgt ctc agt ttc tgt cgt         432
Ala Phe Gln Cys Lys His Ser Met Lys Tyr Arg Leu Ser Phe Cys Arg
         130                 135                 140 aaa acc tgt ggc acc tgt taatgaattc                                      460
Lys Thr Cys Gly Thr Cys
```

-continued

Lys Thr Cys Gly Thr Cys
145

<210> SEQ ID NO 75
<211> LENGTH: 475
<212> TYPE: DNA
<213> ORGANISM: Artificial Sequence
<220> FEATURE:
<223> OTHER INFORMATION: M-G2-H6-G3-SH2(1AB2)-(G4S)2-ShK
<220> FEATURE:
<221> NAME/KEY: exon
<222> LOCATION: (4)..(465)

<400> SEQUENCE: 75

```
cat atg ggt ggt cat cat cat cat cat cat ggt ggt ggt aat tct tta     48
    Met Gly Gly His His His His His His Gly Gly Gly Asn Ser Leu
    1               5                   10                  15 gaa aaa cat tca tgg tat cat ggt cct gta tca cgt aac gca gcc gaa     96
Glu Lys His Ser Trp Tyr His Gly Pro Val Ser Arg Asn Ala Ala Glu
                20                  25                  30 tat ctc tta tct tct ggc att aac ggt agt ttt tta gtc cgc gaa tcc    144
Tyr Leu Leu Ser Ser Gly Ile Asn Gly Ser Phe Leu Val Arg Glu Ser
            35                  40                  45 gaa tct tct cct ggc caa cgc agt atc agt ctc cgt tat gaa ggt cgt    192
Glu Ser Ser Pro Gly Gln Arg Ser Ile Ser Leu Arg Tyr Glu Gly Arg
        50                  55                  60 gtg tat cat tat cgc atc aat acc gct tca gat ggt aaa tta tat gtt    240
Val Tyr His Tyr Arg Ile Asn Thr Ala Ser Asp Gly Lys Leu Tyr Val
65                  70                  75 tcc tcg gaa agt cgt ttc aat acc ctt gcg gaa ctc gtt cat cat cat    288
Ser Ser Glu Ser Arg Phe Asn Thr Leu Ala Glu Leu Val His His His
80                  85                  90                  95 tct act gtg gca gat ggt ctc att aca acg tta cat tat cct gca ccc    336
Ser Thr Val Ala Asp Gly Leu Ile Thr Thr Leu His Tyr Pro Ala Pro
                100                 105                 110 ggc ggt ggt ggc tct ggt ggt ggc gga tcc tgc atc gat aca atc cct    384
Gly Gly Gly Gly Ser Gly Gly Gly Gly Ser Cys Ile Asp Thr Ile Pro
            115                 120                 125 aag tcc cgc tgt act gcc ttt caa tgc aaa cac tca atg aaa tac cgt    432
Lys Ser Arg Cys Thr Ala Phe Gln Cys Lys His Ser Met Lys Tyr Arg
        130                 135                 140 ctc agt ttc tgt cgt aaa acc tgt ggc acc tgt taatgaattc              475
Leu Ser Phe Cys Arg Lys Thr Cys Gly Thr Cys
        145                 150
```

<210> SEQ ID NO 76
<211> LENGTH: 463
<212> TYPE: DNA
<213> ORGANISM: Artificial Sequence
<220> FEATURE:
<223> OTHER INFORMATION: M-G2-H6-G3-SH2(1JYQ)-(G4S)2-ShK
<220> FEATURE:
<221> NAME/KEY: exon
<222> LOCATION: (4)..(453)

<400> SEQUENCE: 76

```
cat atg ggt ggt cat cat cat cat cat cat ggt ggt ggt cct tgg ttt     48
    Met Gly Gly His His His His His His Gly Gly Gly Pro Trp Phe
    1               5                   10                  15 ttt ggt aaa atc cca cgt gcg aaa gct gaa gaa atg ctc tca aaa caa     96
Phe Gly Lys Ile Pro Arg Ala Lys Ala Glu Glu Met Leu Ser Lys Gln
                20                  25                  30 cgt cat gac ggt gca ttc tta att cgt gaa agt gaa tct gct cca ggt    144
Arg His Asp Gly Ala Phe Leu Ile Arg Glu Ser Glu Ser Ala Pro Gly
            35                  40                  45
```

```
gat ttt agt tta agt gtt aaa ttt ggt aat gat gtc caa cat ttt aaa    192
Asp Phe Ser Leu Ser Val Lys Phe Gly Asn Asp Val Gln His Phe Lys
         50                  55                  60 gtc ctt cgt gat ggt gcg ggt aaa tat ttt tta tgg gta gtc aaa ttc    240
Val Leu Arg Asp Gly Ala Gly Lys Tyr Phe Leu Trp Val Val Lys Phe
 65                  70                  75 aat agt ctt aac gaa ctt gtc gat tat cat cgt tcc acc agt gtt agc    288
Asn Ser Leu Asn Glu Leu Val Asp Tyr His Arg Ser Thr Ser Val Ser
 80                  85                  90                  95 cgt aat caa caa att ttt ctc cgc gat att gaa caa ggt ggt ggt ggt    336
Arg Asn Gln Gln Ile Phe Leu Arg Asp Ile Glu Gln Gly Gly Gly Gly
                100                 105                 110 tca gga ggg ggc gga tcc tgc atc gat aca atc cct aag tcc cgc tgt    384
Ser Gly Gly Gly Gly Ser Cys Ile Asp Thr Ile Pro Lys Ser Arg Cys
             115                 120                 125 act gcc ttt caa tgc aaa cac tca atg aaa tac cgt ctc agt ttc tgt    432
Thr Ala Phe Gln Cys Lys His Ser Met Lys Tyr Arg Leu Ser Phe Cys
         130                 135                 140 cgt aaa acc tgt ggc acc tgt taatgaattc                             463
Arg Lys Thr Cys Gly Thr Cys
        145                 150

<210> SEQ ID NO 77
<211> LENGTH: 427
<212> TYPE: DNA
<213> ORGANISM: Artificial Sequence
<220> FEATURE:
<223> OTHER INFORMATION: M-H2-H6-G3-SH3(1PHT)-(G4S)2-ShK
<220> FEATURE:
<221> NAME/KEY: exon
<222> LOCATION: (4)..(417)

<400> SEQUENCE: 77 cat atg ggt ggt cat cat cat cat cat cat ggt ggt ggt tca gca gaa    48
    Met Gly Gly His His His His His His Gly Gly Gly Ser Ala Glu
     1               5                  10                  15 ggt tat caa tat cgt gca tta tat gat tat aaa aaa gaa cgt gaa gaa    96
Gly Tyr Gln Tyr Arg Ala Leu Tyr Asp Tyr Lys Lys Glu Arg Glu Glu
                 20                  25                  30 gat atc gac tta cat ctg gga gac att tta act gtt aat aaa gga agc   144
Asp Ile Asp Leu His Leu Gly Asp Ile Leu Thr Val Asn Lys Gly Ser
             35                  40                  45 tta gtc gct tta gga ttt agt gat ggg caa gag gca cgc cct gaa gaa   192
Leu Val Ala Leu Gly Phe Ser Asp Gly Gln Glu Ala Arg Pro Glu Glu
         50                  55                  60 att gga tgg ttg aat ggt tat aat gaa aca acc ggc gaa cgt ggt gac   240
Ile Gly Trp Leu Asn Gly Tyr Asn Glu Thr Thr Gly Glu Arg Gly Asp
 65                  70                  75 ttt ccg ggt acc tat gta gaa tat atc ggt cgt aaa aaa att agc cct   288
Phe Pro Gly Thr Tyr Val Glu Tyr Ile Gly Arg Lys Lys Ile Ser Pro
 80                  85                  90                  95 gga gga ggg ggg tct gga ggt ggt gga tcc tgc atc gat aca atc cct   336
Gly Gly Gly Gly Ser Gly Gly Gly Gly Ser Cys Ile Asp Thr Ile Pro
                100                 105                 110 aag tcc cgc tgt act gcc ttt caa tgc aaa cac tca atg aaa tac cgt   384
Lys Ser Arg Cys Thr Ala Phe Gln Cys Lys His Ser Met Lys Tyr Arg
             115                 120                 125 ctc agt ttc tgt cgt aaa acc tgt ggc acc tgt taatgaattc            427
Leu Ser Phe Cys Arg Lys Thr Cys Gly Thr Cys
         130                 135

<210> SEQ ID NO 78
```

```
<211> LENGTH: 370
<212> TYPE: DNA
<213> ORGANISM: Artificial Sequence
<220> FEATURE:
<223> OTHER INFORMATION: M-G2-H6-G3-SH3(1WA7)-(G4S)2-ShK
<220> FEATURE:
<221> NAME/KEY: exon
<222> LOCATION: (4)..(360)

<400> SEQUENCE: 78 cat atg ggt ggt cat cat cat cat cat cat ggt ggt ggt cca gaa gaa      48
    Met Gly Gly His His His His His His Gly Gly Gly Pro Glu Glu
    1               5                   10                  15 caa ggt gat att gta gtt gct tta tat cct tat gat ggt att cat cca      96
Gln Gly Asp Ile Val Val Ala Leu Tyr Pro Tyr Asp Gly Ile His Pro
            20                  25                  30 gac gat tta agt ttt aaa aaa ggt gaa aaa atg aaa gtg tta gaa gaa     144
Asp Asp Leu Ser Phe Lys Lys Gly Glu Lys Met Lys Val Leu Glu Glu
        35                  40                  45 cat gga gaa tgg tgg aag gca aaa agt tta tta acg aaa aaa gaa ggt     192
His Gly Glu Trp Trp Lys Ala Lys Ser Leu Leu Thr Lys Lys Glu Gly
    50                  55                  60 ttt att ccg tct aat tat gtg gca aaa tta aat aca gga ggt ggg ggt     240
Phe Ile Pro Ser Asn Tyr Val Ala Lys Leu Asn Thr Gly Gly Gly Gly
65                  70                  75 ggt agt ggg ggg gga gga tcc tgc atc gat aca atc cct aag tcc cgc     288
Gly Ser Gly Gly Gly Gly Ser Cys Ile Asp Thr Ile Pro Lys Ser Arg
80                  85                  90                  95 tgt act gcc ttt caa tgc aaa cac tca atg aaa tac cgt ctc agt ttc     336
Cys Thr Ala Phe Gln Cys Lys His Ser Met Lys Tyr Arg Leu Ser Phe
                100                 105                 110 tgt cgt aaa acc tgt ggc acc tgt taatgaattc                         370
Cys Arg Lys Thr Cys Gly Thr Cys
            115

<210> SEQ ID NO 79
<211> LENGTH: 343
<212> TYPE: DNA
<213> ORGANISM: Artificial Sequence
<220> FEATURE:
<223> OTHER INFORMATION: M-G2-H6-G3-SH3(1X2K)-(G4S)2-ShK
<220> FEATURE:
<221> NAME/KEY: exon
<222> LOCATION: (4)..(333)

<400> SEQUENCE: 79 cat atg ggt ggt cat cat cat cat cat cat ggt ggt ggt aaa gtt ttt      48
    Met Gly Gly His His His His His His Gly Gly Gly Lys Val Phe
    1               5                   10                  15 cgc gca ctt tat acc ttt gaa ccc cgt acc cca gat gaa tta tat ttt      96
Arg Ala Leu Tyr Thr Phe Glu Pro Arg Thr Pro Asp Glu Leu Tyr Phe
            20                  25                  30 gaa gaa ggc gac att att tat att acg gac atg tca gat act aat tgg     144
Glu Glu Gly Asp Ile Ile Tyr Ile Thr Asp Met Ser Asp Thr Asn Trp
        35                  40                  45 tgg aaa gga aca agc aaa ggc cgt act gga ctg atc cca agt aat tac     192
Trp Lys Gly Thr Ser Lys Gly Arg Thr Gly Leu Ile Pro Ser Asn Tyr
    50                  55                  60 gta gca gaa caa gga gga ggt ggc tca gga gga ggt gga tcc tgc atc     240
Val Ala Glu Gln Gly Gly Gly Gly Ser Gly Gly Gly Gly Ser Cys Ile
65                  70                  75 gat aca atc cct aag tcc cgc tgt act gcc ttt caa tgc aaa cac tca     288
Asp Thr Ile Pro Lys Ser Arg Cys Thr Ala Phe Gln Cys Lys His Ser
80                  85                  90                  95
```

-continued

```
atg aaa tac cgt ctc agt ttc tgt cgt aaa acc tgt ggc acc tgt       333
Met Lys Tyr Arg Leu Ser Phe Cys Arg Lys Thr Cys Gly Thr Cys
                100             105             110 taatgaattc                                                        343
```

<210> SEQ ID NO 80
<211> LENGTH: 159
<212> TYPE: PRT
<213> ORGANISM: Artificial Sequence
<220> FEATURE:
<223> OTHER INFORMATION: CH2-OsK1 Fusion Protein

<400> SEQUENCE: 80

Gly Gly His His His His His His Gly Gly Gly Pro Ser Val Phe Leu
1               5                   10                  15

Phe Pro Pro Lys Pro Lys Asp Thr Leu Met Ile Ser Arg Thr Pro Glu
                20                  25                  30

Val Thr Cys Val Val Val Asp Val Ser His Glu Asp Pro Glu Val Lys
            35                  40                  45

Phe Asn Trp Tyr Val Asp Gly Val Glu Val His Asn Ala Lys Thr Lys
        50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Gly
            100                 105                 110

Gly Gly Gly Ser Gly Gly Gly Ser Gly Val Ile Ile Asn Val Lys
        115                 120                 125

Cys Lys Ile Ser Arg Gln Cys Leu Glu Pro Cys Lys Lys Ala Gly Met
    130                 135                 140

Arg Phe Gly Lys Cys Met Asn Gly Lys Cys His Cys Thr Pro Lys
145                 150                 155

<210> SEQ ID NO 81
<211> LENGTH: 155
<212> TYPE: PRT
<213> ORGANISM: Artificial Sequence
<220> FEATURE:
<223> OTHER INFORMATION: FnIII-OsK1 Fusion Protein

<400> SEQUENCE: 81

Gly Gly His His His His His His Gly Gly Gly Thr Val Ser Asp Val
1               5                   10                  15

Pro Arg Asp Leu Glu Val Val Ala Ala Thr Pro Thr Ser Leu Leu Ile
                20                  25                  30

Ser Trp Asp Ala Pro Ala Val Thr Val Arg Tyr Tyr Arg Ile Thr Tyr
            35                  40                  45

Gly Glu Thr Gly Gly Asn Ser Pro Val Gln Glu Phe Thr Val Pro Gly
        50                  55                  60

Ser Lys Ser Thr Ala Thr Ile Ser Gly Leu Lys Pro Gly Val Asp Tyr
65                  70                  75                  80

Thr Ile Thr Val Tyr Ala Val Thr Gly Arg Gly Asp Ser Pro Ala Ser
                85                  90                  95

Ser Lys Pro Ile Ser Ile Asn Tyr Arg Thr Glu Gly Gly Gly Gly Ser
            100                 105                 110

Gly Gly Gly Gly Ser Gly Val Ile Ile Asn Val Lys Cys Lys Ile Ser
        115                 120                 125

```
Arg Gln Cys Leu Glu Pro Cys Lys Lys Ala Gly Met Arg Phe Gly Lys
        130                 135                 140

Cys Met Asn Gly Lys Cys His Cys Thr Pro Lys
145                 150                 155

<210> SEQ ID NO 82
<211> LENGTH: 142
<212> TYPE: PRT
<213> ORGANISM: Artificial Sequence
<220> FEATURE:
<223> OTHER INFORMATION: 1PHT-OSk1 Fusion Protein

<400> SEQUENCE: 82

Gly Gly His His His His His Gly Gly Gly Ser Ala Glu Gly Tyr
1               5                   10                  15

Gln Tyr Arg Ala Leu Tyr Asp Tyr Lys Lys Glu Arg Glu Glu Asp Ile
            20                  25                  30

Asp Leu His Leu Gly Asp Ile Leu Thr Val Asn Lys Gly Ser Leu Val
        35                  40                  45

Ala Leu Gly Phe Ser Asp Gly Gln Glu Ala Arg Pro Glu Glu Ile Gly
    50                  55                  60

Trp Leu Asn Gly Tyr Asn Glu Thr Thr Gly Glu Arg Gly Asp Phe Pro
65                  70                  75                  80

Gly Thr Tyr Val Glu Tyr Ile Gly Arg Lys Lys Ile Ser Pro Gly Gly
                85                  90                  95

Gly Gly Ser Gly Gly Gly Gly Ser Gly Val Ile Ile Asn Val Lys Cys
            100                 105                 110

Lys Ile Ser Arg Gln Cys Leu Glu Pro Cys Lys Lys Ala Gly Met Arg
        115                 120                 125

Phe Gly Lys Cys Met Asn Gly Lys Cys His Cys Thr Pro Lys
    130                 135                 140

<210> SEQ ID NO 83
<211> LENGTH: 157
<212> TYPE: PRT
<213> ORGANISM: Artificial Sequence
<220> FEATURE:
<223> OTHER INFORMATION: 1N7F-OsK1 Fusion Protein

<400> SEQUENCE: 83

Gly Gly His His His His His Gly Gly Gly Ser Ser Gly Ala Ile
1               5                   10                  15

Ile Tyr Thr Val Glu Leu Lys Arg Tyr Gly Gly Pro Leu Gly Ile Thr
            20                  25                  30

Ile Ser Gly Thr Glu Glu Pro Phe Asp Pro Ile Ile Ile Ser Ser Leu
        35                  40                  45

Thr Lys Gly Gly Leu Ala Glu Arg Thr Gly Ala Ile His Ile Gly Asp
    50                  55                  60

Arg Ile Leu Ala Ile Asn Ser Ser Ser Leu Lys Gly Lys Pro Leu Ser
65                  70                  75                  80

Glu Ala Ile His Leu Leu Gln Met Ala Gly Glu Thr Val Thr Leu Lys
                85                  90                  95

Ile Lys Lys Gln Thr Asp Ala Gln Ser Ala Ser Ser Pro Gly Gly Gly
            100                 105                 110

Gly Ser Gly Gly Gly Gly Ser Gly Val Ile Ile Asn Val Lys Cys Lys
        115                 120                 125

Ile Ser Arg Gln Cys Leu Glu Pro Cys Lys Lys Ala Gly Met Arg Phe
    130                 135                 140
```

```
Gly Lys Cys Met Asn Gly Lys Cys His Cys Thr Pro Lys
145                 150                 155
```

<210> SEQ ID NO 84
<211> LENGTH: 114
<212> TYPE: PRT
<213> ORGANISM: Artificial Sequence
<220> FEATURE:
<223> OTHER INFORMATION: 1X2K-OsK1 Fusion Protein

<400> SEQUENCE: 84

```
Gly Gly His His His His His Gly Gly Gly Lys Val Phe Arg Ala
1               5                   10                  15

Leu Tyr Thr Phe Glu Pro Arg Thr Pro Asp Glu Leu Tyr Phe Glu Glu
                20                  25                  30

Gly Asp Ile Ile Tyr Ile Thr Asp Met Ser Asp Thr Asn Trp Trp Lys
            35                  40                  45

Gly Thr Ser Lys Gly Arg Thr Gly Leu Ile Pro Ser Asn Tyr Val Ala
        50                  55                  60

Glu Gln Gly Gly Gly Ser Gly Gly Gly Ser Gly Val Ile Ile
65                  70                  75                  80

Asn Val Lys Cys Lys Ile Ser Arg Gln Cys Leu Glu Pro Cys Lys Lys
                85                  90                  95

Ala Gly Met Arg Phe Gly Lys Cys Met Asn Gly Lys Cys His Cys Thr
            100                 105                 110

Pro Lys
```

<210> SEQ ID NO 85
<211> LENGTH: 150
<212> TYPE: PRT
<213> ORGANISM: Artificial Sequence
<220> FEATURE:
<223> OTHER INFORMATION: 1UEZ-OsK1 Fusion Protein

<400> SEQUENCE: 85

```
Gly Gly His His His His His Gly Gly Gly Pro Gly Glu Val Arg
1               5                   10                  15

Leu Val Ser Leu Arg Arg Ala Lys Ala His Glu Gly Leu Gly Phe Ser
                20                  25                  30

Ile Arg Gly Gly Ser Glu His Gly Val Gly Ile Tyr Val Ser Leu Val
            35                  40                  45

Glu Pro Gly Ser Leu Ala Glu Lys Gly Leu Arg Val Gly Asp Gln
        50                  55                  60

Ile Leu Arg Val Asn Asp Lys Ser Leu Ala Arg Val Thr His Ala Glu
65                  70                  75                  80

Ala Val Lys Ala Leu Lys Gly Ser Lys Lys Leu Val Leu Ser Val Tyr
                85                  90                  95

Ser Ala Gly Arg Ile Pro Gly Gly Gly Ser Gly Gly Gly Ser
            100                 105                 110

Gly Val Ile Ile Asn Val Lys Cys Lys Ile Ser Arg Gln Cys Leu Glu
        115                 120                 125

Pro Cys Lys Lys Ala Gly Met Arg Phe Gly Lys Cys Met Asn Gly Lys
    130                 135                 140

Cys His Cys Thr Pro Lys
145                 150
```

<210> SEQ ID NO 86
<211> LENGTH: 123
<212> TYPE: PRT

<213> ORGANISM: Artificial Sequence
<220> FEATURE:
<223> OTHER INFORMATION: Amino Acid Sequence of
    MK6H-G2-SH3-G5-2X(TMP22-7Q)

<400> SEQUENCE: 86

Met Lys His His His His His Gly Gly Lys Val Phe Arg Ala Leu
1               5                   10                  15

Tyr Thr Phe Glu Pro Arg Thr Pro Asp Glu Leu Tyr Phe Glu Glu Gly
            20                  25                  30

Asp Ile Ile Tyr Ile Thr Asp Met Ser Asp Thr Asn Trp Trp Lys Gly
                35                  40                  45

Thr Ser Lys Gly Arg Gly Leu Ile Pro Ser Asn Tyr Val Ala Glu Gln
        50                  55                  60

Gly Gly Ser Gly Gly Gln Gly Cys Ser Ser Gly Gly Pro Thr Leu Arg
65                  70                  75                  80

Glu Trp Gln Gln Cys Arg Arg Met Gln His Ser Gly Gly Gly Gly
                85                  90                  95

Gly Gly Gly Gln Gly Cys Ser Ser Gly Gly Pro Thr Leu Arg Glu Trp
            100                 105                 110

Gln Gln Cys Arg Arg Met Gln His Ser Gly Gly
            115                 120

<210> SEQ ID NO 87
<211> LENGTH: 160
<212> TYPE: PRT
<213> ORGANISM: Artificial Sequence
<220> FEATURE:
<223> OTHER INFORMATION: MK6H-G2-PDZ-G5-2X(TMP22-7Q) AMINO ACID SEQUENCE

<400> SEQUENCE: 87

Met Lys His His His His His Gly Gly Pro Gly Glu Val Arg Leu
1               5                   10                  15

Val Ser Leu Arg Arg Ala Lys Ala His Glu Gly Leu Gly Phe Ser Ile
            20                  25                  30

Arg Gly Gly Ser Glu His Gly Val Gly Ile Tyr Val Ser Leu Val Glu
        35                  40                  45

Pro Gly Ser Leu Ala Glu Lys Glu Gly Leu Arg Val Gly Asp Gln Ile
    50                  55                  60

Leu Arg Val Asn Asp Lys Ser Leu Ala Arg Val Thr His Ala Glu Ala
65                  70                  75                  80

Val Lys Ala Leu Lys Gly Ser Lys Lys Leu Val Leu Ser Val Tyr Ser
                85                  90                  95

Ala Gly Arg Ile Pro Gly Gly Ser Gly Gly Gln Gly Cys Ser Ser Gly
            100                 105                 110

Gly Pro Thr Leu Arg Glu Trp Gln Gln Cys Arg Arg Met Gln His Ser
        115                 120                 125

Gly Gly Gly Gly Gly Gly Gly Gln Gly Cys Ser Ser Gly Gly Pro
    130                 135                 140

Thr Leu Arg Glu Trp Gln Gln Cys Arg Arg Met Gln His Ser Gly Gly
145                 150                 155                 160

<210> SEQ ID NO 88
<211> LENGTH: 165
<212> TYPE: PRT
<213> ORGANISM: Artificial Sequence
<220> FEATURE:
<223> OTHER INFORMATION: MK6H-G2-Fn3-G5-2X(TMP22-7Q) AMINO ACID SEQUENCE

<400> SEQUENCE: 88

```
Met Lys His His His His His Gly Gly Thr Val Ser Asp Val Pro
1               5                   10                  15

Arg Asp Leu Glu Val Val Ala Ala Thr Pro Thr Ser Leu Leu Ile Ser
            20                  25                  30

Trp Asp Ala Pro Ala Val Thr Val Arg Tyr Tyr Arg Ile Thr Tyr Gly
            35                  40                  45

Glu Thr Gly Gly Asn Ser Pro Val Gln Glu Phe Thr Val Pro Gly Ser
    50                  55                  60

Lys Ser Thr Ala Thr Ile Ser Gly Leu Lys Pro Gly Val Asp Tyr Thr
65                  70                  75                  80

Ile Thr Val Tyr Ala Val Thr Gly Arg Gly Asp Ser Pro Ala Ser Ser
                85                  90                  95

Lys Pro Ile Ser Ile Asn Tyr Arg Thr Glu Gly Gly Ser Gly Gly Gln
            100                 105                 110

Gly Cys Ser Ser Gly Gly Pro Thr Leu Arg Glu Trp Gln Gln Cys Arg
            115                 120                 125

Arg Met Gln His Ser Gly Gly Gly Gly Gly Gly Gln Gly Cys
130                 135                 140

Ser Ser Gly Gly Pro Thr Leu Arg Glu Trp Gln Gln Cys Arg Arg Met
145                 150                 155                 160

Gln His Ser Gly Gly
            165
```

<210> SEQ ID NO 89
<211> LENGTH: 76
<212> TYPE: PRT
<213> ORGANISM: Homo sapiens
<220> FEATURE:
<221> NAME/KEY: MISC_FEATURE
<223> OTHER INFORMATION: HP-76 SUBDOMAIN OF VILLIN HEADPIECE DOMAIN

<400> SEQUENCE: 89

```
Val Phe Asn Ala Asn Ser Asn Leu Ser Ser Gly Pro Leu Pro Ile Phe
1               5                   10                  15

Pro Leu Glu Gln Leu Val Asn Lys Pro Val Glu Leu Pro Glu Gly
            20                  25                  30

Val Asp Pro Ser Arg Lys Glu Glu His Leu Ser Ile Glu Asp Phe Thr
            35                  40                  45

Gln Ala Phe Gly Met Thr Pro Ala Ala Phe Ser Ala Leu Pro Arg Trp
    50                  55                  60

Lys Gln Gln Asn Leu Lys Lys Glu Lys Gly Leu Phe
65                  70                  75
```

<210> SEQ ID NO 90
<211> LENGTH: 76
<212> TYPE: PRT
<213> ORGANISM: Artificial Sequence
<220> FEATURE:
<223> OTHER INFORMATION: HP-76 SUBDOMAIN OF VILLIN HEADPIECE DOMAIN
<220> FEATURE:
<221> NAME/KEY: MISC_FEATURE
<222> LOCATION: (68)..(68)
<223> OTHER INFORMATION: CYSTEINE SUBSTITUTION

<400> SEQUENCE: 90

```
Val Phe Asn Ala Asn Ser Asn Leu Ser Ser Gly Pro Leu Pro Ile Phe
1               5                   10                  15

Pro Leu Glu Gln Leu Val Asn Lys Pro Val Glu Leu Pro Glu Gly
            20                  25                  30
```

Val Asp Pro Ser Arg Lys Glu Glu His Leu Ser Ile Glu Asp Phe Thr
            35                  40                  45

Gln Ala Phe Gly Met Thr Pro Ala Ala Phe Ser Ala Leu Pro Arg Trp
        50                  55                  60

Lys Gln Gln Cys Leu Lys Lys Glu Lys Gly Leu Phe
65                  70                  75

<210> SEQ ID NO 91
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 91

His Gly Glu Gly Thr Phe Thr Ser Asp Val Ser Ser Tyr Leu Glu Gly
1               5                   10                  15

Gln Ala Ala Lys Glu Phe Ile Ala Gln Leu Gln Lys Gly Arg Gly
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 92

His Gly Glu Gly Thr Phe Thr Ser Asp Val Ser Ser Tyr Leu Glu Gly
1               5                   10                  15

Gln Ala Ala Lys Glu Phe Ile Ala Trp Leu Gln Lys Gly Arg Gly
            20                  25                  30

<210> SEQ ID NO 93
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 93

His Asn Glu Thr Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 94
<211> LENGTH: 55
<212> TYPE: PRT
<213> ORGANISM: Homo sapiens
<220> FEATURE:
<221> NAME/KEY: MISC_FEATURE
<223> OTHER INFORMATION: SH3(1X2K)

<400> SEQUENCE: 94

Lys Val Phe Arg Ala Leu Tyr Thr Phe Glu Pro Arg Thr Pro Asp Glu
1               5                   10                  15

Leu Tyr Phe Glu Glu Gly Asp Ile Ile Tyr Ile Thr Asp Met Ser Asp
            20                  25                  30

Thr Asn Trp Trp Lys Gly Thr Ser Lys Gly Arg Thr Gly Leu Ile Pro
        35                  40                  45

```
Ser Asn Tyr Val Ala Glu Gln
    50                  55

<210> SEQ ID NO 95
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 95

His Gly Glu Gly Thr Phe Thr Ser Asp Val Ser Ser Tyr Leu Glu Asn
1               5                   10                  15

Gln Thr Ala Lys Glu Phe Ile Ala Trp Leu Val Lys Gly Arg Gly
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 96

His Gly Glu Gly Thr Phe Thr Ser Asp Val Ser Ser Tyr Leu Glu Gly
1               5                   10                  15

Asn Ala Thr Lys Glu Phe Ile Ala Trp Leu Val Lys Gly Arg Gly
            20                  25                  30

<210> SEQ ID NO 97
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 97

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Asn Gly Thr Gly
            20                  25                  30

<210> SEQ ID NO 98
<211> LENGTH: 31
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 98

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Asn Arg Thr
            20                  25                  30

<210> SEQ ID NO 99
<211> LENGTH: 33
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE
```

```
<400> SEQUENCE: 99

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Asn Gly
            20                  25                  30

Thr

<210> SEQ ID NO 100
<211> LENGTH: 37
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 100

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Thr Gly Asn Gly Thr
        35

<210> SEQ ID NO 101
<211> LENGTH: 37
<212> TYPE: PRT
<213> ORGANISM: Artificial Sequence
<220> FEATURE:
<223> OTHER INFORMATION: GLUCAGON-LIKE PEPTIDE (GLP-1) MIMETIC
      POLYPEPTIDE SEQUENCE

<400> SEQUENCE: 101

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Ser Gly Asn Gly Thr
        35

<210> SEQ ID NO 102
<211> LENGTH: 98
<212> TYPE: PRT
<213> ORGANISM: Homo sapiens
<220> FEATURE:
<221> NAME/KEY: MISC_FEATURE
<223> OTHER INFORMATION: PDZ(1N7F):

<400> SEQUENCE: 102

Ser Ser Gly Ala Ile Ile Tyr Thr Val Glu Leu Lys Arg Tyr Gly Gly
1               5                   10                  15

Pro Leu Gly Ile Thr Ile Ser Gly Thr Glu Glu Pro Phe Asp Pro Ile
            20                  25                  30

Ile Ile Ser Ser Leu Thr Lys Gly Gly Leu Ala Glu Arg Thr Gly Ala
        35                  40                  45

Ile His Ile Gly Asp Arg Ile Leu Ala Ile Asn Ser Ser Ser Leu Lys
    50                  55                  60

Gly Lys Pro Leu Ser Glu Ala Ile His Leu Leu Gln Met Ala Gly Glu
65                  70                  75                  80

Thr Val Thr Leu Lys Ile Lys Lys Gln Thr Asp Ala Gln Ser Ala Ser
                85                  90                  95

Ser Pro
```

```
<210> SEQ ID NO 103
<211> LENGTH: 91
<212> TYPE: PRT
<213> ORGANISM: Homo sapiens
<220> FEATURE:
<221> NAME/KEY: MISC_FEATURE
<223> OTHER INFORMATION: PDZ(1UEZ)

<400> SEQUENCE: 103

Pro Gly Glu Val Arg Leu Val Ser Leu Arg Arg Ala Lys Ala His Glu
1               5                   10                  15

Gly Leu Gly Phe Ser Ile Arg Gly Gly Ser Glu His Gly Val Gly Ile
            20                  25                  30

Tyr Val Ser Leu Val Glu Pro Gly Ser Leu Ala Glu Lys Glu Gly Leu
        35                  40                  45

Arg Val Gly Asp Gln Ile Leu Arg Val Asn Asp Lys Ser Leu Ala Arg
    50                  55                  60

Val Thr His Ala Glu Ala Val Lys Ala Leu Lys Gly Ser Lys Lys Leu
65                  70                  75                  80

Val Leu Ser Val Tyr Ser Ala Gly Arg Ile Pro
                85                  90

<210> SEQ ID NO 104
<211> LENGTH: 94
<212> TYPE: PRT
<213> ORGANISM: Homo sapiens
<220> FEATURE:
<221> NAME/KEY: MISC_FEATURE
<223> OTHER INFORMATION: PDZ(1WFV)

<400> SEQUENCE: 104

Pro Gln Asp Phe Asp Tyr Phe Thr Val Asp Met Glu Lys Gly Ala Lys
1               5                   10                  15

Gly Phe Gly Phe Ser Ile Arg Gly Gly Arg Glu Tyr Lys Met Asp Leu
            20                  25                  30

Tyr Val Leu Arg Leu Ala Glu Asp Gly Pro Ala Ile Arg Asn Gly Arg
        35                  40                  45

Met Arg Val Gly Asp Gln Ile Ile Glu Ile Asn Gly Glu Ser Thr Arg
    50                  55                  60

Asp Met Thr His Ala Arg Ala Ile Glu Leu Ile Lys Ser Gly Gly Arg
65                  70                  75                  80

Arg Val Arg Leu Leu Leu Lys Arg Gly Thr Gly Gln Val Pro
                85                  90

<210> SEQ ID NO 105
<211> LENGTH: 83
<212> TYPE: PRT
<213> ORGANISM: Homo sapiens
<220> FEATURE:
<221> NAME/KEY: MISC_FEATURE
<223> OTHER INFORMATION: SH3(1PHT)

<400> SEQUENCE: 105

Ser Ala Glu Gly Tyr Gln Tyr Arg Ala Leu Tyr Asp Tyr Lys Lys Glu
1               5                   10                  15

Arg Glu Glu Asp Ile Asp Leu His Leu Gly Asp Ile Leu Thr Val Asn
            20                  25                  30

Lys Gly Ser Leu Val Ala Leu Gly Phe Ser Asp Gly Gln Glu Ala Arg
        35                  40                  45

Pro Glu Glu Ile Gly Trp Leu Asn Gly Tyr Asn Glu Thr Thr Gly Glu
```

```
                50                  55                  60
Arg Gly Asp Phe Pro Gly Thr Tyr Val Glu Tyr Ile Gly Arg Lys Lys
 65                  70                  75                  80

Ile Ser Pro

<210> SEQ ID NO 106
<211> LENGTH: 63
<212> TYPE: PRT
<213> ORGANISM: Homo sapiens
<220> FEATURE:
<221> NAME/KEY: MISC_FEATURE
<223> OTHER INFORMATION: SH3(1WA7)

<400> SEQUENCE: 106

Pro Glu Glu Gln Gly Asp Ile Val Val Ala Leu Tyr Pro Tyr Asp Gly
  1               5                  10                  15

Ile His Pro Asp Asp Leu Ser Phe Lys Lys Gly Glu Lys Met Lys Val
                 20                  25                  30

Leu Glu Glu His Gly Glu Trp Trp Lys Ala Lys Ser Leu Leu Thr Lys
             35                  40                  45

Lys Glu Gly Phe Ile Pro Ser Asn Tyr Val Ala Lys Leu Asn Thr
         50                  55                  60

<210> SEQ ID NO 107
<211> LENGTH: 101
<212> TYPE: PRT
<213> ORGANISM: Homo sapiens
<220> FEATURE:
<221> NAME/KEY: MISC_FEATURE
<223> OTHER INFORMATION: TRUNCATED FRAGMENT CH2 DOMAIN OF HUMAN IgG1

<400> SEQUENCE: 107

Gly Pro Ser Val Phe Leu Phe Pro Pro Lys Pro Lys Asp Thr Leu Met
  1               5                  10                  15

Ile Ser Arg Thr Pro Glu Val Thr Cys Val Val Val Asp Val Ser His
                 20                  25                  30

Glu Asp Pro Glu Val Lys Phe Asn Trp Tyr Val Asp Gly Val Glu Val
             35                  40                  45

His Asn Ala Lys Thr Lys Pro Arg Glu Glu Gln Tyr Asn Ser Thr Tyr
         50                  55                  60

Arg Val Val Ser Val Leu Thr Val Leu His Gln Asp Trp Leu Asn Gly
 65                  70                  75                  80

Lys Glu Tyr Lys Cys Lys Val Ser Asn Lys Ala Leu Pro Ala Pro Ile
                 85                  90                  95

Glu Lys Thr Ile Ser
            100

<210> SEQ ID NO 108
<211> LENGTH: 100
<212> TYPE: PRT
<213> ORGANISM: Homo sapiens
<220> FEATURE:
<221> NAME/KEY: MISC_FEATURE
<223> OTHER INFORMATION: TRUNCATED FRAGMENT CH2 DOMAIN OF HUMAN IgG1

<400> SEQUENCE: 108

Pro Ser Val Phe Leu Phe Pro Pro Lys Pro Lys Asp Thr Leu Met Ile
  1               5                  10                  15

Ser Arg Thr Pro Glu Val Thr Cys Val Val Val Asp Val Ser His Glu
                 20                  25                  30

Asp Pro Glu Val Lys Phe Asn Trp Tyr Val Asp Gly Val Glu Val His
```

```
                35                  40                  45
Asn Ala Lys Thr Lys Pro Arg Glu Glu Gln Tyr Asn Ser Thr Tyr Arg
 50                  55                  60

Val Val Ser Val Leu Thr Val Leu His Gln Asp Trp Leu Asn Gly Lys
 65                  70                  75                  80

Glu Tyr Lys Cys Lys Val Ser Asn Lys Ala Leu Pro Ala Pro Ile Glu
                 85                  90                  95

Lys Thr Ile Ser
            100

<210> SEQ ID NO 109
<211> LENGTH: 99
<212> TYPE: PRT
<213> ORGANISM: Homo sapiens
<220> FEATURE:
<221> NAME/KEY: MISC_FEATURE
<223> OTHER INFORMATION: SH2(1AB2)

<400> SEQUENCE: 109

Asn Ser Leu Glu Lys His Ser Trp Tyr His Gly Pro Val Ser Arg Asn
 1               5                  10                  15

Ala Ala Glu Tyr Leu Leu Ser Ser Gly Ile Asn Gly Ser Phe Leu Val
                20                  25                  30

Arg Glu Ser Glu Ser Ser Pro Gly Gln Arg Ser Ile Ser Leu Arg Tyr
            35                  40                  45

Glu Gly Arg Val Tyr His Tyr Arg Ile Asn Thr Ala Ser Asp Gly Lys
 50                  55                  60

Leu Tyr Val Ser Ser Glu Ser Arg Phe Asn Thr Leu Ala Glu Leu Val
 65                  70                  75                  80

His His His Ser Thr Val Ala Asp Gly Leu Ile Thr Thr Leu His Tyr
                 85                  90                  95

Pro Ala Pro

<210> SEQ ID NO 110
<211> LENGTH: 95
<212> TYPE: PRT
<213> ORGANISM: Homo sapiens
<220> FEATURE:
<221> NAME/KEY: MISC_FEATURE
<223> OTHER INFORMATION: SH2(1JYQ)

<400> SEQUENCE: 110

Pro Trp Phe Phe Gly Lys Ile Pro Arg Ala Lys Ala Glu Glu Met Leu
 1               5                  10                  15

Ser Lys Gln Arg His Asp Gly Ala Phe Leu Ile Arg Glu Ser Glu Ser
                20                  25                  30

Ala Pro Gly Asp Phe Ser Leu Ser Val Lys Phe Gly Asn Asp Val Gln
            35                  40                  45

His Phe Lys Val Leu Arg Asp Gly Ala Gly Lys Tyr Phe Leu Trp Val
        50                  55                  60

Val Lys Phe Asn Ser Leu Asn Glu Leu Val Asp Tyr His Arg Ser Thr
 65                  70                  75                  80

Ser Val Ser Arg Asn Gln Gln Ile Phe Leu Arg Asp Ile Glu Gln
                85                  90                  95

<210> SEQ ID NO 111
<211> LENGTH: 38
<212> TYPE: PRT
<213> ORGANISM: Orthochirus scrobiculosus
<220> FEATURE:
```

```
<221> NAME/KEY: MISC_FEATURE
<223> OTHER INFORMATION: OSK1

<400> SEQUENCE: 111

Gly Val Ile Ile Asn Val Lys Cys Lys Ile Ser Arg Gln Cys Leu Glu
1               5                   10                  15

Pro Cys Lys Lys Ala Gly Met Arg Phe Gly Lys Cys Met Asn Gly Lys
            20                  25                  30

Cys His Cys Thr Pro Lys
            35

<210> SEQ ID NO 112
<211> LENGTH: 35
<212> TYPE: PRT
<213> ORGANISM: Stichodactyla helianthus
<220> FEATURE:
<221> NAME/KEY: MISC_FEATURE
<223> OTHER INFORMATION: ShK

<400> SEQUENCE: 112

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```